United States Patent
Mahr et al.

(10) Patent No.: US 12,156,905 B2
(45) Date of Patent: *Dec. 3, 2024

(54) CCR8 PEPTIDE AND T CELLS FOR USE IN IMMUNOTHERAPEUTIC TREATMENT OF VARIOUS CANCERS

(71) Applicant: Immatics Biotechnologies GmbH, Tuebingen (DE)

(72) Inventors: Andrea Mahr, Tuebingen (DE); Toni Weinschenk, Tuebingen (DE); Oliver Schoor, Tuebingen (DE); Jens Fritsche, Tuebingen (DE); Harpreet Singh, Tuebingen (DE)

(73) Assignee: Immatics Biotechnologies GmbH, Tübingen (DE)

( * ) Notice: Subject to any disclaimer, the term of this patent is extended or adjusted under 35 U.S.C. 154(b) by 0 days.

This patent is subject to a terminal disclaimer.

(21) Appl. No.: 18/158,606

(22) Filed: Jan. 24, 2023

(65) Prior Publication Data

US 2023/0226161 A1 Jul. 20, 2023

Related U.S. Application Data

(63) Continuation of application No. 17/711,855, filed on Apr. 1, 2022, which is a continuation of application (Continued)

(30) Foreign Application Priority Data

Aug. 28, 2015 (GB) .................................... 1515321

(51) Int. Cl.
| | | |
|---|---|---|
| A61K 39/00 | (2006.01) | |
| A61P 35/00 | (2006.01) | |
| C07K 7/06 | (2006.01) | |
| C07K 7/08 | (2006.01) | |
| C07K 14/47 | (2006.01) | |
| C07K 14/725 | (2006.01) | |
| C07K 14/74 | (2006.01) | |
| C07K 16/28 | (2006.01) | |
| C07K 16/30 | (2006.01) | |

(Continued)

(52) U.S. Cl.
CPC .......... *A61K 39/0011* (2013.01); *A61P 35/00* (2018.01); *C07K 7/06* (2013.01); *C07K 7/08* (2013.01); *C07K 14/4748* (2013.01); *C07K 14/7051* (2013.01); *C07K 14/70539* (2013.01); *C07K 16/2833* (2013.01); *C07K 16/3076* (2013.01); *C12N 5/0636* (2013.01); *C12N 15/115* (2013.01); *C12Q 1/6886* (2013.01); *G01N 33/57492* (2013.01); *A61K 39/00* (2013.01); *A61K 2039/5158* (2013.01); *C07K 2319/40* (2013.01); *C12N 2310/16* (2013.01); *C12N 2501/50* (2013.01); *C12Q 2600/106* (2013.01); *C12Q 2600/156* (2013.01); *G01N 2333/70539* (2013.01)

(58) Field of Classification Search
CPC ................ A61K 39/0011; A61K 39/00; A61K 2039/5158; A61K 9/0019; A61K 35/17; A61K 38/08; A61K 39/385; A61K 39/39558; A61P 35/00; C07K 7/06; C07K 7/08; C07K 14/4748; C07K 14/7051; C07K 14/70539; C07K 16/2833; C07K 16/3076; C07K 2319/40; C07K 16/32; C12N 5/0636; C12N 15/115; C12N 2310/16; C12N 2501/50; C12N 15/10; C12N 15/11; C12Q 1/6886; C12Q 2600/106; C12Q 2600/156; C12Q 1/6883; G01N 33/57492; G01N 2333/70539
See application file for complete search history.

(56) References Cited

U.S. PATENT DOCUMENTS

| | | |
|---|---|---|
| 6,680,197 B2 | 1/2004 | Jiang et al. |
| 6,897,054 B1 | 5/2005 | Arai et al. |

(Continued)

FOREIGN PATENT DOCUMENTS

| | | |
|---|---|---|
| CN | 101765610 A | 6/2010 |
| EP | 1104808 A1 | 6/2001 |

(Continued)

OTHER PUBLICATIONS

Widdison et al. The bovine chemokine receptors and their mRNA abundance in mononuclear phagocytes. BMC Genomics 11:439-439 (2010).*

(Continued)

*Primary Examiner* — Alana Harris Dent
(74) *Attorney, Agent, or Firm* — McBee Moore & Vanik IP, LLC

(57) ABSTRACT

The present invention relates to peptides, proteins, nucleic acids and cells for use in immunotherapeutic methods. In particular, the present invention relates to the immunotherapy of cancer. The present invention furthermore relates to tumor-associated T-cell peptide epitopes, alone or in combination with other tumor-associated peptides that can for example serve as active pharmaceutical ingredients of vaccine compositions that stimulate anti-tumor immune responses, or to stimulate T cells ex vivo and transfer into patients. Peptides bound to molecules of the major histocompatibility complex (MHC), or peptides as such, can also be targets of antibodies, soluble T-cell receptors, and other binding molecules.

20 Claims, 35 Drawing Sheets
Specification includes a Sequence Listing.

Related U.S. Application Data

No. 17/320,763, filed on May 14, 2021, now Pat. No. 11,793,866, which is a continuation of application No. 17/017,358, filed on Sep. 10, 2020, now Pat. No. 11,065,316, which is a continuation of application No. 16/887,765, filed on May 29, 2020, now Pat. No. 10,898,557, which is a continuation of application No. 16/673,619, filed on Nov. 4, 2019, now Pat. No. 10,695,411, which is a continuation of application No. 15/982,293, filed on May 17, 2018, now Pat. No. 10,576,132, which is a continuation of application No. 15/249,083, filed on Aug. 26, 2016, now Pat. No. 10,335,471.

(60) Provisional application No. 62/211,276, filed on Aug. 28, 2015.

(51) Int. Cl.
*C12N 5/0783* (2010.01)
*C12N 15/115* (2010.01)
*C12Q 1/6886* (2018.01)
*G01N 33/574* (2006.01)

(56) References Cited

U.S. PATENT DOCUMENTS

| | | | |
|---|---|---|---|
| 6,946,256 | B1 | 9/2005 | McKeon et al. |
| 7,807,642 | B2 | 10/2010 | Dengjel |
| 7,833,969 | B2 | 11/2010 | Dengjel |
| 7,833,970 | B2 | 11/2010 | Dengjel |
| 8,080,634 | B2 | 12/2011 | Singh et al. |
| 8,119,139 | B2 | 2/2012 | Weinschenk et al. |
| 8,318,677 | B2 | 11/2012 | Weinschenk et al. |
| 8,653,035 | B2 | 2/2014 | Weinschenk et al. |
| 8,669,230 | B2 | 3/2014 | Singh et al. |
| 8,895,514 | B2 | 11/2014 | Weinschenk et al. |
| 8,961,985 | B2 | 2/2015 | Weinschenk et al. |
| 9,511,128 | B2 | 12/2016 | Singh et al. |
| 9,943,579 | B2 | 4/2018 | Weinschenk et al. |
| 9,950,048 | B2 | 4/2018 | Singh et al. |
| 9,993,540 | B2 | 6/2018 | Weinschenk et al. |
| 10,046,037 | B2 | 8/2018 | Weinschenk et al. |
| 10,047,123 | B2 | 8/2018 | Weinschenk et al. |
| 10,047,124 | B2 | 8/2018 | Weinschenk et al. |
| 10,071,148 | B2 | 9/2018 | Weinschenk et al. |
| 10,100,085 | B2 | 10/2018 | Weinschenk et al. |
| 10,196,432 | B2 | 2/2019 | Dengjel |
| 10,227,381 | B2 | 3/2019 | Weinschenk et al. |
| 10,420,800 | B2 | 9/2019 | Weinschenk et al. |
| 10,618,945 | B2 | 4/2020 | Dengjel |
| 2005/0196754 | A1 | 9/2005 | Drmanac et al. |
| 2008/0206216 | A1 | 8/2008 | Dengjel |
| 2009/0098533 | A1 | 4/2009 | Munnes et al. |
| 2009/0136528 | A1 | 5/2009 | Singh et al. |
| 2011/0111711 | A1 | 5/2011 | Bo |
| 2011/0200626 | A1 | 8/2011 | Tsunoda et al. |
| 2011/0229504 | A1 | 9/2011 | Fritsche et al. |
| 2011/0318380 | A1 | 12/2011 | Brix et al. |
| 2013/0096016 | A1 | 4/2013 | Weinschenk et al. |
| 2014/0010861 | A1 | 1/2014 | Bancel et al. |
| 2014/0271692 | A1 | 9/2014 | Singh et al. |
| 2014/0273275 | A1 | 9/2014 | Jacobs et al. |
| 2016/0009795 | A1 | 1/2016 | Tacha et al. |
| 2016/0051654 | A1 | 2/2016 | Singh et al. |
| 2016/0168200 | A1 | 6/2016 | Weinschenk et al. |
| 2019/0076476 | A1 | 3/2019 | Weinschenk et al. |

FOREIGN PATENT DOCUMENTS

| | | | |
|---|---|---|---|
| EP | 1498424 | A2 | 1/2005 |
| EP | 1760088 | B1 | 3/2008 |
| EP | 1125947 | B1 | 4/2012 |
| WO | 9945954 | A1 | 9/1999 |
| WO | 2003016523 | A1 | 2/2003 |
| WO | 2003062401 | A2 | 7/2003 |
| WO | 2004099243 | A2 | 11/2004 |
| WO | 2005073374 | A1 | 8/2005 |
| WO | 2007028574 | A9 | 5/2008 |
| WO | 2009015842 | A2 | 2/2009 |
| WO | 2010037395 | A2 | 4/2010 |
| WO | 2010037513 | A1 | 4/2010 |
| WO | 2013039477 | A1 | 3/2013 |
| WO | 2013070603 | A1 | 5/2013 |
| WO | 2013151665 | A2 | 10/2013 |
| WO | 2014026277 | A1 | 2/2014 |
| WO | 2015018805 | A1 | 2/2015 |
| WO | 2015092710 | A1 | 6/2015 |
| WO | 2017184590 | A1 | 10/2017 |

OTHER PUBLICATIONS

Research Collaboratory for Structural Bioinformatics (RCSB) Protein Data Bank (PDB).Vyalkvrti. 2 pages. Oct. 20, 2023.*
Peptide Atlas, Exact. Vyalkvrti. 1 page. Oct. 20, 2023.*
Accardi, Luisa, et al. "In vivo antitumor effect of an intracellular single-chain antibody fragment against the E7 oncoprotein of human papillomavirus 16" International Journal of Cancer, vol. 134, No. 11, pp. 2742-2747, Jun. 2014.
Akiyama, Yasuto, et al. "Identification of novel MAGE-A6- and MAGE-A12-derived HLA-A24-restricted cytotoxic T lymphocyte epitopes using an in silico peptide-docking assay" Cancer Immunology Immunotherapy, vol. 61, No. 12, pp. 2311-2319, Dec. 2012.
Ampie, Leonel, et al. "Immunotherapeutic advancements for glioblastoma" Frontiers in Oncology, vol. 5, Article 12, Jan. 2015.
Avigan, David, et al. "Fusion Cell Vaccination of Patients with Metastatic Breast and Renal Cancer Induces Immunological and Clinical Responses" Clinical Cancer Research, vol. 10, pp. 4699-4708, Jul. 15, 2004.
Bassani-Sternberg, Michal, et al. "Direct identification of clinically relevant neoepitopes presented on native human melanoma tissue by mass spectrometry" Nature Communications, vol. 7, Article No. 13404, Nov. 2016.
Beatty, Gregory L., et al. "IFN-g-Dependent Inhibition of Tumor Angiogenesis by Tumor-Infiltrating CD41 T Cells Requires Tumor Responsiveness to IFN-y1" Journal of Immunology, vol. 166, No. 4, pp. 2276-2282, Feb. 15, 2001.
Braumueller, Heidi, et al. "T-helper-1-cell cytokines drive cancer into senescence" Nature, vol. 494, pp. 361-365, Feb. 2013.
Bray, Freddie, et al. "Global estimates of cancer prevalence for 27 sites in the adult population in 2008" International Journal of Cancer, vol. 132, pp. 1133-1145, 2013.
Brossart, Peter and Bevan, Michael J. "Presentation of Exogenous Protein Antigens on Major Histocompatibility Complex Class I Molecules by Dendritic Cells: Pathway of Presentation and Regulation by Cytokines" Blood, vol. 90, No. 4, pp. 1594-1599, Aug. 15, 1997.
Butterfield, Lisa H., et al., "A Phase I/II Trial Testing Immunization of Hepatocellular Carcinoma Patients with Dendritic Cells Pulsed with Four α-Fetoprotein Peptides", Clinical Cancer Research, vol. 12, No. 9, pp. 2817-2825, May 2006.
Butterfield, Lisa H., et al., "Determinant Spreading Associated with Clinical Response in Dendritic Cell-based Immunotherapy for Malignant Melanoma", Clinical Cancer Research, vol. 9, pp. 998-1008, Mar. 2003.
Carballido, Estrella, et al. "Immunomodulatory Drugs and Active Immunotherapy for Chronic Lymphocytic Leukemia" Cancer Control, vol. 19, Issue 1, pp. 4-76, Jan. 2012.
Coosemans, An, et al. "Wilms' Tumor Gene 1 (WT1)-loaded dendritic cell immunotherapy in patients with uterine tumors: a phase I/II clinical trial" Anticancer Research, vol. 33, No. 12, pp. 5495-5500, Dec. 2013.
Corse, Emily, et al., "Strength of TCR-Peptide/MHC interactions and in vivo T cell responses", The Journal of Immunology, vol. 186, No. 9, pp. 5039-5045, May 2011.

(56) References Cited

OTHER PUBLICATIONS

Counter, C.M., "Telomerase activity in normal leukocytes and in hematologic malignancies" Blood, vol. 85, No. 9, pp. 2315-2320, May 1995.
Dengjel, Joern, et al. "Unexpected Abundance of HLA Class II Presented Peptides in Primary Renal Cell Carcinomas" Clinical Cancer Research, vol. 12, No. 14, pp. 4163-4170, Jul. 15, 2006.
Dimarco, Moreno, "The immunopeptidomic landscape of clear cell renal cell carcinoma: identification and characterization of T-cell epitopes for immunotherapeutic approaches," Tuebingen, Germany, 206 pages, Oct. 26, J017.
Economopoulou, Panagiota, et al. "The emerging role of immunotherapy in head and neck squamous cell carcinoma (HNSCC): anti-tumor immunity and clinical applications" Annals of Translational Medicine, vol. 4, No. 9, Article 173, May 2016.
Emens, Leisha A. "Breast cancer immunobiology driving immunotherapy: vaccines and immune checkpoint blockade" Expert Review Anticancer Therapy, vol. 12, No. 12, pp. 1597-1611, Dec. 2012.
Estey, Elihu H. "Acute myeloid leukemia: 2014 update on risk-stratification and management" American Journal of Hematology, vol. 89, No. 11, pp. 1063-1081, Nov. 2014.
ExactPeptideAtlas, Tldeyltyl (SEQ ID No. 80), 1 page, printed Aug. 29, 2022.
Ferlay, J., et al. "Cancer incidence and mortality patterns in Europe: Estimates for 40 countries in 2012" European Journal of Cancer, vol. 49, pp. 1374-1403, Apr. 2013.
Fuge, Oliver, et al. "Immunotherapy for bladder cancer" Research and Reports in Urology, vol. 7, pp. 65-79, May 2015.
Gandhi, Ankit V., et al. "Differential expression of cytochrome P450 omega-hydroxylase isoforms and their association with clinicopathological features in pancreatic ductal adenocarcinoma" Annals Surgical Oncology, vol. 20, Suppl. 3, Dec. 2013.
Ganju, Ramesh K., et al. "Similarity between fluorescein-specific T-cell receptor and antibody in chemical details of antigen recognition" Proc. Natl. Acad. Sci., vol. 89, pp. 11552-11556, Dec. 1992.
Genbank, PRAMEF9, partial [synthetic construct] GenBank: AIC53674. 1, Retrieved from URL: https://ncbi.nlm.nih.gov/protein/AIC53674.1 on Feb. 28, 2023 (1 page).
Giannopolous, K., et al. "Peptide vaccination elicits leukemia-associated antigen-specific cytotoxic CD8+ T-cell responses in patients with chronic lymphocytic leukemia" Leukemia, vol. 24, No. 4, pp. 798-805, Apr. 2010.
Giannopoulos, K., et al. "Expression of RHAMM/CD168 and other tumor-associated antigens in patients with B-cell chronic lymphocytic leukemia" International Journal of Oncology, vol. 29, No. 1, pp. 95-103, Jul. 2006.
Gnjatic, Sacha, et al. "Survey of naturally occurring CD4 T cell responses against NY-ESO-1 in cancer patients: Correlation with antibody responses" PNAS, vol. 100, No. 15, pp. 8862-8867, Jul. 22, 2003.
Goede, Valentin, et al. "Obinutuzumab plus chlorambucil in patients with CLL and coexisting conditions" New England Journal of Medicine, vol. 370, No. 12, pp. 1101-1110, Mar. 2014.
Google Search for "VLSPFILTL", 1 page, Jul. 22, 2020.
Granziero, L., et al. "Survivin is expressed on CD40 stimulation and interfaces proliferation and apoptosis in B-cell chronic lymphocytic leukemia" Blood, vol. 97, No. 9, pp. 27777-27783, May 2001.
Grivas, Petros D., et al. "The biological complexity of urothelial carcinoma: Insights into carcinogenesis, targets and biomarkers of response to therapeutic approaches" Semin Cancer Biol. vol. 35, pp. 125-132, Dec. 2015.
Hagemann, Carsten, et al. "A complete compilation of matrix metalloproteinase expression in human malignant gliomas" World Journal of Clinical Oncology, vol. 3, No. 5, pp. 67-79, May 2012.
Hallek, M., et al. "Immunochemotherapy with fludarabine (F), cyclophosphamide (C), and rituximab (R) (FCR) versus fludarabine and cyclophosphamide (FC) improves response rates and progression-free survival (PFS) of previously untreated patients (pts) with advanced chronic lymphocytic leukemia (CLL)" Blood (ASH Annual Meeting Abstracts), vol. 112, p. 325, 2008 (Abtsract Only).
Harig, S., et al. "Induction of cytotoxic T-cell responses against immunoglobulin V region-derived peptides modified at human leukocyte antigen-A2 binding residues" Blood, vol. 98, No. 10, pp. 29999-3005, Nov. 2001.
Hassan, Chopie, et al. "The human leukocyte antigen-presented ligandome of B lymphocytes" Molecular Cell Proteomics, vol. 12, No. 7, pp. 1829-1843, Jul. 2013.
Hinrichs, Christian S., et al. "Reassessing target antigens for adoptive T-cell therapy" Nat Biotechnol. vol. 31, No. 11, pp. 999-1008, Nov. 2013.
Holtl, Lorenz, et al. "Immunotherapy of Metastatic Renal Cell Carcinoma with Tumor Lysate-pulsed Autologous Dendritic Cells1" Clinical Cancer Research, vol. 8, pp. 3369-3376, Nov. 2002.
Horig, Heidi, et al. "Phase I clinical trial of a recombinant canarypoxvirus (ALVAC) vaccine expressing human carcinoembryonic antigen and the B7.1 co-stimulatory molecule" Cancer Immunology, Immunotherapy, vol. 49, No. 9, pp. 504-514, Nov. 2000.
Hung, Chien-Fu, et al. "Antigen-specific immunotherapy of cervical and ovarian cancer" Immunological Review, vol. 222, pp. 43-69, Apr. 2008.
Hus, Iwona, et al. "Immunotherapy with irradiated autologous leukemic cells in patients with B-CLL in early stages" Oncology Rep. vol. 20, No. 2, pp. 443-451, Aug. 2008.
Hwang. Melissa L., et al. "Cognate memory CD4+ T cells generated with dendritic cell priming influence the expansion, trafficking, and differentiation of secondary CD8+ T cells and enhance tumor control" Journal of Immunology, vol. 179, No. 9, pp. 5829-5838, Nov. 2007.
International Search Report for PCT/EP2016/070146, mailed Feb. 13, 2017.
Jones, Robert T., et al. "Pharmacogenomics: Biomarker-Directed Therapy for Bladder Cancer" Urol. Clim North America, vol. 43, No. 1, pp. 77-86, Feb. 2016.
Kalos, Michael, et al. "T cells with chimeric antigen receptors have potent antitumor effects and can establish memory in patients with advanced leukemia" Science Translational Medicine, vol. 3, No. 95, Aug. 2011.
Kaufman, Howard L., et al. "Combination Chemotherapy and ALVAC-CEA/B7.1Vaccine in Patients with Metastatic Colorectal Cancer" Clinical Cancer Research, vol. 14, No. 15, pp. 4843-4849, Aug. 1, 2008.
Knollman, Hayley, et al. "Muscle-invasive urothelial bladder cancer: an update on systemic therapy" Ther Adv Urol. Vol. 7, No. 6, pp. 312-330, Dec. 2015.
Koido, Shigeo, et al. "Immunotherapy for colorectal cancer" World Journal of Gastroenterology, vol. 19, No. 46, pp. 8531-8542, Dec. 14, 2013.
Krackhardt, Angela M., et al. "Identification of tumor-associated antigens in chronic lymphocytic leukemia by SEREX" Blood, vol. 100, No. 6, pp. 2123-2131, Sep. 2002.
Kronenberger, Konrad, et al. "A Polyvalent Cellular Vaccine Induces T-cell Responses Against Specific Self-antigens Overexpressed in Chronic Lymphocytic B-cell Leukemia" Journal of Immunotherapy, vol. 31, Issue 8, pp. 723-730, Oct. 2008.
Lee, Wei-Chen, et al. , "Vaccination of Advanced Hepatocellular Carcinoma Patients with Tumor Lysate-Pulsed Dendritic Cells: A Clinical Trial" Journal of Immunotherapy, vol. 28, No. 5, pp. 496-504, Sep./Oct. 2005.
Maerten, Angela, et al. "Therapeutic vaccination against metastatic renal cell carcinoma by autologous dendritic cells: preclinical results and outcome of a first clinical phase I/II trial" Cancer Immunology, Immunotherapy, vol. 51, pp. 637-644, Oct. 2002.
Mantia-Smaldone, Gina M., et al. "Immunotherapy in ovarian cancer" Human Vaccin Innumotherapy, vol. 8, No. 9, pp. 1179-1191, Sep. 2012.
Massari, F., et al. "PD-1 blockade therapy in renal cell carcinoma: Current studies and future promises" Cancer Treatment Reviews, vol. 41, No. 2, pp. 114-121, Feb. 2015.
Matsueda, Satoko, et al. "Immunotherapy in gastric cancer" World Journal of Gastroenterology, vol. 20, Issue 7, pp. 1657-1666, Feb. 21, 2014.

(56) References Cited

OTHER PUBLICATIONS

Maus, Marcela V., et al. "Antibody-modified T cells: CARs take the front seat for hematologic malignancies" Blood, vol. 123, No. 17, pp. 2625-2635, Apr. 2014.
Mayr, Christine, et al. "Fibromodulin as a novel tumor-associated antigen (TAA) in chronic lymphocytic leukemia (CLL), which allows expansion of specific CD8+ autologous T lymphocytes" Blood, vol. 105, No. 4, pp. 1566-1573, Feb. 2005.
Mayr, Christine, et al. "MDM2 is recognized as a tumor-associated antigen in chronic lymphocytic leukemia by CD8+ autologous T lymphocytes" Experimental Hematology, vol. 31, No. 1, pp. 44-53, Jan. 2006.
Milner, Elena, et al. "The effect of proteasome inhibition on the generation of the human leukocyte antigen (HLA) peptidome" (and Supplemental Table 3B) Molecular & Cellular Proteomics, vol. 12, No. 7, pp. 1853-1864, Jul. 2013.
Miyagi, Hiromasa, et al. "Expression of human beta-interferon in Namalwa KJM-1 which was adapted to serum-free medium" Cytotechnology, vol. 3, No. 2, pp. 133-140, Mar. 1990.
Mortara, Lorenzo, et al. "CIITA-Induced MHC Class II Expression in Mammary Adenocarcinoma Leads to a Th1Polarization of the Tumor Microenvironment, Tumor Rejection, and Specific Antitumor Memory" Clinical Cancer Research, vol. 12, No. 11, pp. 3435-3443, Jun. 1, 2006.
Moulton, Hong M., et al. "Active Specific Immunotherapy with a beta-Human Chorionic Gonadotropin Peptide Vaccine in Patients with Metastatic Colorectal Cancer: Antibody Response Is Associated with Improved Survival1" Clinical Cancer Research, vol. 8, pp. 2044-2051, Jul. 2002.
Mueller, Martin R., et al. "Induction of chronic lymphocytic leukemia (CLL)-specific CD4- and CD8-mediated T-cell responses using RNA-transfected dendritic cells" Blood, vol. 103, No. 5, pp. 1763-1769, Mar. 2004.
Mumberg, Dominik, et al. "CD41 T cells eliminate MHC class II-negative cancer cells in vivo by indirect effects of IFN-γ" Immunology, vol. 96, pp. 8633-8638, Jul. 1999.
NCBI Blast Protein search results for "FTG36KH2016" 7 sheets, Jul. 1, 2020.
NCBI Blast Protein Sequence for "HGMEU3ED016", 26 pages, Jul. 22, 2020.
NCBI Blast Protein sequence search, 9 pages, Oct. 18, 2020.
NCBI Blast Protein sequence search. 10 pages. Aug. 19, 2022.
NCBI-DNA replication complex GINS protein PSF2 [*Homo sapiens*] protein sequence, NCBI Reference Sequence: NP_05179.1, 3 pages. printed Sep. 8, 2022.
Okuno, Kiyotaka, et al. "Phase I clinical trial of a novel peptide vaccine in combination with UFT/LV for metastatic colorectal cancer" Experimental and Therapeutic Medicine, vol. 2, pp. 73-79, Jan. 2011.
Palma, M., et al. "Development of a dendritic cell-based vaccine for chronic lymphocytic leukemia" Cancer Immunol. Immunother. vol. 57, No. 11, pp. 1705-1710, Nov. 2008.
Palmer, Daniel H., et al., "A phase II study of adoptive immunotherapy using dendritic cells pulsed with tumor lysate in patients with hepatocellular carcinoma", Hepatology, vol. 49, pp. 124-132, Jan. 2009.
Palomba, M. Lia. "Active immunotherapy: current state of the art in vaccine approaches for NHL" Current Oncology Reports, vol. 14, No. 5, pp. 433-440, Oct. 2012.
Parikh, Sameer A., et al. "Frontline chemoimmunotherapy with fludarabine, cyclophosphamide, alemtuzumab, and rituximab for high-risk chronic lymphocytic leukemia" Blood, vol. 118, No. 8, pp. 2062, 2068, Aug. 2011.
PepBank search results for "VHFEDTGKTLLF", 3 sheets, Jul. 1, 2020.
PepBank, 1 page, Jul. 22, 2020.
PepBank, 1 page, Sep. 16, 2019.
Peptide Atlas searches. 2 pages. Aug. 19, 2022.
Peptide Match [PIR-Prot. Inf. Resource], 1 page, Sep. 16, 2019, SYVKVLHHL.
PeptideAtlas "VLSPFILTL", 3 pages, Jul. 22, 2020.
PeptideAtlas search results for "VHFEDTGKLLF", 2 sheets, Jul. 1, 2020.
PeptideAtlas Search, YYMELTKLLL, 1 page. Sep. 7, 2022.
PeptideAtlas, 1 page, Sep. 16, 2019, SYVKVLHHL.
PeptideAtlas, TLDEYLTYL (SEQ ID No. 80), 1 page, printed Aug. 29, 2022.
PeptideAtlasExact sequence alignment, 1 page, Oct. 19, 2020, VYEKNGYIYF.
Phan, Giao Q., et al. "Adoptive cell transfer for patients with metastatic melanoma: the potential and promise of cancer immunotherapy" Cancer Control, vol. 20, No. 4, pp. 289-297, Oct. 2013.
Porter, David L., et al. "Chimeric antigen receptor-modified T cells in chronic lymphoid leukemia" New England Journal of Medicine, vol. 365, No. 8, pp. 725-733, Aug. 2011.
Quinn, David I., et al. "Immunotherapy for castration-resistant prostate cancer: Progress and new paradigms" Urologic Oncology, vol. 33, No. 5, pp. 245-260, May 2015.
Reinisch et al., "Prospective Pilot Study of Recombinant Granulocyte-Macrophage Colony-Stimulating Factor and Interferon-γ in Patients With Inoperable Hepatocellular Carcinoma" Journal of Immunotherapy, vol. 25, No. 6, pp. 489-499, Nov./Dec. 2002.
Reinmuth, Niels, et al. "[Non-small cell lung cancer: news from immunotherapy]" Dtsch Med Wochenschr, vol. 140, No. 5, pp. 329-333, Mar. 2015.
Richards, S., et al. "Chemotherapeutic Options in Chronic Lymphocytic Leukemia: a Meta-analysis of the Randomized Trials" J Natl. Cancer Inst vol. 91, pp. 861-868, May 1999.
Rini, Brian I., et al. "Bevacizumab Plus Interferon Alfa Compared With Interferon Alfa Monotherapy in Patients With Metastatic Renal Cell Carcinoma: CALGB 90206" Journal of Clinical Oncology, vol. 26, No. 33, Nov. 20, 2008.
Robak, Tadeusz, et al. "Anti-CD37 antibodies for chronic lymphocytic leukemia" Expert Opinion on Biological Therapy, vol. 14, No. 5, pp. 651-661, Feb. 2014.
Rock, K.L., et al. "Presentation of exogenous antigen with class I major histocompatibility complex molecules" Science, vol. 249, No. 4971, pp. 918-921, Aug. 1990.
Rouanne, Mathieu, et al. "Novel therapeutic targets in advanced urothelial carcinoma" Critical Review Oncol Hematology, vol. 98, pp. 106-115, Feb. 2016.
Salman, Bulent, et al. "Vaccine therapy for pancreatic cancer" Oncoimmunology, vol. 2, No. 12, article e26662, Dec. 2013.
Sangro, Bruno, et al., "Phase I Trial of Intratumoral Injection of an Adenovirus Encoding Interleukin-12 for Advanced Digestive Tumors", Journal of Clinical Oncology, vol. 22, No. 8, pp. 1389-1397, Apr. 15, 2004.
Sawada, Yu, et al. "A glypican 3-derived peptide vaccine against hepatocellular carcinoma" Oncolnnumology, vol. 1, No. 8, pp. 1448-1450, Nov. 2012.
Schmidt, Susanne M., et al. "Induction of adipophilin-specific cytotoxic T lymphocytes using a novel HLA-A2-binding peptide that mediates tumor cell lysis" Cancer Research, vol. 64, No. 3, pp. 1164-1170, Feb. 2004.
Search Report from GB Application No. 1515321.6, dated Jul. 12, 2016.
Shi, M., "Autologous cytokine-induced killer cell therapy in clinical trial phase I is safe in patients with primary hepatocellular carcinoma", World Journal of Gastroenterology, vol. 10, No. 8, pp. 1146-1151, Apr. 15, 2004.
Siegel, Sandra, et al. "Induction of cytotoxic T-cell responses against the oncofetal antigen-immature laminin receptor for the treatment of hematologic malignancies" Blood, vol. 102, No. 13, pp. 4416-4423, Dec. 2003.
Signori, Emanuela, et al. "The Fourteenth International Conference on Progress in Vaccination Against Cancer (PIVAC-14), Sep. 24-26, 2014, Rome, Italy: rethinking anti-tumor vaccines in a new era of cancer Immunotherapy" Cancer Immunology Immunotherapy, vol. 64, No. 10, pp. 1349-1356, Oct. 2015.

(56) References Cited

OTHER PUBLICATIONS

Singh-Jasuja, Harpreet et al. "!The Tuebingen approach: identification, selection, and validation of tumor-associated HLA peptides for cancer therapy" Cancer Immunology, Immunotherapy, vol. 53, pp. 187-185, Jan. 2004.

Smith, Sheena N., et al. "Changing the peptide specificity of a human T cell receptor by directed evolution" Nat. Commun. vol. 5, Article 5223, Nov. 2014.

Spaner, David E., et al. "A phase I/II trial of oxidized autologous tumor vaccines during the "watch and wait" phase of chronic lymphocytic leukemia" Cancer Immunol. Immunother. vol. 54, No. 7, pp. 635-646, Jul. 2005.

Srivastava, Neeharika, et al. "Update on benefit of immunotherapy and targeted therapy in melanoma: the changing landscape" Cancer Manag Res. vol. 6, pp. 279-289, Jun. 2014.

Stevanovic, Sanja, et al. "Complete regression of metastatic cervical cancer after treatment with human papillomavirus-targeted tumor-infiltrating T cells" Journal of Clinical Oncology, vol. 33, No. 14, pp. 1543-1550, May 2015.

Stintzing, Sebastian. "Management of colorectal cancer" F1000 Prime Reports, vol. 6, No. 108, 2014 (12 pages).

Su, Zhen, et al. "Immunological and clinical responses in metastatic renal cancer patients vaccinated with tumor RNA-transfected dendritic cells" Cancer Research, vol. 63, No. 9, pp. 2127-2133, May 2003.

Takayama, Tadatoshi, et al. "Distribution and therapeutic effect of intraarterially transferred tumor—infiltrating lymphocytes in hepatic malignancies", A Preliminary Report, Cancer, vol. 68, No. 11, pp. 2391-2396, Mar. 19, 1991.

Takayama, Tadatoshi, et al., "Adoptive immunotherapy to lower postsurgical recurrence rates of hepatocellular carcinoma: a randomised trial", The Lancet, vol. 356, pp. 802-807, Sep. 2, 2000.

The Human Protein Atlas: MMP13 protein expression summary, Tissue expression of MMP13, Brain tissue expression of MMP13, 7 pages, printed Oct. 27, 2020.

Toomey, Paul G., et al. "Immunotherapy for Gastrointestinal Malignancies" Cancer Control, vol. 20, No. 1, pp. 32-42, Jan. 2013.

Tran, Eric, et al. "Cancer Immunotherapy Based on Mutation-Specific CD4+ T Cells in a Patient with Epithelial Cancer" Science, vol. 344, No. 6184, pp. 641-645, May 2014.

Udaka, K., et al. "Tolerance to amino acid variations in peptides binding to the major histocompatibility complex class I protein H-2Kb" Journal Biol Chemistry, vol. 270, No. 41, pp. 24130-24134, Oct. 1995.

Vici, Patrizia, et al. "Immunologic treatments for precancerous lesions and uterine cervical cancer" Journal Experimental Clinical Cancer Research, vol. 33, No. 1, Mar. 2014.

Von Rundstedt, Friedrich-Carl, et al. "Bacille-Calmette-Guerin non-responders: how to manage" Transl. Androl. Urol. vol. 4, No. 3, pp. 244-253, Jun. 2015.

Weinschenk, Toni, et al. "Integrated functional genomics approach for the design of patient-individual antitumor vaccines" Cancer Research, vol. 62, No. 20, pp. 5818-5827, Oct. 2002.

Wierda, William G., et al. "Ofatumumab is active in patients with fludarabine-refractory CLL irrespective of prior rituximab: results from the phase 2 international study" Blood, vol. 118, No. 19, pp. 5126-5129, Nov. 2011.

Wilson, Peter M., et al. "Standing the test of time: targeting thymidylate biosynthesis in cancer therapy" Nature, vol. 11, pp. 282-298, May 2014.

Wittig, B., et al. "Therapeutic vaccination against metastatic carcinoma by expression-modulated and immunomodified autologous tumor cells: a first clinical phase I/II trial" Human Gene Therapy, vol. 12, No. 3, pp. 267-278, Feb. 2001.

\* cited by examiner

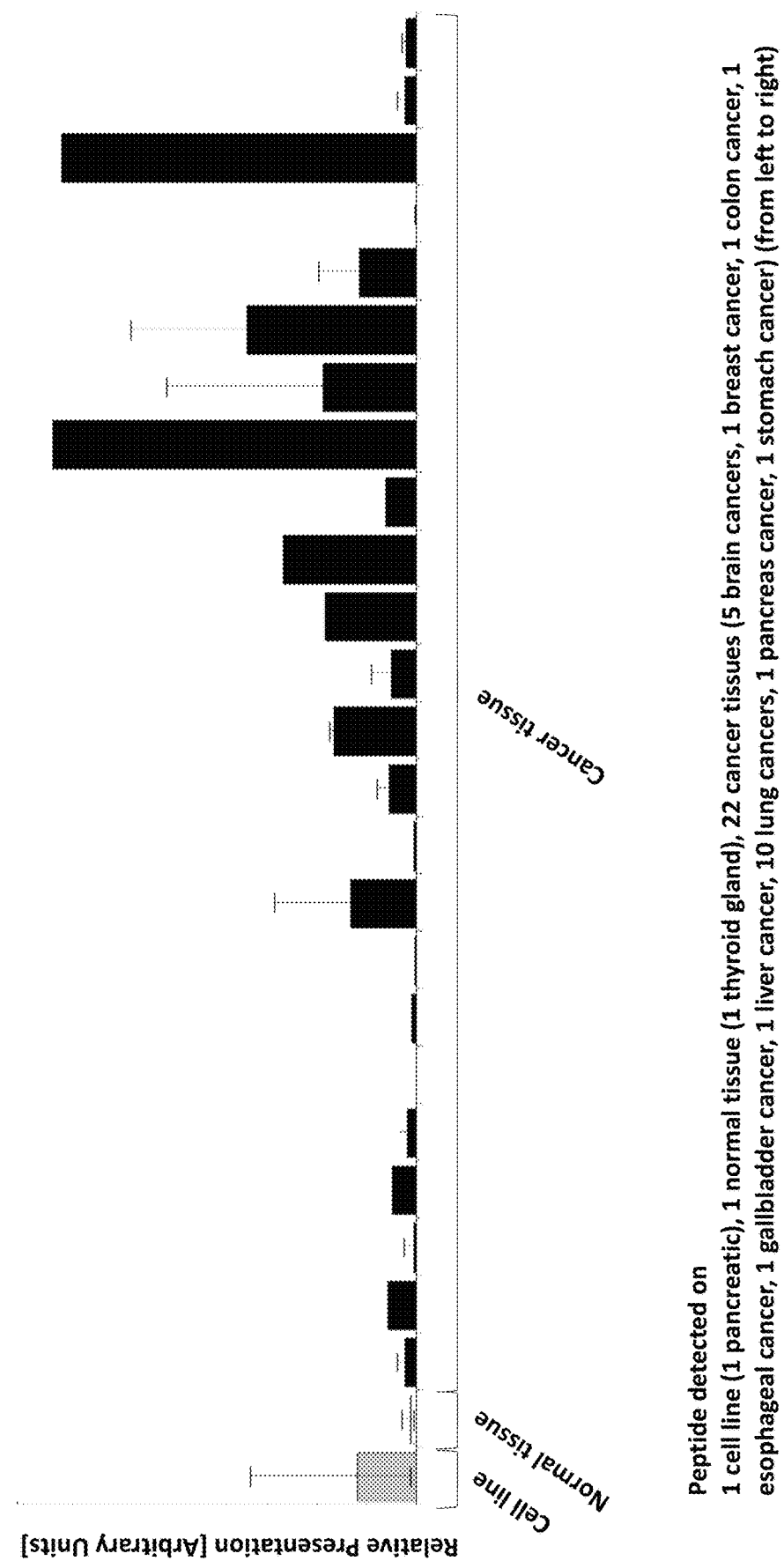

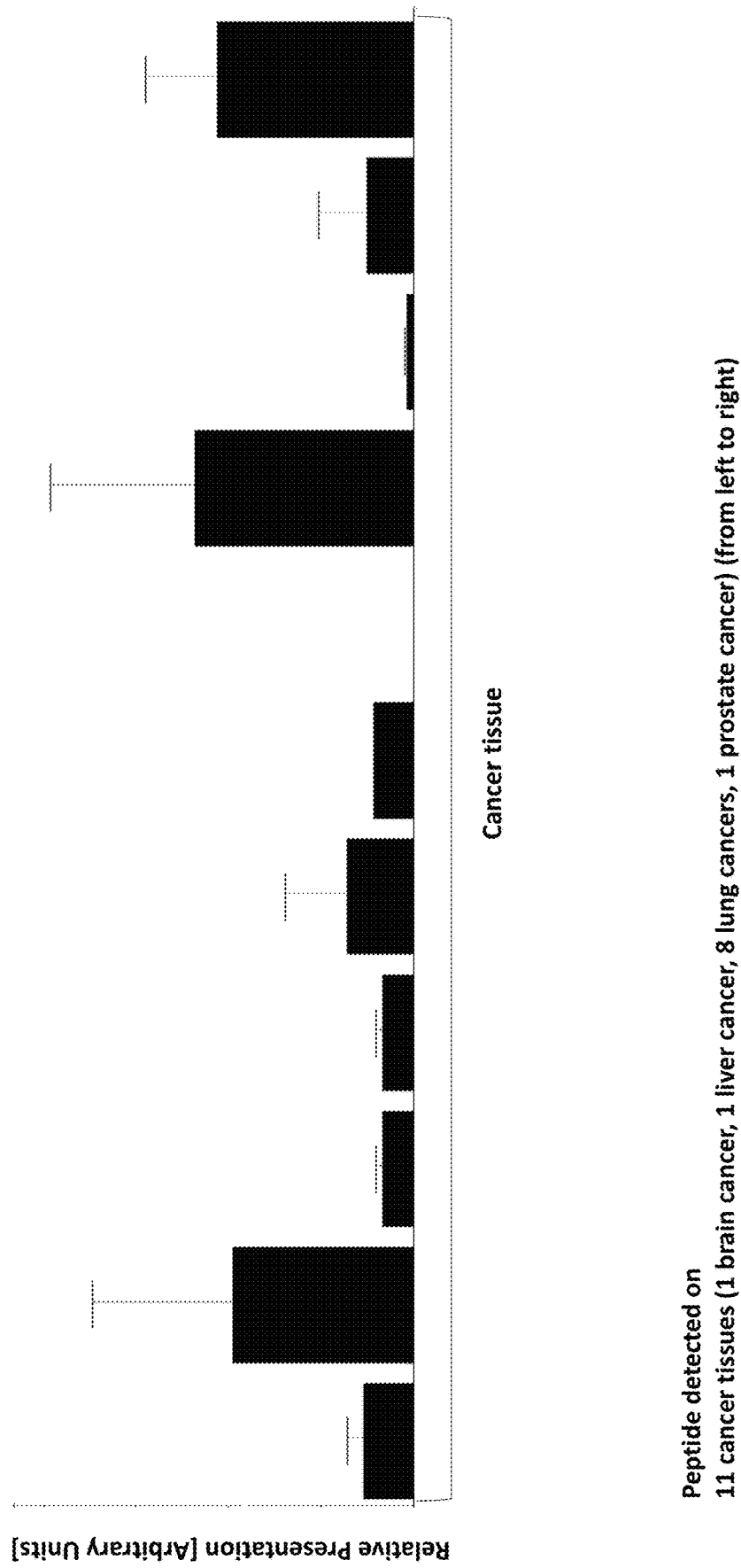

Peptide: EYLDRIGQLFF (A*24)
SEQ ID NO: 131

Peptide: FYINGQYQF (A*24)
SEQ ID NO: 176

Peptide detected on
1 prostate benign hyperplasia, 3 normal tissues (1 kidney, 1 pituitary gland, 1 skin), 67 cancer tissues (4 brain cancers, 2 liver cancers, 42 lung cancers, 12 prostate cancers, 7 stomach cancers) (from left to right)

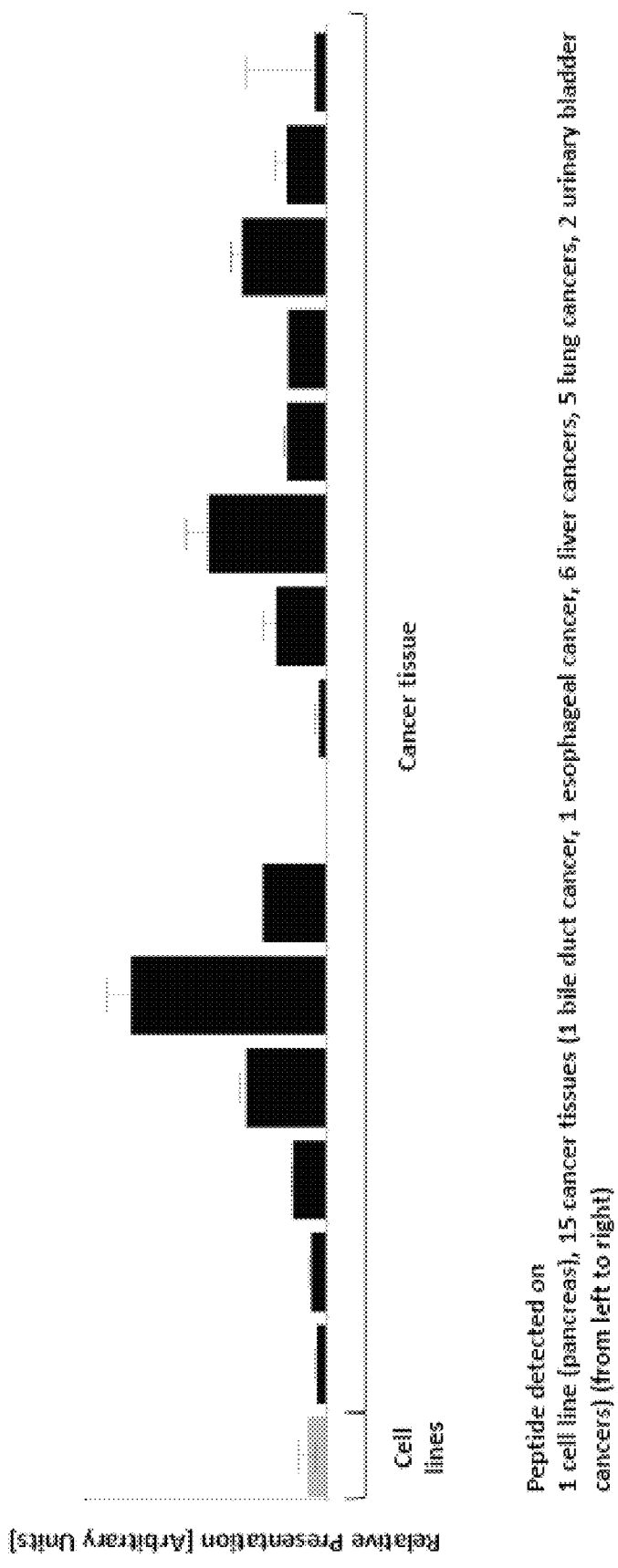

Peptide: YVLPKLYVKL (A*02)
SEQ ID NO: 35

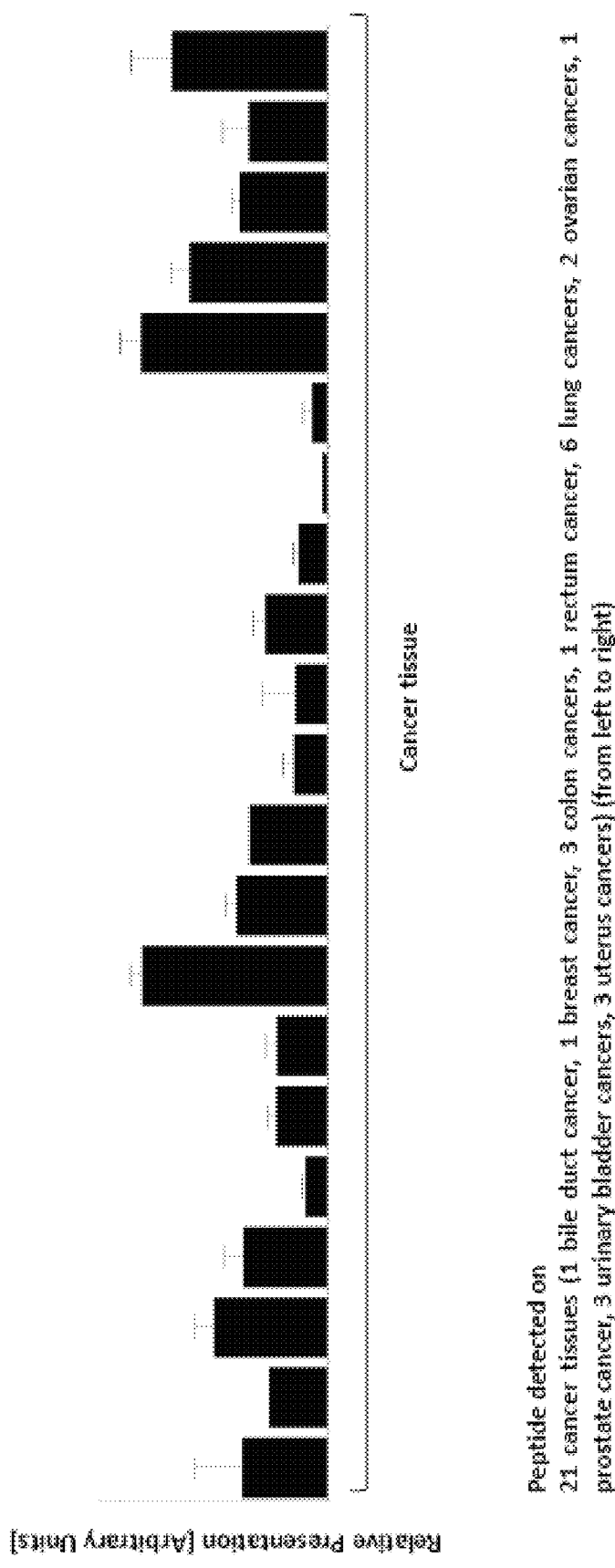

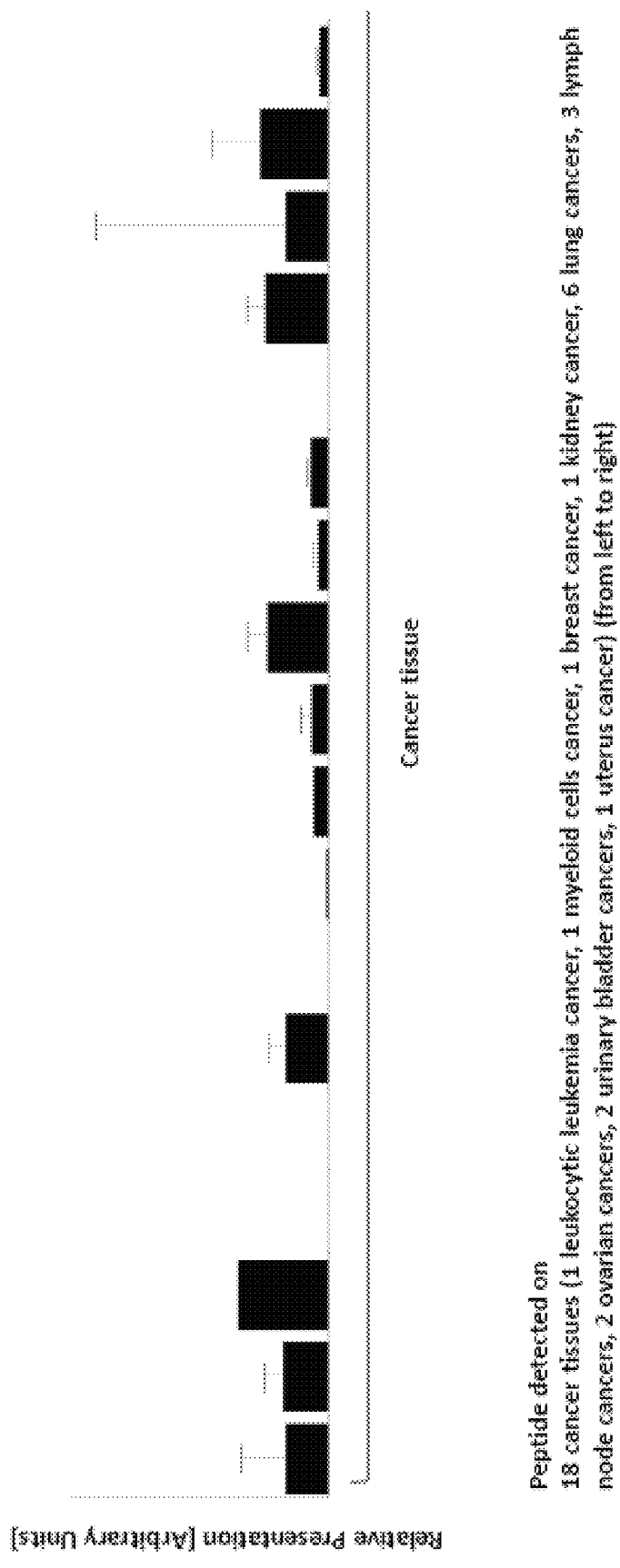

Peptide: SLLSHVIVA (A*02)
SEQ ID NO: 53

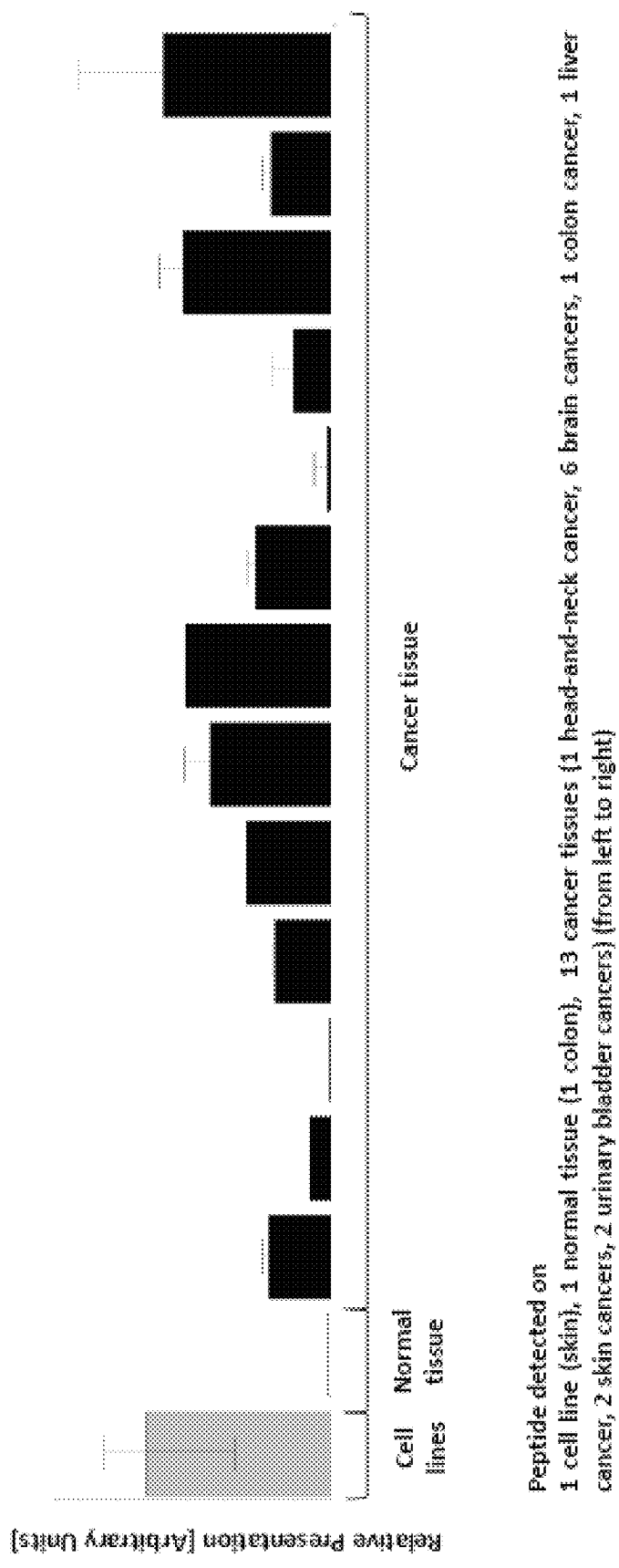

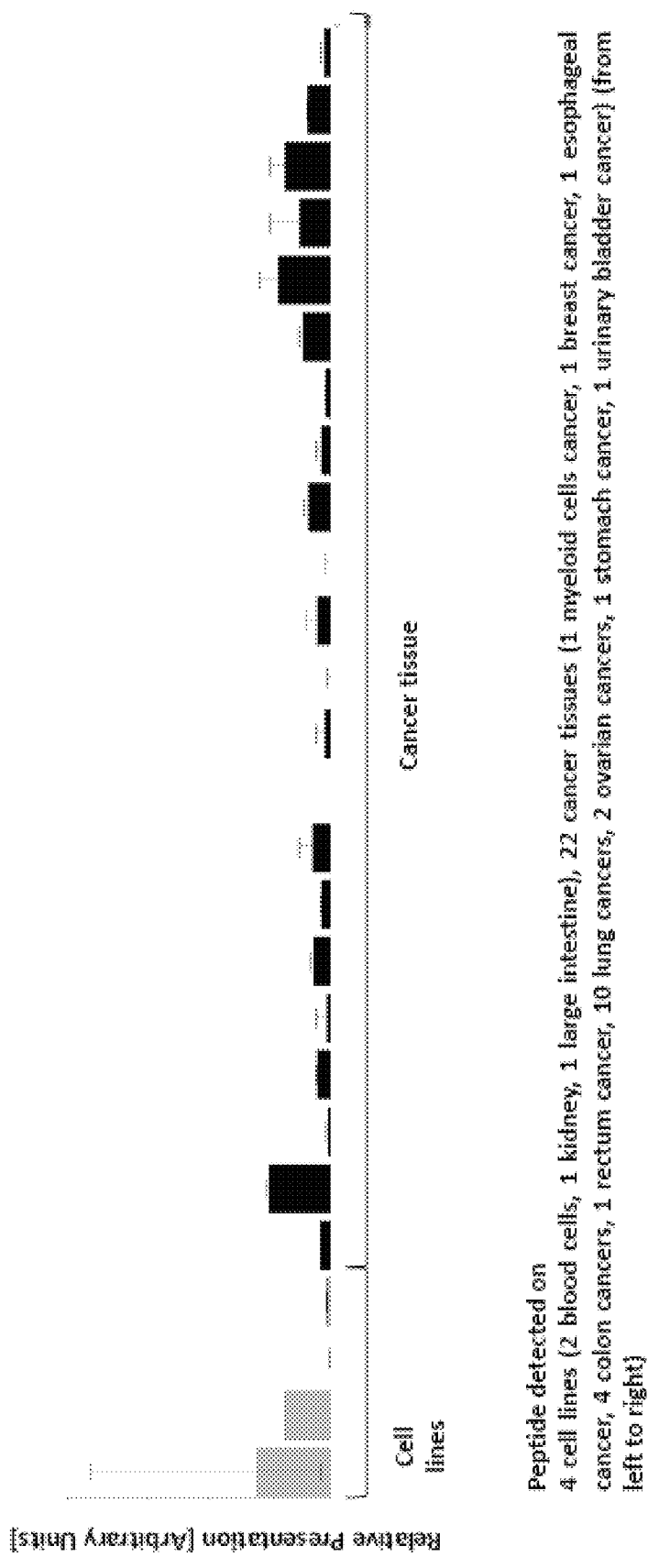

Peptide: VLGPGPPPL (A*02)
SEQ ID NO: 339

Peptide: VYVQILQKL (A*24)
SEQ ID NO: 111

Peptide: IYSFHTLSF (A*24)
SEQ ID NO: 113

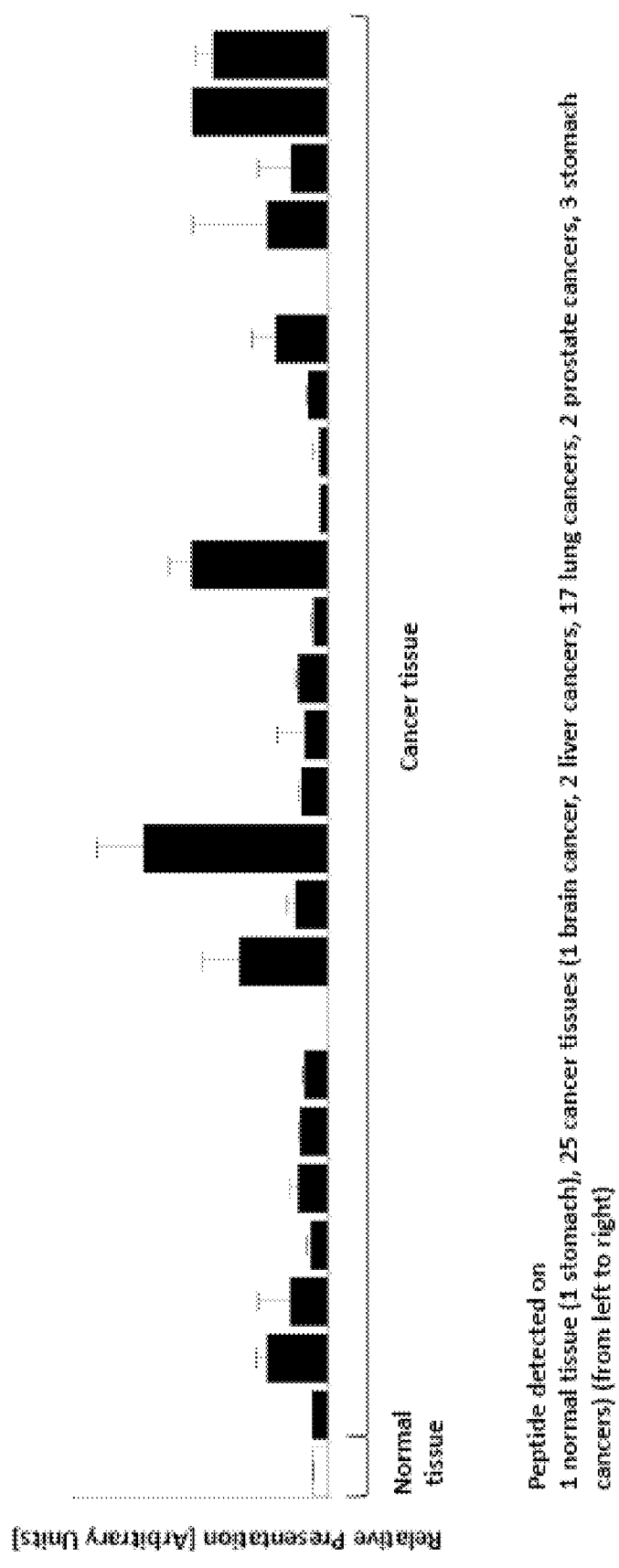

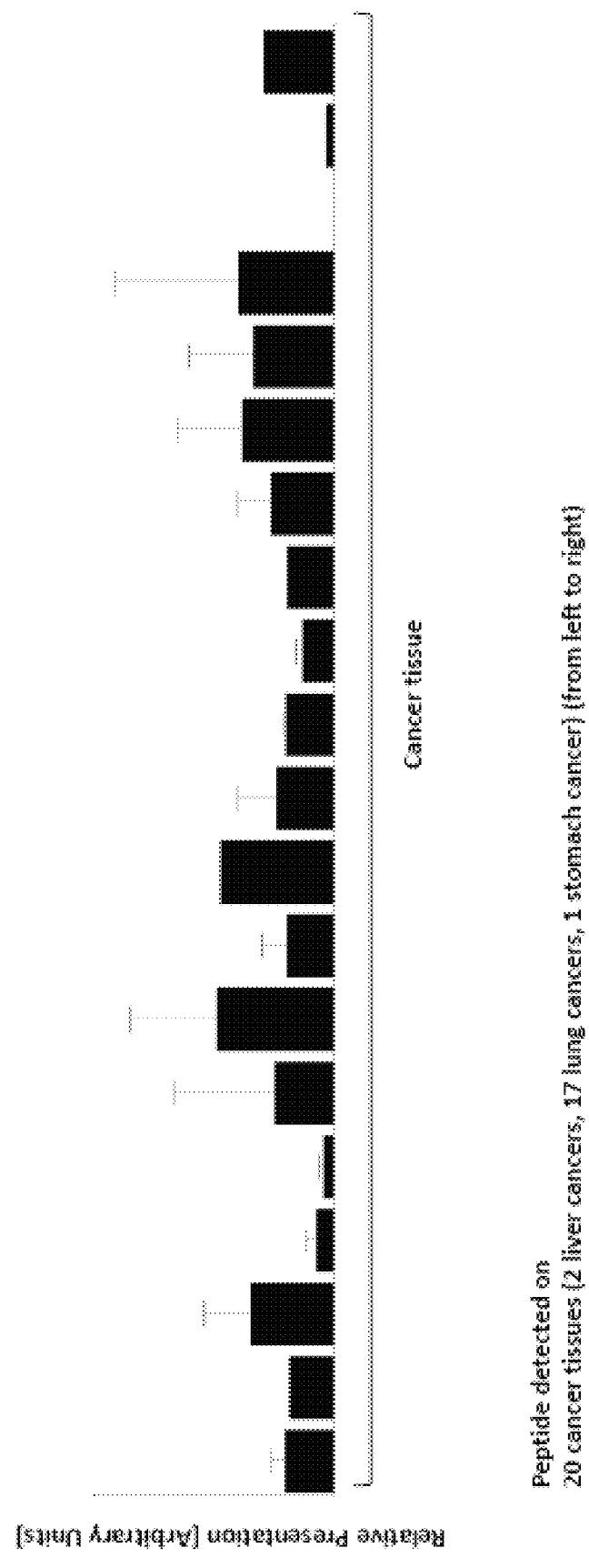

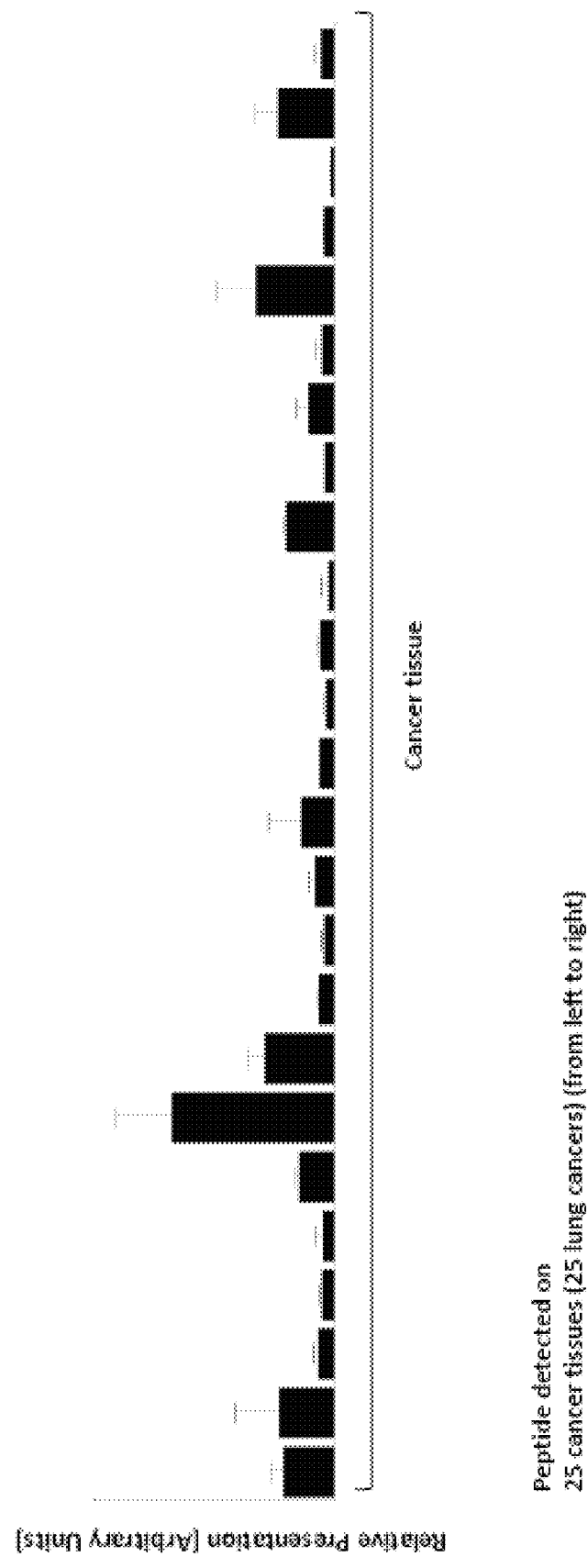

Peptide: SYGTVSQIF (A*24)
SEQ ID NO: 148

Peptide: IYKWITDNF (A*24)
SEQ ID NO: 155

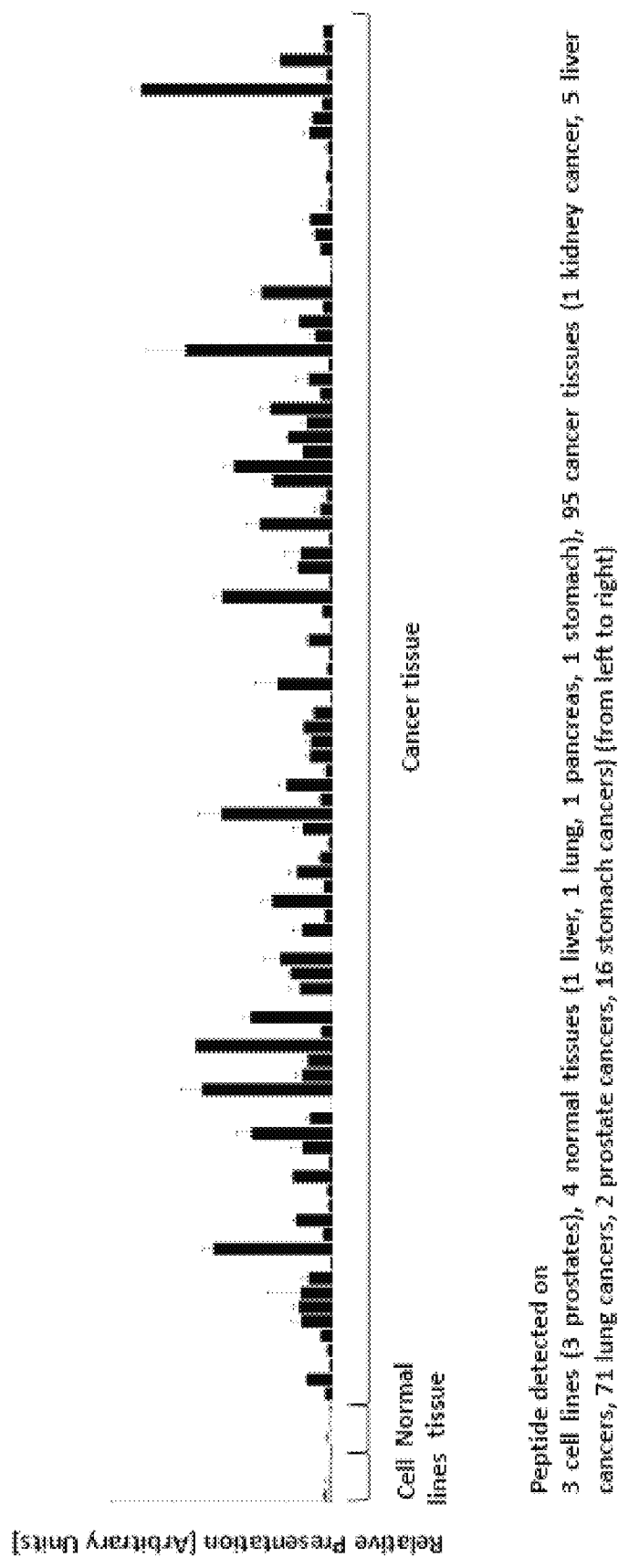

Peptide: EYFTPLLSGQF (A*24)
SEQ ID NO: 165

Peptide: LYSPVPFTL (A*24)
SEQ ID NO: 175

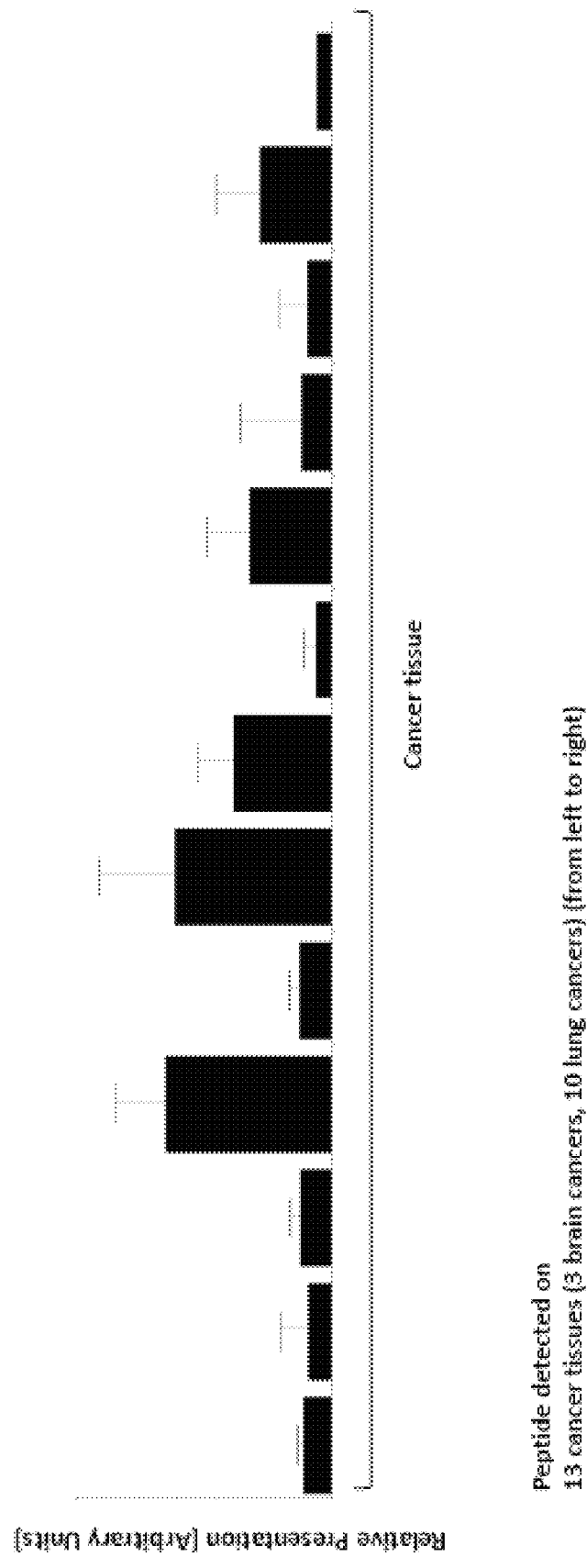

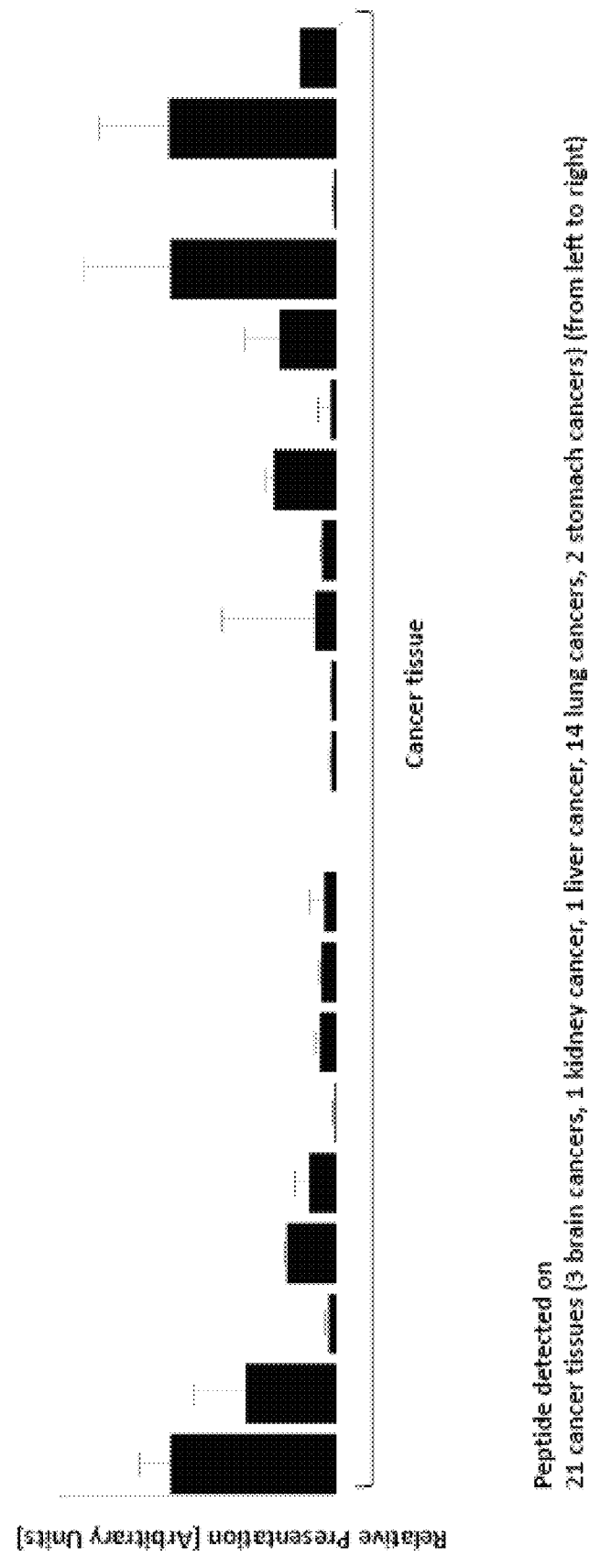

Peptide: VYNEQIRDLL (A*24)
SEQ ID NO: 354

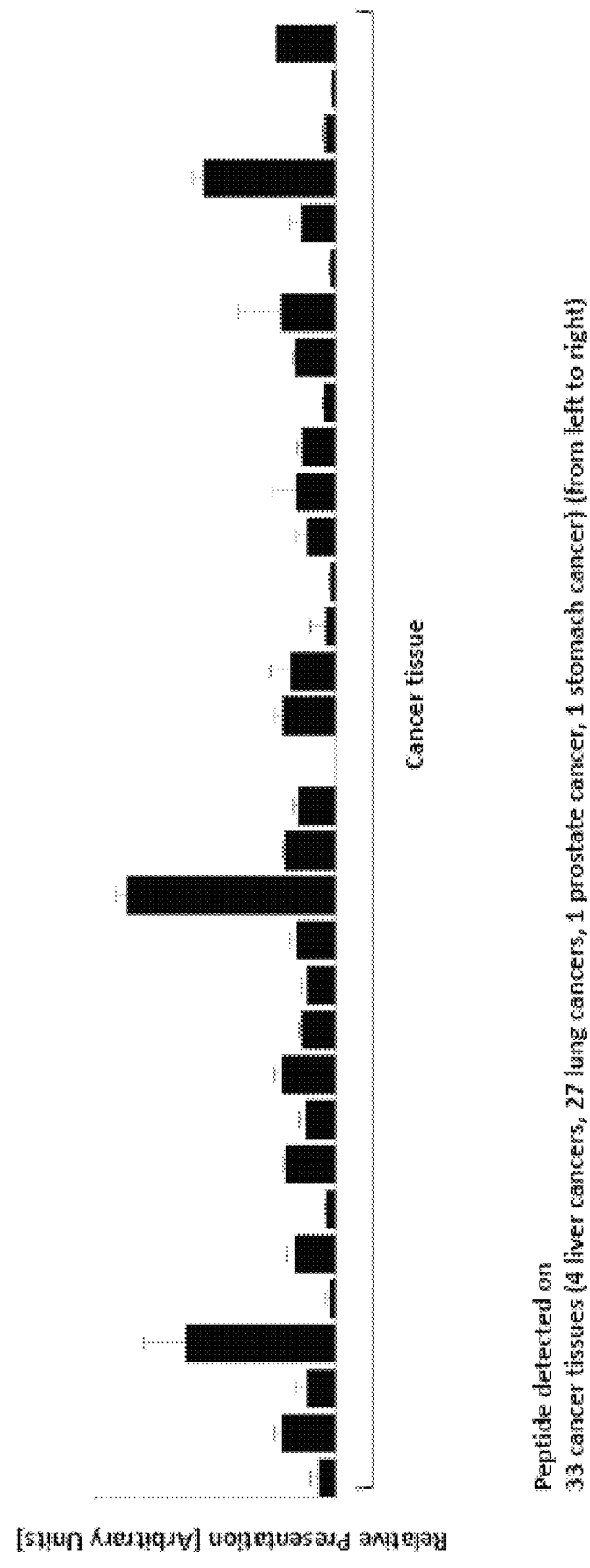

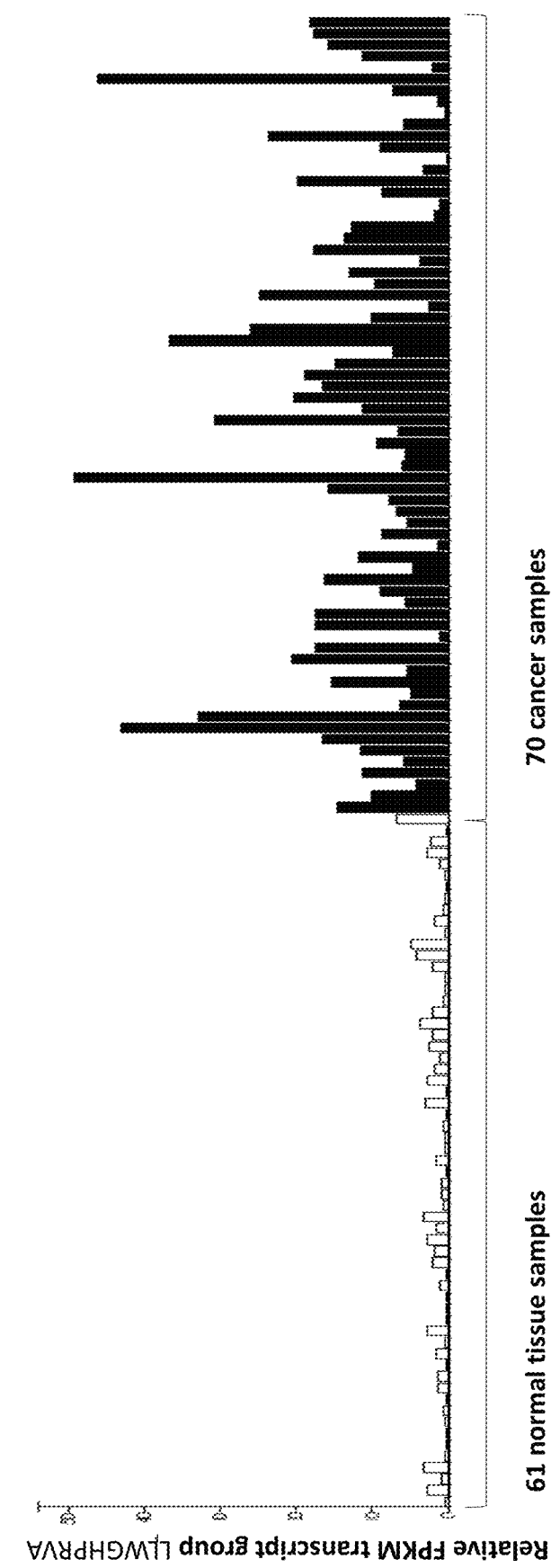

Gene: KIF26B
Peptide: QYLDGTWSL
SEQ ID NO: 114

Gene: IL4I1
Peptide: HYVPATKVF
SEQ ID NO: 164

Gene: TP63
Peptide: LYLENNAQTQF
SEQ ID NO: 193

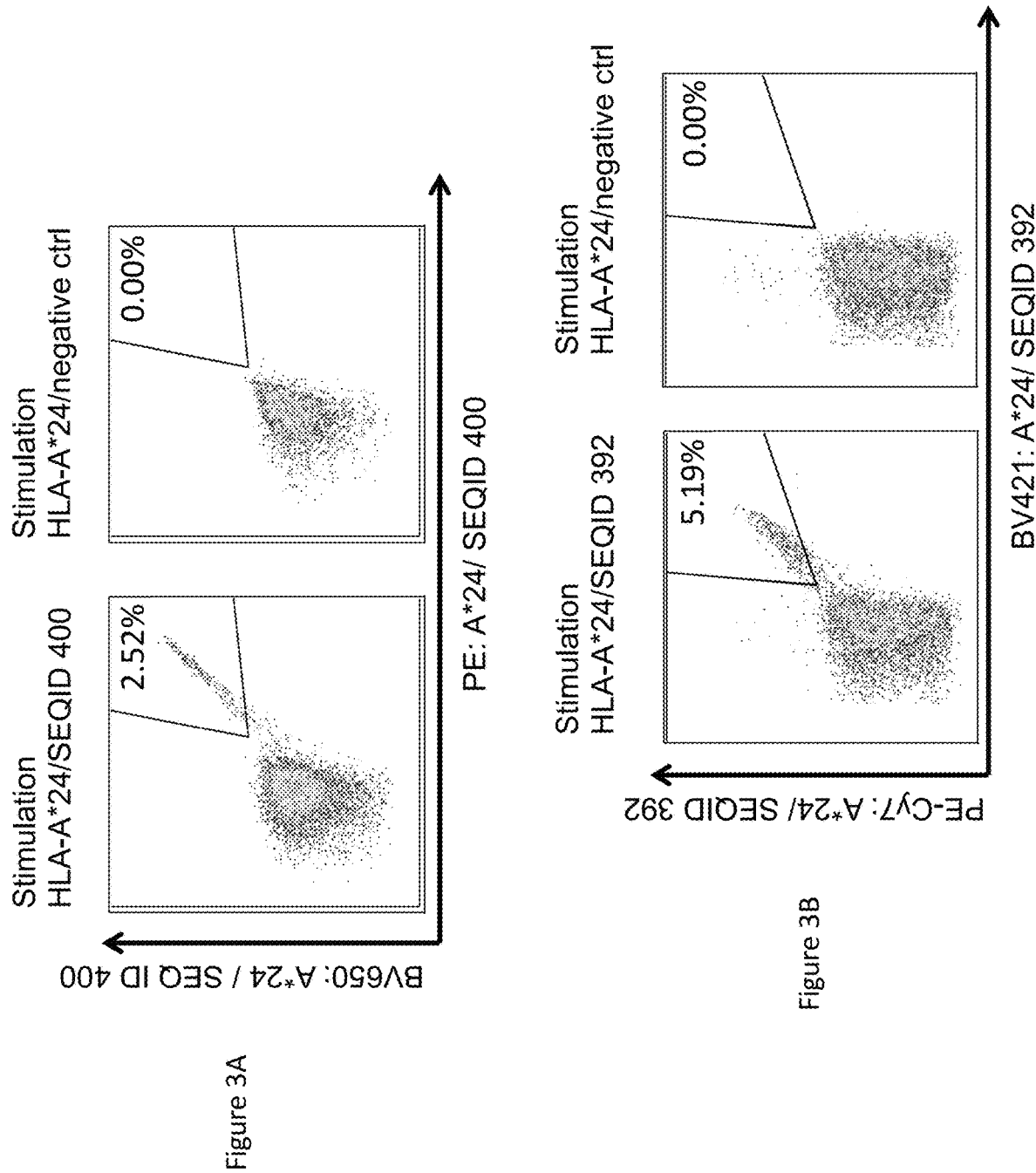

Figure 5A
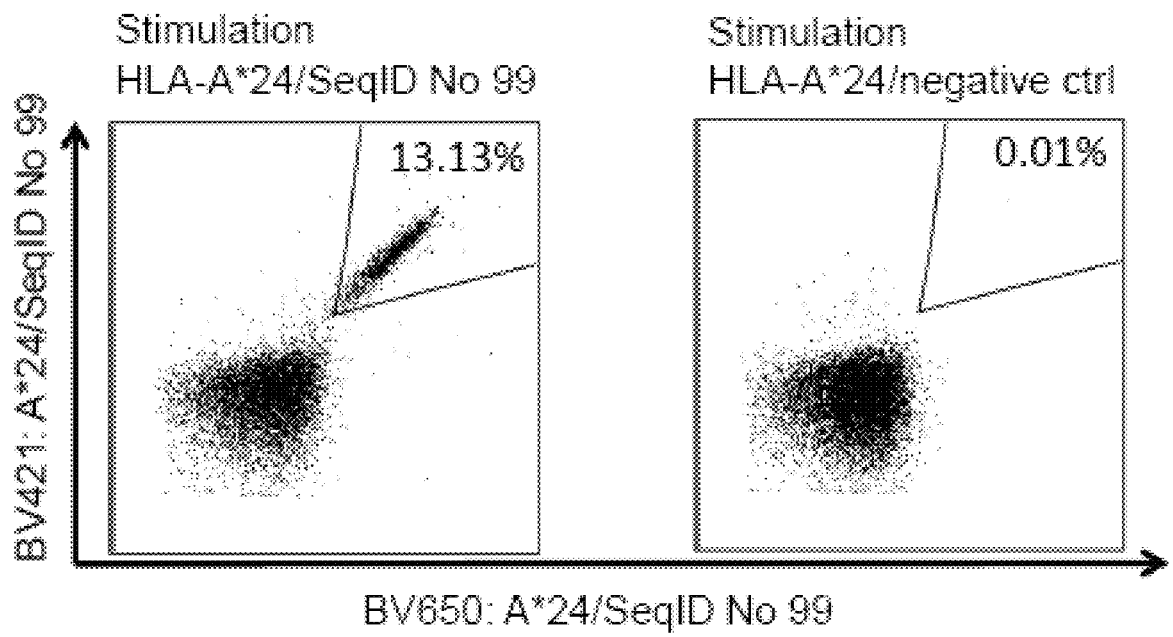
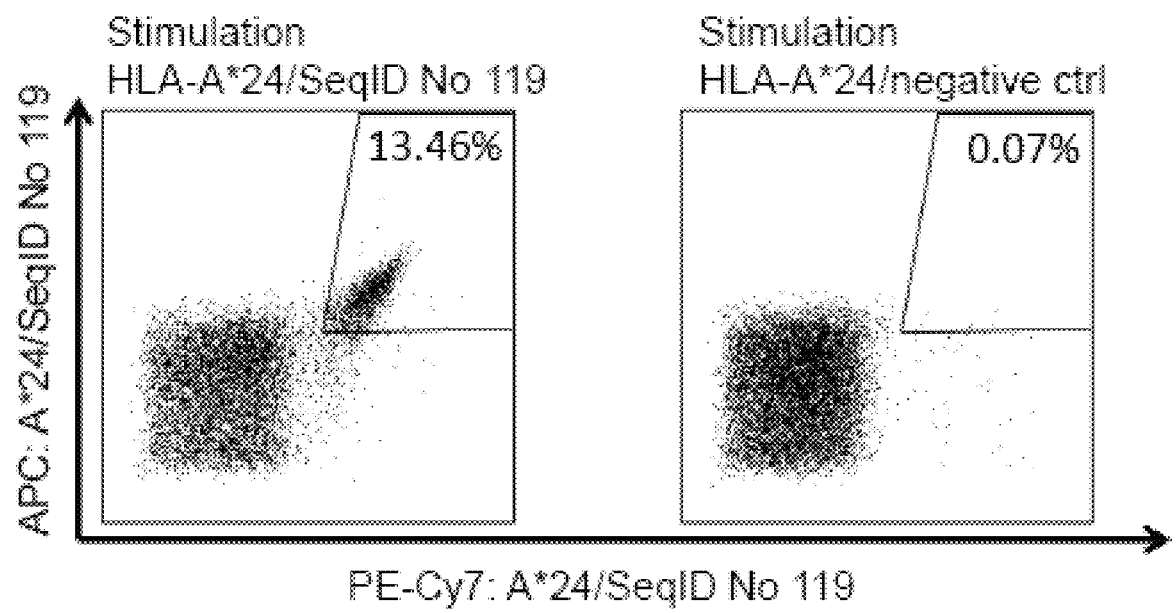
Figure 5B

Figure 5C
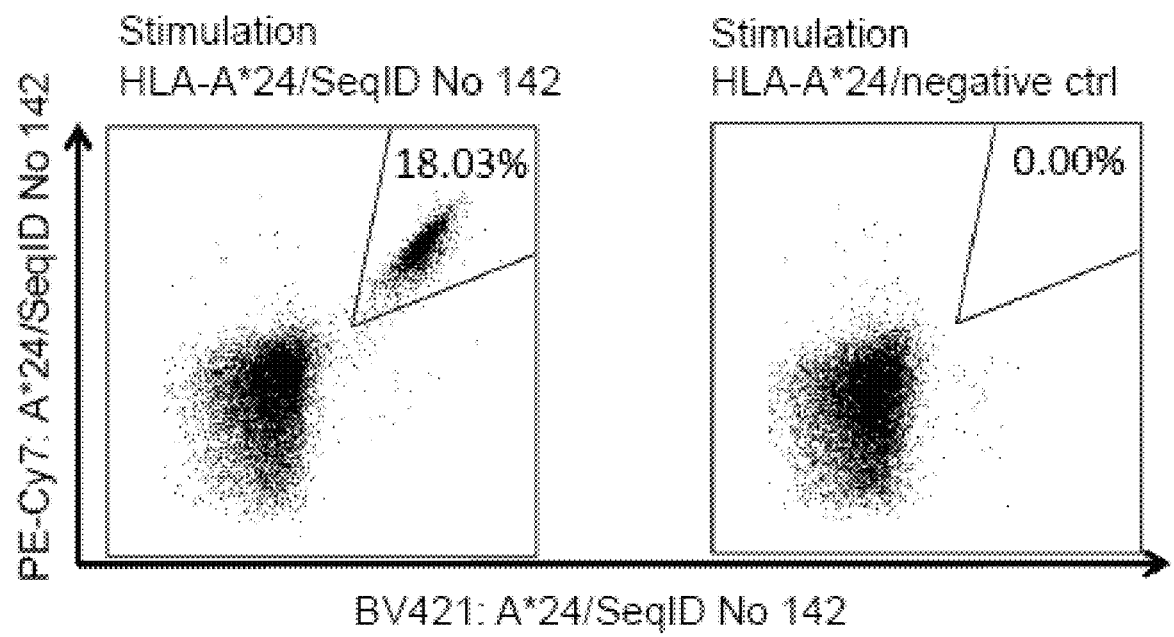
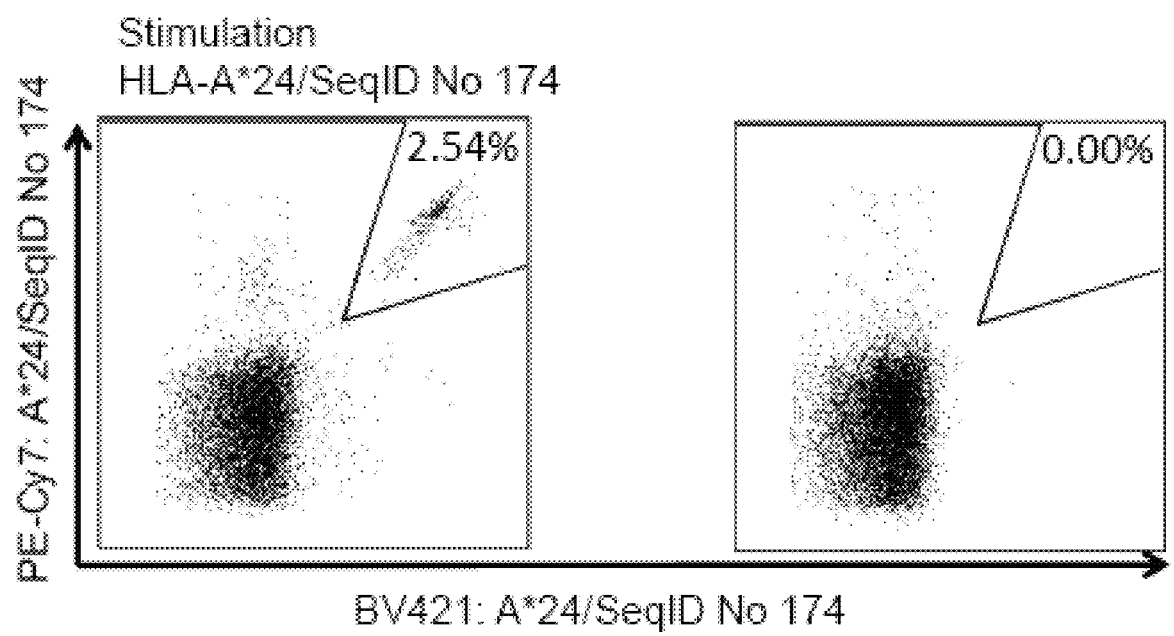
Figure 5D

CCR8 PEPTIDE AND T CELLS FOR USE IN IMMUNOTHERAPEUTIC TREATMENT OF VARIOUS CANCERS

CROSS REFERENCE TO RELATED APPLICATIONS

This application is a a continuation of U.S. patent application Ser. No. 17/711,855, filed Apr. 1, 2022, which is a continuation of U.S. patent application Ser. No. 17/320,763, filed May 14, 2021, which is a continuation of U.S. patent application Ser. No. 17/017,358, filed Sep. 10, 2020, (now U.S. Pat. No. 11,065,316, issued Jul. 20, 2021) which is a continuation of U.S. patent application Ser. No. 16/887,765, filed May 29, 2020, (now U.S. Pat. No. 10,898,557, issued Jan. 26, 2021), which is a continuation of U.S. patent application Ser. No. 16/673,619, filed Nov. 4, 2019 (now U.S. Pat. No. 10,695,411, issued Jun. 30, 2020), which is a continuation of U.S. patent application Ser. No. 15/982,293, filed May 17, 2018 (now U.S. Pat. No. 10,576,132, issued Mar. 3, 2020), which is a continuation of U.S. patent application Ser. No. 15/249,083, filed Aug. 26, 2016 (now U.S. Pat. No. 10,335,471, issued Jul. 2, 2019), which claims the benefit of U.S. Provisional Application Ser. No. 62/211,276, filed 28 Aug. 2015, and Great Britain Application No. 1515321.6, filed 28 Aug. 2015, the content of each of these applications is herein incorporated by reference in their entirety.

This application also is related to PCT/EP2016/070146 filed 26 Aug. 2016, the content of which is incorporated herein by reference in its entirety.

REFERENCE TO SEQUENCE LISTING SUBMITTED AS A COMPLIANT ASCII TEXT FILE (.xml)

Pursuant to the EFS-Web legal framework and 37 CFR §§ 1.821-825 (see MPEP § 2442.03(a)), a Sequence Listing in the form of an ASCII-compliant text file (entitled "2912919-054025_Sequence_Listing_ST26" created on Jan. 23, 2023, and 360,798 bytes in size) is submitted concurrently with the instant application, and the entire contents of the Sequence Listing are incorporated herein by reference.

FIELD

The present invention relates to peptides, proteins, nucleic acids and cells for use in immunotherapeutic methods. In particular, the present invention relates to the immunotherapy of cancer. The present invention furthermore relates to tumor-associated T-cell peptide epitopes, alone or in combination with other tumor-associated peptides that can for example serve as active pharmaceutical ingredients of vaccine compositions that stimulate anti-tumor immune responses, or to stimulate T cells ex vivo and transfer into patients. Peptides bound to molecules of the major histocompatibility complex (MHC), or peptides as such, can also be targets of antibodies, soluble T-cell receptors, and other binding molecules.

The present invention relates to several novel peptide sequences and their variants derived from HLA class I molecules of human tumor cells that can be used in vaccine compositions for eliciting anti-tumor immune responses, or as targets for the development of pharmaceutically/immunologically active compounds and cells.

BACKGROUND OF THE INVENTION

According to the World Health Organization (WHO), cancer ranged among the four major non-communicable deadly diseases worldwide in 2012. For the same year, colorectal cancer, breast cancer and respiratory tract cancers were listed within the top 10 causes of death in high income countries.

Epidemiology

In 2012, 14.1 million new cancer cases, 32.6 million patients suffering from cancer (within 5 years of diagnosis) and 8.2 million cancer deaths were estimated worldwide (Ferlay et al., 2013; Bray et al., 2013).

Within the groups of brain cancer, leukemia and lung cancer, the present application particularly focuses on glioblastoma (GB), chronic lymphocytic leukemia (CLL), and non-small cell and small cell lung cancer (NSCLC and SCLC).

Lung cancer is the most common type of cancer worldwide and the leading cause of death from cancer in many countries.

Breast cancer is an immunogenic cancer entity and different types of infiltrating immune cells in primary tumors exhibit distinct prognostic and predictive significance. A large number of early phase immunotherapy trials have been conducted in breast cancer patients. Most of the completed vaccination studies targeted HER2 and carbohydrate antigens like MUC-1 and revealed rather disappointing results. Clinical data on the effects of immune checkpoint modulation with ipilimumab and other T cell-activating antibodies in breast cancer patients are emerging (Emens, 2012).

Chronic Lymphocytic Leukemia

While CLL is not curable at present, many patients show only slow progression of the disease or worsening of symptoms. As patients do not benefit from an early onset of treatment, the initial approach is "watch and wait" (Richards et al., 1999). For patients with symptomatic or rapidly progressing disease, several treatment options are available. These include chemotherapy, targeted therapy, immune-based therapies like monoclonal antibodies, chimeric antigen-receptors (CARs) and active immunotherapy, and stem cell transplants.

Monoclonal antibodies are widely used in hematologic malignancies. This is due to the knowledge of suitable antigens based on the good characterization of immune cell surface molecules and the accessibility of tumor cells in blood or bone marrow. Common monoclonal antibodies used in CLL therapy target either CD20 or CD52. Rituximab, the first monoclonal anti-CD20 antibody originally approved by the FDA for treatment of NHLs, is now widely used in CLL therapy. Combinational treatment with rituximab/fludarabine/cyclophosphamide leads to higher CR rates and improved overall survival (OS) compared to the combination fludarabine/cyclophosphamide and has become the preferred treatment option (Hallek et al., 2008). Ofatumomab targets CD20 and is used for therapy of refractory CLL patients (Wierda et al., 2011). Obinutuzumab is another monoclonal anti-CD20 antibody used in first-line treatment in combination with chlorambucil (Goede et al., 2014).

Alemtuzumab is an anti-CD52 antibody used for treatment of patients with chemotherapy-resistant disease or patients with poor prognostic factors as del 17p or p53 mutations (Parikh et al., 2011).

Novel monoclonal antibodies target CD37 (otlertuzumab, BI 836826, IMGN529 and (177)Lu-tetulomab) or CD40 (dacetuzumab and lucatumumab) and are tested in preclinical settings (Robak and Robak, 2014).

Several completed and ongoing trials are based on engineered autologous chimeric antigen receptor (CAR)-modified T cells with CD19 specificity (Maus et al., 2014). So far, only the minority of patients showed detectable or persistent CARs. One partial response (PR) and two complete responses (CR) have been detected in the CAR T-cell trials by Porter et al. and Kalos et al. (Kalos et al., 2011; Porter et al., 2011).

Active immunotherapy includes the following strategies: gene therapy, whole modified tumor cell vaccines, DC-based vaccines and tumor associated antigen (TAA)-derived peptide vaccines.

Approaches in gene therapy make use of autologous genetically modified tumor cells. These B-CLL cells are transfected with immuno-(co-)stimulatory genes like IL-2, IL-12, TNF-alpha, GM-CSF, CD80, CD40L, LFA-3 and ICAM-1 to improve antigen presentation and T cell activation (Carballido et al., 2012). While specific T-cell responses and reduction in tumor cells are readily observed, immune responses are only transient.

Several studies have used autologous DCs as antigen presenting cells to elicit anti-tumor responses. DCs have been loaded ex vivo with tumor associated peptides, whole tumor cell lysate and tumor-derived RNA or DNA. Another strategy uses whole tumor cells for fusion with DCs and generation of DC-B-CLL-cell hybrids. Transfected DCs initiated both CD4+ and CD8+ T-cell responses (Muller et al., 2004). Fusion hybrids and DCs loaded with tumor cell lysate or apoptotic bodies increased tumor-specific CD8+ T-cell responses. Patients that showed a clinical response had increased IL-12 serum levels and reduced numbers of Tregs (Palma et al., 2008).

Different approaches use altered tumor cells to initiate or increase CLL-specific immune responses. An example for this strategy is the generation of trioma cells: B-CLL cells are fused to anti-Fc receptor expressing hybridoma cells that have anti-APC specificity. Trioma cells induced CLL-specific T-cell responses in vitro (Kronenberger et al., 2008).

Another strategy makes use of irradiated autologous CLL cells with *Bacillus* Calmette-Guérin as an adjuvant as a vaccine. Several patients showed a reduction in leukocyte levels or stable disease (Hus et al., 2008).

Besides isolated CLL cells, whole blood from CLL patients has been used as a vaccine after preparation in a blood treatment unit. The vaccine elicited CLL-specific T-cell responses and led to partial clinical responses or stable disease in several patients (Spaner et al., 2005).

Several TAAs are over-expressed in CLL and are suitable for vaccinations. These include fibromodulin (Mayr et al., 2005), RHAMM/CD168 (Giannopoulos et al., 2006), MDM2 (Mayr et al., 2006), hTERT (Counter et al., 1995), the oncofetal antigen-immature laminin receptor protein (OFAiLRP) (Siegel et al., 2003), adipophilin (Schmidt et al., 2004), survivin (Granziero et al., 2001), KW1 to KW14 (Krackhardt et al., 2002) and the tumor-derived IgVHCDR3 region (Harig et al., 2001; Carballido et al., 2012). A phase I clinical trial was conducted using the RHAMM-derived R3 peptide as a vaccine. 5 of 6 patients had detectable R3-specific CD8+ T-cell responses (Giannopoulos et al., 2010).

Colorectal Cancer

Depending on the colorectal cancer (CRC) stage, different standard therapies are available for colon and rectal cancer. Standard procedures include surgery, radiation therapy, chemotherapy and targeted therapy for CRC (Berman et al., 2015a; Berman et al., 2015b).

In addition to chemotherapeutic drugs, several monoclonal antibodies targeting the epidermal growth factor receptor (EGFR, cetuximab, panitumumab) or the vascular endothelial growth factor-A (VEGF-A, bevacizumab) are administered to patients with high stage disease. For second-line and later treatment the inhibitor for VEGF aflibercept, the tyrosine kinase inhibitor regorafenib and the thymidylate-synthetase inhibitor TAS-102 and the dUTPase inhibitor TAS-114 can be used (Stintzing, 2014; Wilson et al., 2014).

The most recent clinical trials analyze active immunotherapy as a treatment option against CRC. Those strategies include the vaccination with peptides from tumor-associated antigens (TAAs), whole tumor cells, dendritic cell (DC) vaccines and viral vectors (Koido et al., 2013).

Peptide vaccines have so far been directed against carcinoembryonic antigen (CEA), mucin 1, EGFR, squamous cell carcinoma antigen recognized by T cells 3 (SART3), beta-human chorionic gonadotropin (beta-hCG), Wilms' Tumor antigen 1 (WT1), Survivin-2B, MAGE3, p53, ring finger protein 43 and translocase of the outer mitochondrial membrane 34 (TOMM34), or mutated KRAS. In several phase I and II clinical trials patients showed antigen-specific CTL responses or antibody production. In contrast to immunological responses, many patients did not benefit from peptide vaccines on the clinical level (Koido et al., 2013; Miyagi et al., 2001; Moulton et al., 2002; Okuno et al., 2011).

Dendritic cell vaccines comprise DCs pulsed with either TAA-derived peptides, tumor cell lysates, apoptotic tumor cells, or tumor RNA or DC-tumor cell fusion products. While many patients in phase I/II trials showed specific immunological responses, only the minority had a clinical benefit (Koido et al., 2013).

Whole tumor cell vaccines consist of autologous tumor cells modified to secrete GM-CSF, modified by irradiation or virus-infected, irradiated cells. Most patients showed no clinical benefit in several phase II/III trials (Koido et al., 2013).

Vaccinia virus or replication-defective avian poxvirus encoding CEA as well as B7.1, ICAM-1 and LFA-3 have been used as vehicles in viral vector vaccines in phase I clinical trials. A different study used nonreplicating canarypox virus encoding CEA and B7.1. Besides the induction of CEA-specific T cell responses 40% of patients showed objective clinical responses (Horig et al., 2000; Kaufman et al., 2008).

Esophageal Cancer

The primary treatment strategy for esophageal cancer depends on tumor stage and location, histological type and the medical condition of the patient. Surgery alone is not sufficient, except in a small subgroup of patients with squamous cell carcinoma.

Data on immunotherapeutic approaches in esophageal cancer are scarce, as only a very limited number of early phase clinical trials have been performed. A vaccine consisting of three peptides derived from three different cancer-testis antigens (TTK protein kinase, lymphocyte antigen 6 complex locus K and insulin-like growth factor (IGF)-II mRNA binding protein 3) was administered to patients with advanced esophageal cancer in a phase I trial with moderate results. Intra-tumoral injection of activated T cells after in vitro challenge with autologous malignant cells elicited complete or partial tumor responses in four of eleven patients in a phase I/II study (Toomey et al., 2013).

Gastric Cancer

Gastric cancer (GC) begins in the cells lining the mucosal layer and spreads through the outer layers as it grows. Surgery is the primary treatment and the only curative treatment for gastric cancer. The efficacy of current therapeutic regimens for advanced GC is poor, resulting in low 5-year survival rates Immunotherapy might be an alternative approach to ameliorate the survival of GC patients. Adoptive transfer of tumor-associated lymphocytes and cytokine induced killer cells, peptide-based vaccines targeting HER2/neu, MAGE-3 or vascular endothelial growth factor receptor 1 and 2 and dendritic cell-based vaccines targeting HER2/neu showed promising results in clinical GC trials Immune checkpoint inhibition and engineered T cells might represent additional therapeutic options, which is currently evaluated in pre-clinical and clinical studies (Matsueda and Graham, 2014).

Glioblastoma

The therapeutic options for glioblastoma (WHO grade IV) are very limited. According to the guidelines released by the German Society for Neurology the standard therapy in young patients includes resection or biopsy of the tumor, focal radiation therapy and chemotherapy with temozolomide or CCNU/lomustine or a combination of procarbazine with CCNU and vincristine (PCV). In the USA, Canada and Switzerland treatment with bevacizumab (anti-VEGF-antibody) is also approved for relapse therapy (Leitlinien für Diagnostik and Therapie in der Neurologie, 2014).

Different immunotherapeutic approaches are investigated for the treatment of GB, including immune-checkpoint inhibition, vaccination and adoptive transfer of engineered T cells.

Antibodies directed against inhibitory T cell receptors or their ligands were shown to efficiently enhance T cell-mediated anti-tumor immune responses in different cancer types, including melanoma and bladder cancer. The effects of T cell activating antibodies like ipilimumab and nivolumab are therefore assessed in clinical GB trials, but preliminary data indicate autoimmune-related adverse events.

Different vaccination strategies for GB patients are currently investigated, including peptide-based vaccines, heat-shock protein vaccines, autologous tumor cell vaccines, dendritic cell-based vaccines and viral protein-based vaccines. In these approaches peptides derived from GB-associated proteins like epidermal growth factor receptor variant III (EGFRvIII) or heat shock proteins or dendritic cells pulsed with autologous tumor cell lysate or cytomegalo virus components are applied to induce an anti-tumor immune response in GB patients. Several of these studies reveal good safety and tolerability profiles as well as promising efficacy data.

Adoptive transfer of genetically modified T cells is an additional immunotherapeutic approach for the treatment of GB. Different clinical trials currently evaluate the safety and efficacy of chimeric antigen receptor bearing T cells directed against HER2, IL-13 receptor alpha 2 and EGFRvIII (Ampie et al., 2015).

Liver Cancer

Disease management depends on the tumor stage at the time of diagnosis and the overall condition of the liver. If surgery is not a treatment option, different other therapies are available at hand.

Lately, a limited number of immunotherapy trials for HCC have been conducted. Cytokines have been used to activate subsets of immune cells and/or increase the tumor immunogenicity (Reinisch et al., 2002; Sangro et al., 2004). Other trials have focused on the infusion of Tumor-infiltrating lymphocytes or activated peripheral blood lymphocytes (Shi et al., 2004; Takayama et al., 1991; Takayama et al., 2000b).

So far, a small number of therapeutic vaccination trials have been executed. Butterfield et al. conducted two trials using peptides derived from alpha-fetoprotein (AFP) as a vaccine or DCs loaded with AFP peptides ex vivo (Butterfield et al., 2003; Butterfield et al., 2006). In two different studies, autologous dendritic cells (DCs) were pulsed ex vivo with autologous tumor lysate (Lee et al., 2005) or lysate of the hepatoblastoma cell line HepG2 (Palmer et al., 2009). So far, vaccination trials have only shown limited improvements in clinical outcomes.

Melanoma

The standard therapy in melanoma is complete surgical resection with surrounding healthy tissue. If resection is not complete or not possible at all, patients receive primary radiation therapy, which can be combined with interferon-alpha administration in advanced stages (stages IIB/C and IIIA-C).

Enhancing the anti-tumor immune responses appears to be a promising strategy for the treatment of advanced melanoma. In the United States the immune checkpoint inhibitor ipilimumab as well as the BRAF kinase inhibitors vemurafenib and dabrafenib and the MEK inhibitor trametinib are already approved for the treatment of advanced melanoma. Both approaches increase the patient's anti-tumor immunity-ipilimumab directly by reducing T cell inhibition and the kinase inhibitors indirectly by enhancing the expression of melanocyte differentiation antigens. Additional checkpoint inhibitors (nivolumab and lambrolizumab) are currently investigated in clinical studies with first encouraging results. Additionally, different combination therapies targeting the anti-tumor immune response are tested in clinical trials including ipilimumab plus nivolumab, ipilimumab plus a gp100-derived peptide vaccine, ipilimumab plus dacarbazine, ipilimumab plus IL-2 and iplimumab plus GM-CSF (Srivastava and McDermott, 2014).

Several different vaccination approaches have already been evaluated in patients with advanced melanoma. So far, phase III trials revealed rather disappointing results and vaccination strategies clearly need to be improved. Therefore, new clinical trials, like the OncoVEX GM-CSF trial or the DERMA trial, aim at improving clinical efficacy without reducing tolerability.

Adoptive T cell transfer shows great promise for the treatment of advanced stage melanoma. In vitro expanded autologous tumor infiltrating lymphocytes as well as T cells harboring a high affinity T cell receptor for the cancer-testis antigen NY-ESO-1 had significant beneficial and low toxic effects upon transfer into melanoma patients. Unfortunately, T cells with high affinity T cell receptors for the melanocyte specific antigens MART1 and gp100 and the cancer-testis antigen MAGEA3 induced considerable toxic effects in clinical trials. Thus, adoptive T cell transfer has high therapeutic potential, but safety and tolerability of these treatments needs to be further increased (Phan and Rosenberg, 2013; Hinrichs and Restifo, 2013).

Non-Small Cell Lung Cancer

Treatment options are determined by the type (small cell or non-small cell) and stage of cancer and include surgery, radiation therapy, chemotherapy, and targeted biological therapies such as bevacizumab, erlotinib and gefitinib.

To expand the therapeutic options for NSCLC, different immunotherapeutic approaches have been studied or are still under investigation. While vaccination with L-BLP25 or MAGEA3 failed to demonstrate an vaccine-mediated survival advantage in NSCLC patients, an allogeneic cell line-derived vaccine showed promising results in clinical studies. Additionally, further vaccination trials targeting gangliosides, the epidermal growth factor receptor and several other antigens are currently ongoing. An alternative strategy to enhance the patient's anti-tumor T cell response consists of blocking inhibitory T cell receptors or their ligands with specific antibodies. The therapeutic potential of several of these antibodies, including ipilimumab, nivolumab, pembrolizumab, MPDL3280A and MEDI-4736, in NSCLC is currently evaluated in clinical trials (Reinmuth et al., 2015).

Ovarian Cancer

Surgical resection is the primary therapy in early as well as advanced stage ovarian carcinoma. Surgical removal is followed by systemic chemotherapy with platinum analogs, except for very low grade ovarian cancers (stage IA, grade 1), where post-operative chemotherapy is not indicated.

Immunotherapy appears to be a promising strategy to ameliorate the treatment of ovarian cancer patients, as the presence of pro-inflammatory tumor infiltrating lymphocytes, especially CD8-positive T cells, correlates with good prognosis and T cells specific for tumor-associated antigens can be isolated from cancer tissue.

Therefore, a lot of scientific effort is put into the investigation of different immunotherapies in ovarian cancer. A considerable number of pre-clinical and clinical studies has already been performed and further studies are currently ongoing. Clinical data are available for cytokine therapy, vaccination, monoclonal antibody treatment, adoptive cell transfer and immunomodulation.

Cytokine therapy with interleukin-2, interferon-alpha, interferon-gamma or granulocyte-macrophage colony stimulating factor aims at boosting the patient's own anti-tumor immune response and these treatments have already shown promising results in small study cohorts.

Phase I and II vaccination studies, using single or multiple peptides, derived from several tumor-associated proteins (Her2/neu, NY-ESO-1, p53, Wilms tumor-1) or whole tumor antigens, derived from autologous tumor cells revealed good safety and tolerability profiles, but only low to moderate clinical effects.

Monoclonal antibodies that specifically recognize tumor-associated proteins are thought to enhance immune cell-mediated killing of tumor cells. The anti-CA-125 antibodies oregovomab and abagovomab as well as the anti-EpCAM antibody catumaxomab achieved promising results in phase II and III studies. In contrast, the anti-MUC1 antibody HMFG1 failed to clearly enhance survival in a phase III study.

An alternative approach uses monoclonal antibodies to target and block growth factor and survival receptors on tumor cells. While administration of trastuzumab (anti-HER2/neu antibody) and MOv18 and MORAb-003 (anti-folate receptor alpha antibodies) only conferred limited clinical benefit to ovarian cancer patients, addition of bevacizumab (anti-VEGF antibody) to the standard chemotherapy in advanced ovarian cancer appears to be advantageous.

Adoptive transfer of immune cells achieved heterogeneous results in clinical trials. Adoptive transfer of autologous, in vitro expanded tumor infiltrating T cells was shown to be a promising approach in a pilot trial. In contrast, transfer of T cells harboring a chimeric antigen receptor specific for folate receptor alpha did not induce a significant clinical response in a phase I trial. Dendritic cells pulsed with tumor cell lysate or tumor-associated proteins in vitro were shown to enhance the anti-tumor T cell response upon transfer, but the extent of T cell activation did not correlate with clinical effects. Transfer of natural killer cells caused significant toxicities in a phase II study.

Intrinsic anti-tumor immunity as well as immunotherapy are hampered by an immunosuppressive tumor microenvironment. To overcome this obstacle immunomodulatory drugs, like cyclophosphamide, anti-CD25 antibodies and pegylated liposomal doxorubicin are tested in combination with immunotherapy. Most reliable data are currently available for ipilimumab, an anti-CTLA4 antibody, which enhances T cell activity. Ipilimumab was shown to exert significant anti-tumor effects in ovarian cancer patients (Mantia-Smaldone et al., 2012).

Pancreatic Cancer

Therapeutic options for pancreatic cancer patients are very limited. One major problem for effective treatment is the typically advanced tumor stage at diagnosis. Additionally, pancreatic cancer is rather resistant to chemotherapeutics, which might be caused by the dense and hypovascular desmoplastic tumor stroma.

According to the guidelines released by the German Cancer Society, the German Cancer Aid and the Association of the Scientific Medical Societies in Germany, resection of the tumor is the only available curative treatment option.

Vaccination strategies are investigated as further innovative and promising alternative for the treatment of pancreatic cancer. Peptide-based vaccines targeting KRAS mutations, reactive telomerase, gastrin, survivin, CEA and MUC1 have already been evaluated in clinical trials, partially with promising results. Furthermore, clinical trials for dendritic cell-based vaccines, allogeneic GM-CSF-secreting vaccines and algenpantucel-L in pancreatic cancer patients also revealed beneficial effects of immunotherapy. Additional clinical trials further investigating the efficiency of different vaccination protocols are currently ongoing (Salman et al., 2013).

Prostate Cancer

The therapeutic strategy for prostate cancer mainly depends on the cancer stage. The dendritic cell-based vaccine sipuleucel-T was the first anti-cancer vaccine to be approved by the FDA. Due to its positive effect on survival in patients with CRPC, much effort is put into the development of further immunotherapies. Regarding vaccination strategies, the peptide vaccine prostate-specific antigen (PSA)-TRICOM, the personalized peptide vaccine PPV, the DNA vaccine pTVG-HP and the whole cell vaccine expressing GM-CSF GVAX showed promising results in different clinical trials. Furthermore, dendritic cell-based vaccines other than sipuleucel-T, namely BPX-101 and DCVAC/Pa were shown to elicited clinical responses in prostate cancer patients Immune checkpoint inhibitors like ipilimumab and nivolumab are currently evaluated in clinical studies as monotherapy as well as in combination with other treatments, including androgen deprivation therapy, local radiation therapy, PSA-TRICOM and GVAX. The immunomodulatory substance tasquinimod, which significantly slowed progression and increased progression free survival in a phase II trial, is currently further investigated in a phase III trial. Lenalidomide, another immunomodulator, induced promising effects in early phase clinical studies, but failed to improve survival in a phase III trial. Despite these disappointing results further lenalidomide trials are ongoing (Quinn et al., 2015).

Renal Cell Carcinoma

Initial treatment is most commonly either partial or complete removal of the affected kidney(s) and remains the mainstay of curative treatment (Rini et al., 2008). The known immunogenity of RCC has represented the basis supporting the use of immunotherapy and cancer vaccines in advanced RCC. The interesting correlation between lymphocytes PD-1 expression and RCC advanced stage, grade and prognosis, as well as the selective PD-L1 expression by RCC tumor cells and its potential association with worse clinical outcomes, have led to the development of new anti PD-1/PD-L1 agents, alone or in combination with anti-angiogenic drugs or other immunotherapeutic approaches, for the treatment of RCC (Massari et al., 2015). In advanced RCC, a phase III cancer vaccine trial called TRIST study evaluates whether TroVax (a vaccine using a tumor-associated antigen, 5T4, with a pox virus vector), added to first-line standard of care therapy, prolongs survival of patients with locally advanced or mRCC. Median survival had not been reached in either group with 399 patients (54%) remaining on study however analysis of the data confirms prior clinical results, demonstrating that TroVax is both immunologically active and that there is a correlation between the strength of the 5T4-specific antibody response and improved survival. Further there are several studies searching for peptide vaccines using epitopes being overexpressed in RCC.

Various approaches of tumor vaccines have been under investigation. Studies using whole-tumor approaches, including tumor cell lysates, fusions of dendritic cells with tumor cells, or whole-tumor RNA were done in RCC patients, and remissions of tumor lesions were reported in some of these trials (Avigan et al., 2004; Holtl et al., 2002; Marten et al., 2002; Su et al., 2003; Wittig et al., 2001).

Small Cell Lung Cancer

The treatment and prognosis of SCLC depend strongly on the diagnosed cancer stage Immune therapy presents an excessively investigated field of cancer therapy. Various approaches are studded in the treatment of SCLC. One of the approaches targets the blocking of CTLA-4, a natural human immune suppressor. The inhibition of CTLA-4 intends to boost the immune system to combat the cancer. Recently, the development of promising immune check point inhibitors for treatment of SCLC has been started. Another approach is based on anti-cancer vaccines which is currently available for treatment of SCLC in clinical studies (American Cancer Society, 2015; National Cancer Institute, 2015).

Acute Myeloid Leukemia

One treatment option for AML is targeting CD33 with antibody-drug conjugates (anti-CD33+calechiamicin, SGN-CD33a, anti-CD33+actinium-225), bispecific antibodies (recognition of CD33+CD3 (AMG 330) or CD33+CD16) and chimeric antigen receptors (CARs) (Estey, 2014).

Non-Hodgkin Lymphoma

Treatment of NHL depends on the histologic type and stage (National Cancer Institute, 2015): Spontaneous tumor regression can be observed in lymphoma patients. Therefore, active immunotherapy is a therapy option (Palomba, 2012).

An important vaccination option includes Id vaccines. B lymphocytes express surface immunoglobulins with a specific amino acid sequence in the variable regions of their heavy and light chains, unique to each cell clone (=idiotype, Id). The idiotype functions as a tumor associated antigen.

Passive immunization includes the injection of recombinant murine anti-Id monoclonal antibodies alone or in combination with IFNalpha, IL2 or chlorambucil.

Active immunization includes the injection of recombinant protein (Id) conjugated to an adjuvant (KLH), given together with GM-CSF as an immune adjuvant. Tumor-specific Id is produced by hybridoma cultures or using recombinant DNA technology (plasmids) by bacterial, insect or mammalian cell culture.

Three phase III clinical trials have been conducted (Biovest, Genitope, Favrille). In two trials patients had received rituximab. GM-CSF was administered in all three trials. Biovest used hybridoma-produced protein, Genitope and Favrille used recombinant protein. In all three trials Id was conjugated to KLH. Only Biovest had a significant result.

Vaccines other than Id include the cancer-testis antigens MAGE, NY-ESO1 and PASD-1, the B-cell antigen CD20 or cellular vaccines. The latest mentioned consist of DCs pulsed with apoptotic tumor cells, tumor cell lysate, DC-tumor cell fusion or DCs pulsed with tumor-derived RNA.

In situ vaccination involves the vaccination with intratumoral CpG in combination with chemotherapy or irradiated tumor cells grown in the presence of GM-CSF and collection/expansion/re-infusion of T cells.

Vaccination with antibodies that alter immunologic checkpoints are comprised of anti-CD40, anti-OX40, anti-41BB, anti-CD27, anti-GITR (agonist antibodies that directly enhance anti-tumor response) or anti-PD1, anti-CTLA-4 (blocking antibodies that inhibit the checkpoint that would hinder the immune response). Examples are ipilimumab (anti-CTLA-4) and CT-011 (anti-PD1) (Palomba, 2012).

Uterine Cancer

Treatment of endometrial carcinomas is stage-dependent. The majority of endometrical carcinomas comprises of well to moderately differentiated endometrioid adenocarcinomas which are usually confined to the corpus uteri at diagnosis and can be cured by hysterectomy (World Cancer Report, 2014).

Also therapies for cervical cancer depend on the stage. In early stages, excision is the standard therapy which might be combined with radio-(chemo-) therapy. Primary radio-(chemo-) therapy is chosen at late stages (Stage III and higher), in cases with lymph node infiltration or in cases in which the tumor can not be excised.

There are also some immunotherapeutic approaches that are currently being tested. In a Phase I/II Clinical Trial patients suffering from uterine cancer were vaccinated with autologous dendritic cells (DCs) electroporated with Wilms' tumor gene 1 (WT1) mRNA. Besides one case of local allergic reaction to the adjuvant, no adverse side effects were observed and 3 out of 6 patients showed an immunological response (Coosemans et al., 2013).

As stated above, HPV infections provoke lesions that may ultimately lead to cervical cancer. Therefore, the HPV viral oncoproteins E6 and E7 that are are constitutively expressed in high-grade lesions and cancer and and are required for the onset and maintenance of the malignant phenotype are considered promising targets for immunotherapeutic approaches (Hung et al., 2008; Vici et al., 2014). One study performed Adoptive T-cell therapy (ACT) in patients with metastatic cervical cancer. Patients receive an infusion with E6 and E7 reactive tumor-infiltrating T cells (TILs) resulting in complete regression in 2 and a patial response in 1 out of 9 patients (Stevanovic et al., 2015). Furthermore, an intracellular antibody targeting E7 was reported to block tumor groth in mice (Accardi et al., 2014). Also peptide, DNA and DC-based vaccines targing HPV E6 and E7 are in clinical trials (Vici et al., 2014).

Gallbladder Adenocarcinoma and Cholangiocarcinoma

Cholangiocarcinoma is mostly identified in advanced stages because it is difficult to diagnose. Cholangiocarcinoma is difficult to treat and is usually lethal.

Gallbladder cancer is the most common and aggressive malignancy of the biliary tract worldwide.

Urinary Bladder Cancer

The standard treatment for bladder cancer includes surgery, radiation therapy, chemotherapy and immunotherapy.

At stage 0 and I, the bladder cancer is typically treated by transurethral resection potentially followed by intravesical chemotherapy and optionally combined with intravesical immunotherapeutic treatment with BCG (*bacillus* Calmette-Guérin).

An effective immunotherapeutic approach is established in the treatment of aggressive non-muscle invasive bladder cancer (NMIBC). Thereby, a weakened form of the bacterium *Mycobacterium bovis* (*bacillus* Calmette-Guérin=BCG) is applied as an intravesical solution. The major effect of BCG treatment is a significant long-term (up to 10 years) protection from cancer recurrence and reduced progression rate. In principle, the treatment with BCG induces a local inflammatory response which stimulates the cellular immune response. The immune response to BCG is based on the following key steps: infection of urothelial and bladder cancer cells by BCG, followed by increased expression of antigen-presenting molecules, induction of immune response mediated via cytokine release, induction of antitumor activity via involvement of various immune cells (thereunder cytotoxic T lymphocytes, neutrophils, natural killer cells, and macrophages) (Fuge et al., 2015; Gandhi et al., 2013).

BCG treatment is in general well tolerated by patients but can be fatal especially by the immunocompromised patients. BCG refractory is observed in about 30-40% of patients (Fuge et al., 2015; Steinberg et al., 2016a). The treatment of patients who failed the BCG therapy is challenging. The patients who failed the BCG treatment are at high risk for developing of muscle-invasive disease. Radical cystectomy is the preferable treatment option for non-responders (Steinberg et al., 2016b; von Rundstedt and Lerner, 2015). The FDA approved second line therapy of BCG-failed NMIBC for patients who desire the bladder preservation is the chemotherapeutic treatment with valrubicin. A number of other second line therapies are available or being currently under investigation as well, thereunder immunotherapeutic approaches like combined BCG-interferon or BCG-check point inhibitor treatments, pre-BCG transdermal vaccination, treatment with *Mycobacterium phlei* cell wall-nucleic acid (MCNA) complex, mono- or combination chemotherapy with various agents like mitomycin C, gemcitabine, docetaxel, nab-paclitaxel, epirubicin, mitomycin/gemcitabine, gemcitabine/docetaxel, and device-assisted chemotherapies like thermochemo-, radiochemo-, electromotive or photodynamic therapies (Fuge et al., 2015; Steinberg et al., 2016b; von Rundstedt and Lerner, 2015). Further evaluation of available therapies in clinical trials is still required.

The alternative treatment options for advanced bladder cancer are being investigated in ongoing clinical trials. The current clinical trials focused on the development of molecularly targeted therapies and immunotherapies. The targeted therapies investigate the effects of cancerogenesis related pathway inhibitors (i.e. mTOR, vascular endothelial, fibroblast, or epidermal growth factor receptors, anti-angiogenesis or cell cycle inhibitors) in the treatment of bladder cancer. The development of molecularly targeted therapies remains challenging due to high degree of genetic diversity of bladder cancer. The main focus of the current immunotherapy is the development of checkpoint blockage agents like anti-PD1 monoclonal antibody and adoptive T-cell transfer (Knollman et al., 2015b; Grivas et al., 2015; Jones et al., 2016; Rouanne et al., 2016).

Head and Neck Squamous Cell Carcinoma

Head and neck squamous cell carcinomas (HNSCC) are heterogeneous tumors with differences in epidemiology, etiology and treatment (Economopoulou et al., 2016).

HNSCC is considered an immunosuppressive disease, characterized by the dysregulation of immunocompetent cells and impaired cytokine secretion (Economopoulou et al., 2016). Immunotherapeutic strategies differ between HPV-negative and HPV-positive tumors.

In HPV-positive tumors, the viral oncoproteins E6 and E7 represent good targets, as they are continuously expressed by tumor cells and are essential to maintain the transformation status of HPV-positive cancer cells. Several vaccination therapies are currently under investigation in HPV-positive HNSCC, including DNA vaccines, peptide vaccines and vaccines involving dendritic cells (DCs). Additionally, an ongoing phase II clinical trial investigates the efficacy of lymphodepletion followed by autologous infusion of TILs in patients with HPV-positive tumors (Economopoulou et al., 2016).

In HPV-negative tumors, several immunotherapeutic strategies are currently used and under investigation. The chimeric IgG1 anti-EGFR monoclonal antibody cetuximab has been approved by the FDA in combination with chemotherapy as standard first line treatment for recurring/metastatic HNSCC. Other anti-EGFR monoclonal antibodies, including panitumumab, nimotuzumab and zalutumumab, are evaluated in HNSCC. Several immune checkpoint inhibitors are investigated in clinical trials for their use in HNSCC. They include the following antibodies: Ipilimumab (anti-CTLA-4), tremelimumab (anti-CTLA-4), pembrolizumab (anti-PD-1), nivolumab (anti-PD-1), durvalumab (anti-PD-1), anti-KIR, urelumab (anti-CD137), and anti-LAG-3.

Two clinical studies with HNSCC patients evaluated the use of DCs loaded with p53 peptides or apoptotic tumor cells. The immunological responses were satisfactory and side effects were acceptable.

Several studies have been conducted using adoptive T cell therapy (ACT). T cells were induced against either irradiated autologous tumor cells or EBV. Results in disease control and overall survival were promising (Economopoulou et al., 2016).

Considering the severe side-effects and expense associated with treating cancer, there is a need to identify factors that can be used in the treatment of cancer in general and hepatocellular carcinoma (HCC), colorectal carcinoma (CRC), glioblastoma (GB), gastric cancer (GC), esophageal cancer, non-small cell lung cancer (NSCLC), pancreatic cancer (PC), renal cell carcinoma (RCC), benign prostate hyperplasia (BPH), prostate cancer (PCA), ovarian cancer (OC), melanoma, breast cancer, chronic lymphocytic leukemia (CLL), Merkel cell carcinoma (MCC), small cell lung cancer (SCLC), Non-Hodgkin lymphoma (NHL), acute myeloid leukemia (AML), gallbladder cancer and cholangiocarcinoma (GBC, CCC), urinary bladder cancer (UBC), uterine cancer (UEC), head and neck squamous cell carcinoma (HNSCC), in particular. There is also a need to identify factors representing biomarkers for cancer in general and the above-mentioned cancer types in particular, leading to better diagnosis of cancer, assessment of prognosis, and prediction of treatment success.

Immunotherapy of cancer represents an option of specific targeting of cancer cells while minimizing side effects. Cancer immunotherapy makes use of the existence of tumor associated antigens.

The current classification of tumor associated antigens (TAAs) comprises the following major groups:

a) Cancer-testis antigens: The first TAAs ever identified that can be recognized by T cells belong to this class, which was originally called cancer-testis (CT) antigens because of the expression of its members in histologically different human tumors and, among normal tissues, only in spermatocytes/ spermatogonia of testis and, occasionally, in placenta. Since the cells of testis do not express class I and II HLA molecules, these antigens cannot be recognized by T cells in normal tissues and can therefore be considered as immunologically tumor-specific. Well-known examples for CT antigens are the MAGE family members and NY-ESO-1.

b) Differentiation antigens: These TAAs are shared between tumors and the normal tissue from which the tumor arose. Most of the known differentiation antigens are found in melanomas and normal melanocytes. Many of these melanocyte lineage-related proteins are involved in biosynthesis of melanin and are therefore not tumor specific but nevertheless are widely used for cancer immunotherapy. Examples include, but are not limited to, tyrosinase and Melan-A/MART-1 for melanoma or PSA for prostate cancer.

c) Over-expressed TAAs: Genes encoding widely expressed TAAs have been detected in histologically different types of tumors as well as in many normal tissues, generally with lower expression levels. It is possible that many of the epitopes processed and potentially presented by normal tissues are below the threshold level for T-cell recognition, while their over-expression in tumor cells can trigger an anticancer response by breaking previously established tolerance. Prominent examples for this class of TAAs are Her-2/neu, survivin, telomerase, or WT1.

d) Tumor-specific antigens: These unique TAAs arise from mutations of normal genes (such as β-catenin, CDK4, etc.). Some of these molecular changes are associated with neoplastic transformation and/or progression. Tumor-specific antigens are generally able to induce strong immune responses without bearing the risk for autoimmune reactions against normal tissues. On the other hand, these TAAs are in most cases only relevant to the exact tumor on which they were identified and are usually not shared between many individual tumors. Tumor-specificity (or -association) of a peptide may also arise if the peptide originates from a tumor- (-associated) exon in case of proteins with tumor-specific (-associated) isoforms.

e) TAAs arising from abnormal post-translational modifications: Such TAAs may arise from proteins which are neither specific nor overexpressed in tumors but nevertheless become tumor associated by posttranslational processes primarily active in tumors. Examples for this class arise from altered glycosylation patterns leading to novel epitopes in tumors as for MUC1 or events like protein splicing during degradation which may or may not be tumor specific.

f) Oncoviral proteins: These TAAs are viral proteins that may play a critical role in the oncogenic process and, because they are foreign (not of human origin), they can evoke a T-cell response. Examples of such proteins are the human papilloma type 16 virus proteins, E6 and E7, which are expressed in cervical carcinoma.

T-cell based immunotherapy targets peptide epitopes derived from tumor-associated or tumor-specific proteins, which are presented by molecules of the major histocompatibility complex (MHC). The antigens that are recognized by the tumor specific T lymphocytes, that is, the epitopes thereof, can be molecules derived from all protein classes, such as enzymes, receptors, transcription factors, etc. which are expressed and, as compared to unaltered cells of the same origin, usually up-regulated in cells of the respective tumor.

There are two classes of MHC-molecules, MHC class I and MHC class II. MHC class I molecules are composed of an alpha heavy chain and beta-2-microglobulin, MHC class II molecules of an alpha and a beta chain. Their three-dimensional conformation results in a binding groove, which is used for non-covalent interaction with peptides.

MHC class I molecules can be found on most nucleated cells. They present peptides that result from proteolytic cleavage of predominantly endogenous proteins, defective ribosomal products (DRIPs) and larger peptides. However, peptides derived from endosomal compartments or exogenous sources are also frequently found on MHC class I molecules. This non-classical way of class I presentation is referred to as cross-presentation in the literature (Brossart and Bevan, 1997; Rock et al., 1990). MHC class II molecules can be found predominantly on professional antigen presenting cells (APCs), and primarily present peptides of exogenous or transmembrane proteins that are taken up by APCs e.g. during endocytosis, and are subsequently processed.

Complexes of peptide and MHC class I are recognized by CD8-positive T cells bearing the appropriate T-cell receptor (TCR), whereas complexes of peptide and MHC class II molecules are recognized by CD4-positive-helper-T cells bearing the appropriate TCR. It is well known that the TCR, the peptide and the MHC are thereby present in a stoichiometric amount of 1:1:1.

CD4-positive helper T cells play an important role in inducing and sustaining effective responses by CD8-positive cytotoxic T cells. The identification of CD4-positive T-cell epitopes derived from tumor associated antigens (TAA) is of great importance for the development of pharmaceutical products for triggering anti-tumor immune responses (Gnjatic et al., 2003). At the tumor site, T helper cells, support a cytotoxic T cell- (CTL-) friendly cytokine milieu (Mortara et al., 2006) and attract effector cells, e.g. CTLs, natural killer (NK) cells, macrophages, and granulocytes (Hwang et al., 2007).

In the absence of inflammation, expression of MHC class II molecules is mainly restricted to cells of the immune system, especially professional antigen-presenting cells (APC), e.g., monocytes, monocyte-derived cells, macrophages, dendritic cells. In cancer patients, cells of the tumor have been found to express MHC class II molecules (Dengjel et al., 2006).

Elongated peptides of the invention can act as MHC class II active epitopes.

T-helper cells, activated by MHC class II epitopes, play an important role in orchestrating the effector function of CTLs in anti-tumor immunity. T-helper cell epitopes that trigger a T-helper cell response of the TH1 type support effector functions of CD8-positive killer T cells, which include cytotoxic functions directed against tumor cells displaying tumor-associated peptide/MHC complexes on their cell surfaces. In this way tumor-associated T-helper cell peptide epitopes, alone or in combination with other tumor-associated peptides, can serve as active pharmaceutical ingredients of vaccine compositions that stimulate anti-tumor immune responses.

It was shown in mammalian animal models, e.g., mice, that even in the absence of CD8-positive T lymphocytes, CD4-positive T cells are sufficient for inhibiting manifestation of tumors via inhibition of angiogenesis by secretion of interferon-gamma (IFNγ) (Beatty and Paterson, 2001; Mumberg et al., 1999). There is evidence for CD4 T cells as direct anti-tumor effectors (Braumuller et al., 2013; Tran et al., 2014).

Since the constitutive expression of HLA class II molecules is usually limited to immune cells, the possibility of isolating class II peptides directly from primary tumors was previously not considered possible. However, Dengjel et al.

were successful in identifying a number of MHC Class II epitopes directly from tumors (WO 2007/028574, EP 1 760 088 B1).

Since both types of response, CD8 and CD4 dependent, contribute jointly and synergistically to the anti-tumor effect, the identification and characterization of tumor-associated antigens recognized by either CD8+ T cells (ligand: MHC class I molecule+peptide epitope) or by CD4-positive T-helper cells (ligand: MHC class II molecule+peptide epitope) is important in the development of tumor vaccines.

For an MHC class I peptide to trigger (elicit) a cellular immune response, it also must bind to an MHC-molecule. This process is dependent on the allele of the MHC-molecule and specific polymorphisms of the amino acid sequence of the peptide. MHC-class-I-binding peptides are usually 8-12 amino acid residues in length and usually contain two conserved residues ("anchors") in their sequence that interact with the corresponding binding groove of the MHC-molecule. In this way each MHC allele has a "binding motif" determining which peptides can bind specifically to the binding groove.

In the MHC class I dependent immune reaction, peptides not only have to be able to bind to certain MHC class I molecules expressed by tumor cells, they subsequently also have to be recognized by T cells bearing specific T cell receptors (TCR).

For proteins to be recognized by T-lymphocytes as tumor-specific or -associated antigens, and to be used in a therapy, particular prerequisites must be fulfilled. The antigen should be expressed mainly by tumor cells and not, or in comparably small amounts, by normal healthy tissues. In a preferred embodiment, the peptide should be over-presented by tumor cells as compared to normal healthy tissues. It is furthermore desirable that the respective antigen is not only present in a type of tumor, but also in high concentrations (i.e. copy numbers of the respective peptide per cell). Tumor-specific and tumor-associated antigens are often derived from proteins directly involved in transformation of a normal cell to a tumor cell due to their function, e.g. in cell cycle control or suppression of apoptosis. Additionally, downstream targets of the proteins directly causative for a transformation may be up-regulated and thus may be indirectly tumor-associated. Such indirect tumor-associated antigens may also be targets of a vaccination approach (Singh-Jasuja et al., 2004). It is essential that epitopes are present in the amino acid sequence of the antigen, in order to ensure that such a peptide ("immunogenic peptide"), being derived from a tumor associated antigen, leads to an in vitro or in vivo T-cell-response.

Basically, any peptide able to bind an MHC molecule may function as a T-cell epitope. A prerequisite for the induction of an in vitro or in vivo T-cell-response is the presence of a T cell having a corresponding TCR and the absence of immunological tolerance for this particular epitope.

Therefore, TAAs are a starting point for the development of a T cell based therapy including but not limited to tumor vaccines. The methods for identifying and characterizing the TAAs are usually based on the use of T-cells that can be isolated from patients or healthy subjects, or they are based on the generation of differential transcription profiles or differential peptide expression patterns between tumors and normal tissues. However, the identification of genes over-expressed in tumor tissues or human tumor cell lines, or selectively expressed in such tissues or cell lines, does not provide precise information as to the use of the antigens being transcribed from these genes in an immune therapy. This is because only an individual subpopulation of epitopes of these antigens are suitable for such an application since a T cell with a corresponding TCR has to be present and the immunological tolerance for this particular epitope needs to be absent or minimal. In a very preferred embodiment of the invention it is therefore important to select only those over- or selectively presented peptides against which a functional and/or a proliferating T cell can be found. Such a functional T cell is defined as a T cell, which upon stimulation with a specific antigen can be clonally expanded and is able to execute effector functions ("effector T cell").

In case of targeting peptide-MHC by specific TCRs (e.g. soluble TCRs) and antibodies or other binding molecules (scaffolds) according to the invention, the immunogenicity of the underlying peptides is secondary. In these cases, the presentation is the determining factor.

SUMMARY OF THE INVENTION

In a first aspect of the present invention, the present invention relates to a peptide comprising an amino acid sequence selected from the group consisting of SEQ ID NO: 1 to SEQ ID NO: 388 or a variant sequence thereof which is at least 77%, preferably at least 88%, homologous (preferably at least 77% or at least 88% identical) to SEQ ID NO: 1 to SEQ ID NO: 388, wherein said variant binds to MHC and/or induces T cells cross-reacting with said peptide, or a pharmaceutical acceptable salt thereof, wherein said peptide is not the underlying full-length polypeptide.

While the most important criterion for a peptide to function as cancer therapy target is its over-presentation on primary tumor tissues as compared to normal tissues, also the RNA expression profile of the corresponding gene can help to select appropriate peptides. Particularly, some peptides are hard to detect by mass spectrometry, either due to their chemical properties or to their low copy numbers on cells, and a screening approach focusing on detection of peptide presentation may fail to identify these targets. However, these targets may be detected by an alternative approach starting with analysis of gene expression in normal tissues and secondarily assessing peptide presentation and gene expression in tumors. This approach was realized in this invention using an mRNA database (Lonsdale, 2013) in combination with further gene expression data (including tumor samples), as well as peptide presentation data. If the mRNA of a gene is nearly absent in normal tissues, especially in vital organ systems, targeting the corresponding peptides by even very potent strategies (such as bispecific affinity-optimized antibodies or T-cell receptors), is more likely to be safe. Such peptides, even if identified on only a small percentage of tumor tissues, represent interesting targets. Routine mass spectrometry analysis is not sensitive enough to assess target coverage on the peptide level. Rather, tumor mRNA expression can be used to assess coverage. For detection of the peptide itself, a targeted mass spectrometry approach with higher sensitivity than in the routine screening may be necessary and may lead to a better estimation of coverage on the level of peptide presentation.

The present invention further relates to a peptide of the present invention comprising a sequence that is selected from the group consisting of SEQ ID NO: 1 to SEQ ID NO: 388 or a variant thereof, which is at least 77%, preferably at least 88%, homologous (preferably at least 77% or at least 88% identical) to SEQ ID NO: 1 to SEQ ID NO: 388, wherein said peptide or variant thereof has an overall length of between 8 and 100, preferably between 8 and 30, and most preferred of between 8 and 14 amino acids.

The following tables show the peptides according to the present invention, their respective SEQ ID NOs, and the prospective source (underlying) genes for these peptides. All peptides in Table 1A and Table 2A bind to HLA-A*02. Peptides in Table 1C and Table 2B bind to HLA-A*24. Peptides in Table 1B bind to HLA class II alleles. The peptides in Table 3 are additional peptides that are HLA-A*24 binding and may be useful in combination with the other peptides of the invention.

TABLE 1A

Peptides according to the present invention, HLA-A*02-binding.

| SEQ ID No. | Sequence | GeneID(s) | Official Gene Symbol(s) |
|---|---|---|---|
| 1 | PLWGKVFYL | 10926 | DBF4 |
| 2 | ALYGKLLKL | 157680 | VPS13B |
| 3 | TLLGKQVTL | 157680 | VPS13B |
| 4 | ELAEIVFKV | 203427, 349075, 51373 | SLC25A43, ZNF713, MRPS17 |
| 5 | SLFGQEVYC | 10840 | ALDH1L1 |
| 6 | FLDPAQRDL | 57677 | ZFP14 |
| 7 | AAAAKVPEV | 23382 | AHCYL2 |
| 8 | KLGPFLLNA | 100508781, 653199, 9747 | FAM115B, FAM115A |
| 9 | FLGDYVENL | 54832 | VPS13C |
| 10 | KTLDVFNIIL | 54832 | VPS13C |
| 11 | GVLKVFLENV | 121504, 554313, 8294, 8359, 8360, 8361, 8362, 8363, 8364, 8365, 8366, 8367, 8368, 8370 | HIST4H4, HIST2H4B, HIST1H4I, HIST1H4A, HIST1H4D, HIST1H4F, HIST1H4K, HIST1H4J, HIST1H4C, HIST1H4H, HIST1H4B, HIST1H4E, HIST1H4L, HIST2H4A |
| 12 | GLIYEETRGV | | |
| 13 | VLRDNIQGI | | |
| 14 | LLDHLSFINKI | 64863 | METTL4 |
| 15 | ALGDYVHAC | 4588 | MUC6 |
| 16 | HLYNNEEQV | 101060798, 1645, 8644 | AKR1C1, AKR1C3 |
| 17 | ILHEHHIFL | 4233 | MET |
| 18 | YVLNEEDLQKV | 4233 | MET |
| 19 | TLLPTVLTL | 127707 | KLHDC7A |
| 20 | ALDGHLYAI | 127707 | KLHDC7A |
| 21 | SLYHRVLLY | 57221 | KIAA1244 |
| 22 | MLSDLTLQL | 57221 | KIAA1244 |
| 23 | AQTVVVIKA | 101059911, 4586, 727897 | MUC5AC, MUC5B |
| 24 | FLWNGEDSAL | 4586, 727897 | MUC5AC, MUC5B |
| 25 | IQADDFRTL | 101059911, 4586, 727897 | MUC5AC, MUC5B |
| 26 | KVDGVVIQL | 101059911, 4586, 727897 | MUC5AC, MUC5B |
| 27 | KVFGDLDQV | 169611 | OLFML2A |
| 28 | TLYSMDLMKV | 169611 | OLFML2A |
| 29 | TLCNKTFTA | 26137 | ZBTB20 |
| 30 | TVIDECTRI | 26137 | ZBTB20 |
| 31 | ALSDETKNNWEV | 5591 | PRKDC |
| 32 | ILADEAFFSV | 5591 | PRKDC |

TABLE 1A-continued

Peptides according to the present invention, HLA-A*02-binding.

| SEQ ID No. | Sequence | GeneID(s) | Official Gene Symbol(s) |
|---|---|---|---|
| 33 | LLLPLLPPLSPSLG | 347252 | IGFBPL1 |
| 34 | LLPKKTESHHKT | 8330, 8331 | HIST1H2AK, HIST1H2AJ |
| 35 | YVLPKLYVKL | 100128168, 100996747, 441502, 6231, 643003, 644166, 644928, 644934, 646753, 728937, 729188 | RPS26P39, RPS26P11, RPS26, RPS26P28, RPS26P20, RPS26P15, RPS26P50, RPS26P2, RPS26P25, RPS26P58 |
| 36 | KLYGIEIEV | 56107 | PCDHGA9 |
| 37 | ALINDILGELVKL | 85463 | ZC3H12C |
| 38 | KMQEDLVTL | 781 | CACNA2D1 |
| 39 | ALMAVVSGL | 55103 | RALGPS2 |
| 40 | SLLALPQDLQA | 1364, 1365, 23562, 9074, 9080 | CLDN4, CLDN3, CLDN14, CLDN6, CLDN9 |
| 41 | FVLPLVVTL | 2848 | GPR25 |
| 42 | VLSPFILTL | 113730 | KLHDC7B |
| 43 | LLWAGPVTA | 28603 | TRBV6-4 |
| 44 | GLLWQIIKV | 5357 | PLS1 |
| 45 | VLGPTPELV | 100124692 | |
| 46 | SLAKHGIVAL | 10693 | CCT6B |
| 47 | GLYQAQVNL | 89886 | SLAMF9 |
| 48 | TLDHKPVTV | 203447 | NRK |
| 49 | LLDESKLTL | 64097 | EPB41L4A |
| 50 | EYALLYHTL | 26 | ABP1 |
| 51 | LLLDGDFTL | 347051 | SLC10A5 |
| 52 | ELLSSIFFL | 160418 | TMTC3 |
| 53 | SLLSHVIVA | 545 | ATR |
| 54 | FINPKGNWLL | 3673 | ITGA2 |
| 55 | IASAIVNEL | 57448 | BIRC6 |
| 56 | KILDLTRVL | 79783 | C7orf10 |
| 57 | VLISSTVRL | 166379 | BBS12 |
| 58 | ALDDSLTSL | 2302 | FOXJ1 |
| 59 | ALTKILAEL | 339766 | MROH2A |
| 60 | FLIDTSASM | 203522, 26512 | DDX26B, INTS6 |
| 61 | HLPDFVKQL | 9857 | CEP350 |
| 62 | SLFNQEVQI | 100528032, 22914, 8302 | KLRK1, KLRC4 |
| 63 | TLSSERDFAL | 100293534, 720, 721 | C4A, C4B |
| 64 | GLSSSSYEL | 89866 | SEC16B |
| 65 | KLDGICWQV | 733 | C8G |
| 66 | FITDFYTTV | 80055 | PGAP1 |
| 67 | GVIETVTSL | 79895 | ATP8B4 |

TABLE 1A-continued

Peptides according to the present invention, HLA-A*02-binding.

| SEQ ID No. | Sequence | GeneID(s) | Official Gene Symbol(s) |
|---|---|---|---|
| 68 | ALYGFFFKI | 118663 | BTBD16 |
| 69 | GIYDGILHSI | 158809, 392433 | MAGEB6, MAGEB6P1 |
| 70 | GLFSQHFNL | 1789 | DNMT3B |
| 71 | GLITVDIAL | 84162 | KIAA1109 |
| 72 | GMIGFQVLL | 6006, 6007 | RHCE, RHD |
| 73 | GVPDTIATL | 23120 | ATP10B |
| 74 | ILDETLENV | 167227 | DCP2 |
| 75 | ILDNVKNLL | 4602 | MYB |
| 76 | ILLDESNFNHFL | 222584 | FAM83B |
| 77 | IVLSTIASV | 10559, 154313 | SLC35A1, C6orf165 |
| 78 | LLWGHPRVA | 25878 | MXRA5 |
| 79 | SLVPLQILL | 101060288, 101060295, 101060308, 343068, 343070, 400735, 440560, 440561, 441873, 645359, 653619, 729368 | PRAMEF5, PRAMEF9, PRAMEF4, PRAMEF11, PRAMEF6, PRAMEF15, PRAMEF23 |
| 80 | TLDEYLTYL | 101060308, 343068, 343070, 653619 | PRAMEF5, PRAMEF9, PRAMEF15 |
| 81 | VLFLGKLLV | 204962 | SLC44A5 |
| 82 | VLLRVLIL | 102 | ADAM10 |
| 83 | ELLEYLPQL | 5288 | PIK3C2G |
| 84 | FLEEEITRV | 6570 | SLC18A1 |
| 85 | STLDGSLHAV | 2081 | ERN1 |
| 86 | LLVTSLVVV | 118471, 118472 | PRAP1, ZNF511 |
| 87 | YLTEVFLHVV | 55024 | BANK1 |
| 88 | ILLNTEDLASL | 388015 | RTL1 |
| 89 | YLVAHNLLL | 9365 | KL |
| 90 | GAVAEEVLSSI | 340273 | ABCB5 |
| 91 | SSLEPQIQPV | 23029 | RBM34 |
| 92 | LLRGPPVARA | 3486 | IGFBP3 |
| 93 | SLLTQPIFL | 151295 | SLC23A3 |

TABLE 1B

Peptides according to the present invention, HLA class II binding.

| SEQ ID No. | Sequence | GeneID(s) | Official Gene Symbol(s) |
|---|---|---|---|
| 94 | LKMENKEVLPQLVDAVTS | 4547 | MTTP |
| 95 | GLYLPLFKPSVSTSKAIGGGP | 10165 | SLC25A13 |

TABLE 1C

Peptides according to the present invention, HLA-A*24 binding.

| SEQ ID No. | Sequence | GeneID(s) | Official Gene Symbol(s) |
|---|---|---|---|
| 96 | YYTQYSQTI | 25878 | MXRA5 |
| 97 | TYTFLKETF | 203238 | CCDC171 |
| 98 | VFPRLHNVLF | 9816 | URB2 |

TABLE 1C-continued

Peptides according to the present invention, HLA-A*24 binding.

| SEQ ID No. | Sequence | GeneID(s) | Official Gene Symbol(s) |
|---|---|---|---|
| 99 | QYILAVPVL | 91147 | TMEM67 |
| 100 | VYIESRIGTSTSF | 10112 | KIF20A |
| 101 | IYIPVLPPHL | 163486 | DENND1B |
| 102 | VYPFENFEF | 127700 | OSCP1 |
| 103 | NYIPVKNGKQF | 3096 | HIVEP1 |
| 104 | SYLTWHQQI | 125919 | ZNF543 |
| 105 | IYNETITDLL | 1062 | CENPE |
| 106 | IYNETVRDLL | 3833 | KIFC1 |
| 107 | KYFPYLVVI | 80131 | LRRC8E |
| 108 | PYLVVIHTL | 80131 | LRRC8E |
| 109 | LFITGGQFF | 114134 | SLC2A13 |
| 110 | SYPKIIEEF | 2177 | FANCD2 |
| 111 | VYVQILQKL | 4998 | ORC1 |
| 112 | IYNFVESKL | 4998 | ORC1 |
| 113 | IYSFHTLSF | 55183 | RIF1 |
| 114 | QYLDGTWSL | 55083 | KIF26B |
| 115 | RYLNKSFVL | 63926 | ANKRD5 |
| 116 | AYVIAVHLF | 10178 | TENM1 |
| 117 | IYLSDLTYI | 55103 | RALGPS2 |
| 118 | KYLNSVQYI | 55103 | RALGPS2 |
| 119 | VYRVYVTTF | 57089 | ENTPD7 |
| 120 | GYIEHFSLW | 5069 | PAPPA |
| 121 | RYGLPAAWSTF | 79713 | IGFLR1 |
| 122 | EYQARIPEF | 55758 | RCOR3 |
| 123 | VYTPVLEHL | 5591 | PRKDC |
| 124 | TYKDYVDLF | 5591 | PRKDC |
| 125 | VFSRDFGLLVF | 5591 | PRKDC |
| 126 | PYDPALGSPSRLF | 389058 | SP5 |
| 127 | QYFTGNPLF | 3237 | HOXD11 |
| 128 | VYPFDWQYI | 7941 | PLA2G7 |
| 129 | KYIDYLMTW | 55233, 92597 | MOB1A, MOB1B |
| 130 | VYAHIYHQHF | 55233, 92597 | MOB1A, MOB1B |
| 131 | EYLDRIGQLFF | 51608 | GET4 |
| 132 | RYPALFPVL | 11237 | RNF24 |
| 133 | KYLEDMKTYF | 5273 | SERPINB10 |
| 134 | AYIPTPIYF | 81796 | SLCO5A1 |
| 135 | VYEAMVPLF | 85465 | EPT1 |
| 136 | IYPEWPVVFF | 51146 | A4GNT |
| 137 | EYLHNCSYF | 25909, 285116 | AHCTF1, AHCTF1P1 |
| 138 | VYNAVSTSF | 79915 | ATAD5 |
| 139 | IFGIFPNQF | 79895 | ATP8B4 |
| 140 | RYLINSYDF | 84002 | B3GNT5 |
| 141 | SYNGHLTIWF | 56245 | C21orf62 |
| 142 | VYVDDIYVI | 57082 | CASC5 |
| 143 | KYIFQLNEI | 347475 | CCDC160 |
| 144 | VFASLPGFLF | 1233 | CCR4 |
| 145 | VYALKVRTI | 1237 | CCR8 |
| 146 | NYYERIHAL | 8832 | CD84 |
| 147 | LYLAFPLAF | 253782 | CERS6 |
| 148 | SYGTVSQIF | 23601 | CLEC5A |
| 149 | SYGTVSQI | 23601 | CLEC5A |
| 150 | IYITRQFVQF | 81501 | DCSTAMP |
| 151 | AYISGLDVF | 8632 | DNAH17 |
| 152 | KFFDDLGDELLF | 8632 | DNAH17 |
| 153 | VYVPFGGKSMITF | 146754 | DNAH2 |
| 154 | VYGVPTPHF | 151651 | EFHB |
| 155 | IYKWITDNF | 2302 | FOXJ1 |
| 156 | YYMELTKLLL | 51659 | GINS2 |
| 157 | DYIPASGFALF | 84059 | GPR98 |
| 158, 159 | IYEETRGVLKVF, IYEETRGVL | 121504, 554313, 8294, 8359, 8360, 8361, 8362, 8363, 8364, 8365, 8366, 8367, 8368, 8370 | HIST4H4, HIST2H4B, HIST1H4I, HIST1H4A, HIST1H4D, HIST1H4F, HIST1H4K, HIST1H4J, HIST1H4C, HIST1H4H, HIST1H4B, HIST1H4E, HIST1H4L, HIST2H4A |
| 160 | RYGDGGSSF | 3188 | HNRNPH2 |
| 161 | KYPDIVQQF | 29851 | ICOS |
| 162 | KYTSYILAF | 3458 | IFNG |
| 163 | RYLTISNLQF | 28785 | IGLV4-60 |
| 164 | HYVPATKVF | 259307 | IL4I1 |

TABLE 1C-continued

Peptides according to the present invention, HLA-A*24 binding.

| SEQ ID No. | Sequence | GeneID(s) | Official Gene Symbol(s) |
|---|---|---|---|
| 165 | EYFTPLLSGQF | 55175 | KLHL11 |
| 166 | FYTLPFHLI | 55175 | KLHL11 |
| 167 | RYGFYYVEF | 197021 | LCTL |
| 168 | RYLEAALRL | 10609 | LEPREL4 |
| 169 | NYITKGDVF | 84125 | LRRIQ1 |
| 170 | QYPFHVPLL | 4049 | LTA |
| 171 | NYEDHFPLL | 4109 | MAGEA10 |
| 172 | VFIFKGNEF | 4319 | MMP10 |
| 173 | QYLEKYYNL | 4319 | MMP10 |
| 174 | VYEKNGYIYF | 4322 | MMP13 |
| 175 | LYSPVPFTL | 387521 | TMEM189 |
| 176 | FYINGQYQF | 55728 | N4BP2 |
| 177 | VYFKAGLDVF | 254827 | NAALADL2 |
| 178 | NYSSAVQKF | 4983 | OPHN1 |
| 179 | TYIPVGLGRLL | 58495 | OVOL2 |
| 180 | KYLQVVGMF | 5021 | OXTR |
| 181 | VYPPYLNYL | 5241 | PGR |
| 182 | AYAQLGYLLF | 9033 | PKD2L1 |
| 183 | PYLQDVPRI | 92340 | C17orf72 |
| 184 | IYSVGAFENF | 389677 | RBM12B |
| 185 | QYLVHVNDL | 23322 | RPGRIP1L |
| 186 | VFTTSSNIF | 10371 | SEMA3A |
| 187 | AYAANVHYL | 151473 | SLC16A14 |
| 188 | GYKTFFNEF | 64078 | SLC28A3 |
| 189 | AYFKQSSVF | 54790 | TET2 |
| 190 | LYSELTETL | 54790 | TET2 |
| 191 | TYPDGTYTGRIF | 201633 | TIGIT |
| 192 | RYSTFSEIF | 8277 | TKTL1 |
| 193 | LYLENNAQTQF | 8626 | TP63 |
| 194 | VYQSLSNSL | 286827 | TRIM59 |
| 195 | AYIKGGWIL | 125488 | TTC39C |
| 196 | GYIRGSWQF | 79465 | ULBP3 |
| 197 | IFTDIFHYL | 54464 | XRN1 |
| 198 | DYVGFTLKI | 19 | ABCA1 |
| 199 | SYLNHLNNL | 154664 | ABCA13 |
| 200 | VFIHHLPQF | 116285 | ACSM1 |
| 201 | GYNPNRVFF | 158067 | AK8 |
| 202 | RYVEGIVSL | 246 | ALOX15 |
| 203 | VYNVEVKNAEF | 84250 | ANKRD32 |
| 204 | EYLSTCSKL | 196528 | ARID2 |
| 205 | VYPVVLNQI | 79798 | ARMC5 |
| 206 | NYLDVATFL | 10973 | ASCC3 |
| 207 | LYSDAFKFIVF | 344905 | ATP13A5 |
| 208 | TYLEKIDGF | 100526740, 26024, 9551 | ATP5J2-PTCD1, PTCD1, ATP5J2 |
| 209 | AFIETPIPLF | 631 | BFSP1 |
| 210 | IYAGVGEFSF | 701 | BUB1B |
| 211 | VFKSEGAYF | 375444 | C5orf34 |
| 212 | SYAPPSEDLF | 100533105, 23678 | SGK3 |
| 213 | SYAPPSEDLFL | 100533105, 23678 | SGK3 |
| 214 | KYLMELTLI | 9133 | CCNB2 |
| 215 | SYVASFFLL | 9398 | CD101 |
| 216 | FYVNVKEQF | 79682 | MLF1IP |
| 217 | IYISNSIYF | 54967 | CXorf48 |
| 218 | LYSELNKWSF | 1591 | CYP24A1 |
| 219 | SYLKAVFNL | 163720, 199974 | CYP4Z2P, CYP4Z1 |
| 220 | SYSEIKDFL | 64421 | DCLRE1C |
| 221 | KYIGNLDLL | 8701 | DNAH11 |
| 222 | HYSTLVHMF | 8701 | DNAH11 |
| 223 | TFITQSPLL | 1767 | DNAH5 |
| 224 | PYFFANQEF | 79843 | FAM124B |
| 225 | TYTNTLERL | 55719 | FAM178A |
| 226 | MYLKLVQLF | 2175 | FANCA |
| 227 | IYRFITERF | 2301 | FOXE3 |
| 228 | IYQYVADNF | 2299 | FOXI1 |
| 229 | IYQFVADSF | 344167 | FOXI3 |
| 230 | TYGMVMVTF | 84059 | GPR98 |
| 231 | AFADVSVKF | 84059 | GPR98 |
| 232 | YYLSDSPLL | 51512 | GTSE1 |
| 233 | QYLTAAALHNL | 3552 | IL1A |
| 234 | SYLPAIWLL | 3641 | INSL4 |

TABLE 1C-continued

Peptides according to the present invention, HLA-A*24 binding.

| SEQ ID No. | Sequence | GeneID(s) | Official Gene Symbol(s) |
|---|---|---|---|
| 235 | VYKDSIYYI | 84541 | KBTBD8 |
| 236 | VYLPKIPSW | 157855 | KCNU1 |
| 237 | KYVGQLAVL | 9928 | KIF14 |
| 238 | SYLEKVRQL | 100653049, 3881, 3883, 3884, 3885, 3886 | KRT31, KRT33A, KRT33B, KRT34, KRT35 |
| 239 | VYAIFRILL | 987 | LRBA |
| 240 | YYFFVQEKI | 84944 | MAEL |
| 241 | SYVKVLHHL | 101060230, 4111 | MAGEA12 |
| 242 | VYGEPRELL | 392555, 51438 | MAGEC2 |
| 243 | SYLELANTL | 4163 | MCC |
| 244 | VHFEDTGKTLLF | 4322 | MMP13 |
| 245 | LYPQLFVVL | 377711, 727957 | MROH1 |
| 246 | KYLSVQLTL | 339766 | MROH2A |
| 247 | SFTKTSPNF | 200958 | MUC20 |
| 248 | AFPTFSVQL | 4588 | MUC6 |
| 249 | RYHPTTCTI | 4608 | MYBPH |
| 250 | KYPDIASPTF | 89795 | NAV3 |
| 251 | VYTKALSSL | 64151 | NCAPG |
| 252 | AFGQETNVPLNNF | 4695 | NDUFA2 |
| 253 | IYGFFNENF | 10886 | NPFFR2 |
| 254 | KYLESSATF | 91181 | NUP210L |
| 255 | VYQKIILKF | 139135 | PASD1 |
| 256 | VFGKSAYLF | 118987 | PDZD8 |
| 257 | IFIDNSTQPLHF | 5288 | PIK3C2G |
| 258 | AYAQLGYLL | 9033 | PKD2L1 |
| 259 | YFIKSPPSQLF | 79949 | PLEKHS1 |
| 260 | VYMNVMTRL | 5523 | PPP2R3A |
| 261 | GYIKLINFI | 10196 | PRMT3 |
| 262 | VYSSQFETI | 23362 | PSD3 |
| 263 | RYILENHDF | 442247 | RFPL4B |
| 264 | LYTETRLQF | 26150 | RIBC2 |
| 265 | SYLNEAFSF | 286205 | SCAI |
| 266 | KYTDWTEFL | 57713 | SFMBT2 |
| 267 | SFLNIEKTEILF | 347051 | SLC10A5 |
| 268 | IFITKALQI | 159371 | SLC35G1 |
| 269 | QYPYLQAFF | 146857 | SLFN13 |
| 270 | YYSQESKVLYL | 55181 | SMG8 |
| 271 | RFLMKSYSF | 8435 | SOAT2 |
| 272 | RYVFPLPYL | 8403 | SOX14 |
| 273 | IYGEKLQFIF | 57405 | SPC25 |
| 274 | KQLDIANYELF | 51430 | SUCO |
| 275 | KYGTLDVTF | 255928 | SYT14 |
| 276 | QYLDVLHAL | 51256 | TBC1D7 |
| 277 | FYTFPPFQQL | 6996 | TDG |
| 278 | KYVNLVMYF | 116238 | TLCD1 |
| 279 | VWLPASVLF | 85019 | TMEM241 |
| 280 | TYNPNLQDKL | 5651 | TMPRSS15 |
| 281 | NYSPGLVSLIL | 28677 | TRAV9-2 |
| 282 | NYLVDPVTI | 129868, 653192 | TRIM43, TRIM43B |
| 283 | EYQEIFQQL | 129868, 653192 | TRIM43, TRIM43B |
| 284 | DYLKDPVTI | 391712, 653794 | TRIM61, TRIM60P14 |
| 285 | VYVGDALLHAI | 7223 | TRPC4 |
| 286 | SYGTILSHI | 54986 | ULK4 |
| 287 | IYNPNLLTASKF | 81839 | VANGL1 |
| 288 | VYPDTVALTF | 284403 | WDR62 |
| 289 | FFHEGQYVF | 389668 | XKR9 |
| 290 | KYGDFKLLEF | 143570 | XRRA1 |
| 291 | YYLGSGRETF | 152002 | XXYLT1 |
| 292 | FYPQIINTF | 79776 | ZFHX4 |
| 293 | VYPHFSTTNLI | 79776 | ZFHX4 |
| 294 | RFPVQGTVTF | 79818 | ZNF552 |
| 295 | SYLVIHERI | 84775 | ZNF607 |
| 296 | SYQVIFQHF | 344905 | ATP13A5 |
| 297 | TYIDTRTVF | 827 | CAPN6 |
| 298 | AYKSEVVYF | 441402, 728577, 79937 | CNTNAP3B, CNTNAP3 |
| 299 | KYQYVLNEF | 400823 | FAM177B |
| 300 | TYPSQLPSL | 26290 | GALNT8 |
| 301 | KFDDVTMLF | 2977 | GUCY1A2 |

TABLE 1C-continued

Peptides according to the present invention, HLA-A*24 binding.

| SEQ ID No. | Sequence | GeneID(s) | Official Gene Symbol(s) |
|---|---|---|---|
| 302 | LYLPVHYGF | 253012 | HEPACAM2 |
| 303 | LYSVIKEDF | 285600 | KIAA0825 |
| 304 | EYNEVANLF | 57097 | PARP11 |
| 305 | NYENKQYLF | 144406 | WDR66 |
| 306 | VYPAEQPQI | 2334 | AFF2 |
| 307 | GYAFTLPLF | 440138 | ALG11 |
| 308 | TFDGHGVFF | 29785 | CYP2S1 |
| 309 | KYYRQTLLF | 27042 | DIEXF |
| 310 | IYAPTLLVF | 23341 | DNAJC16 |
| 311 | EYLQNLNHI | 79659 | DYNC2H1 |
| 312 | SYTSVLSRL | 57724 | EPG5 |
| 313 | KYTHFIQSF | 26301 | GBGT1 |
| 314 | RYFKGDYSI | 3709 | ITPR2 |
| 315 | FYIPHVPVSF | 89866 | SEC16B |
| 316 | VYFEGSDFKF | 55164 | SHQ1 |
| 317 | VFDTSIAQLF | 6477 | SIAH1 |
| 318 | TYSNSAFQYF | 28672 | TRAV12-3 |
| 319 | KYSDVKNLI | 57623 | ZFAT |
| 320 | KFILALKVLF | 6790 | AURKA |

TABLE 2A

Additional peptides according to the present invention, HLA-A*02-binding.

| SEQ ID No. | Sequence | GeneID(s) | Official Gene Symbol(s) |
|---|---|---|---|
| 321 | SLWFKPEEL | 4831, 654364 | NME2, NME1-NME2 |
| 322 | ALVSGGVAQA | 64326 | RFWD2 |
| 323 | ILSVVNSQL | 80183 | KIAA0226L |
| 324 | AIFDFCPSV | 23268 | DNMBP |
| 325 | RLLPKVQEV | 168417, 89958 | ZNF679, SAPCD2 |
| 326 | SLLPLVWKI | 1130 | LYST |
| 327 | SIGDIFLKY | 1894 | ECT2 |
| 328 | SVDSAPAAV | 10635 | RAD51AP1 |
| 329 | FAWEPSFRDQV | 1244 | ABCC2 |
| 330 | FLWPKEVEL | 146206 | RLTPR |
| 331 | AIWKELISL | 55183 | RIF1 |
| 332 | AVTKYTSAK | 54145, 85236, 8970 | H2BFS, HIST1H2BK, HIST1H2BJ |
| 333 | GTFLEGVAK | 126328 | NDUFA11 |
| 334 | GRADALRVL | 79713 | IGFLR1 |
| 335 | VLLAAGPSAA | 23225 | NUP210 |
| 336 | GLMDGSPHFL | 157680 | VPS13B |
| 337 | KVLGKIEKV | 987 | LRBA |
| 338 | LLYDGKLSSA | 987 | LRBA |
| 339 | VLGPGPPPL | 254359 | ZDHHC24 |
| 340 | SVAKTILKR | 55233, 92597 | MOB1A, MOB1B |

TABLE 2B

Additional peptides according to the present invention, HLA-A*24-binding.

| SEQ ID No. | Sequence | GeneID(s) | Official Gene Symbol(s) |
|---|---|---|---|
| 341 | SYLTQHQRI | 162655, 344065, 9422 | ZNF519, ZNF264 |
| 342 | NYAFLHRTL | 200316, 9582 | APOBEC3F, APOBEC3B |
| 343 | NYLGGTSTI | 367 | AR |
| 344 | EYNSDLHQF | 699 | BUB1 |
| 345 | EYNSDLHQFF | 699 | BUB1 |
| 346 | IYVIPQPHF | 57082 | CASC5 |
| 347 | VYAEVNSL | 1459 | CSNK2A2 |
| 348 | IYLEHTESI | 2177 | FANCD2 |
| 349 | QYSIISNVF | 28982 | FLVCR1 |
| 350 | KYGNFIDKL | 85865 | GTPBP10 |
| 351 | IFHEVPLKF | 728432, 79664 | NARG2 |
| 352 | QYGGDLTNTF | 3673 | ITGA2 |
| 353 | TYGKIDLGF | 57650 | KIAA1524 |
| 354 | VYNEQIRDLL | 81930 | KIF18A |
| 355 | IYVTGGHLF | 113730 | KLHDC7B |
| 356 | NYMPGQLTI | 346389 | MACC1 |
| 357 | QFITSTNTF | 94025 | MUC16 |

TABLE 2B-continued

Additional peptides according to the present invention, HLA-A*24-binding.

| SEQ ID No. | Sequence | GeneID(s) | Official Gene Symbol(s) |
|---|---|---|---|
| 358 | YYSEVPVKL | 25878 | MXRA5 |
| 359 | NYGVLHVTF | 204801 | NLRP11 |
| 360 | VFSPDGHLF | 143471, 5688 | PSMA8, PSMA7 |
| 361 | TYADIGGLDNQI | 5700 | PSMC1 |
| 362 | VYNYAEQTL | 100526737, 10432, 5936 | RBM14-RBM4, RBM14, RBM4 |
| 363 | SYAELGTTI | 23657 | SLC7A11 |
| 364 | KYLNENQLSQL | 6491 | STIL |
| 365 | VFIDHPVHL | 26011 | TENM4 |
| 366 | QYLELAHSL | 4796 | TONSL |
| 367 | LYQDHMQYI | 7474 | WNT5A |
| 368 | KYQNVKHNL | 79830 | ZMYM1 |
| 369 | VYTHEVVTL | 983 | CDK1 |
| 370 | RFIGIPNQF | 79659 | DYNC2H1 |
| 371 | AYSHLRYVF | 2195 | FAT1 |
| 372 | VYVIEPHSMEF | 23225 | NUP210 |
| 373 | GYISNGELF | 116143, 5534, 5535 | WDR92, PPP3R1, PPP3R2 |
| 374 | VFLPRVTEL | 5591 | PRKDC |
| 375 | KYTDYILKI | 374462 | PTPRQ |
| 376 | VYTPVASRQSL | 56852 | RAD18 |
| 377 | QYTPHSHQF | 57521 | RPTOR |
| 378 | VYIAELEKI | 27127 | SMC1B |
| 379 | VFIAQGYTL | 160418 | TMTC3 |
| 380 | VYTGIDHHW | 25879 | DCAF13 |
| 381 | KYPASSSVF | 3217 | HOXB7 |
| 382 | AYLPPLQQVF | 26523 | EIF2C1 |
| 383 | RYKPGEPITF | 163486 | DENND1B |
| 384 | RYFDVGLHNF | 55733 | HHAT |
| 385 | QYIEELQKF | 55103 | RALGPS2 |
| 386 | TFSDVEAHF | 55609 | ZNF280C |
| 387 | KYTEKLEEI | 95681 | CEP41 |
| 388 | IYGEKTYAF | 5273 | SERPINB10 |

TABLE 3

Peptides useful for cancer therapies according to the invention, e.g. personalized cancer therapies.

| SEQ ID No. | Sequence | GeneID(s) | Official Gene Symbol(s) |
|---|---|---|---|
| 389 | EYLPEFLHTF | 154664 | ABCA13 |
| 390 | RYLWATVTI | 259266 | ASPM |
| 391 | LYQILQGIVF | 983 | CDK1 |
| 392 | RYLDSLKAIVF | 55839 | CENPN |
| 393 | KYIEAIQWI | 81501 | DCSTAMP |
| 394 | FYQPKIQQF | 55215 | FANCI |
| 395 | LYINKANIW | 55632 | G2E3 |
| 396 | YYHFIFTTL | 2899 | GRIK3 |
| 397 | IYNGKLFDL | 11004 | KIF2C |
| 398 | IYNGKLFDLL | 11004 | KIF2C |
| 399 | SYIDVLPEF | 4233 | MET |
| 400 | KYLEKYYNL | 4312 | MMP1 |
| 401 | VFMKDGFFYF | 4312 | MMP1 |
| 402 | VWSDVTPLTF | 4320 | MMP11 |
| 403 | TYKYVDINTF | 4321 | MMP12 |
| 404 | RYLEKFYGL | 4321 | MMP12 |
| 405 | NYPKSIHSF | 4321 | MMP12 |
| 406 | TYSEKTTLF | 94025 | MUC16 |
| 407 | VYGIRLEHF | 83540 | NUF2 |
| 408 | QYASRFVQL | 10733 | PLK4 |
| 409 | YFISHVLAF | 6241 | RRM2 |
| 410 | RFLSGIINF | 83540 | NUF2 |
| 411 | VYIGHTSTI | 23499, 93035 | MACF1, PKHD1L1 |
| 412 | SYNPLWLRI | 259266 | ASPM |
| 413 | NYLLYVSNF | 4486 | MST1R |
| 414 | MYPYIYHVL | 54954 | FAM120C |
| 415 | SYQKVIELF | 55872 | PBK |
| 416 | AYSDGHFLF | 26011 | TENM4 |
| 417 | VYKVVGNLL | 128239 | IQGAP3 |

The present invention furthermore generally relates to the peptides according to the present invention for use in the treatment of proliferative diseases, such as, for example, glioblastoma (GB), breast cancer (BRCA), colorectal cancer (CRC), renal cell carcinoma (RCC), chronic lymphocytic leukemia (CLL), hepatocellular carcinoma (HCC), non-small cell and small cell lung cancer (NSCLC, SCLC), Non-Hodgkin lymphoma (NHL), acute myeloid leukemia (AML), ovarian cancer (OC), pancreatic cancer (PC), prostate cancer (PCA), esophageal cancer including cancer of the gastric-esophageal junction (OSCAR), gallbladder cancer and cholangiocarcinoma (GBC, CCC), melanoma (MEL), gastric cancer (GC), testis cancer (TC), urinary bladder cancer (UBC), head- and neck squamous cell carcinoma (HNSCC), and uterine cancer (UEC).

Particularly preferred are the peptides—alone or in combination—according to the present invention selected from the group consisting of SEQ ID NO: 1 to SEQ ID NO: 388. More preferred are the peptides—alone or in combination—selected from the group consisting of SEQ ID NO: 1 to SEQ ID NO: 295 (see Table 1A, B, C), and their uses in the immunotherapy of glioblastoma, breast cancer, colorectal cancer, renal cell carcinoma, chronic lymphocytic leukemia, hepatocellular carcinoma, non-small cell and small cell lung cancer, Non-Hodgkin lymphoma, acute myeloid leukemia, ovarian cancer, pancreatic cancer, prostate cancer, esophageal cancer including cancer of the gastric-esophageal junction, gallbladder cancer and cholangiocarcinoma, melanoma, gastric cancer, testis cancer, urinary bladder cancer, head- and neck squamous cell carcinoma, or uterine cancer.

Particularly preferred are the peptides—alone or in combination—according to the present invention selected from the group consisting of SEQ ID NO: 70, 80, 323, and 325. More preferred are the peptides—alone or in combination—selected from the group consisting of SEQ ID NO: 70, 80, 323, and 325, and their uses in the immunotherapy of glioblastoma, breast cancer, colorectal cancer, renal cell carcinoma, chronic lymphocytic leukemia, hepatocellular carcinoma, non-small cell and small cell lung cancer, Non-Hodgkin lymphoma, acute myeloid leukemia, ovarian cancer, pancreatic cancer, prostate cancer, esophageal cancer including cancer of the gastric-esophageal junction, gallbladder cancer and cholangiocarcinoma, melanoma, gastric cancer, testis cancer, urinary bladder cancer, head- and neck squamous cell carcinoma, or uterine cancer.

Also preferred are the peptides—alone or in combination—according to the present invention selected from the group consisting of SEQ ID NO: 391, and 403. More preferred are the peptides—alone or in combination—selected from the group consisting of SEQ ID NO: 391, and 403, and their uses in the immunotherapy of glioblastoma, breast cancer, colorectal cancer, renal cell carcinoma, chronic lymphocytic leukemia, hepatocellular carcinoma, non-small cell and small cell lung cancer, Non-Hodgkin lymphoma, acute myeloid leukemia, ovarian cancer, pancreatic cancer, prostate cancer, esophageal cancer including cancer of the gastric-esophageal junction, gallbladder cancer and cholangiocarcinoma, melanoma, gastric cancer, testis cancer, urinary bladder cancer, head- and neck squamous cell carcinoma, or uterine cancer.

As shown in Example 1, many of the peptides according to the present invention are found on various tumor types and can, thus, also be used in the immunotherapy of a variety of indications. Over-expression of the underlying polypeptides in a variety of cancers, as shown in Example 2, hints towards the usefulness of these peptides in various other oncological indications.

Thus, another aspect of the present invention relates to the use of the peptides according to the present invention for the—preferably combined—treatment of a proliferative disease selected from the group of glioblastoma, breast cancer, colorectal cancer, renal cell carcinoma, chronic lymphocytic leukemia, hepatocellular carcinoma, non-small cell and small cell lung cancer, Non-Hodgkin lymphoma, acute myeloid leukemia, ovarian cancer, pancreatic cancer, prostate cancer, esophageal cancer including cancer of the gastric-esophageal junction, gallbladder cancer and cholangiocarcinoma, melanoma, gastric cancer, testis cancer, urinary bladder cancer, head- and neck squamous cell carcinoma, or uterine cancer.

The present invention furthermore relates to peptides according to the present invention that have the ability to bind to a molecule of the human major histocompatibility complex (MHC) class-I or—in an elongated form, such as a length-variant—MHC class-II.

The present invention further relates to the peptides according to the present invention wherein said peptides (each) consist or consist essentially of an amino acid sequence according to SEQ ID NO: 1 to SEQ ID NO: 388.

The present invention further relates to the peptides according to the present invention, wherein said peptide is modified and/or includes non-peptide bonds.

The present invention further relates to the peptides according to the present invention, wherein said peptide is part of a fusion protein, in particular fused to the N-terminal amino acids of the HLA-DR antigen-associated invariant chain (Ii), or fused to (or into the sequence of) an antibody, such as, for example, an antibody that is specific for dendritic cells.

Another embodiment of the present invention relates to a non-naturally occurring peptide wherein said peptide consists or consists essentially of an amino acid sequence according to SEQ ID No: 1 to SEQ ID No: 48 and has been synthetically produced (e.g. synthesized) as a pharmaceutically acceptable salt. Methods to synthetically produce peptides are well known in the art. The salts of the peptides according to the present invention differ substantially from the peptides in their state(s) in vivo, as the peptides as generated in vivo are no salts. The non-natural salt form of the peptide mediates the solubility of the peptide, in particular in the context of pharmaceutical compositions comprising the peptides, e.g. the peptide vaccines as disclosed herein. A sufficient and at least substantial solubility of the peptide(s) is required in order to efficiently provide the peptides to the subject to be treated. Preferably, the salts are pharmaceutically acceptable salts of the peptides. These salts according to the invention include alkaline and earth alkaline salts such as salts of the Hofmeister series comprising as anions $PO_4^{3-}$, $SO_4^{2-}$, $CH_3COO^-$, $Cl^-$, $Br^-$, $NO_3^-$, $ClO_4^-$, $I^-$, $SCN^-$ and as cations $NH_4^+$, $Rb^+$, $K^+$, $Na^+$, $Cs^+$, $Li^+$, $Zn^{2+}$, $Mg^{2+}$, $Ca^{2+}$, $Mn^{2+}$, $Cu^{2+}$ and $Ba^{2+}$. Particularly salts are selected from $(NH_4)_3PO_4$, $(NH_4)_2HPO_4$, $(NH_4)H_2PO_4$, $(NH_4)_2SO_4$, $NH_4CH_3COO$, $NH_4Cl$, $NH_4Br$, $NH_4NO_3$, $NH_4ClO_4$, $NH_4I$, $NH_4SCN$, $Rb_3PO_4$, $Rb_2HPO_4$, $RbH_2PO_4$, $Rb_2SO_4$, $Rb_4CH_3COO$, $Rb_4Cl$, $Rb_4Br$, $Rb_4NO_3$, $Rb_4ClO_4$, $Rb_4I$, $Rb_4SCN$, $K_3PO_4$, $K_2HPO_4$, $KH_2PO_4$, $K_2SO_4$, $KCH_3COO$, $KCl$, $KBr$, $KNO_3$, $KClO_4$, $KI$, $KSCN$, $Na_3PO_4$, $Na_2HPO_4$, $NaH_2PO_4$, $Na_2SO_4$, $NaCH_3COO$, $NaCl$, $NaBr$, $NaNO_3$, $NaClO_4$, $NaI$, $NaSCN$, $ZnCl_2$ $Cs_3PO_4$, $Cs_2HPO_4$, $CsH_2PO_4$, $Cs_2SO_4$, $CsCH_3COO$, $CsCl$, $CsBr$, $CsNO_3$, $CsClO_4$, $CsI$, $CsSCN$, $Li_3PO_4$, $Li_2HPO_4$, $LiH_2PO_4$, $Li_2SO_4$, $LiCH_3COO$, $LiCl$, $LiBr$, $LiNO_3$, $LiClO_4$, $LiI$, $LiSCN$, $Cu_2SO_4$, $Mg_3(PO_4)_2$, $Mg_2HPO_4$, $Mg(H_2PO_4)_2$, $Mg_2SO_4$, $Mg(CH_3COO)_2$, $MgCl_2$, $MgBr_2$, $Mg(NO_3)_2$, $Mg(ClO_4)_2$, $MgI_2$, $Mg(SCN)_2$, $MnCl_2$, $Ca_3(PO_4)$, $Ca_2HPO_4$, $Ca(H_2PO_4)_2$, $CaSO_4$, $Ca(CH_3COO)_2$, $CaCl_2$, $CaBr_2$, $Ca(NO_3)_2$, $Ca(ClO_4)_2$, $CaI_2$, $Ca(SCN)_2$, $Ba_3(PO_4)_2$, $Ba_2HPO_4$, $Ba(H_2PO_4)_2$, $BaSO_4$, $Ba(CH_3COO)_2$, $BaCl_2$, $BaBr_2$, $Ba(NO_3)_2$, $Ba(ClO_4)_2$, $BaI_2$, and $Ba(SCN)_2$. Particularly preferred are NH acetate, $MgCl_2$, $KH_2PO_4$, $Na_2SO_4$, KCl, NaCl, and $CaCl_2$, such as, for example, the chloride or acetate (trifluoroacetate) salts.

Generally, peptides and variants (at least those containing peptide linkages between amino acid residues) may be synthesized by the Fmoc-polyamide mode of solid-phase peptide synthesis as disclosed by Lukas et al. (Lukas et al., 1981) and by references as cited therein. Temporary N-amino group protection is afforded by the 9-fluorenylmethyloxycarbonyl (Fmoc) group. Repetitive cleavage of this highly base-labile protecting group is done using 20% piperidine in N, N-dimethylformamide Side-chain functionalities may be protected as their butyl ethers (in the case of serine threonine and tyrosine), butyl esters (in the case of glutamic acid and aspartic acid), butyloxycarbonyl derivative (in the case of lysine and histidine), trityl derivative (in the case of cysteine) and 4-methoxy-2,3,6-trimethylbenzenesulphonyl derivative (in the case of arginine). Where glutamine or asparagine are C-terminal residues, use is made of the 4,4'-dimethoxybenzhydryl group for protection of the side chain amido functionalities. The solid-phase support is based on a polydimethyl-acrylamide polymer constituted from the three monomers dimethylacrylamide (backbone-monomer), bisacryloylethylene diamine (cross linker) and acryloylsarcosine methyl ester (functionalizing agent). The peptide-to-resin cleavable linked agent used is the acid-labile 4-hydroxymethyl-phenoxyacetic acid derivative. All amino acid derivatives are added as their preformed symmetrical anhydride derivatives with the exception of asparagine and glutamine, which are added using a reversed N, N-dicyclohexyl-carbodiimide/1hydroxybenzotriazole mediated coupling procedure. All coupling and deprotection reactions are monitored using ninhydrine, trinitrobenzene sulphonic acid or isotin test procedures. Upon completion of synthesis, peptides are cleaved from the resin support with concomitant removal of side-chain protecting groups by treatment with 95% trifluoroacetic acid containing a 50% scavenger mix. Scavengers commonly used include ethanedithiol, phenol, anisole and water, the exact choice depending on the constituent amino acids of the peptide being synthesized. Also a combination of solid phase and solution phase methodologies for the synthesis of peptides is possible (see, for example, (Bruckdorfer et al., 2004), and the references as cited therein).

Trifluoroacetic acid is removed by evaporation in vacuo, with subsequent trituration with diethyl ether affording the crude peptide. Any scavengers present are removed by a simple extraction procedure which on lyophilization of the aqueous phase affords the crude peptide free of scavengers. Reagents for peptide synthesis are generally available from e.g. Calbiochem-Novabiochem (Nottingham, UK).

Purification may be performed by any one, or a combination of, techniques such as re-crystallization, size exclusion chromatography, ion-exchange chromatography, hydrophobic interaction chromatography and (usually) reverse-phase high performance liquid chromatography using e.g. acetonitril/water gradient separation.

The present invention further relates to a nucleic acid, encoding the peptides according to the present invention. The present invention further relates to the nucleic acid according to the present invention that is DNA, cDNA, PNA, RNA or combinations thereof.

The present invention further relates to an expression vector capable of expressing and/or expressing a nucleic acid according to the present invention.

The present invention further relates to a peptide according to the present invention, a nucleic acid according to the present invention or an expression vector according to the present invention for use in the treatment of diseases and in medicine, in particular in the treatment of cancer.

The present invention further relates to antibodies that are specific against the peptides according to the present invention or complexes of said peptides according to the present invention with MHC, and methods of making these.

The present invention further relates to T-cell receptors (TCRs), in particular soluble TCR (sTCRs) and cloned TCRs engineered into autologous or allogeneic T cells, and methods of making these, as well as NK cells or other cells bearing said TCR or cross-reacting with said TCRs.

The antibodies and TCRs are additional embodiments of the immunotherapeutic use of the peptides according to the invention at hand.

The present invention further relates to a host cell comprising a nucleic acid according to the present invention or an expression vector as described before. The present invention further relates to the host cell according to the present invention that is an antigen presenting cell, and preferably is a dendritic cell.

The present invention further relates to a method for producing a peptide according to the present invention, said method comprising culturing the host cell according to the present invention, and isolating the peptide from said host cell or its culture medium.

The present invention further relates to said method according to the present invention, wherein the antigen is loaded onto class I or II MHC molecules expressed on the surface of a suitable antigen-presenting cell or artificial antigen-presenting cell by contacting a sufficient amount of the antigen with an antigen-presenting cell.

The present invention further relates to the method according to the present invention, wherein the antigen-presenting cell comprises an expression vector capable of expressing or expressing said peptide containing SEQ ID No. 1 to SEQ ID No.: 388, preferably containing SEQ ID No. 1 to SEQ ID No. 295, or a variant amino acid sequence.

The present invention further relates to activated T cells, produced by the method according to the present invention, wherein said T cell selectively recognizes a cell which expresses a polypeptide comprising an amino acid sequence according to the present invention.

The present invention further relates to a method of killing target cells in a patient which target cells aberrantly express a polypeptide comprising any amino acid sequence according to the present invention, the method comprising administering to the patient an effective number of T cells as produced according to the present invention.

The present invention further relates to the use of any peptide as described, the nucleic acid according to the present invention, the expression vector according to the present invention, the cell according to the present invention, the activated T lymphocyte, the T cell receptor or the antibody or other peptide- and/or peptide-MHC-binding molecules according to the present invention as a medicament or in the manufacture of a medicament. Preferably, said medicament is active against cancer.

Preferably, said medicament is a cellular therapy, a vaccine or a protein based on a soluble TCR or antibody.

The present invention further relates to a use according to the present invention, wherein said cancer cells are glioblastoma, breast cancer, colorectal cancer, renal cell carcinoma, chronic lymphocytic leukemia, hepatocellular carcinoma, non-small cell and small cell lung cancer, Non-Hodgkin lymphoma, acute myeloid leukemia, ovarian cancer, pancreatic cancer, prostate cancer, esophageal cancer including cancer of the gastric-esophageal junction, gallbladder cancer and cholangiocarcinoma, melanoma, gastric cancer, testis cancer, urinary bladder cancer, head and neck squamous cell carcinoma, or uterine cancer.

The present invention further relates to biomarkers based on the peptides according to the present invention, herein called "targets", that can be used in the diagnosis of cancer, preferably of glioblastoma, breast cancer, colorectal cancer, renal cell carcinoma, chronic lymphocytic leukemia, hepatocellular carcinoma, non-small cell and small cell lung cancer, Non-Hodgkin lymphoma, acute myeloid leukemia, ovarian cancer, pancreatic cancer, prostate cancer, esophageal cancer including cancer of the gastric-esophageal junction, gallbladder cancer and cholangiocarcinoma, melanoma, gastric cancer, testis cancer, urinary bladder cancer, head and neck squamous cell carcinoma, or uterine cancer. The marker can be over-presentation of the peptide(s) themselves, or over-expression of the corresponding gene(s). The markers may also be used to predict the probability of success of a treatment, preferably an immunotherapy, and most preferred an immunotherapy targeting the same target that is identified by the biomarker. For example, an antibody or soluble TCR can be used to stain sections of the tumor to detect the presence of a peptide of interest in complex with MHC.

Optionally the antibody carries a further effector function such as an immune stimulating domain or toxin.

The present invention also relates to the use of these novel targets in the context of cancer treatment.

Both therapeutic and diagnostic uses against additional cancerous diseases are disclosed in the following description of the underlying expression products (polypeptides) of the peptides according to the invention.

A4GNT is frequently expressed in pancreatic cancer cells but not peripheral blood cells and quantitative analysis of A4GNT mRNA expressed in the mononuclear cell fraction of peripheral blood will contribute to the detection of pancreatic cancer (Ishizone et al., 2006). A4GNT mRNA was detectable in 80% of patients with an early stage of gastric cancer when the cancer cells were limited to the gastric mucosa, and the expression levels of A4GNT mRNA were increased in association with tumor progression (Shimizu et al., 2003).

The up-regulated expression of ABCC2 in primary fallopian tube carcinomas is associated with poor prognosis (Halon et al., 2013).

In human cancer ADAM10 is up-regulated, with levels generally correlating with parameters of tumor progression and poor outcome. In preclinical models, a selective inhibitor against ADAM10 has been shown to synergize with existing therapies in decreasing tumor growth (Duffy et al., 2009).

AHCYL2 was shown to be down-regulated in colon carcinoma and in a subset of lung carcinomas (Lleonart et al., 2006). mRNA expression of AHCYL2 was described as being potentially associated with the control of p53 function as well as the ras-MAPK pathway, methylation and transcriptional cellular programs, and AHCYL2 may thus be a regulatory suppressor gene involved in human colon and lung tumors (Lleonart et al., 2006).

AKR1C1 plays a role in cisplatin resistance in cervical, ovarian and lung cancer cells which includes mitochondrial membrane depolarization, ROS production and activation of the JNK pathway (Chen et al., 2015). Significantly higher intratumoral levels of AKR1C1 were found in responders to neoadjuvant chemotherapy compared with nonresponders (Hlavac et al., 2014).

Expression of AKR1C3 was shown to be positively correlated with an elevated Gleason score in prostate cancer, indicating that AKR1C3 can serve as a promising biomarker for the progression of prostate cancer (Tian et al., 2014). AKR1C3 was shown to catalyze the reduction of 4-androstene-3,17-dione to testosterone and estrone to 17β-estradiol, which promotes the proliferation of hormone dependent prostate and breast cancers, respectively (Byrns et al., 2011). AKR1C3 was shown to be up-regulated in breast cancer, prostate cancer and skin squamous cell carcinoma (Byrns et al., 2011; Mantel et al., 2014). AKR1C3 was shown to be a marker within a gene signature which is able to discriminate responder patients from non-responders upon chemo-radiotherapy treatment of patients with locally advanced rectal cancer (Agostini et al., 2015). AKR1C3 was shown to be associated with doxorubicin resistance in human breast cancer by activation of anti-apoptosis PTEN/Akt pathway via loss of the tumor suppressor PTEN (Zhong et al., 2015). AKR1C3 was shown to be associated with a higher risk of lung cancer among people from a Chinese county who were exposed to coal emissions (Li et al., 2015a). AKR1C3 was described as a potential therapeutic marker for choriocarcinoma which is also associated with the development of methotrexate resistance in this disease (Zhao et al., 2014a).

The expression of ALDH1L1 was shown to be down-regulated in HCC and gliomas. The down-regulation of ALDH1L1 in those cancers was associated with poorer prognosis and more aggressive phenotype (Chen et al., 2012; Rodriguez et al., 2008).

ALOX15 is present at high levels in prostate cancer (PCa), lung cancer, breast cancer, melanomas, and colonic adenocarcinomas when compared with normal tissues (Kelavkar et al., 2002). ALOX15 enzyme activity contributes to PCa initiation and progression (Kelavkar et al., 2007).

AR has been implicated in the development of various cancers such as prostate, castrate-resistant prostate, breast, glioblastoma multiforme, colon and gastric (Wang et al., 2009b; Yu et al., 2015b; Mehta et al., 2015; Wang et al., 2015a; Sukocheva et al., 2015). In addition to promoting prostate cancer proliferation, androgen signaling through AR leads to apoptosis via inducing the expression of p21 (WAF1/CIP1), a cyclin-dependent kinase inhibitor (Yeh et al., 2000).

Mutations in ARMC5 cause macronodular cortisol-producing neoplasias, bilateral macronodular hyperplasias, primary macronodular adrenal hyperplasia, and meningioma (Espiard and Bertherat, 2015; Kirschner and Stratakis, 2016; Elbelt et al., 2015).

Pharmacogenomic studies reveal correlations between ATAD5 and anticancer agents (Abaan et al., 2013). ATAD5 is significantly up-regulated in malignant peripheral nerve sheath tumors (Pasmant et al., 2011). Hepatitis B virus protein X significantly enhances the expression of ATAD5 in HBV-associated hepatocellular carcinoma (Ghosh et al., 2016). Loss of ATAD5 is embryonically lethal in mice, it acts as tumor suppressor in both mice and humans, and it interacts with components of the human Fanconi Anemia pathway. Furthermore, it may be responsible for some of the phenotypes associated with neurofibromatosis, a hereditary disease with high risk of tumor growth (Gazy et al., 2015; Jenne et al., 2001). Variants of the ATAD5 gene locus are associated with epithelial ovarian cancer risk (Kuchenbaecker et al., 2015). ATAD5 has a bearing on at least one mammalian phenotype of non-small cell lung cancer (Li et al., 2014).

The expression of ATP10B is de-regulated in highly invasive glioma cells and associated with the invasive behavior (Tatenhorst et al., 2004).

ATP8B4 may be a prognostic marker and therapeutic target in multiple myeloma patients and other entities (US Patent No. 20070237770 A1) (Ni et al., 2012).

ATR encodes ATR serine/threonine kinase, which belongs to the PI3/PI4-kinase family Copy number gain, amplification, or translocation of the ATR gene were observed in oral squamous cell carcinoma cell lines (Parikh et al., 2014). It has been demonstrated that truncating ATR mutations in endometrial cancers are associated with reduced disease-free and overall survival (Zighelboim et al., 2009).

B3GNT5 is over-expressed in acute myeloid leukemia, and mouse embryonal carcinoma and its expression is inversely correlated with promotor methylation in glioblastoma (Ogasawara et al., 2011; Etcheverry et al., 2010; Wang et al., 2012). Down-regulation of B3GNT5 through miRNA-203 may contribute to the malignancy of hypopharyngeal squamous cell carcinoma (Wang et al., 2015g). B3GNT5 is associated with breast cancer patient survival (Potapenko et al., 2015).

Bub1 expression is increased in subsets of lymphomas, breast, gastric and prostate cancers. Bub1 over-expression correlates with poor clinical prognosis (Ricke and van Deursen, 2011). Bub1 mutations can be found in colorectal carcinomas exhibiting chromosomal instability (Williams et al., 2007).

C4A has been described as a biomarker for polycystic ovary syndrome and endometrial cancer and experimental data suggest that C4 can mediate cancer growth (Galazis et al., 2013; Rutkowski et al., 2010).

In the acute myelomonocytic leukemia cell line JIH3 a chromosome deletion includes C7orf10 (Pan et al., 2012).

C8 is constitutively expressed by the human hepatoma cell line HepG2 and expression is strongly enhanced after stimulation with the cytokines IL-6, IFN-gamma and IL-1 beta (Scheurer et al., 1997).

Cancer-testis antigen specific primers can detect CASC5 in glioblastoma multiforme, one of the most malignant and aggressive tumors with very poor prognosis. CASC5 has specific binding motifs at the N-terminus (for Bub1 and BubR1) and at the C-terminus (for Zwint-1 and hMis14/hNsl1). Disruption of this connection may be able to lead to tumorigenesis (Kiyomitsu et al., 2011; Jiang et al., 2014c). CASC5 interacts with the tumor suppressor pRb (Bogdanov and Takimoto, 2008). CASC5 is highly expressed in proliferating somatic cells, tumors and healthy human testis (Bogdanov and Takimoto, 2008; Sasao et al., 2004). CASC5 is linked to cell growth suppression and maturation enhancement and its disruption thus may be a key factor for leukemogenesis (Hayette et al., 2000; Bogdanov and Takimoto, 2008; Chinwalla et al., 2003; Kuefer et al., 2003; Yang et al., 2014a).

CCR4 has been described as a prognostic marker in various tumors such as renal cell carcinoma, head and neck squamous cell carcinoma, gastric cancer, breast cancer, colon cancer and Hodgkin lymphoma (Ishida et al., 2006; Olkhanud et al., 2009; Yang et al., 2011; Tsujikawa et al., 2013; Al-haidari et al., 2013; Liu et al., 2014a). Studies have revealed that gastric cancer patients with CCR4-positive tumors had significantly poorer prognosis compared to those with CCR4-negative tumors (Lee et al., 2009a).

CCR8 expression is increased in monocytic and granulocytic myeloid cell subsets in peripheral blood of patients with urothelial and renal carcinomas. Up-regulated expression of CCR8 is also detected within human bladder and renal cancer tissues and primarily limited to tumor-associated macrophages. The CCL1/CCR8 axis is a component of cancer-related inflammation and may contribute to immune evasion (Eruslanov et al., 2013).

A single nucleotide polymorphism in CD101 was shown to be associated with pancreatic cancer risk, but results could not be replicated in a prostate cancer case-control and cohort population, thus, requiring future research in the possible role of CD101 in pancreatic cancer (Reid-Lombardo et al., 2011). CD101 was identified as one gene of a 6-gene signature that discriminated chronic phase from blast crisis chronic myeloid leukemia using a Bayesian model averaging approach (Oehler et al., 2009).

CD84 was described as a CD antigen which is differentially abundant in progressive chronic lymphocytic leukemia as compared to slow-progressive and stable chronic lymphocytic leukemia (Huang et al., 2014). CD84 expression was shown to be significantly elevated from the early stages of chronic lymphocytic leukemia (Binsky-Ehrenreich et al., 2014).

CENPE expression significantly correlated with glioma grade and might complement other parameters for predicting survival time for glioma patients (Bie et al., 2011). CENPE is up-regulated in chemo-resistant epithelial ovarian tumors compared to chemo-sensitive tumors (Ju et al., 2009). CENPE is up-regulated in invasive and aggressive-invasive prolactin pituitary tumors (Wierinckx et al., 2007).

CLDN14 was shown to be up-regulated in gastric cancer (Gao et al., 2013). CLDN14 expression was shown to be associated with lymphatic metastasis in gastric cancer (Gao et al., 2013). CLDN14 was described to play a role in the regulation of tumor blood vessel integrity and angiogenesis in mice (Baker et al., 2013).

CLDN3 is highly differentially expressed in many human tumors and may provide an efficient molecular tool to specifically identify and target biologically aggressive human cancer cells as CLDN3 is a high affinity receptor of *Clostridium perfringens* enterotoxin (Black et al., 2015). CLDN3 is frequently over-expressed in several neoplasias, including ovarian, breast, pancreatic, and prostate cancers (Morin, 2005). CLDN3 was identified as prostate cancer biomarker as it is highly expressed in prostate cancer (Amaro et al., 2014). Decreased expression of CLDN3 is associated with a poor prognosis and EMT in completely resected squamous cell lung carcinoma (Che et al., 2015). CLDN3 inhibits cancer aggressiveness via Wnt-EMT signaling and is a potential prognostic biomarker for hepatocellular carcinoma (Jiang et al., 2014b).

CLDN4 is highly differentially expressed in many human tumors and may provide an efficient molecular tool to specifically identify and target biologically aggressive human cancer cells as CLDN4 is a high affinity receptor of *Clostridium perfringens* enterotoxin (Black et al., 2015). CLDN4 is frequently over-expressed in several neoplasias including ovarian, breast, pancreatic, and prostate cancers (Morin, 2005). An antibody against the extracellular domain of CLDN4 provides pro-chemotherapeutic effects in bladder cancer (Kuwada et al., 2015). High expression of CLDN4 was associated with the more differentiated intestinal-type gastric carcinoma and lost in poorly differentiated diffuse type. Low expression of CLDN4 was related to lymphangiogenesis (Shareef et al., 2015).

CLDN6 expression was shown to be associated with lymph node metastasis and TNM stage in non-small cell lung cancer (Wang et al., 2015f). Furthermore, low expression of CLDN6 was shown to be associated with significantly lower survival rates in patients with non-small cell lung cancer (Wang et al., 2015f). Thus, low CLDN6 expression is an independent prognostic biomarker that indicates worse prognosis in patients with non-small cell lung cancer (Wang et al., 2015f). CLDN6 was shown to be down-regulated in cervical carcinoma and gastric cancer (Zhang et al., 2015; Lin et al., 2013). CLDN6 was shown to be up-regulated in BRCA1-related breast cancer and ovarian papillary serous carcinoma (Wang et al., 2013b; Heerma van Voss et al., 2014). CLDN6 was described as a tumor suppressor for breast cancer (Zhang et al., 2015). Gain of CLDN6 expression in the cervical carcinoma cell lines HeLa and C33A was shown to suppress cell proliferation, colony formation in vitro, and tumor growth in vivo, suggesting that CLDN6 may function as a tumor suppressor in cervical carcinoma cells (Zhang et al., 2015). CLDN6 may play a positive role in the invasion and metastasis of ovarian cancer (Wang et al., 2013b). CLDN6 was shown to be consistently expressed in germ cell tumors and thus is a novel diagnostic marker for primitive germ cell tumors (Ushiku et al., 2012). CLDN6 expression was shown to be positive in most tumors of an assessed set of atypical teratoid/rhabdoid tumors of the central nervous system, with strong CLDN6 positivity being a potential independent prognostic factor for outcome of the disease (Dufour et al., 2012).

CLDN9 was shown to be up-regulated in the metastatic Lewis lung carcinoma cell line p-3LL and in tumors derived from these cells and in pituitary oncocytomas (Sharma et al., 2016; Hong et al., 2014). Knock-down of CLDN9 expression in metastatic Lewis lung carcinoma p-3LL cells was shown to result in significantly reduced motility, invasiveness in vitro and metastasis in vivo, whereas transient over-expression in these cells was shown to enhance their motility (Sharma et al., 2016). Thus, CLDN9 may play an essential role in promoting lung cancer metastasis (Sharma et al., 2016). CLDN9 was shown to be down-regulated in cervical carcinoma tissues (Zhu et al., 2015a). CLDN9 expression was observed to be correlated with lymphatic metastasis of cervical carcinomas (Zhu et al., 2015a). CLDN9 was described as the most significantly altered and up-regulated gene in pituitary oncocytomas with higher expression levels in invasive compared to non-invasive oncocytomas (Hong et al., 2014). Thus, CLDN9 may be an important biomarker for invasive pituitary oncocytomas (Hong et al., 2014). Over-expression of CLDN9 in the gastric adenocarcinoma cell line AGS was shown to enhance invasive potential, cell migration and the proliferation rate and is thus sufficient to enhance tumorigenic properties of a gastric adenocarcinoma cell line (Zavala-Zendejas et al., 2011). Strong CLDN9 expression was shown to be associated with a higher mortality rate in diffuse-type gastric adenocarcinomas compared to the intestinal type and its detection was described as a useful prognostic marker in "intestinal-" and "diffuse-type" gastric adenocarcinomas (Rendon-Huerta et al., 2010).

CLEC5A mRNA expression was shown to be significantly lower in primary acute myeloid leukemia patients samples than in macrophages and granulocytes from healthy donors (Batliner et al., 2011). CLEC5A was described as a novel transcriptional target of the tumor suppressor PU.1 in monocytes/macrophages and granulocytes (Batliner et al., 2011).

DCP2 was identified as miR-224 target that was differentially expressed more than 2-fold in methotrexate resistant human colon cancer cells (Mencia et al., 2011).

DCSTAMP expression is increased in papillary thyroid cancer (Lee et al., 2009b; Kim et al., 2010b). Down-regulation of DCSTAMP leads to a decreased colony formation of MCF-7 cells probably because of decreased proliferation and cell cycle progression as well as increased apoptosis (Zeng et al., 2015). DCSTAMP is over-expressed in peripheral macrophages, and dendritic cells and myeloma plasma cells show high susceptibility to DCSTAMP and are able to transdifferentiate to osteoclasts. Malignant plasma cells expressing cancer stem cell phenotype and high metastasizing capability express osteoclast markers which activate the beta3 transcriptional pathway resulting in ERK1/2 phosphorylation and initiation of bone resorbing activity (Silvestris et al., 2011). Esculetin and parthenolide suppress c-Fos and nuclear factor of activated T cell cl signaling pathway resulting in suppressed DCSTAMP expression, a marker gene for osteoclast differentiation (Ihn et al., 2015; Baek et al., 2015; Cicek et al., 2011; Courtial et al., 2012; Kim et al., 2014a).

SNPs in DENND1B were significantly associated with pancreas cancer risk (Cotterchio et al., 2015).

DNAH17, also known as DNEL2, was described as a homologue to a tumor-antigen identified in melanoma patients (Ehlken et al., 2004). DNAH17 was described as one of several candidate genes mapped to a small chromosome interval associated with sporadic breast and ovarian tumorigenesis, and esophageal cancer in the autosomal dominant disorders hereditary neuralgic amyotrophy and tylosis (Kalikin et al., 1999).

DNAH2 is one of the genes mutated in >10% of patients with chronic myelomonocytic leukemia (Mason et al., 2015). Genes encoding microtubule-associated proteins, such as DNAH2, showed a 10% or higher incidence of genetic aberrations in CpG-island methylator phenotype-positive clear renal cell carcinomas (Arai et al., 2015).

Re-expression of methylation silenced tumor suppressor genes by inhibiting DNMT3B has emerged as an effective strategy against cancer (Singh et al., 2013).

FAM83B mRNA expression was significantly higher in squamous cell carcinoma than in normal lung or adenocarcinoma and FAM83B therefore is a novel biomarker for diagnosis and prognosis (Okabe et al., 2015). FAM83B was identified as an oncogene involved in activating CRAF/MAPK signaling and driving epithelial cell transformation. Elevated expression is associated with elevated tumor grade and decreased overall survival (Cipriano et al., 2014). Elevated FAM83B expression also activates the PI3K/AKT signaling pathway and confers a decreased sensitivity to PI3K, AKT, and mTOR inhibitors (Cipriano et al., 2013).

Down-regulation or dysfunction of FANCD2 due to genetic mutations has been reported in different cancer types including breast cancer, acute lymphatic leukemia and testicular seminomas and is associated with cancer development. Otherwise also re-expression and up-regulation of FANCD2 was shown to be associated with tumor progression and metastasis in gliomas and colorectal cancer (Patil et al., 2014; Shen et al., 2015a; Shen et al., 2015b; Ozawa et al., 2010; Rudland et al., 2010; Zhang et al., 2010a; Smetsers et al., 2012). PI3K/mTOR/Akt pathway promotes FANCD2 inducing the ATM/Chk2 checkpoint as DNA damage response and monoubiquitinilated FANCD2 activates the transcription of the tumor suppressor TAp63 (Shen et al., 2013; Park et al., 2013).

FOXJ1 expression is up-regulated, associated with tumor stage, histologic grade and size and correlated with prognosis in patients with clear cell renal cell carcinoma (Zhu et al., 2015b). Decreased FOXJ1 expression was significantly correlated with clinic stage, lymph node metastasis, and distant metastasis, and lower FOXJ1 expression independently predicted shorter survival time in gastric carcinoma (Wang et al., 2015c). Over-expression of FOXE can promote tumor cell proliferation and cell-cycle transition in hepatocellular carcinoma and is associated with histological grade and poor prognosis (Chen et al., 2013).

High GINS2 transcript level predicts poor prognosis and correlates with high histological grade and endocrine therapy resistance through mammary cancer stem cells in breast cancer patients (Zheng et al., 2014). GINS2 was reported to be present at a high level in lung adenocarcinoma and associated with TNM stages (Liu et al., 2013b). GINS2 express abundantly and abnormally in many malignant solid tumors, such as breast cancer, melanoma and hepatic carcinoma. Further, over-expression of GINS2 could promote proliferation of leukemic cell lines (Zhang et al., 2013a).

GPR98 expression is increased in primary neuroendocrine tumors relative to normal tissue (Sherman et al., 2013). GPR98 was among the genes associated with survival of glioblastoma multiforme (Sadeque et al., 2012). GPR98 displays a transcript regulated by glucocorticoids which are used for the treatment of acute lymphoblastic leukemia as they lead to the induction of apoptosis (Rainer et al., 2012).

GTPBP10 is highly correlated with copy number variation, gene expression, and patient outcome in glioblastoma (Kong et al., 2016).

GTSE1 expression represses apoptotic signaling and confers cisplatin resistance in gastric cancer cells (Subhash et al., 2015). GTSE1 is over-expressed in uterine leiomyosarcoma (ULMS) and participated in cell cycle regulation.

H2BFS was consistently expressed as a significant cluster associated with the low-risk acute lymphoblastic leukemia subgroups (Qiu et al., 2003).

HIST1H2BJ was shown to be down-regulated in brain tumors and was described as potentially useful for developing molecular markers of diagnostic or prognostic value (Luna et al., 2015).

Acetylation of HISTH4A might be a potential target to inactivate embryonic kidney cancer (Wilms tumor) (Yan-Fang et al., 2015).

HIST1H4C may act as risk distinguishing factor for the development of treatment-related myeloid leukemia (Bogni et al., 2006).

HIST1H4F was observed to be hyper-methylated in prostate cancer which might also correlate with the aging of the patient (Kitchen et al., 2016).

A high methylation rate of HIST1H4K was observed in high-grade non-muscle invasive bladder cancer as well as in prostate cancer and is therefore representing a potential biomarker (Payne et al., 2009; Kachakova et al., 2013).

It was shown that HIST1H4L is significantly up-regulated in ERG+ prostate carcinomas (Camoes et al., 2012). HIST1H4L encodes the replication-dependent histone cluster 1, $H_{41}$ that is a member of the histone H4 family (RefSeq, 2002).

HIST2H4B was identified as novel protein in key cellular pathogenic pathways in cells infected with a reovirus subtype that is presently in clinical trials as an anti-cancer oncolytic agent (Berard et al., 2015).

HIST4H4 was one of the genes which showed continuous down-regulation in gastric cancer cells after treatment with immune-conjugates composed of an alpha-emitter and the monoclonal antibody d9MAb that specifically target cells expressing mutant d9-E-cadherin (Seidl et al., 2010). Hyper-methylation of other members of the histon H4 family was significantly associated with shorter relapse-free survival in stage I non-small cell lung cancer (Sandoval et al., 2013).

HIVEP1 was identified as cellular gene disrupted by human T-lymphotropic virus type 1 integration in lymphoma cell lines (Cao et al., 2015). HIVEP1 was associated with the unfavorable 11q deletion and also with the unfavorable Binet stages B and C in chronic lymphocytic leukemia (Aalto et al., 2001).

HNRNPH2 is up-regulated in different cancer types including pancreatic, liver and gastric cancer (Honore et al., 2004; Zeng et al., 2007). HNRNPH2 is involved in splicing of the beta-deletion transcript of hTERT, which is highly expressed in cancer cells and competes and thereby inhibits endogenous telomerase activity (Listerman et al., 2013).

HOXD11 is dysregulated in head and neck squamous cell carcinoma showing strikingly high levels in cell lines and patient tumor samples. Knockdown of HOXD11 reduced invasion (Sharpe et al., 2014). HOXD11 is significantly up-regulated in oral squamous cell carcinoma (Rodini et al., 2012). HOXD11 is aberrantly methylated in human breast cancers (Miyamoto et al., 2005). The HOXD11 gene is fused to the NUP98 gene in acute myeloid leukemia with t(2;11)(q31;p15) (Taketani et al., 2002).

ICOS acts as a ligand of programmed death-1 (PD-1) on T cells, induces the immune escape of cancer cells and also acts as a receptor mediating anti-apoptotic effects on cancer cells (Yang et al., 2015c). Murine tumor models have provided significant support for the targeting of multiple immune checkpoints involving ICOS during tumor growth (Leung and Suh, 2014). ICOS+ cell infiltration correlates with adverse patient prognosis, identifying ICOS as a new target for cancer immunotherapy (Faget et al., 2013). ICOS can enhance the cytotoxic effect of cytokine-induced killer cells against cholangiocarcinoma both in vitro and in vivo (He et al., 2011).

Intratumoral expression of IFNG was shown to be associated with expression of MHC Class II molecules and a more aggressive phenotype in human melanomas (Brocker et al., 1988). Autocrine IFNG signaling was shown to enhance experimental metastatic ability of IFNG gene-transfected mammary adenocarcinoma cells, and was attributed to increased resistance to NK cells (Lollini et al., 1993).

Triple-negative breast cancer has high tumor expression of IGFBP3 associated with markers of poor prognosis (Marzec et al., 2015). A novel cell death receptor that binds specifically to IGFBP3 was identified and might be used in breast cancer treatment (Mohanraj and Oh, 2011). IGFBP3 exhibits pro-survival and growth-promoting properties in vitro (Johnson and Firth, 2014). IGFBP3 is an independent marker of recurrence of the urothelial cell carcinomas (Phe et al., 2009).

IGFBPL1 is a regulator of insulin-growth factors and is down-regulated in breast cancer cell lines by aberrant hypermethylation. Methylation in IGFBPL1 was clearly associated with worse overall survival and disease-free survival (Smith et al., 2007).

IGFLR1 is mutated in colorectal cancer (Donnard et al., 2014). IGFLR1 has structural similarity with the tumor necrosis factor receptor family (Lobito et al., 2011).

IL4I1 protein expression is very frequent in tumors. IL4I1 was detected in tumor-associated macrophages of different tumor entities, in neoplastic cells from lymphomas and in rare cases of solid cancers mainly mesothelioma (Carbonnelle-Puscian et al., 2009). IL4I1 up-regulation in human Th17 cells limits their T-cell receptor (TCR)-mediated expansion by blocking the molecular pathway involved in the activation of the IL-2 promoter and by maintaining high levels of Tob1, which impairs entry into the cell cycle (Santarlasci et al., 2014).

IQGAP3 is over-expressed in lung cancer and is associated with tumor cell growth, migration and invasion. Furthermore, it is up-regulated by chromosomal amplification in hepatocellular carcinoma and the expression of IQGAP3 is increased in p53-mutated colorectal cancer patients with poor survival (Katkoori et al., 2012; Yang et al., 2014b; Skawran et al., 2008). IQGAP3 is modulating the EGFR/Ras/ERK signaling cascade and interacts with Rac/Cdc42 (Yang et al., 2014b; Kunimoto et al., 2009).

Elevated levels of ITGA2 were found in the highly invasive and metastatic melanoma cell lines compared with normal cultured melanocytes and non-metastatic melanoma cell lines (van Muijen et al., 1995). The adhesion molecule ITGA2 was up-regulated by IFN-gamma, TNF-alpha, and IL-1-beta in melanoma cells (Garbe and Krasagakis, 1993). Transfection of ITGA2 into human rhabdomyosarcoma cells which do not express ITGA2, potentiated the frequency of metastases in various organs (Matsuura et al., 1995).

KCNU1 is located on chromosome 8p in an area that is frequently involved in complex chromosomal rearrangements in breast cancer (Gelsi-Boyer et al., 2005). KCNU1 is one of the top 25 over-expressed extracellular membrane proteins in hepatoblastomas of pediatric cancer samples (Orentas et al., 2012).

KIAA0226L is thought to be a tumor suppressor gene and is hyper-methylated in cervical cancer. Re-activation of KIAA0226L leads to decreased cell growth, viability, and colony formation (Huisman et al., 2015; Eijsink et al., 2012; Huisman et al., 2013). The methylation pattern of KIAA0226L can be used to differ between precursor lesions and normal cervix cancer (Milutin et al., 2015). The methylation pattern of KIAA0226L cannot be used as specific biomarker for cervical cancer (Sohrabi et al., 2014). Re-activation of KIAA0226L partially de-methylates its pro-motor region and also decreases repressive histone methylations (Huisman et al., 2013).

KIAA1244 over-expression is one of the important mechanisms causing the activation of the estrogen/ERalpha signaling pathway in the hormone-related growth of breast cancer cells (Kim et al., 2009). Inhibiting the interaction between KIAA1244 and PHB2 may be a new therapeutic strategy for the treatment of luminal-type breast cancer (Yoshimaru et al., 2013).

KIAA1524 encodes Cancerous Inhibitor of Protein Phosphatase 2A (CIP2A). A critical role of CIP2A has been shown among other for NSCLC, HCC, HNSCC, bladder, pancreatic, cervical, breast, prostate, ovarian and colorectal cancers (Ventela et al., 2015; Ma et al., 2014; Guo et al., 2015b; Rincon et al., 2015; Guo et al., 2015c; Wu et al., 2015; Peng et al., 2015; Lei et al., 2014; Liu et al., 2014c; Farrell et al., 2014; Fang et al., 2012; He et al., 2012; Bockelman et al., 2012).

KIF18A was shown to be over-expressed in hepatocellular cancer, which correlated with significantly shorter disease free and overall survival. Thus, KIF18A might be a biomarker for hepatocellular cancer diagnosis and an independent predictor of disease free and overall survival after surgical resection (Liao et al., 2014). KIF18A expression is up-regulated in specific subtypes of synovial sarcoma (Przybyl et al., 2014). Estrogen strongly induces KIF18A expression in breast cancer, which is associated with increased proliferation and reduced apoptosis (Zou et al., 2014).

Over-expression of KIF20A was detected in pancreatic ductal adenocarcinoma, melanoma, bladder cancer, non-small cell lung cancer and cholangiocellular carcinoma (Imai et al., 2011; Yamashita et al., 2012; Stangel et al., 2015). Recently, it was reported that patients with pancreatic ductal adenocarcinoma vaccinated with a KIF20A-derived peptide exhibited better prognosis compared to the control group (Asahara et al., 2013). In addition, silencing of KIF20A resulted in an inhibition of proliferation, motility, and invasion of pancreatic cancer cell lines (Stangel et al., 2015).

High expression of KIF26B in breast cancer associates with poor prognosis (Wang et al., 2013c). KIF26B up-regulation was significantly correlated with tumor size analysing CRC tumor tissues and paired adjacent normal mucosa. KIF26B plays an important role in colorectal carcinogenesis and functions as a novel prognostic indicator and a potential therapeutic target for CRC (Wang et al., 2015d).

KIF2C was shown to be involved in directional migration and invasion of tumor cells (Ritter et al., 2015). Over-expression of KIF2C was shown to be associated with lymphatic invasion and lymph node metastasis in gastric and colorectal cancer patients (Ritter et al., 2015). KIF2C was shown to be up-regulated in oral tongue cancer (Wang et al., 2014a). High expression of KIF2C was shown to be associated with lymph node metastasis and tumor staging in squamous cell carcinoma of the oral tongue (Wang et al., 2014a). Silencing of KIF2C was shown to result in suppressed proliferation and migration of the human oral squamous cell carcinoma cell line Tca8113 (Wang et al., 2014a). Mutation of KIF2C was described as being associated with colorectal cancer (Kumar et al., 2013).

KIFC1 was shown to be essential for proper spindle assembly, stable pole-focusing and survival of cancer cells independently from number of formed centrosomes (normal or supernumerary centrisomes). KIFC1 expression was shown to be up-regulated in breast cancer, particularly in estrogen receptor negative, progesterone receptor negative and triple negative breast cancer, and 8 human breast cancer cell lines. In estrogen receptor-positive breast cancer cells, KIFC1 was one of 19 other kinesins whose expression was strongly induced by estrogen. In breast cancer, the overexpression of KIFC1 and its nuclear accumulation was shown to correlate with histological grade and predict poor progression-free and overall survival. In breast cancer cell lines, the overexpression of KIFC1 was shown to mediate the resistance to docetaxel. The KIFC1 silencing negatively affected the breast cancer cell viability (Zou et al., 2014; Pannu et al., 2015; De et al., 2009; Li et al., 2015b). KIFC1 was shown to be overexpressed in ovarian cancer which was associated with tumor aggressiveness, advanced tumor grade and stage. KIFC1 was identified as one of three genes, whose higher expression in primary NSCLC tumors indicated the higher risk for development of brain metastasis (Grinberg-Rashi et al., 2009).

KL was described as a tumor suppressor which suppresses the epithelial to mesenchymal transition in cervical cancer and which functions as a tumor suppressor in several types of human cancers by inhibiting insulin/IGF1, p53/p21, and Wnt signaling (Xie et al., 2013; Qureshi et al., 2015). KL was described as an aberrantly expressed gene in a number of cancers, including breast cancer, lung cancer and hepatocellular carcinoma (Zhou and Wang, 2015). KL was described to be down-regulated in pancreatic cancer, hepatocellular carcinoma, and other tumors (Zhou and Wang, 2015). KL was described as a novel biomarker for cancer whose down-regulation was described to result in promoted proliferation and reduced apoptosis of cancer cells. In this context Wnt/B-catenin signaling is one of several relevant signaling pathways (Zhou and Wang, 2015). A KL gene polymorphism was shown to be associated with increased risk of colorectal cancer (Liu et al., 2015).

KLHDC7B is associated with cervical squamous cell carcinoma and is a potential biomarker for cervical squamous cell carcinoma (Guo et al., 2015a).

KLHL genes are responsible for several Mendelian diseases and have been associated with cancer (Dhanoa et al., 2013).

Focal expression of KRT31 was observed in invasive onychocytic carcinoma originating from nail matrix keratinocytes (Wang et al., 2015e). Pilomatricomas are tumors that emulate the differentiation of matrix cells of the hair follicle, showing cortical differentiation, with sequential over-expression of KRT35 and KRT31 keratins (Battistella et al., 2014).

KRT35 was one of the most frequently and most strongly expressed hair keratins in pilomatrixomas. Pilomatricomas are tumors that emulate the differentiation of matrix cells of the hair follicle, showing cortical differentiation, with sequential over-expression of KRT35 and KRT31 keratins (Battistella et al., 2014).

Knockdown of LCTL allowed hTERT to immortalize human colonic epithelial cells (Kim et al., 2011).

Researchers have observed that inhibition of LRBA expression by RNA interference, or by a dominant-negative mutant, resulted in the growth inhibition of cancer cells. These findings imply that deregulated expression of LRBA contributes to the altered growth properties of a cancer cell (Wang et al., 2004).

LRRC8E is over-expressed in osteosarcoma and neuroblastoma tissues in comparison to normal samples (Orentas et al., 2012).

LTA polymorphisms contributed to the increased risk of cancers (Huang et al., 2013a). Bone resorbing factors like LTA are produced by certain solid and hematologic cancers and have also been implicated in tumour-induced hypercalcemia (Goni and Tolis, 1993). There is a link between the LTA to LTbetaR signaling axis and cancer (Drutskaya et al., 2010). B-cell-derived lymphotoxin promotes castration-resistant prostate cancer (Ammirante et al., 2010).

MACC1 is over-expressed in many cancer entities including gastric, colorectal, lung and breast cancer and is associated with cancer progression, metastasis and poor survival of patients (Huang et al., 2013b; Ma et al., 2013a; Stein, 2013; Wang et al., 2015b; Wang et al., 2015h; Ilm et al., 2015). MACC1 promotes carcinogenesis through targeting beta-catenin and PI3K/AKT signaling pathways, which leads to an increase of c-Met and beta-catenin and their downstream target genes including c-Myc, cyclin D1, caspase9, BAD and MMP9 (Zhen et al., 2014; Yao et al., 2015).

MAGEA10 encodes MAGE family member A10, implicated in some hereditary disorders, such as dyskeratosis congenital (RefSeq, 2002). By a vaccine directed against MAGEA10 and two other cancer-testis antigens, all of which are known to be targets of cytotoxic-T-lymphocyte responses, more than two-thirds of breast cancers would be covered (Taylor et al., 2007). MAGEA10 was expressed in 36.7% of the tumor tissues from hepatocellular carcinoma patients; however, it was not expressed in the para-cancer tissues (Chen et al., 2003). MAGEA10 was expressed in 14% of 79 lung cancer tissues (Kim et al., 2012).

MAGEB6 was identified as new MAGE gene not expressed in normal tissues, except for testis, and expressed in tumors of different histological origins (Lucas et al., 2000). MAGEB6 was found frequently expressed in head and neck squamous cell carcinoma and mRNA positivity presented significant associations with recognized clinical features for poor outcome (Zamuner et al., 2015).

MCC interacts with beta-catenin and re-expression of MCC in colorectal cancer cells specifically inhibits Wnt signaling (Fukuyama et al., 2008). The MCC gene is in close linkage with the adenomatous polyposis coli gene on chromosome 5, in a region of frequent loss of heterozygosity (LOH) in colorectal cancer (Kohonen-Corish et al., 2007). LOH of MCC gene could be found in both early and advanced stages of gastric, lung, esophageal and breast cancers (Wang et al., 1999a; Medeiros et al., 1994).

MET was shown to be up-regulated in dedifferentiated liposarcoma and is associated with melanocytic tumors, hepatocellular carcinoma, non-small cell lung cancer, hereditary papillary kidney cancers and gastric adenocarcinomas (Petrini, 2015; Finocchiaro et al., 2015; Steinway et al., 2015; Bill et al., 2015; Yeh et al., 2015).

The expression of MMP10 in oral squamous cell carcinoma was intensive and in verrucous carcinoma was moderate (Kadeh et al., 2015). MMP10 contributes to hepatocarcinogenesis in a novel crosstalk with the stromal derived factor 1/C-X-C chemokine receptor 4 axis (Garcia-Irigoyen et al., 2015). *Helicobacter pylori* infection promotes the invasion and metastasis of gastric cancer through increasing the expression of MMP10 (Jiang et al., 2014a). MMP10 promotes tumor progression through regulation of angiogenic and apoptotic pathways in cervical tumors (Zhang et al., 2014).

The elevated level of preoperative MMP13 was found to associate with tumor progression and poor survival in patients with esophageal squamous cell carcinoma (Jiao et al., 2014). PAI-1, a target gene of miR-143, regulates invasion and lung metastasis via enhancement of MMP13 expression and secretion in human osteosarcoma cells, suggesting that these molecules could be potential therapeutic target genes for preventing lung metastasis in osteosarcoma patients (Hirahata et al., 2016). MMP13 is already upregulated in Oral lichen planus (OLP) which has been classified as a pre-malignant condition for oral squamous cell carcinoma (OSCC) (Agha-Hosseini and Mirzaii-Dizgah, 2015). MMP13 plays a potentially unique physiological role in the regeneration of osteoblast-like cells (Ozeki et al., 2016).

MUC5AC is de-regulated in a variety of cancer types including colorectal, gastric, lung and pancreatic cancer. Depletion or low expression in colorectal and gastric tumors is associated with a more aggressive behavior and poor prognosis. Over-expression in lung cancer results in an increased likelihood of recurrence and metastases (Yonezawa et al., 1999; Kocer et al., 2002; Kim et al., 2014b; Yu et al., 1996).

MUC5B is over-expressed in different cancer entities including colorectal, lung and breast cancer and is associated with tumor progression (Sonora et al., 2006; Valque et al., 2012; Walsh et al., 2013; Nagashio et al., 2015). MUC5B can be repressed under the influence of methylation and can be up-regulated by ATF-1, c-Myc, NFkappaB, Sp1, CREB, TTF-11 and GCR (Perrais et al., 2001; Van, I et al., 2000).

Genetic variants of MUC6 have been reported to modify the risk of developing gastric cancer (Resende et al., 2011). In salivary gland tumors the expression patterns of MUC6 appear to be very closely correlated with the histopathological tumor type indicating their potential use to improve diagnostic accuracy (Mahomed, 2011). Studies have identified a differential expression of MUC6 in breast cancer tissues when compared with the non-neoplastic breast tissues (Mukhopadhyay et al., 2011).

A Chinese study identified MXRA5 as the second most frequently mutated gene in non-small cell lung cancer (Xiong et al., 2012). In colon cancer, MXRA5 was shown to be over-expressed and might serve as a biomarker for early diagnosis and omental metastasis (Zou et al., 2002; Wang et al., 2013a).

MYB can be converted into an oncogenic transforming protein through a few mutations (Zhou and Ness, 2011). MYB is known as oncogene and is associated with apoptosis, cell cycle control, cell growth/angiogenesis and cell adhesion by regulating expression of key target genes such as cyclooxygenase-2, Bcl-2, BclX(L) and c-Myc (Ramsay et al., 2003; Stenman et al., 2010). The oncogenic fusion protein MYB-NFIB and MYB over-expression are found in adenoid cystic carcinoma of the salivary gland and breast, pediatric diffuse gliomas, acute myeloid leukemia and pancreatic cancer (Wallrapp et al., 1999; Pattabiraman and Gonda, 2013; Nobusawa et al., 2014; Chae et al., 2015; Marchio et al., 2010). By the synergy between MYB and beta-Catenin during Wnt signaling, MYB is associated with colon tumorigenesis (Burgess et al., 2011). Since MYB is a direct target of estrogen signaling anti-MYB therapy is considered for ER-positive breast tumors (Gonda et al., 2008).

N4BP2 has a potential role in the development of nasopharyngeal carcinoma. There is a statistically relevant difference in two different haplotype blocks which correlate with the risk of sporadic nasopharyngeal carcinoma. Furthermore, N4BP2 is over-expressed in these tumor tissues relative to paired normal tissues (Zheng et al., 2007).

In a multistage, case-only genome-wide association study of 12,518 prostate cancer cases, NAALADL2 was identified as a locus associated with Gleason score, a pathological measure of disease aggressiveness (Berndt et al., 2015). NAALADL2 is over-expressed in prostate and colon cancer and promotes a pro-migratory and pro-metastatic phenotype associated with poor survival (Whitaker et al., 2014).

NCAPG is down-regulated in patients with multiple myeloma, acute myeloid leukemia, and leukemic cells from blood or myeloma cells (Cohen et al., 2014). NCAPG may be a multi-drug resistant gene in colorectal cancer (Li et al., 2012a). NCAPG is highly up-regulated in the chromophobe subtype of human cell carcinoma but not in conventional human renal cell carcinoma (Kim et al., 2010a). Up-regulation of NCAPG is associated with melanoma progression (Ryu et al., 2007). NCAPG is associated with uveal melanoma (Van Ginkel et al., 1998). NCAPG shows variable expression in different tumor cells (Jager et al., 2000).

NRK encodes Nik related kinase, a protein kinase required for JNK activation which may be involved in the induction of actin polymerization in late embryogenesis (RefSeq, 2002). NRK activates the c-Jun N-terminal kinase signaling pathway and may be involved in the regulation of actin cytoskeletal organization in skeletal muscle cells through cofilin phosphorylation (Nakano et al., 2003).

NUP210 was shown to be a candidate gene carrying polymorphisms associated with the risk of colorectal cancer (Landi et al., 2012). NUP210 was shown to be up-regulated in cervical cancer and suggested to play a role in the early phase of tumorigenesis (Rajkumar et al., 2011).

ORC1 was shown to be over-expressed in tumor-derived cell lines and is predicted to be a biomarker in prostate cancer as well as in leukemia (Struyf et al., 2003; Zimmerman et al., 2013; Young et al., 2014). Through its interaction with histone acetyltranferases such as HBO1, ORC1 exerts oncogenic functions in breast cancer (Wang et al., 2010).

Non-carrier of heterozygous mutations in two SNPs in OSCP1 might be a biomarker for susceptibility for non-viral liver carcinoma (Toda et al., 2014).

OVOL2 induces mesenchymal-epithelial transition resulting in decreased metastasis (Roca et al., 2013). OVOL2 inhibits c-Myc and Notch1 (Wells et al., 2009). OVOL2 is hyper-methylated in colorectal cancer resulting in its inability to inhibit Wnt signaling (Ye et al., 2016). Over-expression of OVOL2 decreased cell migration and invasion, reduced markers for epithelial-mesenchymal transition, and suppressed metastasis (Ye et al., 2016). OVOL2 is down-regulated in colorectal cancer and is inversely correlated with tumor stage (Ye et al., 2016). OVOL2 is regulated by Wnt signaling pathway (Ye et al., 2016).

OXTR is significantly over-expressed in primary small bowel and pancreatic neuroendocrine tumors, small cell carcinoma of the lung, ovarian carcinoma as well as in prostate cancer, mediating cell migration and metastasis (Morita et al., 2004; Zhong et al., 2010; Carr et al., 2012; Carr et al., 2013; Pequeux et al., 2002). However, OXTR1 possesses also an inhibitory effect on proliferation of neoplastic cells of either epithelial, nervous or bone origin, which is thought to be dependent on the receptor localization on the membrane (Casson et al., 2004).

PAPPA represents a metastasis-related gene occurring in a range of cancer types such as NSCLC and hepatocellular carcinoma, where it is positively associated to growth (VEGF and IGF-I) and transcription factors (NF-kappaB p50, NF-kappaB p65, HIF-1alpha) (Salim et al., 2013; Iunusova et al., 2013; Engelmann et al., 2015). PAPPA regulates mitotic progression through modulating the IGF-1 signaling pathway in breast cancer and ovarian cancer cells, where it is predominantly found at the primary site (Boldt and Conover, 2011; Loddo et al., 2014; Becker et al., 2015; Iunusova et al., 2014).

PGAP1 is down-regulated in the adenocarcinoma cell line AsPC-1 (Yang et al., 2016).

PGR is highly associated with breast cancer initiation and progression, where it activates MAPK and PI3K/AKT pathways as well as the expression of Growth Factors Receptors (GFR) (Jaiswal et al., 2014; Piasecka et al., 2015). PGR (besides HER and estrogen receptor) acts as a classification factor helping to distinguish between three different subtypes of breast cancer (Safarpour and Tavassoli, 2015).

PLA2G7 has strong influence on lipid metabolism in breast, ovarian, melanoma and prostate cancer cells, where a blockage of the enzyme leads to impaired cancer pathogenicity (Vainio et al., 2011a; Massoner et al., 2013; Kohnz et al., 2015). PLA2G7 is highly associated with prostate cancer and is therefore representing a potential biomarker for this type of cancer (Vainio et al., 2011b).

PPP3R1 is up-regulated in hepatocellular carcinoma cells affecting up to 10 different signaling pathways (Zekri et al., 2008).

PRKDC is a frequently mutated gene in endometriosis-associated ovarian cancer and breast cancer (Er et al., 2016; Wheler et al., 2015). PRKDC is up-regulated in cancerous tissues compared with normal tissues in colorectal carcinoma. Patients with high PRKDC expression show poorer overall survival (Sun et al., 2016).

An up-regulated expression of PSMA7T was found in metastatic lung cancer, castration-recurrent prostate cancer (CRPC) as well as in primary colorectal cancer, where it increases the risk of liver metastasis (Hu et al., 2008; Hu et al., 2009; Romanuik et al., 2010; Cai et al., 2010). It was also shown that the amount of PSMA7T correlates with the transactivation of the androgen receptor (AR) in androgen/AR-mediated prostate tumor growth (Ogiso et al., 2002).

It was shown that PSMC1 is able to influence cell growth and is therefore representing a potential anti-cancer target in prostate cancer, multiple myeloma and glioblastoma cells (Dahlman et al., 2012; Kim et al., 2008).

RAD18 is implicated in tumorigenesis due to its well-known function in DNA damage bypass, post-replication repair and homologous recombination (Ting et al., 2010). RAD18 Arg302Gln polymorphism is associated with the risk for colorectal cancer and non-small-cell lung cancer (Kanzaki et al., 2008; Kanzaki et al., 2007). RAD18 mediates resistance to ionizing radiation in human glioma cells and knockdown of RAD18 disrupts homologous recombination-mediated repair, resulting in increased accumulation of double strand breaks (Xie et al., 2014). Using melanoma tissue microarray, it was shown that nuclear RAD18 expression was up-regulated in primary and metastatic melanoma compared to dysplastic nevi (Wong et al., 2012).

RAD51AP1 was shown to be associated with radiation exposure papillary thyroid cancer (Handkiewicz-Junak et al., 2016) Amplification of RAD51AP1 was shown to be correlated with cell immortality and a shorter survival time in ovarian cancer (Sankaranarayanan et al., 2015). RAD51AP1 was described as commonly over-expressed in tumor cells and tissues and disruption of RAD51AP1 function was suggested to be a promising approach in targeted tumor therapy (Parplys et al., 2014). RAD51AP1 transcription was shown to be directly stimulated by the tumor suppressor MEN1 (Fang et al., 2013). RAD51AP1 was shown to be up-regulated in intrahepatic cholangiocarcinoma, human papillomavirus-positive squamous cell carcinoma of the head and neck and in BRCA1-deficient compared to sporadic breast tumors (Martinez et al., 2007; Martin et al., 2007; Obama et al., 2008). Suppression of RAD51AP1 was shown to result in growth suppression in intrahepatic cholangiocarcinoma cells, suggesting its involvement in the development and/or progression of intrahepatic cholangiocarcinoma (Obama et al., 2008).

Knock-down of RBM14 was shown to block glioblastoma multiforme re-growth after irradiation in vivo (Yuan et al., 2014). RBM14 was shown to be down-regulated in renal cell carcinoma (Kang et al., 2008). RBM14 was described as a potential tumor suppressor in renal carcinoma which inhibits G(1)-S transition in human kidney cells and suppresses anchorage-independent growth and xenograft tumor formation in part by down-regulation of the proto-oncogene c-myc (Kang et al., 2008). RBM14 was shown to be involved in the migration-enhancing action of PEAS and MCF7 human cancer cells (Verreman et al., 2011). The RBM14 gene was shown to be amplified in a subset of primary human cancers including non-small cell lung carcinoma, squamous cell skin carcinoma and lymphoma (Sui et al., 2007).

RBM4 is involved in regulatory splicing mechanisms of pre-messenger RNA suppressing proliferation and migration of various cancer cells (Lin et al., 2014; Wang et al., 2014c). Dysregulations of BBM4 activity were found in cervical, breast, lung, colon, ovarian and rectal cancers (Liang et al., 2015; Markus et al., 2016).

Serum RCOR3 levels in liver cancer patients were significantly lower than those in the patients with moderate chronic hepatitis B and with mild chronic hepatitis B (Xue et al., 2011).

Down-regulation of RFWD2 is correlated with poor prognosis in gastric cancer (Sawada et al., 2013). RFWD2 directly interacts with p27 and the de-regulation of this interaction is involved in tumorigenesis (Choi et al., 2015b; Choi et al., 2015a; Marine, 2012). Up-regulation of RFWD2 is correlated with poor prognosis in bladder cancer, gastric cancer, and triple-negative breast cancer (Ouyang et al., 2015; Li et al., 2016; Li et al., 2012c).

RIF1 is highly expressed in human breast tumors, encodes an anti-apoptotic factor required for DNA repair and is a potential target for cancer treatment (Wang et al., 2009a). The role of RIF1 in the maintenance of genomic integrity has been expanded to include the regulation of chromatin structure, replication timing and intra-S phase checkpoint (Kumar and Cheok, 2014).

In patients diagnosed with visceral multicentric infantile myofibromatosis novel homozygous variants in the RLTPR gene were identified (Linhares et al., 2014).

RNF24 was shown to be up-regulated in esophageal adenocarcinoma and plays a critical role in the progression of Barrett's esophagus to esophageal adenocarcinoma (Wang et al., 2014b). RNF24 was shown to be differentially expressed depending on certain risk factors in oral squamous cell carcinoma (Cheong et al., 2009).

RPGRIP1L suppresses anchorage-independent growth partly through the mitotic checkpoint protein Mad2 and is a candidate tumor suppressor gene in human hepatocellular carcinoma (Lin et al., 2009).

Over-expression of Rtl1 in the livers of adult mice resulted in highly penetrant tumor formation and over-expression of RTL1 was detected in 30% of analyzed human hepatocellular carcinoma samples (Riordan et al., 2013). Transcriptional activity of the imprinted gene RTL1 was assessed in a panel of 32 Wilms tumors and a massive over-expression was detected compared to normal renal tissue (Hubertus et al., 2011).

SAPCD2 (also called p42.3 or C9orf140) encodes a protein initially found to be expressed in gastric cancer, but not in normal gastric mucosa (Xu et al., 2007). SAPCD2 is over-expressed in different cancer entities including colorectal, gastric, hepatocellular and brain cancer and high SAPCD2 levels are associated with tumor progression (Sun et al., 2013; Weng et al., 2014; Wan et al., 2014). The optimal pathway of SAPCD2 gene in protein regulatory network in gastric cancer is Ras protein, Raf-1 protein, MEK, MAPK kinase, MAPK, tubulin, spindle protein, centromere protein and tumor (Zhang et al., 2012a; Weng et al., 2014).

Lower expression of SEMA3A was shown to be correlated with shorter overall survival and had independent prognostic importance in patients with head and neck squamous cell carcinoma (Wang et al., 2016). Over-expression of SEMA3A was shown to suppress migration, invasion and epithelial-to-mesenchymal transition due in part to the inhibition of NF-kB and SNAI2 in head and neck squamous cell carcinoma cell lines (Wang et al., 2016). Thus, SEMA3A serves as a tumor suppressor in head and neck squamous cell carcinoma and may be a new target for the treatment of this disease (Wang et al., 2016). SEMA3A expression was shown to be significantly reverse associated with metastasis in hepatocellular carcinoma (Yan-Chun et al., 2015). SEMA3A was described as being down-regulated in numerous types of cancer, including prostate cancer, breast cancer, glioma, epithelial ovarian carcinoma and gastric cancer (Jiang et al., 2015a; Tang et al., 2014). Low SEMA3A expression was shown to be correlated with poor differentiation, vascular invasion, depth of invasion, lymph node metastasis, distant metastasis, advanced TNM stage and poor prognosis in gastric cancer (Tang et al., 2014). SEMA3A was described as a candidate tumor suppressor and potential prognostic biomarker in gastric carcinogenesis (Tang et al., 2014).

It was shown that missense variations in the SERPINB10 gene possess tumorigenic features leading to an increased risk of prostate cancer (Shioji et al., 2005). In addition, SERPINB10 expression is significantly up-regulated in metastatic mammary tumors (Klopfleisch et al., 2010).

Expression level of SLC16A14 is significantly associated with progression-free survival and presents a novel putative marker for the progression of epithelial ovarian cancer (Elsnerova et al., 2016).

SLC18A1 was showing lower expression in unfavorable neuroblastoma tumor types as compared to favorable ones (Wilzen et al., 2009).

SLC25A43 was identified as a regulator of cell cycle progression and proliferation through a putative mitochondrial checkpoint in breast cancer cell lines (Gabrielson et al., 2016). SLC25A43 affects drug efficacy and cell cycle regulation following drug exposure in breast cancer cell lines (Gabrielson and Tina, 2013).

SLC28A3 was shown to be down-regulated in pancreatic ductal adenocarcinoma (Mohelnikova-Duchonova et al., 2013). SLC28A3 is associated with clinical outcome in metastatic breast cancer treated with paclitaxel and gemcitabine chemotherapy, overall survival in gemcitabine treated non-small cell lung cancer and overall survival in gemcitabine-based chemoradiation treated pancreatic adenocarcinoma (Li et al., 2012b; Lee et al., 2014b; Marechal et al., 2009). SLC28A3 is associated with fludarabine resistance in chronic lymphocytic leukemia and drug resistance in T-cell leukemia (Karim et al., 2011; Fernandez-Calotti et al., 2012).

SLC2A13 was consistently increased in the sphere-forming cells in the primary cultures of oral squamous cell carcinoma samples and confocal microscopy revealed that SLC2A13-expressing cells were embedded in the limited areas of tumor tissue as a cluster suggesting that SLC2A13 can be a potential marker for cancer stem cells (Lee et al., 2011). SLC2A13 was identified as gene associated with non-small-cell lung cancer promotion and progression (Bankovic et al., 2010).

Inhibition of SLC35A1 was shown to reduce cancer cell sialylation and decrease the metastatic potential of cancer cells (Maggioni et al., 2014).

SLC7A11 was shown to be down-regulated in drug resistant variants of the W1 ovarian cancer cell line and thus might play a role in cancer cell drug resistance (Januchowski et al., 2013). SLC7A11 was described to modulate tumor microenvironment, leading to a growth advantage for cancer (Savaskan and Eyupoglu, 2010). SLC7A11 was described to be involved in neurodegenerative processes in glioma (Savaskan et al., 2015). SLC7A11 was shown to be repressed by p53 in the context of ferroptosis, and the p53-SLC7A11 axis was described as preserved in the p53 (3KR) mutant, and contributes to its ability to suppress tumorigenesis in the absence of the classical tumor suppression mechanisms (Jiang et al., 2015b). SLC7A11 was described as the functional subunit of system Xc- whose function is increased in aggressive breast cancer cells (Linher-Melville et al., 2015). High membrane staining for SLC7A11 in cisplatin-resistant bladder cancer was shown to be associated with a poorer clinical outcome and SLC7A11 inhibition was described as a promising therapeutic approach to the treatment of this disease (Drayton et al., 2014). SLC7A11 was shown to be differentially expressed in the human promyelocytic leukemia cell line HL-60 that had been exposed to benzene and its metabolites and thus highlights a potential association of SLC7A11 with leukemogenesis (Sarma et al., 2011). Disruption of SLC7A11 was described to result in growth inhibition of a variety of carcinomas, including lymphoma, glioma, prostate and breast cancer (Chen et al., 2009). Inhibition of SLC7A11 was shown to inhibit cell invasion in the esophageal cancer cell line KYSE150 in vitro and its experimental metastasis in nude mice and thus establishes a role of SLC7A11 in tumor metastasis (Chen et al., 2009).

SLCO5A1 is located at the plasma membrane and may contribute to chemoresistance of small cell lung carcinoma by affecting the intracellular transport of drugs (Olszewski-Hamilton et al., 2011). SLCO5A1 is the most prominent organic anion transporting polypeptide in metastatic small cell lung cancer and the mRNA level of SLCO5A1 is highly increased in hepatic tumors and breast cancer (Kindla et al., 2011; Wlcek et al., 2011; Brenner et al., 2015). Gene fusions in oropharyngeal squamous cell carcinoma are associated with down-regulation of SLCO5A1 (Guo et al., 2016).

SP5 was down-regulated after depletion of beta-catenin in colorectal cancer cell lines and is a novel direct downstream target in the Wnt signaling pathway (Takahashi et al., 2005). The over-expression of SP5 demonstrated activation of the beta-catenin pathway in rare human pancreatic neoplasms (Cavard et al., 2009). In human colorectal carcinoma cells displaying de-regulated Wnt signaling, monensin reduced the intracellular levels of β-catenin leading to a decrease in the expression of Wnt signaling target genes such as SP5 and a decreased cell proliferation rate (Tumova et al., 2014).

STIL is among the genes with copy number alterations and copy-neutral losses of heterozygosity in 15 cortisol-secreting adrenocortical adenomas (Ronchi et al., 2012). Chromosomal deletions that fuse this gene and the adjacent locus commonly occur in T cell leukemias, and are thought to arise through illegitimate V-(D)-J recombination events (Karrman et al., 2009; Alonso et al., 2012).

An elevated expression of TBC1D7 was found in the majority of lung cancers and immunohistochemical staining suggested an association of TBC1D7 expression with poor prognosis for NSCLC patients (Sato et al., 2010). Over-expression of TBC7 enhanced ubiquitination of TSC1 and increased phosphorylation of S6 protein by S6 kinase, that is located in the mTOR-signaling pathway (Nakashima et al., 2007).

TDG influences the Wnt signaling pathway in an up-regulating manner via interaction with the transcription factor TCF4 and is thought to be a potential biomarker for colorectal cancer (Xu et al., 2014). On the other hand, a reduced expression of TDG leads to an impaired base excision repair (BER) pathway with strong oncogenic features (van de Klundert et al., 2012). A down-regulation of the protein was observed in early breast cancer esophageal squamous cell carcinoma (ESCC) as well as in gastric cancer (Li et al., 2013; Du et al., 2015; Yang et al., 2015a).

Among the four most frequently mutated genes was TENM4 showing protein-changing mutations in primary CNS lymphomas (Vater et al., 2015). MDA-MB-175 cell line contains a chromosomal translocation that leads to the fusion of TENM4 and receptors of the ErbB family Chimeric genes were also found in neuroblastomas (Wang et al., 1999b; Boeva et al., 2013).

TET2 is a critical regulator for hematopoietic stem cell homeostasis whose functional impairment leads to hematological malignancies (Nakajima and Kunimoto, 2014). TET2 mutations have an adverse impact on prognosis and may help to justify risk-adapted therapeutic strategies for patients with acute myeloid leukemia (Liu et al., 2014b). Nuclear localization of TET2 was lost in a significant portion of colorectal cancer tissues, in association with metastasis (Huang et al., 2016).

TKTL1 is associated with the development and progression of multiple tumor types such as esophageal squamous cell carcinoma, oral squamous cell carcinoma, lung cancer, colorectal cancer and non-small cell lung cancer (Kayser et al., 2011; Bentz et al., 2013; Grimm et al., 2014).

TMEM67 functions in centriole migration to the apical membrane and formation of the primary cilium. Defects in this gene are a cause of Meckel syndrome type 3 (MKS3) and Joubert syndrome type 6 (JBTS6) (RefSeq, 2002). TMEM67 is involved in cilia formation and defective cilia may cause ocular coloboma, tongue tumors, and medulloblastoma (Yang et al., 2015b; Parisi, 2009).

TONSL is involved in lung and esophageal carcinogenesis by stabilizing the oncogenic protein MMS22L (Nguyen et al., 2012). Further interactions were shown between TONSL and BRCA1, which acts as a breast and ovarian tumor suppressor (Hill et al., 2014).

TP63 translocation was described as an event in a subset of anaplastic lymphoma kinase-positive anaplastic large cell lymphomas which is associated with an aggressive course of the disease (Hapgood and Savage, 2015). TP63 was described to play a complex role in cancer due to its involvement in epithelial differentiation, cell cycle arrest and apoptosis (Lin et al., 2015). The TP63 isoform TAp63 was described to be over-expressed in hematological malignancies while TP63 missense mutations have been reported in squamous cancers and TP63 translocations in lymphomas and some lung adenocarcinomas (Orzol et al., 2015). Aberrant splicing resulting in the over-expression of the TP63 isoform DeltaNp63 was described to be frequently found in human cancers such as cutaneous squamous cell carcinoma, where it is likely to favor tumor initiation and progression (Missero and Antonini, 2014; Inoue and Fry, 2014).

TRIM59 promotes proliferation and migration of non-small cell lung cancer cells by up-regulating cell cycle related proteins (Zhan et al., 2015). The putative ubiquitin ligase TRIM59 is up-regulated in gastric tumors compared with non-tumor tissues and levels of TRIM59 correlate with tumor progression and patient survival times. TRIM59 interacts with P53, promoting its ubiquitination and degradation, and TRIM59 might promote gastric carcinogenesis via this mechanism (Zhou et al., 2014).

TRPC4 was found to be up-regulated in lung cancer, ovarian cancer, head and neck cancer, kidney cancer and non-small cell lung cancer (Zhang et al., 2010b; Zeng et al., 2013a; Jiang et al., 2013; Park et al., 2016).

ULBP3 is expressed soluble and membrane bound isoform in many tumor cells. Pediatric acute lymphoblastic leukemia blasts express significantly higher levels of ULBP3 compared to adult blasts (Torelli et al., 2014). Much higher expression levels of ULBP3 were found in the leukemia cell line K562 compared to other leukemia cell lines. Furthermore, it can be found in both leukemia cell lines and primary malignant leukemic cells (Ma et al., 2013b). The ULBP3 locus is methylated in colorectal cancer cell lines (Bormann et al., 2011). Increased mRNA levels and surface expression levels of ULBP3 have been detected in the human lung cancer cell line SW-900 (Park et al., 2011). ULBP3 has a higher surface expression in leukemic cells (Ogbomo et al., 2008). ULBP3 levels in different tumor cell lines correlate with NK cell cytotoxicity, however, ULBP3 seems not to be suitable as biomarker (Wang et al., 2008; Linkov et al., 2009). ULBP3 is not expressed in the human nasopharyngeal carcinoma cell line CNE2 (Mei et al., 2007). ULBP3 is expressed in ovarian cancer and inversely correlated with patient survival (Carlsten et al., 2007; McGilvray et al., 2010). B cells express ULBP3 in non-Hodgkin's lymphoma or it can be found in peripheral blood, bone marrow, or lymph nodes (Catellani et al., 2007). ULBP3 is expressed in breast cancer, the glioblastoma cell line U251, human brain tumors, and in head and neck squamous cell carcinoma (Eisele et al., 2006; Butler et al., 2009; Bryant et al., 2011; de Kruijf et al., 2012). Tumor cells express soluble and surface ULBP3 to regulate NK cell activity (Mou et al., 2014). ULBP3 is over-expressed in certain epithelial tumors. Furthermore, the ULBP3 level in cancer patient sera is elevated compared to healthy donors (Mou et al., 2014).

VPS13B alleles are mutated in small cell lung cancers (Iwakawa et al., 2015). Mutations of VPS13B were observed in gastric and colorectal cancers (An et al., 2012).

Frameshift mutations of VPS13C were found in gastric and colorectal cancers with microsatellite instability (An et al., 2012).

WDR62 expression was significantly increased in gastric cancer tissues and cell lines and was associated with poor differentiation and prognosis. Further, WDR62 expression was elevated in multidrug resistant cells (Zeng et al., 2013b). WDR62 over-expression is related to centrosome amplification and may be a novel useful differentiation biomarker and a potential therapy target for ovarian cancer (Zhang et al., 2013b).

Exosome-bound WDR92 inhibits breast cancer cell invasion by degrading amphiregulin mRNA (Saeki et al., 2013). WDR92 potentiates apoptosis induced by tumor necrosis factor-alpha and cycloheximide (Ni et al., 2009).

WNT5A belongs to the WNT gene family that consists of structurally related genes which encode secreted signaling proteins. These proteins have been implicated in oncogenesis and in several developmental processes, including regulation of cell fate and patterning during embryogenesis. The WNT5A gene encodes a member of the WNT family that signals through both the canonical and non-canonical WNT pathways. This protein is a ligand for the seven transmembrane receptor frizzled-5 and the tyrosine kinase orphan receptor 2. This protein plays an essential role in regulating developmental pathways during embryogenesis. This protein may also play a role in oncogenesis (RefSeq, 2002). WNT5A is over-expressed in CRC and had a concordance rate of 76% between the primary tumor and metastatic site (Lee et al., 2014a). WNT5A is up-regulated and a key regulator of the epithelial-to-mesenchymal transition and metastasis in human gastric carcinoma cells, nasopharyngeal carcinoma and pancreatic cancer (Kanzawa et al., 2013; Zhu et al., 2014; Bo et al., 2013).

XRN1 is likely involved in a number of regulatory mRNA pathways in astrocytes and astrocytoma cells (Moser et al., 2007). Knockdown of XRN1 inhibited androgen receptor expression in prostate cancer cells and plays an important role in miR-204/XRN1 axis in prostate adenocarcinoma (Ding et al., 2015).

Genome-wide association studies identified gene polymorphisms in XXYLT1. It has been proposed that these polymorphisms are susceptibility loci for non-small cell lung cancer development (Zhang et al., 2012b).

ZBTB20 promotes cell proliferation in non-small cell lung cancer through repression of FoxO1 (Zhao et al., 2014b). ZBTB20 expression is increased in hepatocellular carcinoma and associated with poor prognosis (Wang et al., 2011c). Polymorphism in ZBTB20 gene is associated with gastric cancer (Song et al., 2013).

ZFHX4 is thought to regulate cell differentiation and its suppression is linked to glioma-free survival (Chudnovsky et al., 2014). Papillary tumors of the pineal region show high expression levels of ZFHX4 (Fevre-Montange et al., 2006). ZFHX4 was found to be a basal cell carcinoma susceptibility locus (Stacey et al., 2015).

ZMYM1 is a major interactor of ZNF131 which acts in estrogen signaling and breast cancer proliferation (Oh and Chung, 2012; Kim et al., 2016).

DETAILED DESCRIPTION OF THE INVENTION

Stimulation of an immune response is dependent upon the presence of antigens recognized as foreign by the host immune system. The discovery of the existence of tumor associated antigens has raised the possibility of using a host's immune system to intervene in tumor growth. Various mechanisms of harnessing both the humoral and cellular arms of the immune system are currently being explored for cancer immunotherapy.

Specific elements of the cellular immune response are capable of specifically recognizing and destroying tumor cells. The isolation of T-cells from tumor-infiltrating cell populations or from peripheral blood suggests that such cells play an important role in natural immune defense against cancer. CD8-positive T-cells in particular, which recognize class I molecules of the major histocompatibility complex (MHC)-bearing peptides of usually 8 to 10 amino acid residues derived from proteins or defect ribosomal products (DRIPS) located in the cytosol, play an important role in this response. The MHC-molecules of the human are also designated as human leukocyte-antigens (HLA).

As used herein and except as noted otherwise all terms are defined as given below.

The term "T-cell response" shall mean that the specific proliferation and activation of effector functions induced by a peptide in vitro or in vivo. For MHC class I restricted cytotoxic T cells, effector functions may be lysis of peptide-pulsed, peptide-precursor pulsed or naturally peptide-presenting target cells, secretion of cytokines, preferably Interferon-gamma, TNF-alpha, or IL-2 induced by peptide, secretion of effector molecules, preferably granzymes or perforins induced by peptide, or degranulation.

The term "peptide" is used herein to designate a series of amino acid residues, connected one to the other typically by peptide bonds between the alpha-amino and carbonyl groups of the adjacent amino acids. The peptides are preferably 9 amino acids in length, but can be as short as 8 amino acids in length, and as long as 10, 11, 12, 13 or 14 amino acids or longer, and in case of MHC class II peptides (elongated variants of the peptides of the invention) they can be as long as 15, 16, 17, 18, 19 or 20 or more amino acids in length.

Furthermore, the term "peptide" shall include salts of a series of amino acid residues, connected one to the other typically by peptide bonds between the alpha-amino and carbonyl groups of the adjacent amino acids. Preferably, the salts are pharmaceutical acceptable salts of the peptides, such as, for example, the chloride or acetate (trifluoroacetate) salts. It has to be noted that the salts of the peptides according to the present invention differ substantially from the peptides in their state(s) in vivo, as the peptides are not salts in vivo.

The term "peptide" shall also include "oligopeptide". The term "oligopeptide" is used herein to designate a series of amino acid residues, connected one to the other typically by peptide bonds between the alpha-amino and carbonyl groups of the adjacent amino acids. The length of the oligopeptide is not critical to the invention, as long as the correct epitope or epitopes are maintained therein. The oligopeptides are typically less than about 30 amino acid residues in length, and greater than about 15 amino acids in length.

The term "polypeptide" designates a series of amino acid residues, connected one to the other typically by peptide bonds between the alpha-amino and carbonyl groups of the adjacent amino acids. The length of the polypeptide is not critical to the invention as long as the correct epitopes are maintained. In contrast to the terms peptide or oligopeptide, the term polypeptide is meant to refer to molecules containing more than about 30 amino acid residues.

A peptide, oligopeptide, protein or polynucleotide coding for such a molecule is "immunogenic" (and thus is an "immunogen" within the present invention), if it is capable of inducing an immune response. In the case of the present invention, immunogenicity is more specifically defined as the ability to induce a T-cell response. Thus, an "immunogen" would be a molecule that is capable of inducing an immune response, and in the case of the present invention, a molecule capable of inducing a T-cell response. In another aspect, the immunogen can be the peptide, the complex of the peptide with MHC, oligopeptide, and/or protein that is used to raise specific antibodies or TCRs against it.

A class I T cell "epitope" requires a short peptide that is bound to a class I MHC receptor, forming a ternary complex (MHC class I alpha chain, beta-2-microglobulin, and peptide) that can be recognized by a T cell bearing a matching T-cell receptor binding to the MHC/peptide complex with appropriate affinity. Peptides binding to MHC class I molecules are typically 8-14 amino acids in length, and most typically 9 amino acids in length.

In humans there are three different genetic loci that encode MHC class I molecules (the MHC-molecules of the human are also designated human leukocyte antigens (HLA)): HLA-A, HLA-B, and HLA-C. HLA-A*01, HLA-A*02, and HLA-B*07 are examples of different MHC class I alleles that can be expressed from these loci.

TABLE 4

Expression frequencies F of HLA-A*02 and HLA-A*24 and the most frequent HLA-DR serotypes. Frequencies are deduced from haplotype frequencies Gf within the American population adapted from Mori et al. (Mori et al., 1997) employing the Hardy-Weinberg formula $F = 1 - (1-Gf)^2$. Combinations of A*02 or A*24 with certain HLA-DR alleles might be enriched or less frequent than expected from their single frequencies due to linkage disequilibrium. For details refer to Chanock et al. (Chanock et al., 2004).

| Allele | Population | Calculated phenotype from allele frequency |
|---|---|---|
| A*02 | Caucasian (North America) | 49.1% |
| A*02 | African American (North America) | 34.1% |
| A*02 | Asian American (North America) | 43.2% |

TABLE 4-continued

Expression frequencies F of HLA-A*02 and HLA-A*24 and the most frequent HLA-DR serotypes. Frequencies are deduced from haplotype frequencies Gf within the American population adapted from Mori et al. (Mori et al., 1997) employing the Hardy-Weinberg formula $F = 1 - (1-Gf)^2$. Combinations of A*02 or A*24 with certain HLA-DR alleles might be enriched or less frequent than expected from their single frequencies due to linkage disequilibrium. For details refer to Chanock et al. (Chanock et al., 2004).

| Allele | Population | Calculated phenotype from allele frequency |
|---|---|---|
| A*02 | Latin American (North American) | 48.3% |
| DR1 | Caucasian (North America) | 19.4% |
| DR2 | Caucasian (North America) | 28.2% |
| DR3 | Caucasian (North America) | 20.6% |
| DR4 | Caucasian (North America) | 30.7% |
| DR5 | Caucasian (North America) | 23.3% |
| DR6 | Caucasian (North America) | 26.7% |
| DR7 | Caucasian (North America) | 24.8% |
| DR8 | Caucasian (North America) | 5.7% |
| DR9 | Caucasian (North America) | 2.1% |
| DR1 | African (North) American | 13.20% |
| DR2 | African (North) American | 29.80% |
| DR3 | African (North) American | 24.80% |
| DR4 | African (North) American | 11.10% |
| DR5 | African (North) American | 31.10% |
| DR6 | African (North) American | 33.70% |
| DR7 | African (North) American | 19.20% |
| DR8 | African (North) American | 12.10% |
| DR9 | African (North) American | 5.80% |
| DR1 | Asian (North) American | 6.80% |
| DR2 | Asian (North) American | 33.80% |
| DR3 | Asian (North) American | 9.20% |
| DR4 | Asian (North) American | 28.60% |
| DR5 | Asian (North) American | 30.00% |
| DR6 | Asian (North) American | 25.10% |
| DR7 | Asian (North) American | 13.40% |
| DR8 | Asian (North) American | 12.70% |
| DR9 | Asian (North) American | 18.60% |
| DR1 | Latin (North) American | 15.30% |
| DR2 | Latin (North) American | 21.20% |
| DR3 | Latin (North) American | 15.20% |
| DR4 | Latin (North) American | 36.80% |
| DR5 | Latin (North) American | 20.00% |
| DR6 | Latin (North) American | 31.10% |
| DR7 | Latin (North) American | 20.20% |
| DR8 | Latin (North) American | 18.60% |
| DR9 | Latin (North) American | 2.10% |
| A*24 | Philippines | 65% |
| A*24 | Russia Nenets | 61% |
| A*24:02 | Japan | 59% |
| A*24 | Malaysia | 58% |
| A*24:02 | Philippines | 54% |
| A*24 | India | 47% |
| A*24 | South Korea | 40% |
| A*24 | Sri Lanka | 37% |
| A*24 | China | 32% |
| A*24:02 | India | 29% |
| A*24 | Australia West | 22% |
| A*24 | USA | 22% |
| A*24 | Russia Samara | 20% |
| A*24 | South America | 20% |
| A*24 | Europe | 18% |

The peptides of the invention, preferably when included into a vaccine of the invention as described herein preferably bind to A*02, A*24 or class II alleles, as specified. A vaccine may also include pan-binding MHC class II peptides. Therefore, the vaccine of the invention can be used to treat cancer in patients that are A*02 positive, whereas no selection for MHC class II allotypes is necessary due to the pan-binding nature of these peptides.

If A*02 peptides of the invention are combined with peptides binding to another allele, for example A*24, a higher percentage of any patient population can be treated compared with addressing either MHC class I allele alone. While in most populations less than 50% of patients could be addressed by either allele alone, a vaccine comprising HLA-A*24 and HLA-A*02 epitopes can treat at least 60% of patients in any relevant population. Specifically, the following percentages of patients will be positive for at least one of these alleles in various regions: USA 61%, Western Europe 62%, China 75%, South Korea 77%, Japan 86%.

In a preferred embodiment, the term "nucleotide sequence" refers to a heteropolymer of deoxyribonucleotides.

The nucleotide sequence coding for a particular peptide, oligopeptide, or polypeptide may be naturally occurring or they may be synthetically constructed. Generally, DNA segments encoding the peptides, polypeptides, and proteins of this invention are assembled from cDNA fragments and short oligonucleotide linkers, or from a series of oligonucleotides, to provide a synthetic gene that is capable of being expressed in a recombinant transcriptional unit comprising regulatory elements derived from a microbial or viral operon.

As used herein the term "a nucleotide coding for (or encoding) a peptide" refers to a nucleotide sequence coding for the peptide including artificial (man-made) start and stop codons compatible for the biological system the sequence is to be expressed by, for example, a dendritic cell or another cell system useful for the production of TCRs.

As used herein, reference to a nucleic acid sequence includes both single stranded and double stranded nucleic acid. Thus, for example for DNA, the specific sequence, unless the context indicates otherwise, refers to the single strand DNA of such sequence, the duplex of such sequence with its complement (double stranded DNA) and the complement of such sequence.

The term "coding region" refers to that portion of a gene which either naturally or normally codes for the expression product of that gene in its natural genomic environment, i.e., the region coding in vivo for the native expression product of the gene.

The coding region can be derived from a non-mutated ("normal"), mutated or altered gene, or can even be derived from a DNA sequence, or gene, wholly synthesized in the laboratory using methods well known to those of skill in the art of DNA synthesis.

The term "expression product" means the polypeptide or protein that is the natural translation product of the gene and any nucleic acid sequence coding equivalents resulting from genetic code degeneracy and thus coding for the same amino acid(s).

The term "fragment", when referring to a coding sequence, means a portion of DNA comprising less than the complete coding region, whose expression product retains essentially the same biological function or activity as the expression product of the complete coding region.

The term "DNA segment" refers to a DNA polymer, in the form of a separate fragment or as a component of a larger DNA construct, which has been derived from DNA isolated at least once in substantially pure form, i.e., free of contaminating endogenous materials and in a quantity or concentration enabling identification, manipulation, and recovery of the segment and its component nucleotide sequences by standard biochemical methods, for example, by using a cloning vector. Such segments are provided in the form of an open reading frame uninterrupted by internal non-translated sequences, or introns, which are typically present in eukaryotic genes. Sequences of non-translated DNA may be present downstream from the open reading frame, where the same do not interfere with manipulation or expression of the coding regions.

The term "primer" means a short nucleic acid sequence that can be paired with one strand of DNA and provides a free 3'-OH end at which a DNA polymerase starts synthesis of a deoxyribonucleotide chain.

The term "promoter" means a region of DNA involved in binding of RNA polymerase to initiate transcription.

The term "isolated" means that the material is removed from its original environment (e.g., the natural environment, if it is naturally occurring). For example, a naturally-occurring polynucleotide or polypeptide present in a living animal is not isolated, but the same polynucleotide or polypeptide, separated from some or all of the coexisting materials in the natural system, is isolated. Such polynucleotides could be part of a vector and/or such polynucleotides or polypeptides could be part of a composition, and still be isolated in that such vector or composition is not part of its natural environment.

The polynucleotides, and recombinant or immunogenic polypeptides, disclosed in accordance with the present invention may also be in "purified" form. The term "purified" does not require absolute purity; rather, it is intended as a relative definition, and can include preparations that are highly purified or preparations that are only partially purified, as those terms are understood by those of skill in the relevant art. For example, individual clones isolated from a cDNA library have been conventionally purified to electrophoretic homogeneity. Purification of starting material or natural material to at least one order of magnitude, preferably two or three orders, and more preferably four or five orders of magnitude is expressly contemplated. Furthermore, a claimed polypeptide which has a purity of preferably 99.999%, or at least 99.99% or 99.9%; and even desirably 99% by weight or greater is expressly encompassed.

The nucleic acids and polypeptide expression products disclosed according to the present invention, as well as expression vectors containing such nucleic acids and/or such polypeptides, may be in "enriched form". As used herein, the term "enriched" means that the concentration of the material is at least about 2, 5, 10, 100, or 1000 times its natural concentration (for example), advantageously 0.01%, by weight, preferably at least about 0.1% by weight. Enriched preparations of about 0.5%, 1%, 5%, 10%, and 20% by weight are also contemplated. The sequences, constructs, vectors, clones, and other materials comprising the present invention can advantageously be in enriched or isolated form. The term "active fragment" means a fragment, usually of a peptide, polypeptide or nucleic acid sequence, that generates an immune response (i.e., has immunogenic activity) when administered, alone or optionally with a suitable adjuvant or in a vector, to an animal, such as a mammal, for example, a rabbit or a mouse, and also including a human, such immune response taking the form of stimulating a T-cell response within the recipient animal, such as a human. Alternatively, the "active fragment" may also be used to induce a T-cell response in vitro.

As used herein, the terms "portion", "segment" and "fragment", when used in relation to polypeptides, refer to a continuous sequence of residues, such as amino acid residues, which sequence forms a subset of a larger sequence. For example, if a polypeptide were subjected to treatment with any of the common endopeptidases, such as trypsin or chymotrypsin, the oligopeptides resulting from such treatment would represent portions, segments or fragments of the starting polypeptide. When used in relation to polynucleotides, these terms refer to the products produced by treatment of said polynucleotides with any of the endonucleases.

In accordance with the present invention, the term "percent identity" or "percent identical", when referring to a sequence, means that a sequence is compared to a claimed or described sequence after alignment of the sequence to be compared (the "Compared Sequence") with the described or claimed sequence (the "Reference Sequence"). The percent identity is then determined according to the following formula:

$$\text{percent identity} = 100[1-(C/R)]$$

wherein C is the number of differences between the Reference Sequence and the Compared Sequence over the length of alignment between the Reference Sequence and the Compared Sequence, wherein
(i) each base or amino acid in the Reference Sequence that does not have a corresponding aligned base or amino acid in the Compared Sequence and
(ii) each gap in the Reference Sequence and
(iii) each aligned base or amino acid in the Reference Sequence that is different from an aligned base or amino acid in the Compared Sequence, constitutes a difference and
(iiii) the alignment has to start at position 1 of the aligned sequences;
and R is the number of bases or amino acids in the Reference Sequence over the length of the alignment with the Compared Sequence with any gap created in the Reference Sequence also being counted as a base or amino acid.

If an alignment exists between the Compared Sequence and the Reference Sequence for which the percent identity as calculated above is about equal to or greater than a specified minimum Percent Identity then the Compared Sequence has the specified minimum percent identity to the Reference Sequence even though alignments may exist in which the herein above calculated percent identity is less than the specified percent identity.

As mentioned above, the present invention thus provides a peptide comprising a sequence that is selected from the group of consisting of SEQ ID NO: 1 to SEQ ID NO: 388 or a variant thereof which is 88% homologous to SEQ ID NO: 1 to SEQ ID NO: 388, or a variant thereof that will induce T cells cross-reacting with said peptide. The peptides of the invention have the ability to bind to a molecule of the human major histocompatibility complex (MHC) class-I or elongated versions of said peptides to class II.

In the present invention, the term "homologous" refers to the degree of identity (see percent identity above) between sequences of two amino acid sequences, i.e. peptide or polypeptide sequences. The aforementioned "homology" is determined by comparing two sequences aligned under optimal conditions over the sequences to be compared. Such a sequence homology can be calculated by creating an alignment using, for example, the ClustalW algorithm. Commonly available sequence analysis software, more specifically, Vector NTI, GENETYX or other tools are provided by public databases.

A person skilled in the art will be able to assess, whether T cells induced by a variant of a specific peptide will be able to cross-react with the peptide itself (Appay et al., 2006; Colombetti et al., 2006; Fong et al., 2001; Zaremba et al., 1997).

By a "variant" of the given amino acid sequence the inventors mean that the side chains of, for example, one or two of the amino acid residues are altered (for example by replacing them with the side chain of another naturally occurring amino acid residue or some other side chain) such that the peptide is still able to bind to an HLA molecule in substantially the same way as a peptide consisting of the given amino acid sequence in consisting of SEQ ID NO: 1 to SEQ ID NO: 388. For example, a peptide may be modified so that it at least maintains, if not improves, the ability to interact with and bind to the binding groove of a suitable MHC molecule, such as HLA-A*02 or -DR, and in that way it at least maintains, if not improves, the ability to bind to the TCR of activated T cells.

These T cells can subsequently cross-react with cells and kill cells that express a polypeptide that contains the natural amino acid sequence of the cognate peptide as defined in the aspects of the invention. As can be derived from the scientific literature and databases (Rammensee et al., 1999; Godkin et al., 1997), certain positions of HLA binding peptides are typically anchor residues forming a core sequence fitting to the binding motif of the HLA receptor, which is defined by polar, electrophysical, hydrophobic and spatial properties of the polypeptide chains constituting the binding groove. Thus, one skilled in the art would be able to modify the amino acid sequences set forth in SEQ ID NO: 1 to SEQ ID NO 388, by maintaining the known anchor residues, and would be able to determine whether such variants maintain the ability to bind MHC class I or II molecules. The variants of the present invention retain the ability to bind to the TCR of activated T cells, which can subsequently cross-react with and kill cells that express a polypeptide containing the natural amino acid sequence of the cognate peptide as defined in the aspects of the invention.

The original (unmodified) peptides as disclosed herein can be modified by the substitution of one or more residues at different, possibly selective, sites within the peptide chain, if not otherwise stated. Preferably those substitutions are located at the end of the amino acid chain. Such substitutions may be of a conservative nature, for example, where one amino acid is replaced by an amino acid of similar structure and characteristics, such as where a hydrophobic amino acid is replaced by another hydrophobic amino acid. Even more conservative would be replacement of amino acids of the same or similar size and chemical nature, such as where leucine is replaced by isoleucine. In studies of sequence variations in families of naturally occurring homologous proteins, certain amino acid substitutions are more often tolerated than others, and these are often show correlation with similarities in size, charge, polarity, and hydrophobicity between the original amino acid and its replacement, and such is the basis for defining "conservative substitutions."

Conservative substitutions are herein defined as exchanges within one of the following five groups: Group 1-small aliphatic, nonpolar or slightly polar residues (Ala, Ser, Thr, Pro, Gly); Group 2-polar, negatively charged residues and their amides (Asp, Asn, Glu, Gln); Group 3-polar, positively charged residues (His, Arg, Lys); Group 4-large, aliphatic, nonpolar residues (Met, Leu, Ile, Val, Cys); and Group 5-large, aromatic residues (Phe, Tyr, Trp).

Less conservative substitutions might involve the replacement of one amino acid by another that has similar characteristics but is somewhat different in size, such as replacement of an alanine by an isoleucine residue. Highly non-conservative replacements might involve substituting an acidic amino acid for one that is polar, or even for one that is basic in character. Such "radical" substitutions cannot, however, be dismissed as potentially ineffective since chemical effects are not totally predictable and radical substitutions might well give rise to serendipitous effects not otherwise predictable from simple chemical principles.

Of course, such substitutions may involve structures other than the common L-amino acids. Thus, D-amino acids might be substituted for the L-amino acids commonly found in the antigenic peptides of the invention and yet still be encompassed by the disclosure herein. In addition, non-standard amino acids (i.e., other than the common naturally occurring proteinogenic amino acids) may also be used for substitution purposes to produce immunogens and immunogenic polypeptides according to the present invention.

If substitutions at more than one position are found to result in a peptide with substantially equivalent or greater antigenic activity as defined below, then combinations of those substitutions will be tested to determine if the combined substitutions result in additive or synergistic effects on the antigenicity of the peptide. At most, no more than 4 positions within the peptide would be simultaneously substituted.

A peptide consisting essentially of the amino acid sequence as indicated herein can have one or two non-anchor amino acids (see below regarding the anchor motif) exchanged without that the ability to bind to a molecule of the human major histocompatibility complex (MHC) class-I or -II is substantially changed or is negatively affected, when compared to the non-modified peptide.

In another embodiment, in a peptide consisting essentially of the amino acid sequence as indicated herein, one or two amino acids can be exchanged with their conservative exchange partners (see herein below) without that the ability to bind to a molecule of the human major histocompatibility complex (MHC) class-I or —II is substantially changed, or is negatively affected, when compared to the non-modified peptide.

The amino acid residues that do not substantially contribute to interactions with the T-cell receptor can be modified by replacement with other amino acids whose incorporation do not substantially affect T-cell reactivity and does not eliminate binding to the relevant MHC. Thus, apart from the proviso given, the peptide of the invention may be any peptide (by which term the inventors include oligopeptide or polypeptide), which includes the amino acid sequences or a portion or variant thereof as given.

TABLE 5

Preferred variants and motifs of the HLA-A*02-peptides according to SEQ ID NO: 2, 4, and 6.

| | Position | | | | | | | | |
|---|---|---|---|---|---|---|---|---|---|
| | 1 | 2 | 3 | 4 | 5 | 6 | 7 | 8 | 9 |
| SEQ ID NO. 4 Variants | E | L | A | E | I | V | F | K | V |
| | | | | | | | | | I |
| | | | | | | | | | L |
| | | | | | | | | | A |
| | | M | | | | | | | I |
| | | M | | | | | | | L |
| | | M | | | | | | | |
| | | M | | | | | | | A |
| | | A | | | | | | | I |
| | | A | | | | | | | L |
| | | A | | | | | | | |
| | | A | | | | | | | A |
| | | V | | | | | | | I |
| | | V | | | | | | | L |
| | | V | | | | | | | |
| | | V | | | | | | | A |
| | | T | | | | | | | I |
| | | T | | | | | | | L |
| | | T | | | | | | | |
| | | T | | | | | | | A |
| | | Q | | | | | | | I |
| | | Q | | | | | | | L |
| | | Q | | | | | | | |
| | | Q | | | | | | | A |
| SEQ ID NO 2 Variants | A | L | Y | G | K | L | L | K | L |
| | | | | | | | | | V |
| | | | | | | | | | I |
| | | | | | | | | | A |
| | | M | | | | | | | V |
| | | M | | | | | | | I |
| | | M | | | | | | | |
| | | M | | | | | | | A |
| | | A | | | | | | | V |
| | | A | | | | | | | I |
| | | A | | | | | | | |
| | | A | | | | | | | A |
| | | V | | | | | | | V |
| | | V | | | | | | | I |

TABLE 5-continued

Preferred variants and motifs of the HLA-A*02-peptides according to SEQ ID NO: 2, 4, and 6.

| | Position | | | | | | | | |
|---|---|---|---|---|---|---|---|---|---|
| | 1 | 2 | 3 | 4 | 5 | 6 | 7 | 8 | 9 |
| | | V | | | | | | | |
| | | V | | | | | | | A |
| | | T | | | | | | | V |
| | | T | | | | | | | I |
| | | T | | | | | | | |
| | | T | | | | | | | A |
| | | Q | | | | | | | V |
| | | Q | | | | | | | I |
| | | Q | | | | | | | |
| SEQ ID NO. 6 Variants | F | L | D | P | A | Q | R | D | L |
| | | | | | | | | | V |
| | | | | | | | | | I |
| | | | | | | | | | A |
| | | M | | | | | | | V |
| | | M | | | | | | | I |
| | | M | | | | | | | |
| | | M | | | | | | | A |
| | | A | | | | | | | V |
| | | A | | | | | | | I |
| | | A | | | | | | | |
| | | A | | | | | | | A |
| | | V | | | | | | | V |
| | | V | | | | | | | I |
| | | V | | | | | | | |
| | | V | | | | | | | A |
| | | T | | | | | | | V |
| | | T | | | | | | | I |
| | | T | | | | | | | |
| | | T | | | | | | | A |
| | | Q | | | | | | | V |
| | | Q | | | | | | | I |
| | | Q | | | | | | | |
| | | Q | | | | | | | A |

TABLE 6

Preferred variants and motifs of the HLA-A*24-binding peptides according to SEQ ID NO: 98, 114, and 158.

| | Position | | | | | | | | | | | |
|---|---|---|---|---|---|---|---|---|---|---|---|---|
| | 1 | 2 | 3 | 4 | 5 | 6 | 7 | 8 | 9 | 10 | 11 | 12 |
| SEQ ID 158 Variant | I | Y | E | E | T | R | G | V | L | K | V | F |
| | | | | | | | | | | | | I |
| | | | | | | | | | | | | L |
| | | F | | | | | | | | | | |
| | | F | | | | | | | | | | I |
| | | F | | | | | | | | | | L |
| SEQ ID 114 Variant | Q | Y | L | D | G | T | W | S | L | | | |
| | | | | | | | | | I | | | |
| | | | | | | | | | F | | | |
| | | F | | | | | | | | | | |
| | | F | | | | | | | | I | | |
| | | F | | | | | | | | F | | |
| SEQ ID 98 Variant | V | F | P | R | L | H | N | V | L | F | | |
| | | Y | | | | | | | | I | | |
| | | Y | | | | | | | | L | | |
| | | Y | | | | | | | | | | |
| | | | | | | | | | | I | | |
| | | | | | | | | | | L | | |

Longer (elongated) peptides may also be suitable. It is possible that MHC class I epitopes, although usually between 8 and 11 amino acids long, are generated by peptide processing from longer peptides or proteins that include the actual epitope. It is preferred that the residues that flank the actual epitope are residues that do not substantially affect proteolytic cleavage necessary to expose the actual epitope during processing.

The peptides of the invention can be elongated by up to four amino acids, that is 1, 2, 3 or 4 amino acids can be added to either end in any combination between 4:0 and 0:4. Combinations of the elongations according to the invention can be found in Table 7.

TABLE 7

Combinations of the elongations of peptides of the invention

| C-terminus | N-terminus |
|---|---|
| 4 | 0 |
| 3 | 0 or 1 |
| 2 | 0 or 1 or 2 |
| 1 | 0 or 1 or 2 or 3 |
| 0 | 0 or 1 or 2 or 3 or 4 |

| N-terminus | C-terminus |
|---|---|
| 4 | 0 |
| 3 | 0 or 1 |
| 2 | 0 or 1 or 2 |
| 1 | 0 or 1 or 2 or 3 |
| 0 | 0 or 1 or 2 or 3 or 4 |

The amino acids for the elongation/extension can be the peptides of the original sequence of the protein or any other amino acid(s). The elongation can be used to enhance the stability or solubility of the peptides.

Thus, the epitopes of the present invention may be identical to naturally occurring tumor-associated or tumor-specific epitopes or may include epitopes that differ by no more than four residues from the reference peptide, as long as they have substantially identical antigenic activity.

In an alternative embodiment, the peptide is elongated on either or both sides by more than four amino acids, preferably to a total length of up to 30 amino acids. This may lead to MHC class II binding peptides. Binding to MHC class II can be tested by methods known in the art.

Accordingly, the present invention provides peptides and variants of MHC class I epitopes, wherein the peptide or variant has an overall length of between 8 and 100, preferably between 8 and 30, and most preferred between 8 and 14, namely 8, 9, 10, 11, 12, 13, 14 amino acids, in case of the elongated class II binding peptides the length can also be 15, 16, 17, 18, 19, 20, 21 or 22 amino acids.

Of course, the peptide or variant according to the present invention will have the ability to bind to a molecule of the human major histocompatibility complex (MHC) class I or II. Binding of a peptide or a variant to a MHC complex may be tested by methods known in the art.

Preferably, when the T cells specific for a peptide according to the present invention are tested against the substituted peptides, the peptide concentration at which the substituted peptides achieve half the maximal increase in lysis relative to background is no more than about 1 mM, preferably no more than about 1 µM, more preferably no more than about 1 nM, and still more preferably no more than about 100 pM, and most preferably no more than about 10 pM. It is also preferred that the substituted peptide be recognized by T cells from more than one individual, at least two, and more preferably three individuals.

In a particularly preferred embodiment of the invention the peptide consists or consists essentially of an amino acid sequence according to SEQ ID NO: 1 to SEQ ID NO: 388.

"Consisting essentially of" shall mean that a peptide according to the present invention, in addition to the sequence according to any of SEQ ID NO: 1 to SEQ ID NO 388 or a variant thereof contains additional N- and/or C-terminally located stretches of amino acids that are not necessarily forming part of the peptide that functions as an epitope for MHC molecules epitope.

Nevertheless, these stretches can be important to provide an efficient introduction of the peptide according to the present invention into the cells. In one embodiment of the present invention, the peptide is part of a fusion protein which comprises, for example, the 80 N-terminal amino acids of the HLA-DR antigen-associated invariant chain (p33, in the following "Ii") as derived from the NCBI, GenBank Accession number X00497. In other fusions, the peptides of the present invention can be fused to an antibody as described herein, or a functional part thereof, in particular into a sequence of an antibody, so as to be specifically targeted by said antibody, or, for example, to or into an antibody that is specific for dendritic cells as described herein.

In addition, the peptide or variant may be modified further to improve stability and/or binding to MHC molecules in order to elicit a stronger immune response. Methods for such an optimization of a peptide sequence are well known in the art and include, for example, the introduction of reverse peptide bonds or non-peptide bonds.

In a reverse peptide bond amino acid residues are not joined by peptide (—CO—NH—) linkages but the peptide bond is reversed. Such retro-inverso peptidomimetics may be made using methods known in the art, for example such as those described in Meziere et al (1997) (Meziere et al., 1997), incorporated herein by reference. This approach involves making pseudopeptides containing changes involving the backbone, and not the orientation of side chains. Meziere et al. (Meziere et al., 1997) show that for MHC binding and T helper cell responses, these pseudopeptides are useful. Retro-inverse peptides, which contain NH—CO bonds instead of CO—NH peptide bonds, are much more resistant to proteolysis.

A non-peptide bond is, for example, —$CH_2$—NH, —$CH_2$S—, —$CH_2CH_2$—, —CH=CH—, —$COCH_2$—, —CH(OH)$CH_2$—, and —$CH_2$SO—. U.S. Pat. No. 4,897, 445 provides a method for the solid phase synthesis of non-peptide bonds (—$CH_2$—NH) in polypeptide chains which involves polypeptides synthesized by standard procedures and the non-peptide bond synthesized by reacting an amino aldehyde and an amino acid in the presence of NaCNBH$_3$.

Peptides comprising the sequences described above may be synthesized with additional chemical groups present at their amino and/or carboxy termini, to enhance the stability, bioavailability, and/or affinity of the peptides. For example, hydrophobic groups such as carbobenzoxyl, dansyl, or t-butyloxycarbonyl groups may be added to the peptides' amino termini. Likewise, an acetyl group or a 9-fluorenyl-methoxy-carbonyl group may be placed at the peptides' amino termini. Additionally, the hydrophobic group, t-butyloxycarbonyl, or an amido group may be added to the peptides' carboxy termini.

Further, the peptides of the invention may be synthesized to alter their steric configuration. For example, the D-isomer of one or more of the amino acid residues of the peptide may be used, rather than the usual L-isomer. Still further, at least one of the amino acid residues of the peptides of the invention may be substituted by one of the well-known non-naturally occurring amino acid residues. Alterations such as these may serve to increase the stability, bioavailability and/or binding action of the peptides of the invention.

Similarly, a peptide or variant of the invention may be modified chemically by reacting specific amino acids either before or after synthesis of the peptide. Examples for such modifications are well known in the art and are summarized e.g. in R. Lundblad, Chemical Reagents for Protein Modification, 3rd ed. CRC Press, 2004 (Lundblad, 2004), which is incorporated herein by reference. Chemical modification of amino acids includes but is not limited to, modification by acylation, amidination, pyridoxylation of lysine, reductive alkylation, trinitrobenzylation of amino groups with 2,4,6-trinitrobenzene sulphonic acid (TNBS), amide modification of carboxyl groups and sulphydryl modification by performic acid oxidation of cysteine to cysteic acid, formation of mercurial derivatives, formation of mixed disulphides with other thiol compounds, reaction with maleimide, carboxymethylation with iodoacetic acid or iodoacetamide and carbamoylation with cyanate at alkaline pH, although without limitation thereto. In this regard, the skilled person is referred to Chapter 15 of Current Protocols In Protein Science, Eds. Coligan et al. (John Wiley and Sons NY 1995-2000) (Coligan et al., 1995) for more extensive methodology relating to chemical modification of proteins.

Briefly, modification of e.g. arginyl residues in proteins is often based on the reaction of vicinal dicarbonyl compounds such as phenylglyoxal, 2,3-butanedione, and 1,2-cyclohexanedione to form an adduct. Another example is the reaction of methylglyoxal with arginine residues. Cysteine can be modified without concomitant modification of other nucleophilic sites such as lysine and histidine. As a result, a large number of reagents are available for the modification of cysteine. The websites of companies such as Sigma-Aldrich provide information on specific reagents.

Selective reduction of disulfide bonds in proteins is also common. Disulfide bonds can be formed and oxidized during the heat treatment of biopharmaceuticals. Woodward's Reagent K may be used to modify specific glutamic acid residues. N-(3-(dimethylamino)propyl)-N'-ethylcarbodiimide can be used to form intra-molecular crosslinks between a lysine residue and a glutamic acid residue. For example, diethylpyrocarbonate is a reagent for the modification of histidyl residues in proteins. Histidine can also be modified using 4-hydroxy-2-nonenal. The reaction of lysine residues and other α-amino groups is, for example, useful in binding of peptides to surfaces or the cross-linking of proteins/peptides. Lysine is the site of attachment of poly(ethylene)glycol and the major site of modification in the glycosylation of proteins. Methionine residues in proteins can be modified with e.g. iodoacetamide, bromoethylamine, and chloramine T.

Tetranitromethane and N-acetylimidazole can be used for the modification of tyrosyl residues. Cross-linking via the formation of dityrosine can be accomplished with hydrogen peroxide/copper ions.

Recent studies on the modification of tryptophan have used N-bromosuccinimide, 2-hydroxy nitrobenzyl bromide or 3-bromo-3-methyl-2-(2-nitrophenylmercapto)-3H-indole (BPNS-skatole).

Successful modification of therapeutic proteins and peptides with PEG is often associated with an extension of circulatory half-life while cross-linking of proteins with glutaraldehyde, polyethylene glycol diacrylate and formaldehyde is used for the preparation of hydrogels. Chemical modification of allergens for immunotherapy is often achieved by carbamylation with potassium cyanate.

A peptide or variant, wherein the peptide is modified or includes non-peptide bonds is a preferred embodiment of the invention. Generally, peptides and variants (at least those containing peptide linkages between amino acid residues) may be synthesized by the Fmoc-polyamide mode of solid-phase peptide synthesis as disclosed by Lukas et al. (Lukas et al., 1981) and by references as cited therein. Temporary N-amino group protection is afforded by the 9-fluorenylmethyloxycarbonyl (Fmoc) group. Repetitive cleavage of this highly base-labile protecting group is done using 20% piperidine in N, N-dimethylformamide Side-chain functionalities may be protected as their butyl ethers (in the case of serine threonine and tyrosine), butyl esters (in the case of glutamic acid and aspartic acid), butyloxycarbonyl derivative (in the case of lysine and histidine), trityl derivative (in the case of cysteine) and 4-methoxy-2,3,6-trimethylbenzenesulphonyl derivative (in the case of arginine). Where glutamine or asparagine are C-terminal residues, use is made of the 4,4'-dimethoxybenzhydryl group for protection of the side chain amido functionalities. The solid-phase support is based on a polydimethyl-acrylamide polymer constituted from the three monomers dimethylacrylamide (backbone-monomer), bisacryloylethylene diamine (cross linker) and acryloylsarcosine methyl ester (functionalizing agent). The peptide-to-resin cleavable linked agent used is the acid-labile 4-hydroxymethyl-phenoxyacetic acid derivative. All amino acid derivatives are added as their preformed symmetrical anhydride derivatives with the exception of asparagine and glutamine, which are added using a reversed N, N-dicyclohexyl-carbodiimide/1hydroxybenzotriazole mediated coupling procedure. All coupling and deprotection reactions are monitored using ninhydrin, trinitrobenzene sulphonic acid or isotin test procedures. Upon completion of synthesis, peptides are cleaved from the resin support with concomitant removal of side-chain protecting groups by treatment with 95% trifluoroacetic acid containing a 50% scavenger mix. Scavengers commonly used include ethanedithiol, phenol, anisole and water, the exact choice depending on the constituent amino acids of the peptide being synthesized. Also a combination of solid phase and solution phase methodologies for the synthesis of peptides is possible (see, for example, (Bruckdorfer et al., 2004), and the references as cited therein).

Trifluoroacetic acid is removed by evaporation in vacuo, with subsequent trituration with diethyl ether affording the crude peptide. Any scavengers present are removed by a simple extraction procedure which on lyophilization of the aqueous phase affords the crude peptide free of scavengers. Reagents for peptide synthesis are generally available from e.g. Calbiochem-Novabiochem (Nottingham, UK).

Purification may be performed by any one, or a combination of, techniques such as re-crystallization, size exclusion chromatography, ion-exchange chromatography, hydrophobic interaction chromatography and (usually) reverse-phase high performance liquid chromatography using e.g. acetonitrile/water gradient separation.

Analysis of peptides may be carried out using thin layer chromatography, electrophoresis, in particular capillary electrophoresis, solid phase extraction (CSPE), reverse-phase high performance liquid chromatography, amino-acid analysis after acid hydrolysis and by fast atom bombardment (FAB) mass spectrometric analysis, as well as MALDI and ESI-Q-TOF mass spectrometric analysis.

For the identification of peptides of the present invention, a database of RNA expression data (Lonsdale, 2013) from about 3000 normal (healthy) tissue samples was screened for genes with near-absent expression in vital organ systems, and low expression in other important organ systems. Then, cancer-associated peptides derived from the protein products of these genes were identified by mass spectrometry using the XPRESIDENT™ platform as described herein.

In order to select over-presented peptides, a presentation profile was calculated showing the median sample presentation as well as replicate variation. The profile juxtaposes samples of the tumor entity of interest to a baseline of normal tissue samples. Each of these profiles can then be consolidated into an over-presentation score by calculating the p-value of a Linear Mixed-Effects Model (Pinheiro et al., 2015) adjusting for multiple testing by False Discovery Rate (Benjamini and Hochberg, 1995) (cf. Example 1).

For the identification and relative quantitation of HLA ligands by mass spectrometry, HLA molecules from shock-frozen tissue samples were purified and HLA-associated peptides were isolated. The isolated peptides were separated and sequences were identified by online nano-electrospray-ionization (nanoESI) liquid chromatography-mass spectrometry (LC-MS) experiments. The resulting peptide sequences were verified by comparison of the fragmentation pattern of natural tumor-associated peptides (TUMAPs) recorded from cancer samples (N=377 A*02-positive samples from 370 donors, N=204 A*24-positive samples) with the fragmentation patterns of corresponding synthetic reference peptides of identical sequences. Since the peptides were directly identified as ligands of HLA molecules of primary tumors, these results provide direct evidence for the natural processing and presentation of the identified peptides on primary cancer tissue obtained from 574 cancer patients.

The discovery pipeline XPRESIDENT® v2.1 (see, for example, US 2013-0096016, which is hereby incorporated by reference in its entirety) allows the identification and selection of relevant over-presented peptide vaccine candidates based on direct relative quantitation of HLA-restricted peptide levels on cancer tissues in comparison to several different non-cancerous tissues and organs. This was achieved by the development of label-free differential quantitation using the acquired LC-MS data processed by a proprietary data analysis pipeline, combining algorithms for sequence identification, spectral clustering, ion counting, retention time alignment, charge state deconvolution and normalization.

Presentation levels including error estimates for each peptide and sample were established. Peptides exclusively presented on tumor tissue and peptides over-presented in tumor versus non-cancerous tissues and organs have been identified.

HLA-peptide complexes from tissue samples were purified and HLA-associated peptides were isolated and analyzed by LC-MS (see examples). All TUMAPs contained in the present application were identified with this approach on primary cancer samples, confirming their presentation on primary glioblastoma, breast cancer, colorectal cancer, renal cell carcinoma, chronic lymphocytic leukemia, hepatocellular carcinoma, non-small cell and small cell lung cancer, Non-Hodgkin lymphoma, acute myeloid leukemia, ovarian cancer, pancreatic cancer, prostate cancer, esophageal cancer including cancer of the gastric-esophageal junction, gallbladder cancer and cholangiocarcinoma, melanoma, gastric cancer, testis cancer, urinary bladder cancer, or uterine cancer.

TUMAPs as identified on multiple cancer and normal tissues were quantified using ion-counting of label-free LC-MS data. The method assumes that LC-MS signal areas of a peptide correlate with its abundance in the sample. All quantitative signals of a peptide in various LC-MS experiments were normalized based on central tendency, averaged per sample and merged into a bar plot, called presentation profile. The presentation profile consolidates different analysis methods like protein database search, spectral clustering, charge state deconvolution (decharging) and retention time alignment and normalization.

Furthermore, the discovery pipeline XPRESIDENT® v2.1 allows the direct absolute quantitation of MHC-, preferably HLA-restricted, peptide levels on cancer or other infected tissues. Briefly, the total cell count was calculated from the total DNA content of the analyzed tissue sample. The total peptide amount for a TUMAP in a tissue sample was measured by nanoLC-MS/MS as the ratio of the natural TUMAP and a known amount of an isotope-labeled version of the TUMAP, the so-called internal standard. The efficiency of TUMAP isolation was determined by spiking peptide:MHC complexes of all selected TUMAPs into the tissue lysate at the earliest possible point of the TUMAP isolation procedure and their detection by nanoLC-MS/MS following completion of the peptide isolation procedure. The total cell count and the amount of total peptide were calculated from triplicate measurements per tissue sample. The peptide-specific isolation efficiencies were calculated as an average from 10 spike experiments each measured as a triplicate (see Example 6 and Table 14).

This combined analysis of RNA expression and mass spectrometry data resulted in the 417 peptides of the present invention.

The present invention provides peptides that are useful in treating cancers/tumors, preferably glioblastoma, breast cancer, colorectal cancer, renal cell carcinoma, chronic lymphocytic leukemia, hepatocellular carcinoma, non-small cell and small cell lung cancer, Non-Hodgkin lymphoma, acute myeloid leukemia, ovarian cancer, pancreatic cancer, prostate cancer, esophageal cancer including cancer of the gastric-esophageal junction, gallbladder cancer and cholangiocarcinoma, melanoma, gastric cancer, testis cancer, urinary bladder cancer, head and neck squamous cell carcinoma, and uterine cancer that over- or exclusively present the peptides of the invention. These peptides were shown by mass spectrometry to be naturally presented by HLA molecules on primary human cancer samples.

Many of the source gene/proteins (also designated "full-length proteins" or "underlying proteins") from which the peptides are derived were shown to be highly over-expressed in cancer compared with normal tissues—"normal tissues" in relation to this invention shall mean either healthy cells or tissue derived from the same organ as the tumor, or other normal tissue cells, demonstrating a high degree of tumor association of the source genes (see Example 2). Moreover, the peptides themselves are strongly over-presented on tumor tissue—"tumor tissue" in relation to this invention shall mean a sample from a patient suffering from cancer, but not on normal tissues (see, e.g., Example 1).

HLA-bound peptides can be recognized by the immune system, specifically T lymphocytes. T cells can destroy the cells presenting the recognized HLA/peptide complex, e.g. glioblastoma, breast cancer, colorectal cancer, renal cell carcinoma, chronic lymphocytic leukemia, hepatocellular carcinoma, non-small cell and small cell lung cancer, Non-Hodgkin lymphoma, acute myeloid leukemia, ovarian cancer, pancreatic cancer, prostate cancer, esophageal cancer including cancer of the gastric-esophageal junction, gallbladder cancer and cholangiocarcinoma, melanoma, gastric cancer, testis cancer, urinary bladder cancer, head and neck squamous cell carcinoma, or uterine cancer cells presenting the derived peptides.

The peptides of the present invention have been shown to be capable of stimulating T cell responses and/or are overpresented and thus can be used for the production of antibodies and/or TCRs, such as soluble TCRs, according to the present invention (see Example 3). Furthermore, the peptides when complexed with the respective MHC can be used for the production of antibodies and/or TCRs, in particular sTCRs, according to the present invention, as well. Respective methods are well known to the person of skill, and can be found in the respective literature as well. Thus, the peptides of the present invention are useful for generating an immune response in a patient by which tumor cells can be destroyed. An immune response in a patient can be induced by direct administration of the described peptides or suitable precursor substances (e.g. elongated peptides, proteins, or nucleic acids encoding these peptides) to the patient, ideally in combination with an agent enhancing the immunogenicity (i.e. an adjuvant). The immune response originating from such a therapeutic vaccination can be expected to be highly specific against tumor cells because the target peptides of the present invention are not presented on normal tissues in comparable copy numbers, preventing the risk of undesired autoimmune reactions against normal cells in the patient.

The present description further relates to T-cell receptors (TCRs) comprising an alpha chain and a beta chain ("alpha/beta TCRs"). Also provided are peptides capable of binding to TCRs and antibodies when presented by an MHC molecule. The present description also relates to nucleic acids, vectors and host cells for expressing TCRs and peptides of the present description; and methods of using the same.

The term "T-cell receptor" (abbreviated TCR) refers to a heterodimeric molecule comprising an alpha polypeptide chain (alpha chain) and a beta polypeptide chain (beta chain), wherein the heterodimeric receptor is capable of binding to a peptide antigen presented by an HLA molecule. The term also includes so-called gamma/delta TCRs.

In one embodiment the description provides a method of producing a TCR as described herein, the method comprising culturing a host cell capable of expressing the TCR under conditions suitable to promote expression of the TCR.

The description in another aspect relates to methods according to the description, wherein the antigen is loaded onto class I or II MHC molecules expressed on the surface of a suitable antigen-presenting cell or artificial antigen-presenting cell by contacting a sufficient amount of the antigen with an antigen-presenting cell or the antigen is loaded onto class I or II MHC tetramers by tetramerizing the antigen/class I or II MHC complex monomers.

The alpha and beta chains of alpha/beta TCR's, and the gamma and delta chains of gamma/delta TCRs, are generally regarded as each having two "domains", namely variable and constant domains. The variable domain consists of a concatenation of variable region (V), and joining region (J). The variable domain may also include a leader region (L). Beta and delta chains may also include a diversity region (D). The alpha and beta constant domains may also include C-terminal transmembrane (TM) domains that anchor the alpha and beta chains to the cell membrane.

With respect to gamma/delta TCRs, the term "TCR gamma variable domain" as used herein refers to the concatenation of the TCR gamma V (TRGV) region without leader region (L), and the TCR gamma J (TRGJ) region, and the term TCR gamma constant domain refers to the extracellular TRGC region, or to a C-terminal truncated TRGC sequence. Likewise the term "TCR delta variable domain" refers to the concatenation of the TCR delta V (TRDV) region without leader region (L) and the TCR delta D/J (TRDD/TRDJ) region, and the term "TCR delta constant domain" refers to the extracellular TRDC region, or to a C-terminal truncated TRDC sequence.

TCRs of the present description preferably bind to a peptide-HLA molecule complex with a binding affinity (KD) of about 100 μM or less, about 50 μM or less, about 25 μM or less, or about 10 μM or less. More preferred are high affinity TCRs having binding affinities of about 1 μM or less, about 100 nM or less, about 50 nM or less, about 25 nM or less. Non-limiting examples of preferred binding affinity ranges for TCRs of the present invention include about 1 nM to about 10 nM; about 10 nM to about 20 nM; about 20 nM to about 30 nM; about 30 nM to about 40 nM; about 40 nM to about 50 nM; about 50 nM to about 60 nM; about 60 nM to about 70 nM; about 70 nM to about 80 nM; about 80 nM to about 90 nM; and about 90 nM to about 100 nM.

As used herein in connect with TCRs of the present description, "specific binding" and grammatical variants thereof are used to mean a TCR having a binding affinity (KD) for a peptide-HLA molecule complex of 100 μM or less.

Alpha/beta heterodimeric TCRs of the present description may have an introduced disulfide bond between their constant domains. Preferred TCRs of this type include those which have a TRAC constant domain sequence and a TRBC1 or TRBC2 constant domain sequence except that Thr 48 of TRAC and Ser 57 of TRBC1 or TRBC2 are replaced by cysteine residues, the said cysteines forming a disulfide bond between the TRAC constant domain sequence and the TRBC1 or TRBC2 constant domain sequence of the TCR.

With or without the introduced inter-chain bond mentioned above, alpha/beta hetero-dimeric TCRs of the present description may have a TRAC constant domain sequence and a TRBC1 or TRBC2 constant domain sequence, and the TRAC constant domain sequence and the TRBC1 or TRBC2 constant domain sequence of the TCR may be linked by the native disulfide bond between Cys4 of exon 2 of TRAC and Cys2 of exon 2 of TRBC1 or TRBC2.

TCRs of the present description may comprise a detectable label selected from the group consisting of a radionuclide, a fluorophore and biotin. TCRs of the present description may be conjugated to a therapeutically active agent, such as a radionuclide, a chemotherapeutic agent, or a toxin.

In an embodiment, a TCR of the present description having at least one mutation in the alpha chain and/or having at least one mutation in the beta chain has modified glycosylation compared to the unmutated TCR.

In an embodiment, a TCR comprising at least one mutation in the TCR alpha chain and/or TCR beta chain has a binding affinity for, and/or a binding half-life for, an peptide-HLA molecule complex, which is at least double that of a TCR comprising the unmutated TCR alpha chain and/or unmutated TCR beta chain. Affinity-enhancement of tumor-specific TCRs, and its exploitation, relies on the existence of a window for optimal TCR affinities. The existence of such a window is based on observations that TCRs specific for HLA-A2-restricted pathogens have KD values that are generally about 10-fold lower when compared to TCRs specific for HLA-A2-restricted tumor-associated self-antigens. It is now known, although tumor antigens have the potential to be immunogenic, because tumors arise from the individual's own cells only mutated proteins or proteins with altered translational processing will be seen as foreign by the immune system. Antigens that are upregulated or overexpressed (so called self-antigens) will not necessarily induce a functional immune response against the tumor: T-cells expressing TCRs that are highly reactive to these antigens will have been negatively selected within the thymus in a process known as central tolerance, meaning that only T-cells with low-affinity TCRs for self-antigens remain. Therefore, affinity of TCRs or variants of the present description to the peptides according to the invention can be enhanced by methods well known in the art.

The present description further relates to a method of identifying and isolating a TCR according to the present description, said method comprising incubating PBMCs from HLA-A*02-negative healthy donors with A2/peptide monomers, incubating the PBMCs with tetramer-phycoerythrin (PE) and isolating the high avidity T-cells by fluo-rescence activated cell sorting (FACS)-Calibur analysis.

The present description further relates to a method of identifying and isolating a TCR according to the present description, said method comprising obtaining a transgenic mouse with the entire human TCRαβ gene loci (1.1 and 0.7 Mb), whose T-cells express a diverse human TCR repertoire that compensates for mouse TCR deficiency, immunizing the mouse with peptide of interest, incubating PBMCs obtained from the transgenic mice with tetramer-phycoerythrin (PE), and isolating the high avidity T-cells by fluorescence activated cell sorting (FACS)—Calibur analysis.

In one aspect, to obtain T-cells expressing TCRs of the present description, nucleic acids encoding TCR-alpha and/or TCR-beta chains of the present description are cloned into expression vectors, such as gamma retrovirus or lentivirus. The recombinant viruses are generated and then tested for functionality, such as antigen specificity and functional avidity. An aliquot of the final product is then used to transduce the target T-cell population (generally purified from patient PBMCs), which is expanded before infusion into the patient. In another aspect, to obtain T-cells expressing TCRs of the present description, TCR RNAs are synthesized by techniques known in the art, e.g., in vitro transcription sys-tems. The in vitro-synthesized TCR RNAs are then introduced into primary CD8+ T-cells obtained from healthy donors by electroporation to re-express tumor specific TCR-alpha and/or TCR-beta chains.

To increase the expression, nucleic acids encoding TCRs of the present description may be operably linked to strong promoters, such as retroviral long terminal repeats (LTRs), cytomegalovirus (CMV), murine stem cell virus (MSCV) U3, phosphoglycerate kinase (PGK), β-actin, ubiquitin, and a simian virus 40 (SV40)/CD43 composite promoter, elongation factor (EF)-1a and the spleen focus-forming virus (SFFV) promoter. In a preferred embodiment, the promoter is heterologous to the nucleic acid being expressed. In addition to strong promoters, TCR expression cassettes of the present description may contain additional elements that can enhance transgene expression, including a central polypurine tract (cPPT), which promotes the nuclear translocation of lentiviral constructs (Follenzi et al., 2000), and the woodchuck hepatitis virus posttranscriptional regulatory element (wPRE), which increases the level of transgene expression by increasing RNA stability (Zufferey et al., 1999).

The alpha and beta chains of a TCR of the present invention may be encoded by nucleic acids located in separate vectors, or may be encoded by polynucleotides located in the same vector.

Achieving high-level TCR surface expression requires that both the TCR-alpha and TCR-beta chains of the introduced TCR be transcribed at high levels. To do so, the TCR-alpha and TCR-beta chains of the present description may be cloned into bi-cistronic constructs in a single vector, which has been shown to be capable of over-coming this obstacle. The use of a viral intraribosomal entry site (IRES) between the TCR-alpha and TCR-beta chains results in the coordinated expression of both chains, because the TCR-alpha and TCR-beta chains are generated from a single transcript that is broken into two proteins during translation, ensuring that an equal molar ratio of TCR-alpha and TCR-beta chains are produced. (Schmitt et al. 2009).

Nucleic acids encoding TCRs of the present description may be codon optimized to increase expression from a host cell. Redundancy in the genetic code allows some amino acids to be encoded by more than one codon, but certain codons are less "op-timal" than others because of the relative availability of matching tRNAs as well as other factors (Gustafsson et al., 2004). Modifying the TCR-alpha and TCR-beta gene sequences such that each amino acid is encoded by the optimal codon for mammalian gene expression, as well as eliminating mRNA instability motifs or cryptic splice sites, has been shown to significantly enhance TCR-alpha and TCR-beta gene expression (Scholten et al., 2006).

Furthermore, mispairing between the introduced and endogenous TCR chains may result in the acquisition of specificities that pose a significant risk for autoimmunity. For example, the formation of mixed TCR dimers may reduce the number of CD3 molecules available to form properly paired TCR complexes, and therefore can significantly decrease the functional avidity of the cells expressing the introduced TCR (Kuball et al., 2007).

To reduce mispairing, the C-terminus domain of the introduced TCR chains of the present description may be modified in order to promote interchain affinity, while decreasing the ability of the introduced chains to pair with the endogenous TCR. These strategies may include replacing the human TCR-alpha and TCR-beta C-terminus domains with their murine counterparts (murinized C-terminus domain); generating a second interchain disulfide bond in the C-terminus domain by introducing a second cysteine residue into both the TCR-alpha and TCR-beta chains of the introduced TCR (cysteine modification); swapping interacting residues in the TCR-alpha and TCR-beta chain C-terminus domains ("knob-in-hole"); and fusing the variable domains of the TCR-alpha and TCR-beta chains directly to CD3ζ (CD3ζ fusion). (Schmitt et al. 2009).

In an embodiment, a host cell is engineered to express a TCR of the present description. In preferred embodiments, the host cell is a human T-cell or T-cell progenitor. In some embodiments the T-cell or T-cell progenitor is obtained from a cancer patient. In other embodiments the T-cell or T-cell progenitor is obtained from a healthy donor. Host cells of the present description can be allogeneic or autologous with respect to a patient to be treated. In one embodiment, the host is a gamma/delta T-cell transformed to express an alpha/beta TCR.

A "pharmaceutical composition" is a composition suitable for administration to a human being in a medical setting. Preferably, a pharmaceutical composition is sterile and produced according to GMP guidelines.

The pharmaceutical compositions comprise the peptides either in the free form or in the form of a pharmaceutically acceptable salt (see also above). As used herein, "a pharmaceutically acceptable salt" refers to a derivative of the disclosed peptides wherein the peptide is modified by making acid or base salts of the agent. For example, acid salts are prepared from the free base (typically wherein the neutral form of the drug has a neutral —NH2 group) involving reaction with a suitable acid. Suitable acids for preparing acid salts include both organic acids, e.g., acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methane sulfonic acid, ethane sulfonic acid, p-toluenesulfonic acid, salicylic acid, and the like, as well as inorganic acids, e.g., hydrochloric acid, hydrobromic acid, sulfuric acid, nitric acid phosphoric acid and the like. Conversely, preparation of basic salts of acid moieties which may be present on a peptide are prepared using a pharmaceutically acceptable base such as sodium hydroxide, potassium hydroxide, ammonium hydroxide, calcium hydroxide, trimethylamine or the like.

In an especially preferred embodiment, the pharmaceutical compositions comprise the peptides as salts of acetic acid (acetates), trifluoro acetates or hydrochloric acid (chlorides).

Preferably, the medicament of the present invention is an immunotherapeutic, such as a vaccine. It may be administered directly into the patient, into the affected organ or systemically i.d., i.m., s.c., i.p. and i.v., or applied ex vivo to cells derived from the patient or a human cell line which are subsequently administered to the patient, or used in vitro to select a subpopulation of immune cells derived from the patient, which are then re-administered to the patient. If the nucleic acid is administered to cells in vitro, it may be useful for the cells to be transfected so as to co-express immune-stimulating cytokines, such as interleukin-2. The peptide may be substantially pure, or combined with an immune-stimulating adjuvant (see below) or used in combination with immune-stimulatory cytokines, or be administered with a suitable delivery system, for example liposomes. The peptide may also be conjugated to a suitable carrier such as keyhole limpet haemocyanin (KLH) or mannan (see WO 95/18145 and (Longenecker et al., 1993)). The peptide may also be tagged, may be a fusion protein, or may be a hybrid molecule. The peptides whose sequence is given in the present invention are expected to stimulate CD4 or CD8 T cells. However, stimulation of CD8 T cells is more efficient in the presence of help provided by CD4 T-helper cells. Thus, for MHC Class I epitopes that stimulate CD8 T cells the fusion partner or sections of a hybrid molecule suitably provide epitopes which stimulate CD4-positive T cells. CD4- and CD8-stimulating epitopes are well known in the art and include those identified in the present invention.

In one aspect, the vaccine comprises at least one peptide having the amino acid sequence set forth SEQ ID No. 1 to SEQ ID No. 388, and at least one additional peptide, preferably two to 50, more preferably two to 25, even more preferably two to 20 and most preferably two, three, four, five, six, seven, eight, nine, ten, eleven, twelve, thirteen, fourteen, fifteen, sixteen, seventeen or eighteen peptides. The peptide(s) may be derived from one or more specific TAAs and may bind to MHC class I molecules.

A further aspect of the invention provides a nucleic acid (for example a polynucleotide) encoding a peptide or peptide variant of the invention. The polynucleotide may be, for example, DNA, cDNA, PNA, RNA or combinations thereof, either single- and/or double-stranded, or native or stabilized forms of polynucleotides, such as, for example, polynucleotides with a phosphorothioate backbone and it may or may not contain introns so long as it codes for the peptide. Of course, only peptides that contain naturally occurring amino acid residues joined by naturally occurring peptide bonds are encodable by a polynucleotide. A still further aspect of the invention provides an expression vector capable of expressing a polypeptide according to the invention.

A variety of methods have been developed to link polynucleotides, especially DNA, to vectors for example via complementary cohesive termini. For instance, complementary homopolymer tracts can be added to the DNA segment to be inserted to the vector DNA. The vector and DNA segment are then joined by hydrogen bonding between the complementary homopolymeric tails to form recombinant DNA molecules.

Synthetic linkers containing one or more restriction sites provide an alternative method of joining the DNA segment to vectors. Synthetic linkers containing a variety of restriction endonuclease sites are commercially available from a number of sources including International Biotechnologies Inc. New Haven, CN, USA.

A desirable method of modifying the DNA encoding the polypeptide of the invention employs the polymerase chain reaction as disclosed by Saiki R K, et al. (Saiki et al., 1988). This method may be used for introducing the DNA into a suitable vector, for example by engineering in suitable restriction sites, or it may be used to modify the DNA in other useful ways as is known in the art. If viral vectors are used, pox- or adenovirus vectors are preferred.

The DNA (or in the case of retroviral vectors, RNA) may then be expressed in a suitable host to produce a polypeptide comprising the peptide or variant of the invention. Thus, the DNA encoding the peptide or variant of the invention may be used in accordance with known techniques, appropriately modified in view of the teachings contained herein, to construct an expression vector, which is then used to transform an appropriate host cell for the expression and production of the polypeptide of the invention. Such techniques include those disclosed, for example, in U.S. Pat. Nos. 4,440,859, 4,530,901, 4,582,800, 4,677,063, 4,678,751, 4,704,362, 4,710,463, 4,757,006, 4,766,075, and 4,810,648.

The DNA (or in the case of retroviral vectors, RNA) encoding the polypeptide constituting the compound of the invention may be joined to a wide variety of other DNA sequences for introduction into an appropriate host. The companion DNA will depend upon the nature of the host, the manner of the introduction of the DNA into the host, and whether episomal maintenance or integration is desired.

Generally, the DNA is inserted into an expression vector, such as a plasmid, in proper orientation and correct reading frame for expression. If necessary, the DNA may be linked to the appropriate transcriptional and translational regulatory control nucleotide sequences recognized by the desired host, although such controls are generally available in the expression vector. The vector is then introduced into the host through standard techniques. Generally, not all of the hosts will be transformed by the vector. Therefore, it will be necessary to select for transformed host cells. One selection technique involves incorporating into the expression vector a DNA sequence, with any necessary control elements, that codes for a selectable trait in the transformed cell, such as antibiotic resistance.

Alternatively, the gene for such selectable trait can be on another vector, which is used to co-transform the desired host cell.

Host cells that have been transformed by the recombinant DNA of the invention are then cultured for a sufficient time and under appropriate conditions known to those skilled in the art in view of the teachings disclosed herein to permit the expression of the polypeptide, which can then be recovered.

Many expression systems are known, including bacteria (for example *E. coli* and *Bacillus subtilis*), yeasts (for example *Saccharomyces cerevisiae*), filamentous fungi (for example *Aspergillus* spec.), plant cells, animal cells and insect cells. Preferably, the system can be mammalian cells such as CHO cells available from the ATCC Cell Biology Collection.

A typical mammalian cell vector plasmid for constitutive expression comprises the CMV or SV40 promoter with a suitable poly A tail and a resistance marker, such as neomycin. One example is pSVL available from Pharmacia, Piscataway, NJ, USA. An example of an inducible mammalian expression vector is pMSG, also available from Pharmacia. Useful yeast plasmid vectors are pRS403-406 and pRS413-416 and are generally available from Stratagene Cloning Systems, La Jolla, CA 92037, USA. Plasmids pRS403, pRS404, pRS405 and pRS406 are Yeast Integrating plasmids (YIps) and incorporate the yeast selectable markers HIS3, TRP1, LEU2 and URA3. Plasmids pRS413-416 are Yeast Centromere plasmids (Ycps). CMV promoter-based vectors (for example from Sigma-Aldrich) provide transient or stable expression, cytoplasmic expression or secretion, and N-terminal or C-terminal tagging in various combinations of FLAG, 3×FLAG, c-myc or MAT. These fusion proteins allow for detection, purification and analysis of recombinant protein. Dual-tagged fusions provide flexibility in detection.

The strong human cytomegalovirus (CMV) promoter regulatory region drives constitutive protein expression levels as high as 1 mg/L in COS cells. For less potent cell lines, protein levels are typically ~0.1 mg/L. The presence of the SV40 replication origin will result in high levels of DNA replication in SV40 replication permissive COS cells. CMV vectors, for example, can contain the pMB1 (derivative of pBR322) origin for replication in bacterial cells, the b-lactamase gene for ampicillin resistance selection in bacteria, hGH polyA, and the f1 origin. Vectors containing the pre-pro-trypsin leader (PPT) sequence can direct the secretion of FLAG fusion proteins into the culture medium for purification using ANTI-FLAG antibodies, resins, and plates. Other vectors and expression systems are well known in the art for use with a variety of host cells.

In another embodiment two or more peptides or peptide variants of the invention are encoded and thus expressed in a successive order (similar to "beads on a string" constructs). In doing so, the peptides or peptide variants may be linked or fused together by stretches of linker amino acids, such as for example LLLLLL, or may be linked without any additional peptide(s) between them. These constructs can also be used for cancer therapy, and may induce immune responses both involving MHC I and MHC II.

The present invention also relates to a host cell transformed with a polynucleotide vector construct of the present invention. The host cell can be either prokaryotic or eukaryotic. Bacterial cells may be preferred prokaryotic host cells in some circumstances and typically are a strain of *E. coli* such as, for example, the *E. coli* strains DH5 available from Bethesda Research Laboratories Inc., Bethesda, MD, USA, and RR1 available from the American Type Culture Collection (ATCC) of Rockville, MD, USA (No ATCC 31343). Preferred eukaryotic host cells include yeast, insect and mammalian cells, preferably vertebrate cells such as those from a mouse, rat, monkey or human fibroblastic and colon cell lines. Yeast host cells include YPH499, YPH500 and YPH501, which are generally available from Stratagene Cloning Systems, La Jolla, CA 92037, USA. Preferred mammalian host cells include Chinese hamster ovary (CHO) cells available from the ATCC as CCL61, NIH Swiss mouse embryo cells NIH/3T3 available from the ATCC as CRL 1658, monkey kidney-derived COS-1 cells available from the ATCC as CRL 1650 and 293 cells which are human embryonic kidney cells. Preferred insect cells are Sf9 cells which can be transfected with baculovirus expression vectors. An overview regarding the choice of suitable host cells for expression can be found in, for example, the textbook of Paulina Balbás and Argelia Lorence "Methods in Molecular Biology Recombinant Gene Expression, Reviews and Protocols," Part One, Second Edition, ISBN 978-1-58829-262-9, and other literature known to the person of skill.

Transformation of appropriate cell hosts with a DNA construct of the present invention is accomplished by well-known methods that typically depend on the type of vector used. With regard to transformation of prokaryotic host cells, see, for example, Cohen et al. (Cohen et al., 1972) and (Green and Sambrook, 2012). Transformation of yeast cells is described in Sherman et al. (Sherman et al., 1986). The method of Beggs (Beggs, 1978) is also useful. With regard to vertebrate cells, reagents useful in transfecting such cells, for example calcium phosphate and DEAE-dextran or liposome formulations, are available from Stratagene Cloning Systems, or Life Technologies Inc., Gaithersburg, MD 20877, USA. Electroporation is also useful for transforming and/or transfecting cells and is well known in the art for transforming yeast cell, bacterial cells, insect cells and vertebrate cells.

Successfully transformed cells, i.e. cells that contain a DNA construct of the present invention, can be identified by well-known techniques such as PCR. Alternatively, the presence of the protein in the supernatant can be detected using antibodies.

It will be appreciated that certain host cells of the invention are useful in the preparation of the peptides of the invention, for example bacterial, yeast and insect cells. However, other host cells may be useful in certain therapeutic methods. For example, antigen-presenting cells, such as dendritic cells, may usefully be used to express the peptides of the invention such that they may be loaded into appropriate MHC molecules. Thus, the current invention provides a host cell comprising a nucleic acid or an expression vector according to the invention.

In a preferred embodiment the host cell is an antigen presenting cell, in particular a dendritic cell or antigen presenting cell. APCs loaded with a recombinant fusion protein containing prostatic acid phosphatase (PAP) were approved by the U.S. Food and Drug Administration (FDA) on Apr. 29, 2010, to treat asymptomatic or minimally symptomatic metastatic HRPC (Sipuleucel-T) (Rini et al., 2006; Small et al., 2006).

A further aspect of the invention provides a method of producing a peptide or its variant, the method comprising culturing a host cell and isolating the peptide from the host cell or its culture medium.

In another embodiment the peptide, the nucleic acid or the expression vector of the invention are used in medicine. For example, the peptide or its variant may be prepared for intravenous (i.v.) injection, sub-cutaneous (s.c.) injection, intradermal (i.d.) injection, intraperitoneal (i.p.) injection, intramuscular (i.m.) injection. Preferred methods of peptide injection include s.c., i.d., i.p., i.m., and i.v. Preferred methods of DNA injection include i.d., i.m., s.c., i.p. and i.v. Doses of e.g. between 50 µg and 1.5 mg, preferably 125 µg to 500 µg, of peptide or DNA may be given and will depend on the respective peptide or DNA. Dosages of this range were successfully used in previous trials (Walter et al., 2012).

The polynucleotide used for active vaccination may be substantially pure, or contained in a suitable vector or delivery system. The nucleic acid may be DNA, cDNA, PNA, RNA or a combination thereof. Methods for designing and introducing such a nucleic acid are well known in the art. An overview is provided by e.g. Teufel et al. (Teufel et al., 2005). Polynucleotide vaccines are easy to prepare, but the mode of action of these vectors in inducing an immune response is not fully understood. Suitable vectors and delivery systems include viral DNA and/or RNA, such as systems based on adenovirus, vaccinia virus, retroviruses, herpes virus, adeno-associated virus or hybrids containing elements of more than one virus. Non-viral delivery systems include cationic lipids and cationic polymers and are well known in the art of DNA delivery. Physical delivery, such as via a "gene-gun", may also be used. The peptide or peptides encoded by the nucleic acid may be a fusion protein, for example with an epitope that stimulates T cells for the respective opposite CDR as noted above.

The medicament of the invention may also include one or more adjuvants. Adjuvants are substances that non-specifically enhance or potentiate the immune response (e.g., immune responses mediated by CD8-positive T cells and helper-T (TH) cells to an antigen, and would thus be considered useful in the medicament of the present invention. Suitable adjuvants include, but are not limited to, 1018 ISS, aluminum salts, AMPLIVAX®, AS15, BCG, CP-870, 893, CpG7909, CyaA, dSLIM, flagellin or TLR5 ligands derived from flagellin, FLT3 ligand, GM-CSF, IC30, IC31, Imiquimod (ALDARA®), resiquimod, ImuFact IMP321, Interleukins as IL-2, IL-13, IL-21, Interferon-alpha or -beta, or pegylated derivatives thereof, IS Patch, ISS, ISCOMA-TRIX, ISCOMs, JuvImmune®, LipoVac, MALP2, MF59, monophosphoryl lipid A, Montanide IMS 1312, Montanide ISA 206, Montanide ISA 50V, Montanide ISA-51, water-in-oil and oil-in-water emulsions, OK-432, OM-174, OM-197-MP-EC, ONTAK, OspA, PepTel® vector system, poly(lactid co-glycolid) [PLG]-based and dextran microparticles, talactoferrin SRL172, Virosomes and other Virus-like particles, YF-17D, VEGF trap, R848, beta-glucan, Pam3Cys, Aquila's QS21 stimulon, which is derived from saponin, mycobacterial extracts and synthetic bacterial cell wall mimics, and other proprietary adjuvants such as Ribi's Detox, Quil, or Superfos. Adjuvants such as Freund's or GM-CSF are preferred. Several immunological adjuvants (e.g., MF59) specific for dendritic cells and their preparation have been described previously (Allison and Krummel, 1995). Also cytokines may be used. Several cytokines have been directly linked to influencing dendritic cell migration to lymphoid tissues (e.g., TNF-), accelerating the maturation of dendritic cells into efficient antigen-presenting cells for T-lymphocytes (e.g., GM-CSF, IL-1 and IL-4) (U.S. Pat. No. 5,849,589, specifically incorporated herein by reference in its entirety) and acting as immunoadjuvants (e.g., IL-12, IL-15, IL-23, IL-7, IFN-alpha. IFN-beta) (Gabrilovich et al., 1996).

CpG immunostimulatory oligonucleotides have also been reported to enhance the effects of adjuvants in a vaccine setting. Without being bound by theory, CpG oligonucleotides act by activating the innate (non-adaptive) immune system via Toll-like receptors (TLR), mainly TLR9. CpG triggered TLR9 activation enhances antigen-specific humoral and cellular responses to a wide variety of antigens, including peptide or protein antigens, live or killed viruses, dendritic cell vaccines, autologous cellular vaccines and polysaccharide conjugates in both prophylactic and therapeutic vaccines. More importantly it enhances dendritic cell maturation and differentiation, resulting in enhanced activation of TH1 cells and strong cytotoxic T-lymphocyte (CTL) generation, even in the absence of CD4 T cell help. The TH1 bias induced by TLR9 stimulation is maintained even in the presence of vaccine adjuvants such as alum or incomplete Freund's adjuvant (IFA) that normally promote a TH2 bias. CpG oligonucleotides show even greater adjuvant activity when formulated or co-administered with other adjuvants or in formulations such as microparticles, nanoparticles, lipid emulsions or similar formulations, which are especially necessary for inducing a strong response when the antigen is relatively weak. They also accelerate the immune response and enable the antigen doses to be reduced by approximately two orders of magnitude, with comparable antibody responses to the full-dose vaccine without CpG in some experiments (Krieg, 2006). U.S. Pat. No. 6,406,705 B1 describes the combined use of CpG oligonucleotides, non-nucleic acid adjuvants and an antigen to induce an antigen-specific immune response. A CpG TLR9 antagonist is dSLIM (double Stem Loop Immunomodulator) by Mologen (Berlin, Germany) which is a preferred component of the pharmaceutical composition of the present invention. Other TLR binding molecules such as RNA binding TLR 7, TLR 8 and/or TLR 9 may also be used.

Other examples for useful adjuvants include, but are not limited to chemically modified CpGs (e.g. CpR, Idera), dsRNA analogues such as Poly(I:C) and derivates thereof (e.g. AmpliGen®, Hiltonol®, poly-(ICLC), poly(IC-R), poly(I:C12U), non-CpG bacterial DNA or RNA as well as immunoactive small molecules and antibodies such as cyclophosphamide, sunitinib, Bevacizumab®, celebrex, NCX-4016, sildenafil, tadalafil, vardenafil, sorafenib, temozolomide, temsirolimus, XL-999, CP-547632, pazopanib, VEGF Trap, ZD2171, AZD2171, anti-CTLA4, other antibodies targeting key structures of the immune system (e.g. anti-CD40, anti-TGFbeta, anti-TNFalpha receptor) and SC58175, which may act therapeutically and/or as an adjuvant. The amounts and concentrations of adjuvants and additives useful in the context of the present invention can readily be determined by the skilled artisan without undue experimentation.

Preferred adjuvants are anti-CD40, imiquimod, resiquimod, GM-CSF, cyclophosphamide, sunitinib, bevacizumab, interferon-alpha, CpG oligonucleotides and derivates, poly-(I:C) and derivates, RNA, sildenafil, and particulate formulations with PLG or virosomes.

In a preferred embodiment, the pharmaceutical composition according to the invention the adjuvant is selected from the group consisting of colony-stimulating factors, such as Granulocyte Macrophage Colony Stimulating Factor (GM-CSF, sargramostim), cyclophosphamide, imiquimod, resiquimod, and interferon-alpha.

In a preferred embodiment, the pharmaceutical composition according to the invention the adjuvant is selected from the group consisting of colony-stimulating factors, such as Granulocyte Macrophage Colony Stimulating Factor (GM-CSF, sargramostim), cyclophosphamide, imiquimod and resiquimod. In a preferred embodiment of the pharmaceutical composition according to the invention, the adjuvant is cyclophosphamide, imiquimod or resiquimod. Even more preferred adjuvants are Montanide IMS 1312, Montanide ISA 206, Montanide ISA 50V, Montanide ISA-51, poly-ICLC (Hiltonol®) and anti-CD40 mAB, or combinations thereof.

This composition is used for parenteral administration, such as subcutaneous, intradermal, intramuscular or oral administration. For this, the peptides and optionally other molecules are dissolved or suspended in a pharmaceutically acceptable, preferably aqueous carrier. In addition, the composition can contain excipients, such as buffers, binding agents, blasting agents, diluents, flavors, lubricants, etc. The peptides can also be administered together with immune stimulating substances, such as cytokines. An extensive listing of excipients that can be used in such a composition, can be, for example, taken from A. Kibbe, Handbook of Pharmaceutical Excipients (Kibbe, 2000). The composition can be used for a prevention, prophylaxis and/or therapy of adenomatous or cancerous diseases. Exemplary formulations can be found in, for example, EP2112253.

It is important to realize that the immune response triggered by the vaccine according to the invention attacks the cancer in different cell-stages and different stages of development. Furthermore different cancer associated signaling pathways are attacked. This is an advantage over vaccines that address only one or few targets, which may cause the tumor to easily adapt to the attack (tumor escape). Furthermore, not all individual tumors express the same pattern of antigens. Therefore, a combination of several tumor-associated peptides ensures that every single tumor bears at least some of the targets. The composition is designed in such a way that each tumor is expected to express several of the antigens and cover several independent pathways necessary for tumor growth and maintenance. Thus, the vaccine can easily be used "off-the-shelf" for a larger patient population. This means that a pre-selection of patients to be treated with the vaccine can be restricted to HLA typing, does not require any additional biomarker assessments for antigen expression, but it is still ensured that several targets are simultaneously attacked by the induced immune response, which is important for efficacy (Bancherau et al., 2001; Walter et al., 2012).

As used herein, the term "scaffold" refers to a molecule that specifically binds to an (e.g. antigenic) determinant. In one embodiment, a scaffold is able to direct the entity to which it is attached (e.g. a (second) antigen binding moiety) to a target site, for example to a specific type of tumor cell or tumor stroma bearing the antigenic determinant (e.g. the complex of a peptide with MHC, according to the application at hand). In another embodiment a scaffold is able to activate signaling through its target antigen, for example a T cell receptor complex antigen. Scaffolds include but are not limited to antibodies and fragments thereof, antigen binding domains of an antibody, comprising an antibody heavy chain variable region and an antibody light chain variable region, binding proteins comprising at least one ankyrin repeat motif and single domain antigen binding (SDAB) molecules, aptamers, (soluble) TCRs and (modified) cells such as allogenic or autologous T cells. To assess whether a molecule is a scaffold binding to a target, binding assays can be performed.

"Specific" binding means that the scaffold binds the peptide-MHC-complex of interest better than other naturally occurring peptide-MHC-complexes, to an extent that a scaffold armed with an active molecule that is able to kill a cell bearing the specific target is not able to kill another cell without the specific target but presenting other peptide-MHC complex(es). Binding to other peptide-MHC complexes is irrelevant if the peptide of the cross-reactive peptide-MHC is not naturally occurring, i.e. not derived from the human HLA-peptidome. Tests to assess target cell killing are well known in the art. They should be performed using target cells (primary cells or cell lines) with unaltered peptide-MHC presentation, or cells loaded with peptides such that naturally occurring peptide-MHC levels are reached.

Each scaffold can comprise a labelling which provides that the bound scaffold can be detected by determining the presence or absence of a signal provided by the label. For example, the scaffold can be labelled with a fluorescent dye or any other applicable cellular marker molecule. Such marker molecules are well known in the art. For example a fluorescence-labelling, for example provided by a fluorescence dye, can provide a visualization of the bound aptamer by fluorescence or laser scanning microscopy or flow cytometry.

Each scaffold can be conjugated with a second active molecule such as for example IL-21, anti-CD3, anti-CD28.

For further information on polypeptide scaffolds see for example the background section of WO 2014/071978A1 and the references cited therein.

The present invention further relates to aptamers. Aptamers (see for example WO 2014/191359 and the literature as cited therein) are short single-stranded nucleic acid molecules, which can fold into defined three-dimensional structures and recognize specific target structures. They have appeared to be suitable alternatives for developing targeted therapies. Aptamers have been shown to selectively bind to a variety of complex targets with high affinity and specificity.

Aptamers recognizing cell surface located molecules have been identified within the past decade and provide means for developing diagnostic and therapeutic approaches. Since aptamers have been shown to possess almost no toxicity and immunogenicity they are promising candidates for biomedical applications. Indeed aptamers, for example prostate-specific membrane-antigen recognizing aptamers, have been successfully employed for targeted therapies and shown to be functional in xenograft in vivo models. Furthermore, aptamers recognizing specific tumor cell lines have been identified.

DNA aptamers can be selected to reveal broad-spectrum recognition properties for various cancer cells, and particularly those derived from solid tumors, while non-tumorigenic and primary healthy cells are not recognized. If the identified aptamers recognize not only a specific tumor sub-type but rather interact with a series of tumors, this renders the aptamers applicable as so-called broad-spectrum diagnostics and therapeutics.

Further, investigation of cell-binding behavior with flow cytometry showed that the aptamers revealed very good apparent affinities that are within the nanomolar range.

Aptamers are useful for diagnostic and therapeutic purposes. Further, it could be shown that some of the aptamers are taken up by tumor cells and thus can function as molecular vehicles for the targeted delivery of anti-cancer agents such as siRNA into tumor cells.

Aptamers can be selected against complex targets such as cells and tissues and complexes of the peptides comprising, preferably consisting of, a sequence according to any of SEQ ID NO 1 to SEQ ID NO 388, according to the invention at hand with the MHC molecule, using the cell-SELEX (Systematic Evolution of Ligands by Exponential enrichment) technique.

The peptides of the present invention can be used to generate and develop specific antibodies against MHC/peptide complexes. These can be used for therapy, targeting toxins or radioactive substances to the diseased tissue. Another use of these antibodies can be targeting radionuclides to the diseased tissue for imaging purposes such as PET. This use can help to detect small metastases or to determine the size and precise localization of diseased tissues.

Therefore, it is a further aspect of the invention to provide a method for producing a recombinant antibody specifically binding to a human major histocompatibility complex (MHC) class I or II being complexed with a HLA-restricted antigen, the method comprising immunizing a genetically engineered non-human mammal comprising cells expressing said human major histocompatibility complex (MHC) class I or II with a soluble form of a MHC class I or II molecule being complexed with said HLA-restricted antigen; isolating mRNA molecules from antibody producing cells of said non-human mammal; producing a phage display library displaying protein molecules encoded by said mRNA molecules; and isolating at least one phage from said phage display library, said at least one phage displaying said antibody specifically binding to said human major histocompatibility complex (MHC) class I or II being complexed with said HLA-restricted antigen.

It is a further aspect of the invention to provide an antibody that specifically binds to a human major histocompatibility complex (MHC) class I or II being complexed with a HLA-restricted antigen, wherein the antibody preferably is a polyclonal antibody, monoclonal antibody, bispecific antibody and/or a chimeric antibody.

Respective methods for producing such antibodies and single chain class I major histocompatibility complexes, as well as other tools for the production of these antibodies are disclosed in WO 03/068201, WO 2004/084798, WO 01/72768, WO 03/070752, and in publications (Cohen et al., 2003a; Cohen et al., 2003b; Denkberg et al., 2003), which for the purposes of the present invention are all explicitly incorporated by reference in their entireties.

Preferably, the antibody is binding with a binding affinity of below 20 nanomolar, preferably of below 10 nanomolar, to the complex, which is also regarded as "specific" in the context of the present invention.

The present invention relates to a peptide comprising a sequence that is selected from the group consisting of SEQ ID NO: 1 to SEQ ID NO: 388, or a variant thereof which is at least 88% homologous (preferably identical) to SEQ ID NO: 1 to SEQ ID NO: 388 or a variant thereof that induces T cells cross-reacting with said peptide, wherein said peptide is not the underlying full-length polypeptide.

The present invention further relates to a peptide comprising a sequence that is selected from the group consisting of SEQ ID NO: 1 to SEQ ID NO: 388 or a variant thereof which is at least 88% homologous (preferably identical) to SEQ ID NO: 1 to SEQ ID NO: 388, wherein said peptide or variant has an overall length of between 8 and 100, preferably between 8 and 30, and most preferred between 8 and 14 amino acids.

The present invention further relates to the peptides according to the invention that have the ability to bind to a molecule of the human major histocompatibility complex (MHC) class-I or -II.

The present invention further relates to the peptides according to the invention wherein the peptide consists or consists essentially of an amino acid sequence according to SEQ ID NO: 1 to SEQ ID NO: 388.

The present invention further relates to the peptides according to the invention, wherein the peptide is (chemically) modified and/or includes non-peptide bonds.

The present invention further relates to the peptides according to the invention, wherein the peptide is part of a fusion protein, in particular comprising N-terminal amino acids of the HLA-DR antigen-associated invariant chain (Ii), or wherein the peptide is fused to (or into) an antibody, such as, for example, an antibody that is specific for dendritic cells.

The present invention further relates to a nucleic acid, encoding the peptides according to the invention, provided that the peptide is not the complete (full) human protein.

The present invention further relates to the nucleic acid according to the invention that is DNA, cDNA, PNA, RNA or combinations thereof.

The present invention further relates to an expression vector capable of expressing or expressing a nucleic acid according to the present invention.

The present invention further relates to a peptide according to the present invention, a nucleic acid according to the present invention or an expression vector according to the present invention for use in medicine, in particular in the treatment of cancers such as glioblastoma, breast cancer, colorectal cancer, renal cell carcinoma, chronic lymphocytic leukemia, hepatocellular carcinoma, non-small cell and small cell lung cancer, Non-Hodgkin lymphoma, acute myeloid leukemia, ovarian cancer, pancreatic cancer, prostate cancer, esophageal cancer including cancer of the gastric-esophageal junction, gallbladder cancer and cholangio-carcinoma, melanoma, gastric cancer (GC), testis cancer (TC), urinary bladder cancer (UBC), head and neck squamous cell carcinoma (HNSCC), or uterine cancer (UEC).

The present invention further relates to a host cell comprising a nucleic acid according to the invention or an expression vector according to the invention.

The present invention further relates to the host cell according to the present invention that is an antigen presenting cell, and preferably a dendritic cell.

The present invention further relates to a method of producing a peptide according to the present invention, said method comprising culturing the host cell according to the present invention, and isolating the peptide from said host cell or its culture medium.

The present invention further relates to the method according to the present invention, wherein the antigen is loaded onto class I or II MHC molecules expressed on the surface of a suitable antigen-presenting cell by contacting a sufficient amount of the antigen with an antigen-presenting cell.

The present invention further relates to the method according to the invention, wherein the antigen-presenting cell comprises an expression vector capable of expressing said peptide containing SEQ ID NO: 1 to SEQ ID NO: 388 or said variant amino acid sequence.

The present invention further relates to activated T cells, produced by the method according to the present invention, wherein said T cells selectively recognizes a cell which aberrantly expresses a polypeptide comprising an amino acid sequence according to the present invention.

The present invention further relates to a method of killing target cells in a patient which target cells aberrantly express a polypeptide comprising any amino acid sequence according to the present invention, the method comprising administering to the patient an effective number of T cells as according to the present invention.

The present invention further relates to the use of any peptide described, a nucleic acid according to the present invention, an expression vector according to the present invention, a cell according to the present invention, or an activated cytotoxic T lymphocyte according to the present invention as a medicament or in the manufacture of a medicament. The present invention further relates to a use according to the present invention, wherein the medicament is active against cancer.

The present invention further relates to a use according to the invention, wherein the medicament is a vaccine. The present invention further relates to a use according to the invention, wherein the medicament is active against cancer.

The present invention further relates to a use according to the invention, wherein said cancer cells are solid or hematological tumor cells such as glioblastoma, breast cancer, colorectal cancer, renal cell carcinoma, chronic lymphocytic leukemia, hepatocellular carcinoma, non-small cell and small cell lung cancer, Non-Hodgkin lymphoma, acute myeloid leukemia, ovarian cancer, pancreatic cancer, prostate cancer, esophageal cancer including cancer of the gastric-esophageal junction, gallbladder cancer and cholangiocarcinoma, melanoma, gastric cancer, testis cancer, urinary bladder cancer, head and neck squamous cell carcinoma (HNSCC), or uterine cancer.

The present invention further relates to particular marker proteins and biomarkers based on the peptides according to the present invention, herein called "targets" that can be used in the diagnosis and/or prognosis of glioblastoma, breast cancer, colorectal cancer, renal cell carcinoma, chronic lymphocytic leukemia, hepatocellular carcinoma, non-small cell and small cell lung cancer, Non-Hodgkin lymphoma, acute myeloid leukemia, ovarian cancer, pancreatic cancer, prostate cancer, esophageal cancer including cancer of the gastric-esophageal junction, gallbladder cancer and cholangiocarcinoma, melanoma, gastric cancer, testis cancer, urinary bladder cancer, head and neck squamous cell carcinoma (HNSCC), or uterine cancer. The present invention also relates to the use of these novel targets for cancer treatment.

The term "antibody" or "antibodies" is used herein in a broad sense and includes both polyclonal and monoclonal antibodies. In addition to intact or "full" immunoglobulin molecules, also included in the term "antibodies" are fragments (e.g. CDRs, Fv, Fab and Fc fragments) or polymers of those immunoglobulin molecules and humanized versions of immunoglobulin molecules, as long as they exhibit any of the desired properties (e.g., specific binding of a glioblastoma, breast cancer, colorectal cancer, renal cell carcinoma, chronic lymphocytic leukemia, hepatocellular carcinoma, non-small cell and small cell lung cancer, Non-Hodgkin lymphoma, acute myeloid leukemia, ovarian cancer, pancreatic cancer, prostate cancer, esophageal cancer including cancer of the gastric-esophageal junction, gallbladder cancer and cholangiocarcinoma, melanoma, gastric cancer, testis cancer, urinary bladder cancer, head and neck squamous cell carcinoma (HNSCC), or uterine cancer marker (poly)peptide, delivery of a toxin to a cancer cell expressing a cancer marker gene at an increased level, and/or inhibiting the activity of a cancer marker polypeptide) according to the invention.

Whenever possible, the antibodies of the invention may be purchased from commercial sources. The antibodies of the invention may also be generated using well-known methods. The person of skill will understand that either full length glioblastoma, breast cancer, colorectal cancer, renal cell carcinoma, chronic lymphocytic leukemia, hepatocellular carcinoma, non-small cell and small cell lung cancer, Non-Hodgkin lymphoma, acute myeloid leukemia, ovarian cancer, pancreatic cancer, prostate cancer, esophageal cancer including cancer of the gastric-esophageal junction, gallbladder cancer and cholangiocarcinoma, melanoma, gastric cancer, testis cancer, urinary bladder cancer, head and neck squamous cell carcinoma (HNSCC), or uterine cancer marker polypeptides or fragments thereof may be used to generate the antibodies of the invention. A polypeptide to be used for generating an antibody of the invention may be partially or fully purified from a natural source, or may be produced using recombinant DNA techniques.

For example, a cDNA encoding a peptide according to the present invention, such as a peptide according to SEQ ID NO: 1 to SEQ ID NO: 388 polypeptide, or a variant or fragment thereof, can be expressed in prokaryotic cells (e.g., bacteria) or eukaryotic cells (e.g., yeast, insect, or mammalian cells), after which the recombinant protein can be purified and used to generate a monoclonal or polyclonal antibody preparation that specifically bind the marker polypeptide for above-mentioned cancers used to generate the antibody according to the invention.

One of skill in the art will realize that the generation of two or more different sets of monoclonal or polyclonal antibodies maximizes the likelihood of obtaining an antibody with the specificity and affinity required for its intended use (e.g., ELISA, immunohistochemistry, in vivo imaging, immunotoxin therapy). The antibodies are tested for their desired activity by known methods, in accordance with the purpose for which the antibodies are to be used (e.g., ELISA, immunohistochemistry, immunotherapy, etc.; for further guidance on the generation and testing of antibodies, see, e.g., Greenfield, 2014 (Greenfield, 2014)). For example, the antibodies may be tested in ELISA assays or, Western blots, immunohistochemical staining of formalin-fixed cancers or frozen tissue sections. After their initial in vitro characterization, antibodies intended for therapeutic or in vivo diagnostic use are tested according to known clinical testing methods.

The term "monoclonal antibody" as used herein refers to an antibody obtained from a substantially homogeneous population of antibodies, i.e.; the individual antibodies comprising the population are identical except for possible naturally occurring mutations that may be present in minor amounts. The monoclonal antibodies herein specifically include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired antagonistic activity (U.S. Pat. No. 4,816,567, which is hereby incorporated in its entirety).

Monoclonal antibodies of the invention may be prepared using hybridoma methods. In a hybridoma method, a mouse or other appropriate host animal is typically immunized with an immunizing agent to elicit lymphocytes that produce or are capable of producing antibodies that will specifically bind to the immunizing agent. Alternatively, the lymphocytes may be immunized in vitro.

The monoclonal antibodies may also be made by recombinant DNA methods, such as those described in U.S. Pat. No. 4,816,567. DNA encoding the monoclonal antibodies of the invention can be readily isolated and sequenced using conventional procedures (e.g., by using oligonucleotide probes that are capable of binding specifically to genes encoding the heavy and light chains of murine antibodies).

In vitro methods are also suitable for preparing monovalent antibodies. Digestion of antibodies to produce fragments thereof, particularly Fab fragments, can be accomplished using routine techniques known in the art. For instance, digestion can be performed using papain. Examples of papain digestion are described in WO 94/29348 and U.S. Pat. No. 4,342,566. Papain digestion of antibodies typically produces two identical antigen binding fragments, called Fab fragments, each with a single antigen binding site, and a residual Fc fragment. Pepsin treatment yields a F(ab')2 fragment and a pFc' fragment.

The antibody fragments, whether attached to other sequences or not, can also include insertions, deletions, substitutions, or other selected modifications of particular regions or specific amino acids residues, provided the activity of the fragment is not significantly altered or impaired compared to the non-modified antibody or antibody fragment. These modifications can provide for some additional property, such as to remove/add amino acids capable of disulfide bonding, to increase its bio-longevity, to alter its secretory characteristics, etc. In any case, the antibody fragment must possess a bioactive property, such as binding activity, regulation of binding at the binding domain, etc. Functional or active regions of the antibody may be identified by mutagenesis of a specific region of the protein, followed by expression and testing of the expressed polypeptide. Such methods are readily apparent to a skilled practitioner in the art and can include site-specific mutagenesis of the nucleic acid encoding the antibody fragment.

The antibodies of the invention may further comprise humanized antibodies or human antibodies. Humanized forms of non-human (e.g., murine) antibodies are chimeric immunoglobulins, immunoglobulin chains or fragments thereof (such as Fv, Fab, Fab' or other antigen-binding subsequences of antibodies) which contain minimal sequence derived from non-human immunoglobulin. Humanized antibodies include human immunoglobulins (recipient antibody) in which residues from a complementary determining region (CDR) of the recipient are replaced by residues from a CDR of a non-human species (donor antibody) such as mouse, rat or rabbit having the desired specificity, affinity and capacity. In some instances, Fv framework (FR) residues of the human immunoglobulin are replaced by corresponding non-human residues. Humanized antibodies may also comprise residues which are found neither in the recipient antibody nor in the imported CDR or framework sequences. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin.

Methods for humanizing non-human antibodies are well known in the art. Generally, a humanized antibody has one or more amino acid residues introduced into it from a source which is non-human. These non-human amino acid residues are often referred to as "import" residues, which are typically taken from an "import" variable domain. Humanization can be essentially performed by substituting rodent CDRs or CDR sequences for the corresponding sequences of a human antibody. Accordingly, such "humanized" antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

Transgenic animals (e.g., mice) that are capable, upon immunization, of producing a full repertoire of human antibodies in the absence of endogenous immunoglobulin production can be employed. For example, it has been described that the homozygous deletion of the antibody heavy chain joining region gene in chimeric and germ-line mutant mice results in complete inhibition of endogenous antibody production. Transfer of the human germ-line immunoglobulin gene array in such germ-line mutant mice will result in the production of human antibodies upon antigen challenge. Human antibodies can also be produced in phage display libraries.

Antibodies of the invention are preferably administered to a subject in a pharmaceutically acceptable carrier. Typically, an appropriate amount of a pharmaceutically-acceptable salt is used in the formulation to render the formulation isotonic. Examples of the pharmaceutic ally-acceptable carrier include saline, Ringer's solution and dextrose solution. The pH of the solution is preferably from about 5 to about 8, and more preferably from about 7 to about 7.5. Further carriers include sustained release preparations such as semipermeable matrices of solid hydrophobic polymers containing the antibody, which matrices are in the form of shaped articles, e.g., films, liposomes or microparticles. It will be apparent to those persons skilled in the art that certain carriers may be more preferable depending upon, for instance, the route of administration and concentration of antibody being administered.

The antibodies can be administered to the subject, patient, or cell by injection (e.g., intravenous, intraperitoneal, subcutaneous, intramuscular), or by other methods such as infusion that ensure its delivery to the bloodstream in an effective form. The antibodies may also be administered by intratumoral or peritumoral routes, to exert local as well as systemic therapeutic effects. Local or intravenous injection is preferred.

Effective dosages and schedules for administering the antibodies may be determined empirically, and making such determinations is within the skill in the art. Those skilled in the art will understand that the dosage of antibodies that must be administered will vary depending on, for example, the subject that will receive the antibody, the route of administration, the particular type of antibody used and other drugs being administered. A typical daily dosage of the antibody used alone might range from about 1 (μg/kg to up to 100 mg/kg of body weight or more per day, depending on the factors mentioned above. Following administration of an antibody, preferably for treating glioblastoma, breast cancer, colorectal cancer, renal cell carcinoma, chronic lymphocytic leukemia, hepatocellular carcinoma, non-small cell and small cell lung cancer, Non-Hodgkin lymphoma, acute myeloid leukemia, ovarian cancer, pancreatic cancer, prostate cancer, esophageal cancer including cancer of the gastric-esophageal junction, gallbladder cancer and cholangiocarcinoma, melanoma, gastric cancer, testis cancer, urinary bladder cancer, head and neck squamous cell carcinoma (HNSCC), or uterine cancer, the efficacy of the therapeutic antibody can be assessed in various ways well known to the skilled practitioner. For instance, the size, number, and/or distribution of cancer in a subject receiving treatment may be monitored using standard tumor imaging techniques. A therapeutically-administered antibody that arrests tumor growth, results in tumor shrinkage, and/or prevents the development of new tumors, compared to the disease course that would occurs in the absence of antibody administration, is an efficacious antibody for treatment of cancer.

It is a further aspect of the invention to provide a method for producing a soluble T-cell receptor (sTCR) recognizing a specific peptide-MHC complex. Such soluble T-cell receptors can be generated from specific T-cell clones, and their affinity can be increased by mutagenesis targeting the complementarity-determining regions. For the purpose of T-cell receptor selection, phage display can be used (US 2010/0113300, (Liddy et al., 2012)). For the purpose of stabilization of T-cell receptors during phage display and in case of practical use as drug, alpha and beta chain can be linked e.g. by non-native disulfide bonds, other covalent bonds (single-chain T-cell receptor), or by dimerization domains (Boulter et al., 2003; Card et al., 2004; Willcox et al., 1999). The T-cell receptor can be linked to toxins, drugs, cytokines (see, for example, US 2013/0115191), domains recruiting effector cells such as an anti-CD3 domain, etc., in order to execute particular functions on target cells. Moreover, it could be expressed in T cells used for adoptive transfer. Further information can be found in WO 2004/033685A1 and WO 2004/074322A1. A combination of sTCRs is described in WO 2012/056407A1. Further methods for the production are disclosed in WO 2013/057586A1.

In addition, the peptides and/or the TCRs or antibodies or other binding molecules of the present invention can be used to verify a pathologist's diagnosis of a cancer based on a biopsied sample.

The antibodies or TCRs may also be used for in vivo diagnostic assays. Generally, the antibody is labeled with a radionucleotide (such as $^{111}$In, $^{99}$Tc, $^{14}$C, $^{131}$I, $^{3}$H, $^{32}$P or $^{35}$S) so that the tumor can be localized using immunoscintiography. In one embodiment, antibodies or fragments thereof bind to the extracellular domains of two or more targets of a protein selected from the group consisting of the above-mentioned proteins, and the affinity value (Kd) is less than 1×10 μM.

Antibodies for diagnostic use may be labeled with probes suitable for detection by various imaging methods. Methods for detection of probes include, but are not limited to, fluorescence, light, confocal and electron microscopy; magnetic resonance imaging and spectroscopy; fluoroscopy, computed tomography and positron emission tomography. Suitable probes include, but are not limited to, fluorescein, rhodamine, eosin and other fluorophores, radioisotopes, gold, gadolinium and other lanthanides, paramagnetic iron, fluorine-18 and other positron-emitting radionuclides. Additionally, probes may be bi- or multi-functional and be detectable by more than one of the methods listed. These antibodies may be directly or indirectly labeled with said probes. Attachment of probes to the antibodies includes covalent attachment of the probe, incorporation of the probe into the antibody, and the covalent attachment of a chelating compound for binding of probe, amongst others well recognized in the art. For immunohistochemistry, the disease tissue sample may be fresh or frozen or may be embedded in paraffin and fixed with a preservative such as formalin. The fixed or embedded section contains the sample are contacted with a labeled primary antibody and secondary antibody, wherein the antibody is used to detect the expression of the proteins in situ.

Another aspect of the present invention includes an in vitro method for producing activated T cells, the method comprising contacting in vitro T cells with antigen loaded human MHC molecules expressed on the surface of a suitable antigen-presenting cell for a period of time sufficient to activate the T cell in an antigen specific manner, wherein the antigen is a peptide according to the invention. Preferably a sufficient amount of the antigen is used with an antigen-presenting cell.

Preferably the mammalian cell lacks or has a reduced level or function of the TAP peptide transporter. Suitable cells that lack the TAP peptide transporter include T2, RMA-S and *Drosophila* cells. TAP is the transporter associated with antigen processing.

The human peptide loading deficient cell line T2 is available from the American Type Culture Collection, 12301 Parklawn Drive, Rockville, MD 20852, USA under Catalogue No CRL 1992; the *Drosophila* cell line Schneider line 2 is available from the ATCC under Catalogue No CRL 19863; the mouse RMA-S cell line is described in Ljunggren et al. (Ljunggren and Karre, 1985).

Preferably, before transfection the host cell expresses substantially no MHC class I molecules. It is also preferred that the stimulator cell expresses a molecule important for providing a co-stimulatory signal for T-cells such as any of B7.1, B7.2, ICAM-1 and LFA 3. The nucleic acid sequences of numerous MHC class I molecules and of the co-stimulator molecules are publicly available from the GenBank and EMBL databases.

In case of a MHC class I epitope being used as an antigen, the T cells are CD8-positive T cells.

If an antigen-presenting cell is transfected to express such an epitope, preferably the cell comprises an expression vector capable of expressing a peptide containing SEQ ID NO: 1 to SEQ ID NO: 388, or a variant amino acid sequence thereof.

A number of other methods may be used for generating T cells in vitro. For example, autologous tumor-infiltrating lymphocytes can be used in the generation of CTL. Plebanski et al. (Plebanski et al., 1995) made use of autologous peripheral blood lymphocytes (PLBs) in the preparation of T cells. Furthermore, the production of autologous T cells by pulsing dendritic cells with peptide or polypeptide, or via infection with recombinant virus is possible. Also, B cells can be used in the production of autologous T cells. In addition, macrophages pulsed with peptide or polypeptide, or infected with recombinant virus, may be used in the preparation of autologous T cells. S. Walter et al. (Walter et al., 2003) describe the in vitro priming of T cells by using artificial antigen presenting cells (aAPCs), which is also a suitable way for generating T cells against the peptide of choice. In the present invention, aAPCs were generated by the coupling of preformed MHC:peptide complexes to the surface of polystyrene particles (microbeads) by biotin:streptavidin biochemistry. This system permits the exact control of the MHC density on aAPCs, which allows to selectively elicit high- or low-avidity antigen-specific T cell responses with high efficiency from blood samples. Apart from MHC:peptide complexes, aAPCs should carry other proteins with co-stimulatory activity like anti-CD28 antibodies coupled to their surface. Furthermore such aAPC-based systems often require the addition of appropriate soluble factors, e. g. cytokines, like interleukin-12.

Allogeneic cells may also be used in the preparation of T cells and a method is described in detail in WO 97/26328, incorporated herein by reference. For example, in addition to *Drosophila* cells and T2 cells, other cells may be used to present antigens such as CHO cells, baculovirus-infected insect cells, bacteria, yeast, vaccinia-infected target cells. In addition plant viruses may be used (see, for example, Porta et al. (Porta et al., 1994) which describes the development of cowpea mosaic virus as a high-yielding system for the presentation of foreign peptides.

The activated T cells that are directed against the peptides of the invention are useful in therapy. Thus, a further aspect of the invention provides activated T cells obtainable by the foregoing methods of the invention.

Activated T cells, which are produced by the above method, will selectively recognize a cell that aberrantly expresses a polypeptide that comprises an amino acid sequence of SEQ ID NO: 1 to SEQ ID NO 388.

Preferably, the T cell recognizes the cell by interacting through its TCR with the HLA/peptide-complex (for example, binding). The T cells are useful in a method of killing target cells in a patient whose target cells aberrantly express a polypeptide comprising an amino acid sequence of the invention wherein the patient is administered an effective number of the activated T cells. The T cells that are administered to the patient may be derived from the patient and activated as described above (i.e. they are autologous T cells). Alternatively, the T cells are not from the patient but are from another individual. Of course, it is preferred if the individual is a healthy individual. By "healthy individual" the inventors mean that the individual is generally in good health, preferably has a competent immune system and, more preferably, is not suffering from any disease that can be readily tested for, and detected.

In vivo, the target cells for the CD8-positive T cells according to the present invention can be cells of the tumor (which sometimes express MHC class II) and/or stromal cells surrounding the tumor (tumor cells) (which sometimes also express MHC class II; (Dengjel et al., 2006)).

The T cells of the present invention may be used as active ingredients of a therapeutic composition. Thus, the invention also provides a method of killing target cells in a patient whose target cells aberrantly express a polypeptide comprising an amino acid sequence of the invention, the method comprising administering to the patient an effective number of T cells as defined above.

By "aberrantly expressed" the inventors also mean that the polypeptide is over-expressed compared to levels of expression in normal tissues or that the gene is silent in the tissue from which the tumor is derived but in the tumor it is expressed. By "over-expressed" the inventors mean that the polypeptide is present at a level at least 1.2-fold of that present in normal tissue; preferably at least 2-fold, and more preferably at least 5-fold or 10-fold the level present in normal tissue.

T cells may be obtained by methods known in the art, e.g. those described above.

Protocols for this so-called adoptive transfer of T cells are well known in the art. Reviews can be found in: Gattioni et al. and Morgan et al. (Gattinoni et al., 2006; Morgan et al., 2006).

Another aspect of the present invention includes the use of the peptides complexed with MHC to generate a T-cell receptor whose nucleic acid is cloned and is introduced into a host cell, preferably a T cell. This engineered T cell can then be transferred to a patient for therapy of cancer.

Any molecule of the invention, i.e. the peptide, nucleic acid, antibody, expression vector, cell, activated T cell, T-cell receptor or the nucleic acid encoding it, is useful for the treatment of disorders, characterized by cells escaping an immune response. Therefore any molecule of the present invention may be used as medicament or in the manufacture of a medicament. The molecule may be used by itself or combined with other molecule(s) of the invention or (a) known molecule(s).

The present invention is further directed at a kit comprising:
(a) a container containing a pharmaceutical composition as described above, in solution or in lyophilized form;
(b) optionally a second container containing a diluent or reconstituting solution for the lyophilized formulation; and
(c) optionally, instructions for (i) use of the solution or (ii) reconstitution and/or use of the lyophilized formulation.

The kit may further comprise one or more of (iii) a buffer, (iv) a diluent, (v) a filter, (vi) a needle, or (v) a syringe. The container is preferably a bottle, a vial, a syringe or test tube; and it may be a multi-use container. The pharmaceutical composition is preferably lyophilized.

Kits of the present invention preferably comprise a lyophilized formulation of the present invention in a suitable container and instructions for its reconstitution and/or use. Suitable containers include, for example, bottles, vials (e.g. dual chamber vials), syringes (such as dual chamber syringes) and test tubes. The container may be formed from a variety of materials such as glass or plastic. Preferably the kit and/or container contain/s instructions on or associated with the container that indicates directions for reconstitution and/or use. For example, the label may indicate that the lyophilized formulation is to be reconstituted to peptide concentrations as described above. The label may further indicate that the formulation is useful or intended for subcutaneous administration.

The container holding the formulation may be a multi-use vial, which allows for repeat administrations (e.g., from 2-6 administrations) of the reconstituted formulation. The kit may further comprise a second container comprising a suitable diluent (e.g., sodium bicarbonate solution).

Upon mixing of the diluent and the lyophilized formulation, the final peptide concentration in the reconstituted formulation is preferably at least 0.15 mg/mL/peptide (=75 µg) and preferably not more than 3 mg/mL/peptide (=1500 µg). The kit may further include other materials desirable from a commercial and user standpoint, including other buffers, diluents, filters, needles, syringes, and package inserts with instructions for use.

Kits of the present invention may have a single container that contains the formulation of the pharmaceutical compositions according to the present invention with or without other components (e.g., other compounds or pharmaceutical compositions of these other compounds) or may have distinct container for each component.

Preferably, kits of the invention include a formulation of the invention packaged for use in combination with the co-administration of a second compound (such as adjuvants (e.g. GM-CSF), a chemotherapeutic agent, a natural product, a hormone or antagonist, an anti-angiogenesis agent or inhibitor, an apoptosis-inducing agent or a chelator) or a pharmaceutical composition thereof. The components of the kit may be pre-complexed or each component may be in a separate distinct container prior to administration to a patient. The components of the kit may be provided in one or more liquid solutions, preferably, an aqueous solution, more preferably, a sterile aqueous solution. The components of the kit may also be provided as solids, which may be converted into liquids by addition of suitable solvents, which are preferably provided in another distinct container.

The container of a therapeutic kit may be a vial, test tube, flask, bottle, syringe, or any other means of enclosing a solid or liquid. Usually, when there is more than one component, the kit will contain a second vial or other container, which allows for separate dosing. The kit may also contain another container for a pharmaceutically acceptable liquid. Preferably, a therapeutic kit will contain an apparatus (e.g., one or more needles, syringes, eye droppers, pipette, etc.), which enables administration of the agents of the invention that are components of the present kit.

The present formulation is one that is suitable for administration of the peptides by any acceptable route such as oral (enteral), nasal, ophthal, subcutaneous, intradermal, intramuscular, intravenous or transdermal. Preferably, the administration is s.c., and most preferably i.d. administration may be by infusion pump.

Since the peptides of the invention were isolated from glioblastoma, breast cancer, colorectal cancer, renal cell carcinoma, chronic lymphocytic leukemia, hepatocellular carcinoma, non-small cell and small cell lung cancer, Non-Hodgkin lymphoma, acute myeloid leukemia, ovarian cancer, pancreatic cancer, prostate cancer, esophageal cancer including cancer of the gastric-esophageal junction, gallbladder cancer and cholangiocarcinoma, melanoma, gastric cancer, testis cancer, urinary bladder cancer, or uterine cancer, the medicament of the invention is preferably used to treat glioblastoma, breast cancer, colorectal cancer, renal cell carcinoma, chronic lymphocytic leukemia, hepatocellular carcinoma, non-small cell and small cell lung cancer, Non-Hodgkin lymphoma, acute myeloid leukemia, ovarian cancer, pancreatic cancer, prostate cancer, esophageal cancer including cancer of the gastric-esophageal junction, gallbladder cancer and cholangiocarcinoma, melanoma, gastric cancer, testis cancer, urinary bladder cancer, head and neck squamous cell carcinoma (HNSCC), or uterine cancer.

The present invention further relates to a method for producing a personalized pharmaceutical for an individual patient comprising manufacturing a pharmaceutical composition comprising at least one peptide selected from a warehouse of pre-screened TUMAPs, wherein the at least one peptide used in the pharmaceutical composition is selected for suitability in the individual patient. In one embodiment, the pharmaceutical composition is a vaccine. The method could also be adapted to produce T cell clones for down-stream applications, such as TCR isolations, or soluble antibodies, and other treatment options.

A "personalized pharmaceutical" shall mean specifically tailored therapies for one individual patient that will only be used for therapy in such individual patient, including actively personalized cancer vaccines and adoptive cellular therapies using autologous patient tissue.

As used herein, the term "warehouse" shall refer to a group or set of peptides that have been pre-screened for immunogenicity and/or over-presentation in a particular tumor type. The term "warehouse" is not intended to imply that the particular peptides included in the vaccine have been pre-manufactured and stored in a physical facility, although that possibility is contemplated. It is expressly contemplated that the peptides may be manufactured de novo for each individualized vaccine produced, or may be pre-manufactured and stored. The warehouse (e.g. in the form of a database) is composed of tumor-associated peptides which were highly overexpressed in the tumor tissue of glioblastoma, breast cancer, colorectal cancer, renal cell carcinoma, chronic lymphocytic leukemia, hepatocellular carcinoma, non-small cell and small cell lung cancer, Non-Hodgkin lymphoma, acute myeloid leukemia, ovarian cancer, pancreatic cancer, prostate cancer, esophageal cancer including cancer of the gastric-esophageal junction, gallbladder cancer and cholangiocarcinoma, melanoma, gastric cancer, testis cancer, urinary bladder cancer, head and neck squamous cell carcinoma (HNSCC), or uterine cancer patients with various HLA-A HLA-B and HLA-C alleles. It may contain MHC class I and MHC class II peptides or elongated MHC class I peptides. In addition to the tumor associated peptides collected from several cancer tissues, the warehouse may contain HLA-A*02 and HLA-A*24 marker peptides. These peptides allow comparison of the magnitude of T-cell immunity induced by TUMAPS in a quantitative manner and hence allow important conclusion to be drawn on the capacity of the vaccine to elicit anti-tumor responses. Secondly, they function as important positive control peptides derived from a "non-self" antigen in the case that any vaccine-induced T-cell responses to TUMAPs derived from "self" antigens in a patient are not observed. And thirdly, it may allow conclusions to be drawn, regarding the status of immunocompetence of the patient.

TUMAPs for the warehouse are identified by using an integrated functional genomics approach combining gene expression analysis, mass spectrometry, and T-cell immunology (XPresident®). The approach assures that only TUMAPs truly present on a high percentage of tumors but not or only minimally expressed on normal tissue, are chosen for further analysis. For initial peptide selection, glioblastoma, breast cancer, colorectal cancer, renal cell carcinoma, chronic lymphocytic leukemia, hepatocellular carcinoma, non-small cell and small cell lung cancer, Non-Hodgkin lymphoma, acute myeloid leukemia, ovarian cancer, pancreatic cancer, prostate cancer, esophageal cancer including cancer of the gastric-esophageal junction, gallbladder cancer and cholangiocarcinoma, melanoma, gastric cancer, testis cancer, urinary bladder cancer, head and neck squamous cell carcinoma (HNSCC), and uterine cancer samples from patients and blood from healthy donors were analyzed in a stepwise approach:

1. HLA ligands from the malignant material were identified by mass spectrometry
2. Genome-wide messenger ribonucleic acid (mRNA) expression analysis was used to identify genes over-expressed in the malignant tissue compared with a range of normal organs and tissues
3. Identified HLA ligands were compared to gene expression data. Peptides over-presented or selectively presented on tumor tissue, preferably encoded by selectively expressed or over-expressed genes as detected in step 2 were considered suitable TUMAP candidates for a multi-peptide vaccine.
4. Literature research was performed in order to identify additional evidence supporting the relevance of the identified peptides as TUMAPs
5. The relevance of over-expression at the mRNA level was confirmed by redetection of selected TUMAPs from step 3 on tumor tissue and lack of (or infrequent) detection on healthy tissues.
6. In order to assess, whether an induction of in vivo T-cell responses by the selected peptides may be feasible, in vitro immunogenicity assays were performed using human T cells from healthy donors as well as from cancer patients.

In an aspect, the peptides are pre-screened for immunogenicity before being included in the warehouse. By way of example, and not limitation, the immunogenicity of the peptides included in the warehouse is determined by a method comprising in vitro T-cell priming through repeated stimulations of CD8+ T cells from healthy donors with artificial antigen presenting cells loaded with peptide/MHC complexes and anti-CD28 antibody.

This method is preferred for rare cancers and patients with a rare expression profile. In contrast to multi-peptide cocktails with a fixed composition as currently developed, the warehouse allows a significantly higher matching of the actual expression of antigens in the tumor with the vaccine. Selected single or combinations of several "off-the-shelf" peptides will be used for each patient in a multitarget approach. In theory an approach based on selection of e.g. 5 different antigenic peptides from a library of 50 would already lead to approximately 17 million possible drug product (DP) compositions.

In an aspect, the peptides are selected for inclusion in the vaccine based on their suitability for the individual patient based on the method according to the present invention as described herein, or as below.

The HLA phenotype, transcriptomic and peptidomic data is gathered from the patient's tumor material, and blood samples to identify the most suitable peptides for each patient containing "warehouse" and patient-unique (i.e. mutated) TUMAPs. Those peptides will be chosen, which are selectively or over-expressed in the patients tumor and, where possible, show strong in vitro immunogenicity if tested with the patients' individual PBMCs.

Preferably, the peptides included in the vaccine are identified by a method comprising: (a) identifying tumor-associated peptides (TUMAPs) presented by a tumor sample from the individual patient; (b) comparing the peptides identified in (a) with a warehouse (database) of peptides as described above; and (c) selecting at least one peptide from the warehouse (database) that correlates with a tumor-associated peptide identified in the patient. For example, the TUMAPs presented by the tumor sample are identified by: (a1) comparing expression data from the tumor sample to expression data from a sample of normal tissue corresponding to the tissue type of the tumor sample to identify proteins that are over-expressed or aberrantly expressed in the tumor sample; and (a2) correlating the expression data with sequences of MHC ligands bound to MHC class I and/or class II molecules in the tumor sample to identify MHC ligands derived from proteins over-expressed or aberrantly expressed by the tumor. Preferably, the sequences of MHC ligands are identified by eluting bound peptides from MHC molecules isolated from the tumor sample, and sequencing the eluted ligands. Preferably, the tumor sample and the normal tissue are obtained from the same patient.

In addition to, or as an alternative to, selecting peptides using a warehousing (database) model, TUMAPs may be identified in the patient de novo, and then included in the vaccine. As one example, candidate TUMAPs may be identified in the patient by (a1) comparing expression data from the tumor sample to expression data from a sample of normal tissue corresponding to the tissue type of the tumor sample to identify proteins that are over-expressed or aberrantly expressed in the tumor sample; and (a2) correlating the expression data with sequences of MHC ligands bound to MHC class I and/or class II molecules in the tumor sample to identify MHC ligands derived from proteins over-expressed or aberrantly expressed by the tumor. As another example, proteins may be identified containing mutations that are unique to the tumor sample relative to normal corresponding tissue from the individual patient, and TUMAPs can be identified that specifically target the mutation. For example, the genome of the tumor and of corresponding normal tissue can be sequenced by whole genome sequencing: For discovery of non-synonymous mutations in the protein-coding regions of genes, genomic DNA and RNA are extracted from tumor tissues and normal non-mutated genomic germline DNA is extracted from peripheral blood mononuclear cells (PBMCs). The applied NGS approach is confined to the re-sequencing of protein coding regions (exome re-sequencing). For this purpose, exonic DNA from human samples is captured using vendor-supplied target enrichment kits, followed by sequencing with e.g. a HiSeq2000 (Illumina). Additionally, tumor mRNA is sequenced for direct quantification of gene expression and validation that mutated genes are expressed in the patients' tumors. The resultant millions of sequence reads are processed through software algorithms. The output list contains mutations and gene expression. Tumor-specific somatic mutations are determined by comparison with the PBMC-derived germline variations and prioritized. The de novo identified peptides can then be tested for immunogenicity as described above for the warehouse, and candidate TUMAPs possessing suitable immunogenicity are selected for inclusion in the vaccine.

In one exemplary embodiment, the peptides included in the vaccine are identified by: (a) identifying tumor-associated peptides (TUMAPs) presented by a tumor sample from the individual patient by the method as described above; (b) comparing the peptides identified in a) with a warehouse of peptides that have been prescreened for immunogenicity and overpresentation in tumors as compared to corresponding normal tissue; (c) selecting at least one peptide from the warehouse that correlates with a tumor-associated peptide identified in the patient; and (d) optionally, selecting at least one peptide identified de novo in (a) confirming its immunogenicity.

In one exemplary embodiment, the peptides included in the vaccine are identified by: (a) identifying tumor-associated peptides (TUMAPs) presented by a tumor sample from the individual patient; and (b) selecting at least one peptide identified de novo in (a) and confirming its immunogenicity.

Once the peptides for a personalized peptide based vaccine are selected, the vaccine is produced.

The vaccine preferably is a liquid formulation consisting of the individual peptides dissolved in between 20-40% DMSO, preferably about 30-35% DMSO, such as about 33% DMSO.

Each peptide to be included into a product is dissolved in DMSO. The concentration of the single peptide solutions has to be chosen depending on the number of peptides to be included into the product. The single peptide-DMSO solutions are mixed in equal parts to achieve a solution containing all peptides to be included in the product with a concentration of ~2.5 mg/ml per peptide. The mixed solution is then diluted 1:3 with water for injection to achieve a concentration of 0.826 mg/ml per peptide in 33% DMSO. The diluted solution is filtered through a 0.22 µm sterile filter. The final bulk solution is obtained.

Final bulk solution is filled into vials and stored at −20° C. until use. One vial contains 700 µL solution, containing 0.578 mg of each peptide. Of this, 500 µL (approx. 400 µg per peptide) will be applied for intradermal injection.

In addition to being useful for treating cancer, the peptides of the present invention are also useful as diagnostics. Since the peptides were generated from glioblastoma, breast cancer, colorectal cancer, renal cell carcinoma, chronic lymphocytic leukemia, hepatocellular carcinoma, non-small cell and small cell lung cancer, Non-Hodgkin lymphoma, acute myeloid leukemia, ovarian cancer, pancreatic cancer, prostate cancer, esophageal cancer including cancer of the gastric-esophageal junction, gallbladder cancer and cholangiocarcinoma, melanoma, gastric cancer, testis cancer, urinary bladder cancer, head and neck squamous cell carcinoma (HNSCC), or uterine cancer samples and since it was determined that these peptides are not or at lower levels present in normal tissues, these peptides can be used to diagnose the presence of a cancer.

The presence of claimed peptides on tissue biopsies in blood samples can assist a pathologist in diagnosis of cancer. Detection of certain peptides by means of antibodies, mass spectrometry or other methods known in the art can tell the pathologist that the tissue sample is malignant or inflamed or generally diseased, or can be used as a biomarker for glioblastoma, breast cancer, colorectal cancer, renal cell carcinoma, chronic lymphocytic leukemia, hepatocellular carcinoma, non-small cell and small cell lung cancer, Non-Hodgkin lymphoma, acute myeloid leukemia, ovarian cancer, pancreatic cancer, prostate cancer, esophageal cancer including cancer of the gastric-esophageal junction, gallbladder cancer and cholangiocarcinoma, melanoma, gastric cancer, testis cancer, urinary bladder cancer, head and neck squamous cell carcinoma (HNSCC), or uterine cancer. Presence of groups of peptides can enable classification or sub-classification of diseased tissues.

The detection of peptides on diseased tissue specimen can enable the decision about the benefit of therapies involving the immune system, especially if T-lymphocytes are known or expected to be involved in the mechanism of action. Loss of MHC expression is a well described mechanism by which infected of malignant cells escape immuno-surveillance. Thus, presence of peptides shows that this mechanism is not exploited by the analyzed cells.

The peptides of the present invention might be used to analyze lymphocyte responses against those peptides such as T cell responses or antibody responses against the peptide or the peptide complexed to MHC molecules. These lymphocyte responses can be used as prognostic markers for decision on further therapy steps. These responses can also be used as surrogate response markers in immunotherapy approaches aiming to induce lymphocyte responses by different means, e.g. vaccination of protein, nucleic acids, autologous materials, adoptive transfer of lymphocytes. In gene therapy settings, lymphocyte responses against peptides can be considered in the assessment of side effects. Monitoring of lymphocyte responses might also be a valuable tool for follow-up examinations of transplantation therapies, e.g. for the detection of graft versus host and host versus graft diseases.

The present invention will now be described in the following examples which describe preferred embodiments thereof, and with reference to the accompanying figures, nevertheless, without being limited thereto. For the purposes of the present invention, all references as cited herein are incorporated by reference in their entireties.

BRIEF DESCRIPTION OF THE DRAWINGS

FIGS. 1A-1Z show the over-presentation of various peptides in normal tissues (white bars) and different cancers (black bars). FIG. 1A) Gene symbol: IGFBPL1, Peptide: LLPLLPPLSPSLG (SEQ ID NO: 33)—Tissues from left to right: 1 cell line (1 pancreatic), 1 normal tissue (1 thyroid gland), 22 cancer tissues (5 brain cancers, 1 breast cancer, 1 colon cancer, 1 esophageal cancer, 1 gallbladder cancer, 1 liver cancer, 10 lung cancers, 1 pancreas cancer, 1 stomach cancer); FIG. 1B) Gene symbol: HIVEP1, Peptide: NYIPVKNGKQF (SEQ ID NO: 103)—Tissues from left to right: 11 cancer tissues (1 brain cancer, 1 liver cancer, 8 lung cancers, 1 prostate cancer); FIGS. 1E) to Z) show the over-presentation of various peptides in different cancer tissues compared to normal tissues. The analyses included data from more than 440 normal tissue samples, and 526 cancer samples. Shown are only samples where the peptide was found to be presented. FIG. 1E) Gene symbol: AKR1C1, AKR1C3, Peptide: HLYNNEEQV (SEQ ID NO: 16)—Tissues from left to right: 1 cell line (pancreas), 15 cancer tissues (1 bile duct cancer, 1 esophageal cancer, 6 liver cancers, S lung cancers, 2 urinary bladder cancers); FIG. 1G) Gene symbol: CLDN4, CLDN3, CLDN14, CLDN6, CLDN9, Peptide: SLLALPQDLQA (SEQ ID NO: 40)—Tissues from left to right: 21 cancer tissues (1 bile duct cancer, 1 breast cancer, 3 colon cancers, 1 rectum cancer, 6 lung cancers, 2 ovarian cancers, 1 prostate cancer, 3 urinary bladder cancers, 3 uterus cancers); FIG. 1H) Gene symbol: KLHDC7B, Peptide: VLSPFILTL (SEQ ID NO: 42)—Tissues from left to right: 18 cancer tissues (1 leukocytic leukemia cancer, 1 myeloid cells cancer, 1 breast cancer, 1 kidney cancer, 6 lung cancers, 3 lymph node cancers, 2 ovarian cancers, 2 urinary bladder cancers, 1 uterus cancer); FIG. 1J) Gene symbol: PGAP1, Peptide: FITDFYTTV (SEQ ID NO: 66)—Tissues from left to right: 1 cell line (skin), 1 normal tissue (1 colon), 13 cancer tissues (1 head-and-neck cancer, 6 brain cancers, 1 colon cancer, 1 liver cancer, 2 skin cancers, 2 urinary bladder cancers); FIG. 1K) Gene symbol: ZNF679, SAPCD2, Peptide: RLLPKVQEV (SEQ ID NO: 325)—Tissues from left to right: 4 cell lines (2 blood cells, 1 kidney, 1 large intestine), 22 cancer tissues (1 myeloid cells cancer, 1 breast cancer, 1 esophageal cancer, 4 colon cancers, 1 rectum cancer, 10 lung cancers, 2 ovarian cancers, 1 stomach cancer, 1 urinary bladder cancer); FIG. 1O) Gene symbol: ANKRD5, Peptide: RYLNKSFVL (SEQ ID NO: 115)—Tissues from left to right: 1 normal tissue (1 stomach), 25 cancer tissues (1 brain cancer, 2 liver cancers, 17 lung cancers, 2 prostate cancers, 3 stomach cancers); FIG. 1P) Gene symbol: IGFLR1, Peptide: RYGLPAAWSTF (SEQ ID NO: 121)—Tissues from left to right: 20 cancer tissues (2 liver cancers, 17 lung cancers, 1 stomach cancer); FIG. 1Q) Gene symbol:

CCR8, Peptide: VYALKVRTI (SEQ ID NO: 145)—Tissues from left to right: 25 cancer tissues (25 lung cancers); FIG. 1T) Gene symbol: IFNG, Peptide: KYTSYILAF (SEQ ID NO: 162)—Tissues from left to right: 3 cell lines (3 prostates), 4 normal tissues (1 liver, 1 lung, 1 pancreas, 1 stomach), 95 cancer tissues (1 kidney cancer, 5 liver cancers, 71 lung cancers, 2 prostate cancers, 16 stomach cancers); FIG. 1W) Gene symbol: BUB1, Peptide: EYNSDLHQFF (SEQ ID NO: 345)—Tissues from left to right: 13 cancer tissues (3 brain cancers, 10 lung cancers); FIG. 1X) Gene symbol: CASC5, Peptide: IYVIPQPHF (SEQ ID NO: 346)—Tissues from left to right: 21 cancer tissues (3 brain cancers, 1 kidney cancer, 1 liver cancer, 14 lung cancers, 2 stomach cancers); FIG. 1Z) Gene symbol: PSMA8, PSMA7, Peptide: VFSPDGHLF (SEQ ID NO: 360)—Tissues from left to right: 33 cancer tissues (4 liver cancers, 27 lung cancers, 1 prostate cancer, 1 stomach cancer).

FIGS. 2A-2D show exemplary expression profiles of source genes of the present invention that are highly overexpressed or exclusively expressed in different cancers in a panel of normal tissues (white bars) and different cancer samples (black bars). FIG. 2A) Gene symbol: MXRA5—Tissues from left to right: 61 normal tissue samples (6 arteries, 1 brain, 1 heart, 2 livers, 2 lungs, 2 veins, 1 adipose tissue, 1 adrenal gland, 5 bone marrows, 1 cartilage, 1 colon, 1 esophagus, 2 gallbladders, 1 kidney, 6 lymph nodes, 1 pancreas, 1 pituitary gland, 1 rectum, 1 skeletal muscle, 1 skin, 1 small intestine, 1 spleen, 1 stomach, 1 thymus, 1 thyroid gland, 5 tracheas, 1 urinary bladder, 1 breast, 5 ovaries, 3 placentas, 1 prostate, 1 testis, 1 uterus) and 70 cancer samples (10 breast cancers, 11 lung cancers, 12 ovary cancers, 11 esophageal cancers, 26 pancreas cancers); FIG. 2B) Gene symbol: KIF26B—Tissues from left to right: 61 normal tissue samples (6 arteries, 1 brain, 1 heart, 2 livers, 2 lungs, 2 veins, 1 adipose tissue, 1 adrenal gland, 5 bone marrows, 1 cartilage, 1 colon, 1 esophagus, 2 gallbladders, 1 kidney, 6 lymph nodes, 1 pancreas, 1 pituitary gland, 1 rectum, 1 skeletal muscle, 1 skin, 1 small intestine, 1 spleen, 1 stomach, 1 thymus, 1 thyroid gland, 5 tracheas, 1 urinary bladder, 1 breast, 5 ovaries, 3 placentas, 1 prostate, 1 testis, 1 uterus) and 58 cancer samples (10 breast cancers, 11 lung cancers, 11 esophageal cancers, 26 pancreas cancers); FIG. 2C) Gene symbol: IL4I1—Tissues from left to right: 61 normal tissue samples (6 arteries, 1 brain, 1 heart, 2 livers, 2 lungs, 2 veins, 1 adipose tissue, 1 adrenal gland, 5 bone marrows, 1 cartilage, 1 colon, 1 esophagus, 2 gallbladders, 1 kidney, 6 lymph nodes, 1 pancreas, 1 pituitary gland, 1 rectum, 1 skeletal muscle, 1 skin, 1 small intestine, 1 spleen, 1 stomach, 1 thymus, 1 thyroid gland, 5 tracheas, 1 urinary bladder, 1 breast, 5 ovaries, 3 placentas, 1 prostate, 1 testis, 1 uterus) and 34 cancer samples (11 lung cancers, 12 ovary cancers, 11 esophageal cancers); FIG. 2D) Gene symbol: TP63—Tissues from left to right: 61 normal tissue samples (6 arteries, 1 brain, 1 heart, 2 livers, 2 lungs, 2 veins, 1 adipose tissue, 1 adrenal gland, 5 bone marrows, 1 cartilage, 1 colon, 1 esophagus, 2 gallbladders, 1 kidney, 6 lymph nodes, 1 pancreas, 1 pituitary gland, 1 rectum, 1 skeletal muscle, 1 skin, 1 small intestine, 1 spleen, 1 stomach, 1 thymus, 1 thyroid gland, 5 tracheas, 1 urinary bladder, 1 breast, 5 ovaries, 3 placentas, 1 prostate, 1 testis, 1 uterus) and 11 esophageal cancer samples FIGS. 3A-3B show exemplary immunogenicity data: flow cytometry results after peptide-specific multimer staining.

FIGS. 5A-5D show exemplary results of peptide-specific in vitro CD8+ T cell responses of a healthy HLA-A*24+ donor. CD8+ T cells were primed using artificial APCs coated with anti-CD28 mAb and HLA-A*24 in complex with SEQ ID NO: 99 peptide (FIG. 5A, left panel), SEQ ID NO: 119 peptide (FIG. 5B, left panel), SEQ ID NO: 142 peptide (FIG. 5C, left panel) and SEQ ID NO: 174 peptide (FIG. 5D, left panel), respectively. After three cycles of stimulation, the detection of peptide-reactive cells was performed by 2D multimer staining with A*24/SEQ ID NO: 99 (FIG. 5A), A*24/SEQ ID NO: 119 (B), A*24/SEQ ID NO: 142 (C) or A*24/SEQ ID NO: 174 (FIG. 5D). Right panels (FIGS. 5A, 5B, 5C and 5D) show control staining of cells stimulated with irrelevant A*24/peptide complexes. Viable singlet cells were gated for CD8+ lymphocytes. Boolean gates helped excluding false-positive events detected with multimers specific for different peptides. Frequencies of specific multimer+ cells among CD8+ lymphocytes are indicated.

EXAMPLES

Example 1

Figure 1C:
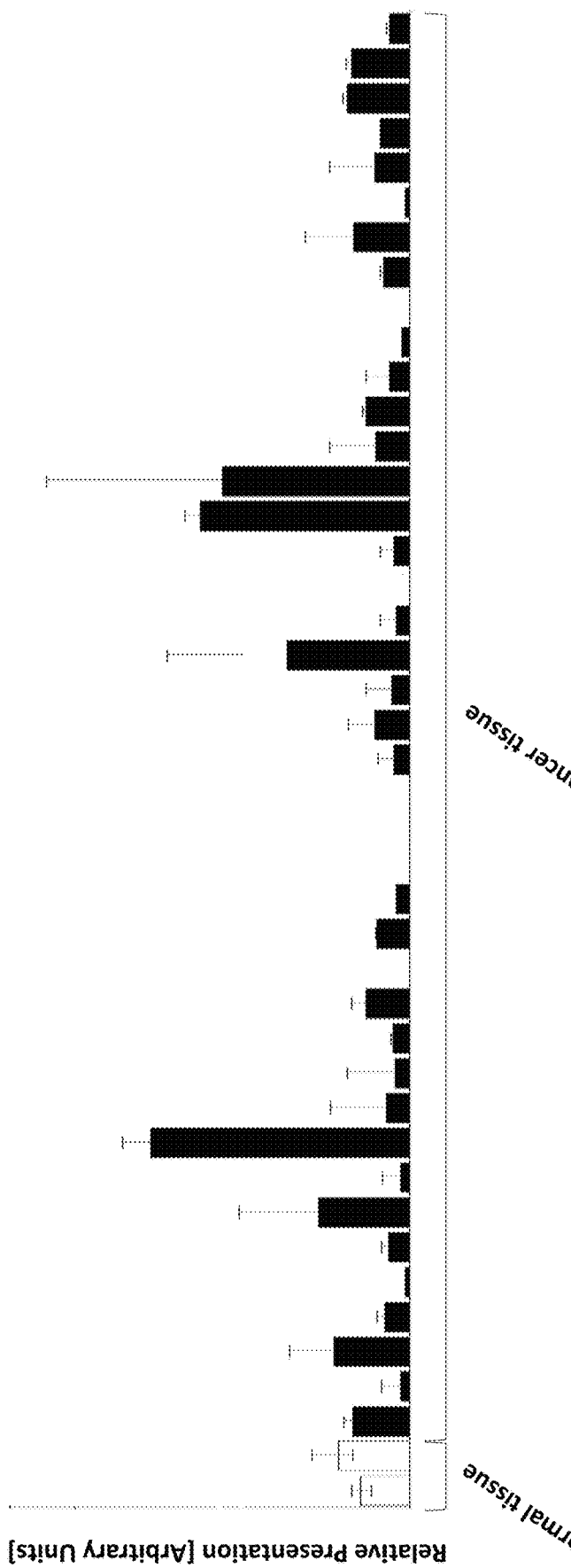
FIG. 1C) Gene symbol: GET4, Peptide: EYLDRIGQLFF (SEQ ID NO: 131)—Tissues from left to right: 2 normal tissues (1 kidney, 1 lung), 41 cancer tissues (2 brain cancers, 1 kidney cancer, 3 liver cancers, 29 lung cancers, 2 prostate cancers, 4 stomach cancers)
Figure 1D:
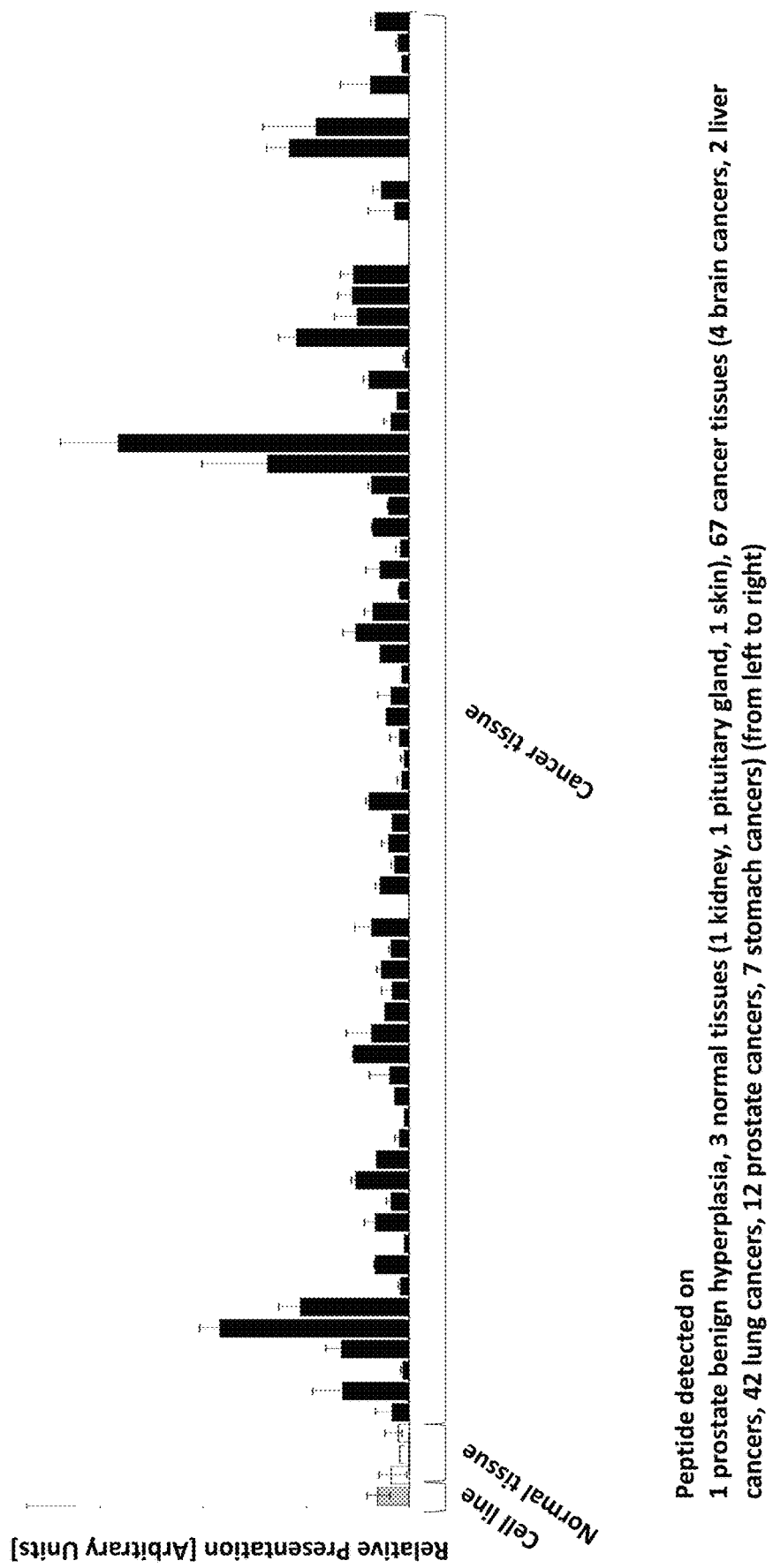
FIG. 1D) Gene symbol: N4BP2, Peptide: FYINGQYQF (SEQ ID NO: 176)—Tissues from left to right: 1 cell line (1 prostate), 3 normal tissues (1 kidney, 1 pituitary gland, 1 skin), 67 cancer tissues (4 brain cancers, 2 liver cancers, 42 lung cancers, 12 prostate cancers, 7 stomach cancers).
Figure 1F:
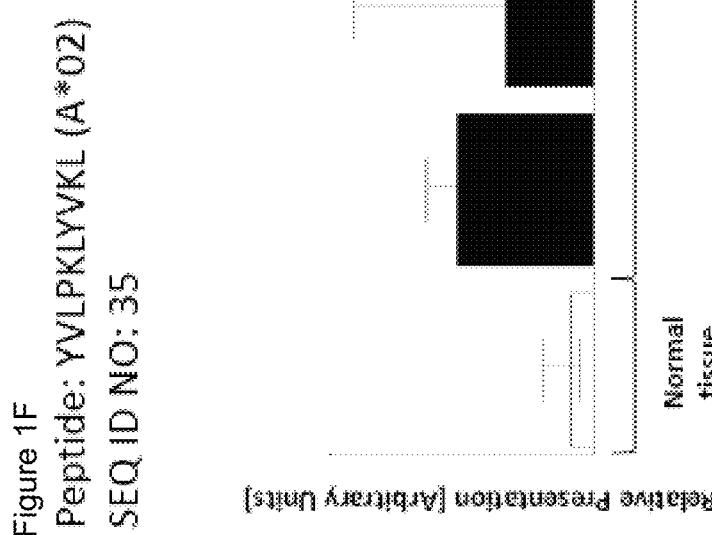
FIG. 1F) Gene symbol: RPS26P39, RPS26P11, RPS26, RPS26P28, RPS26P20, RPS26P15, RPS26P50, RPS26P2, RPS26P25, RPS26P58, Peptide: YVLPKLYVKL (SEQ ID NO: 35)—Tissues from left to right: 1 normal tissue (1 leukocyte sample), 8 cancer tissues (1 head-and-neck cancer, 3 leukocytic leukemia cancers, 1 myeloid cells cancer, 1 gallbladder cancer, 1 colon cancer, 1 lymph node cancer)
Figure 1I:
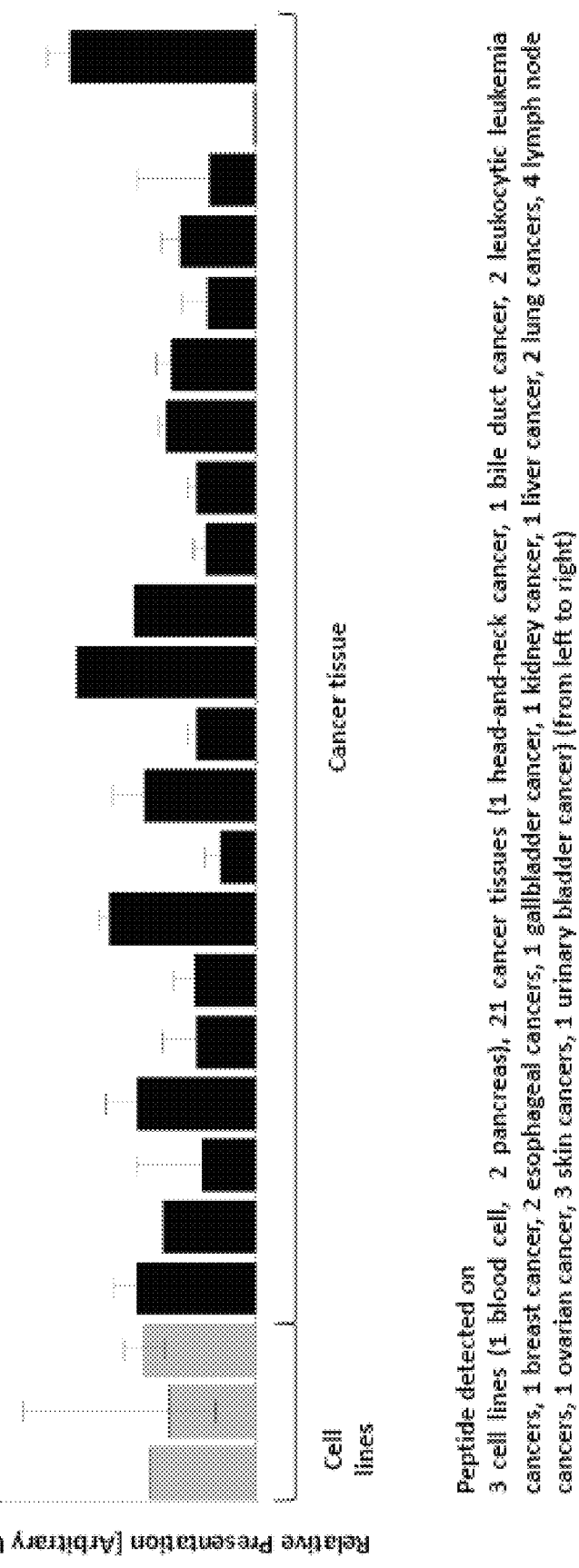
FIG. 1I) Gene symbol: ATR, Peptide: SLLSHVIVA (SEQ ID NO: 53)—Tissues from left to right: 3 cell lines (1 blood cell, 2 pancreas), 21 cancer tissues (1 head-and-neck cancer, 1 bile duct cancer, 2 leukocytic leukemia cancers, 1 breast cancer, 2 esophageal cancers, 1 gallbladder cancer, 1 kidney cancer, 1 liver cancer, 2 lung cancers, 4 lymph node cancers, 1 ovarian cancer, 3 skin cancers, 1 urinary bladder cancer)
Figure 1L:
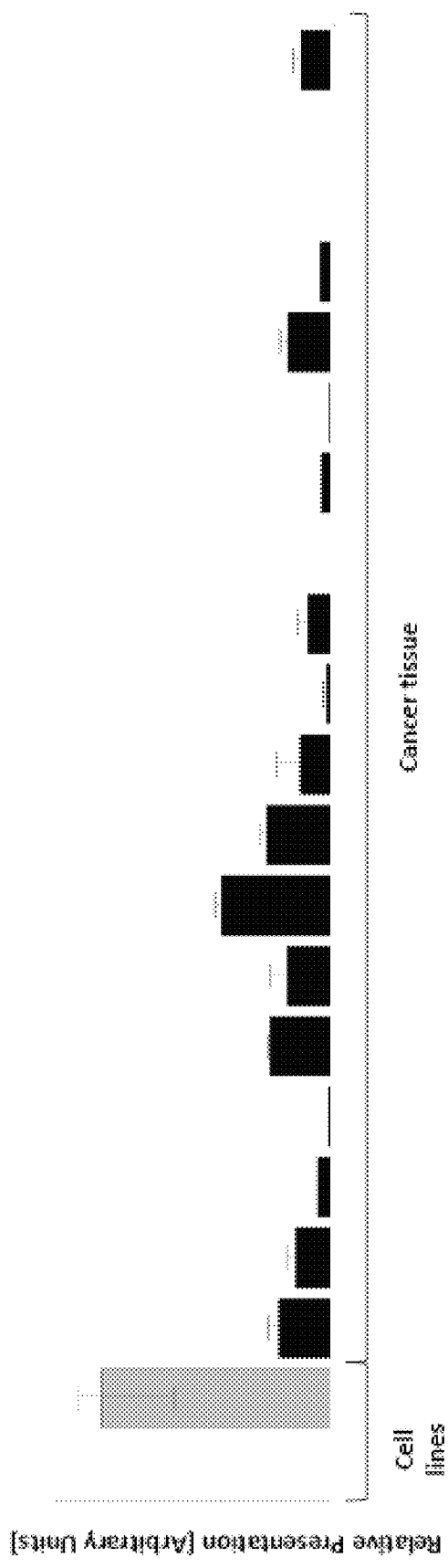
FIG. 1L) Gene symbol: ZDHHC24, Peptide: VLGPGPPPL (SEQ ID NO: 339)—Tissues from left to right: 2 cell lines (1 kidney, 1 pancreas), 19 cancer tissues (4 leukocytic leukemia cancers, 1 myeloid cells cancer, 1 bone marrow cancer, 2 brain cancers, 1 liver cancer, 2 lung cancers, 6 lymph node cancers, 1 skin cancer, 1 uterus cancer)
Figure 1M:
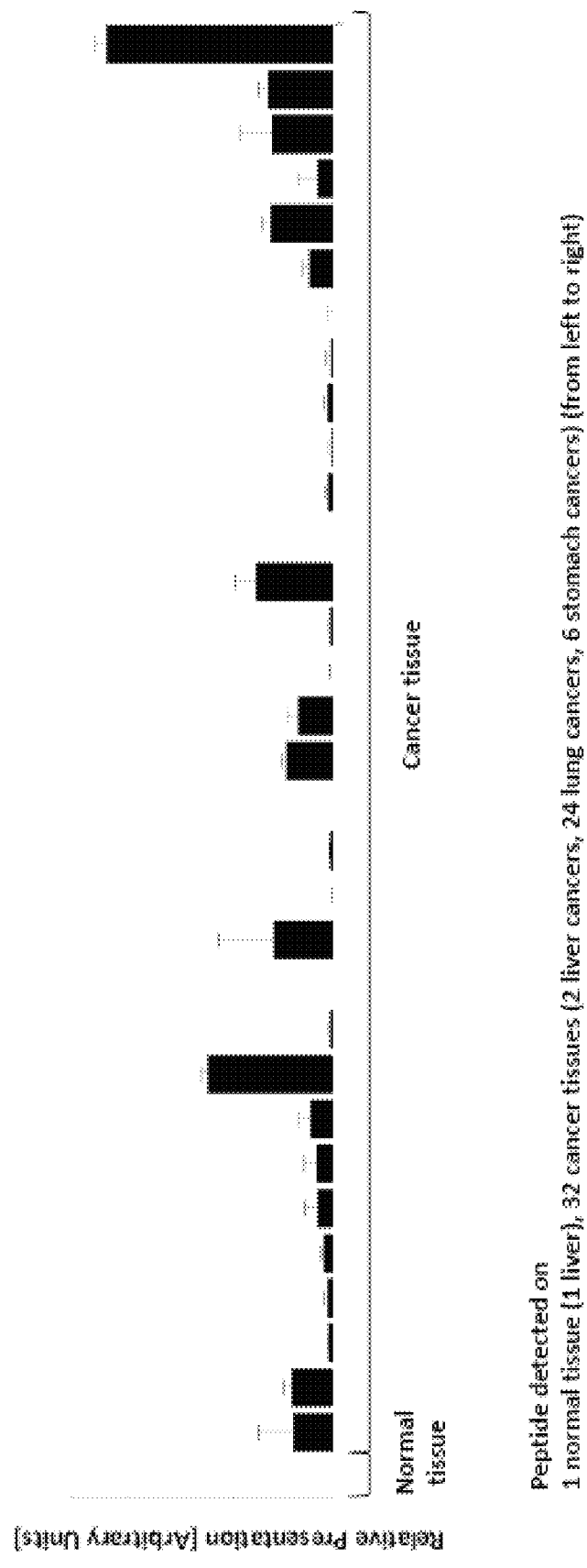
FIG. 1M) Gene symbol: ORC1, Peptide: VYVQILQKL (SEQ ID NO: 111)—Tissues from left to right: 1 normal tissue (1 liver), 32 cancer tissues (2 liver cancers, 24 lung cancers, 6 stomach cancers)
Figure 1N:
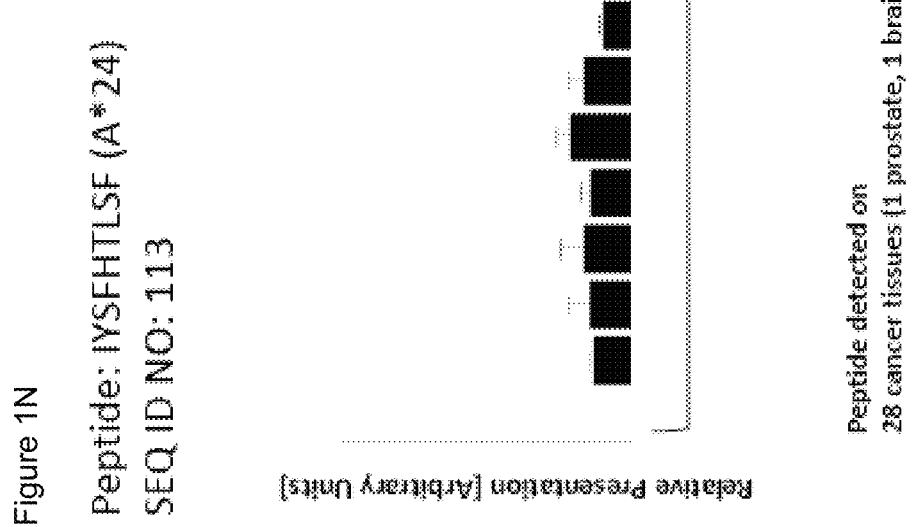
FIG. 1N) Gene symbol: RIF1, Peptide: IYSFHTLSF (SEQ ID NO: 113)—Tissues from left to right: 28 cancer tissues (1 prostate, 1 brain cancer, 25 lung cancers, 2 stomach cancers)
Figure 1R:
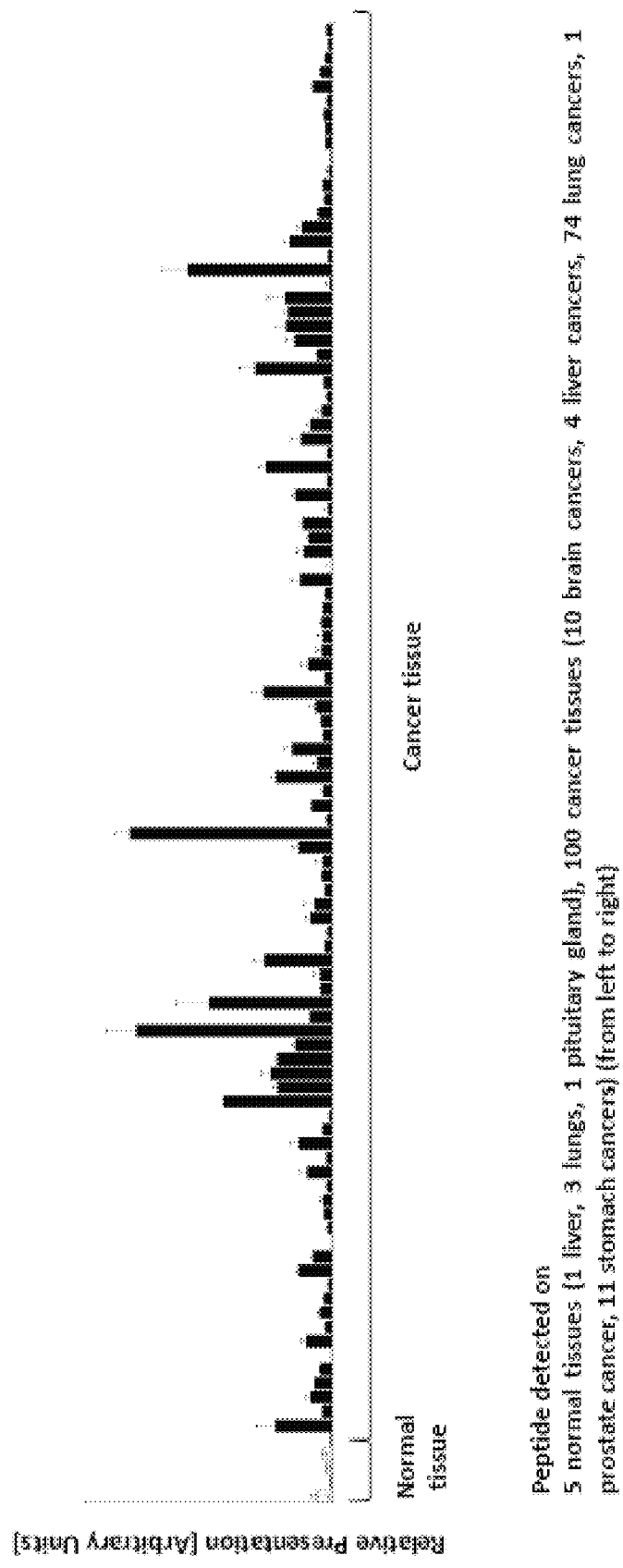
FIG. 1R) Gene symbol: CLEC5A, Peptide: SYGTVSQIF (SEQ ID NO: 148)—Tissues from left to right: 5 normal tissues (1 liver, 3 lungs, 1 pituitary gland), 100 cancer tissues (10 brain cancers, 4 liver cancers, 74 lung cancers, 1 prostate cancer, 11 stomach cancers)
Figure 1S:
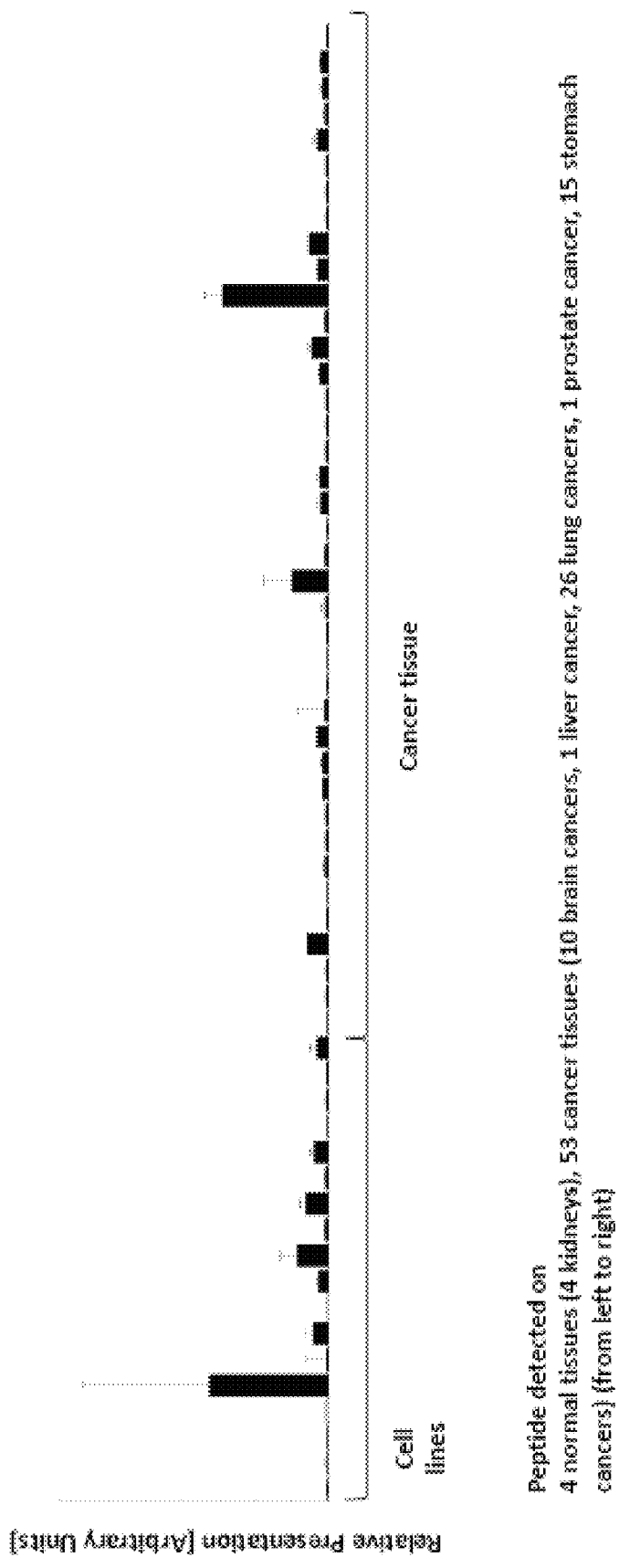
FIG. 1S) Gene symbol: FOXJ1, Peptide: IYKWITDNF (SEQ ID NO: 155)—Tissues from left to right: 4 normal tissues (4 kidneys), 53 cancer tissues (10 brain cancers, 1 liver cancer, 26 lung cancers, 1 prostate cancer, 15 stomach cancers)
Figure 1U:
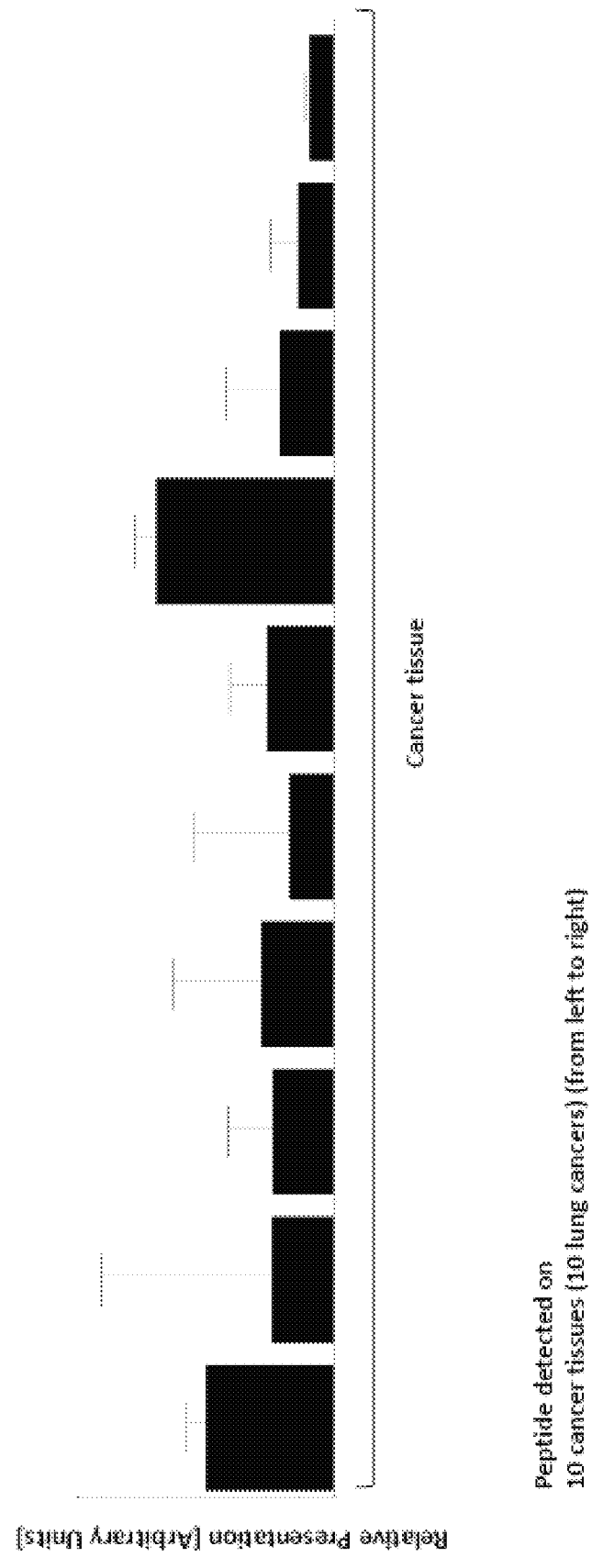
FIG. 1U) Gene symbol: KLHL11, Peptide: EYFTPLLSGQF (SEQ ID NO: 165)—Tissues from left to right: 10 cancer tissues (10 lung cancers)
Figure 1V:
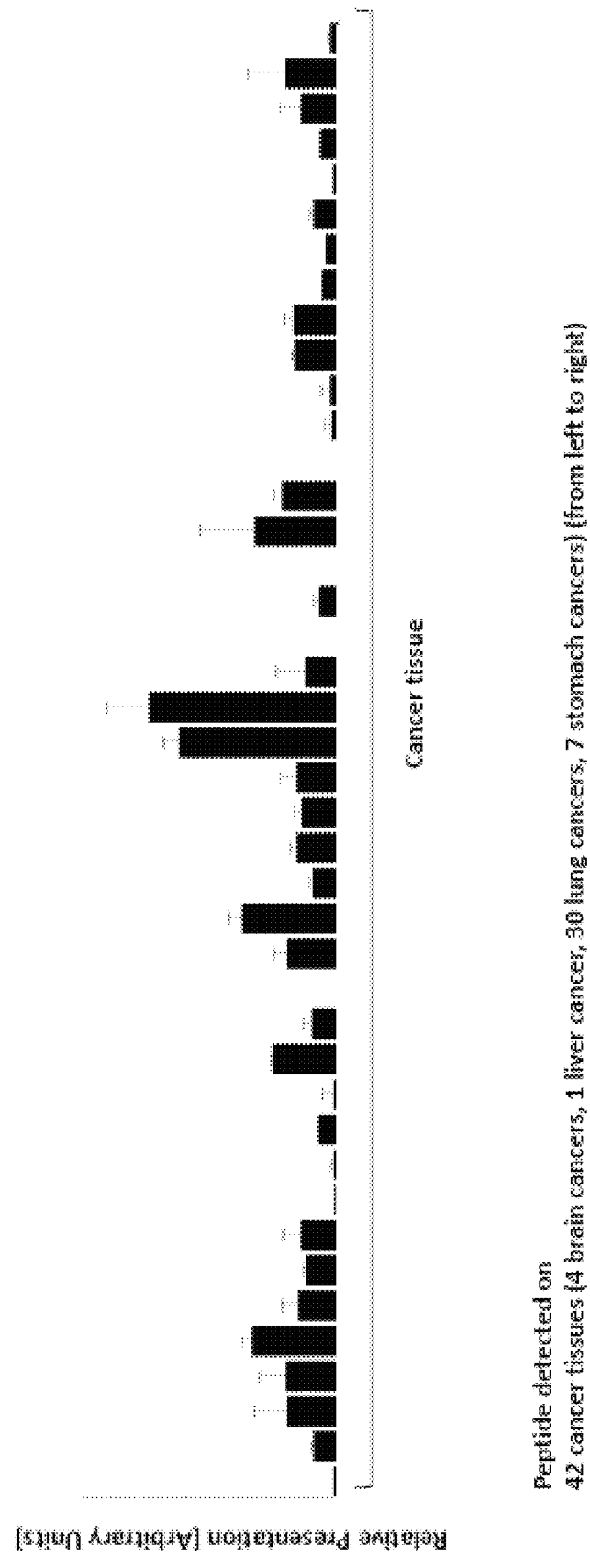
FIG. 1V) Gene symbol: TMEM189, Peptide: LYSPVPFTL (SEQ ID NO: 175)—Tissues from left to right: 42 cancer tissues (4 brain cancers, 1 liver cancer, 30 lung cancers, 7 stomach cancers)
Figure 1Y:
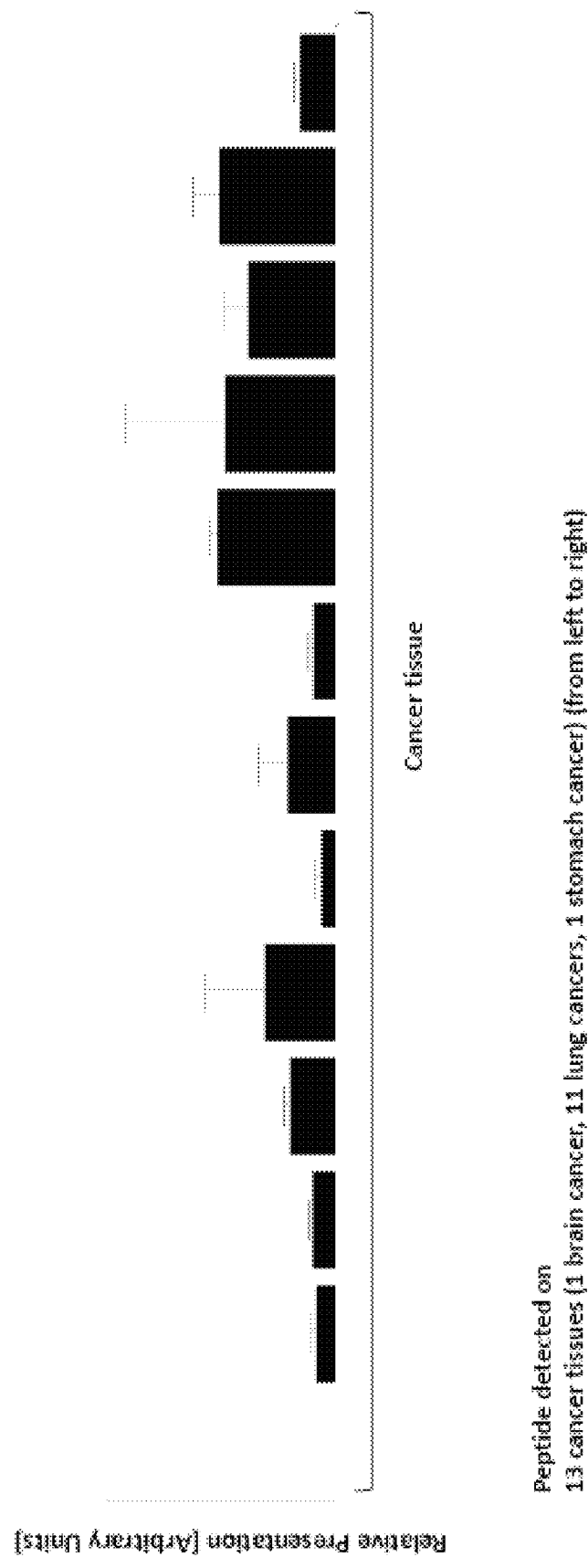
FIG. 1Y) Gene symbol: KIF18A, Peptide: VYNEQIRDLL (SEQ ID NO: 354)—Tissues from left to right: 13 cancer tissues (1 brain cancer, 11 lung cancers, 1 stomach cancer)
Figure 2B:
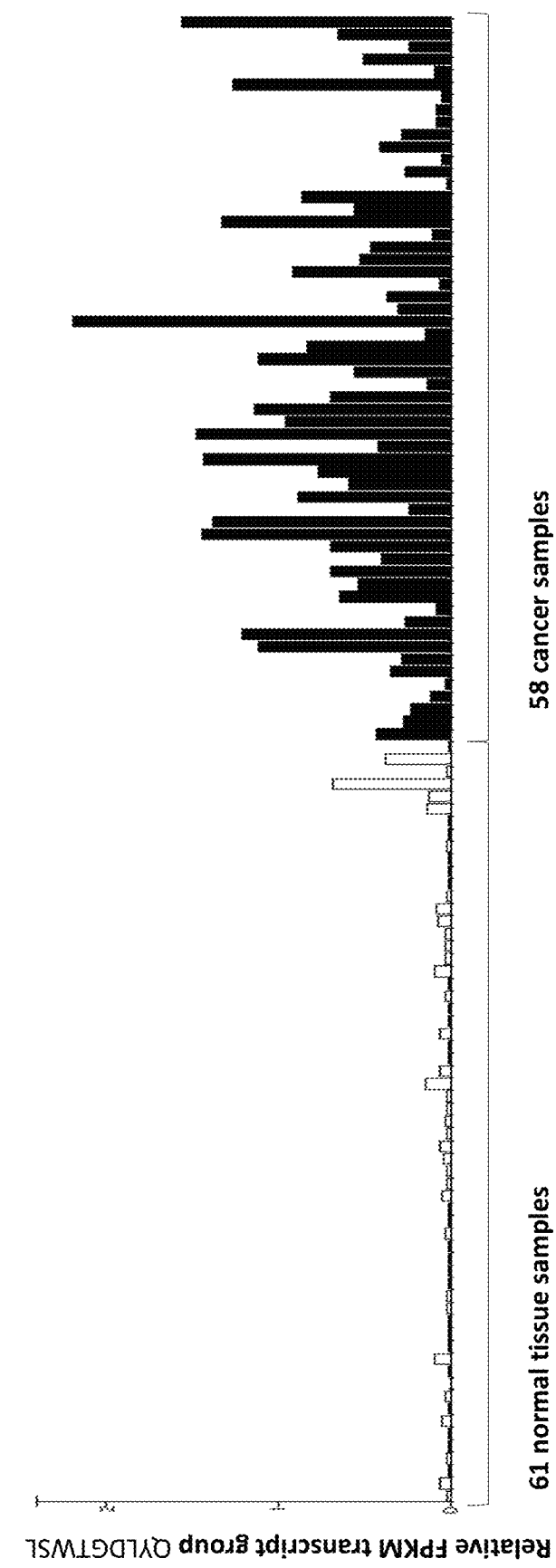
Figure 2C:
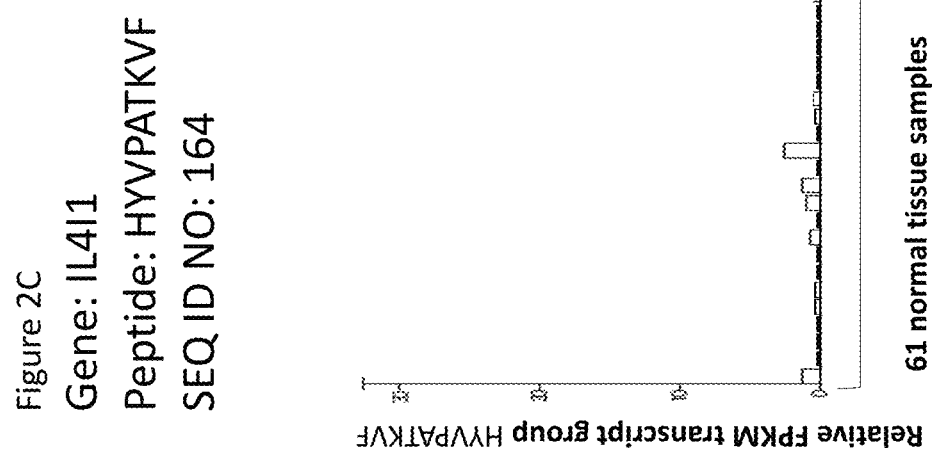
Figure 2D:
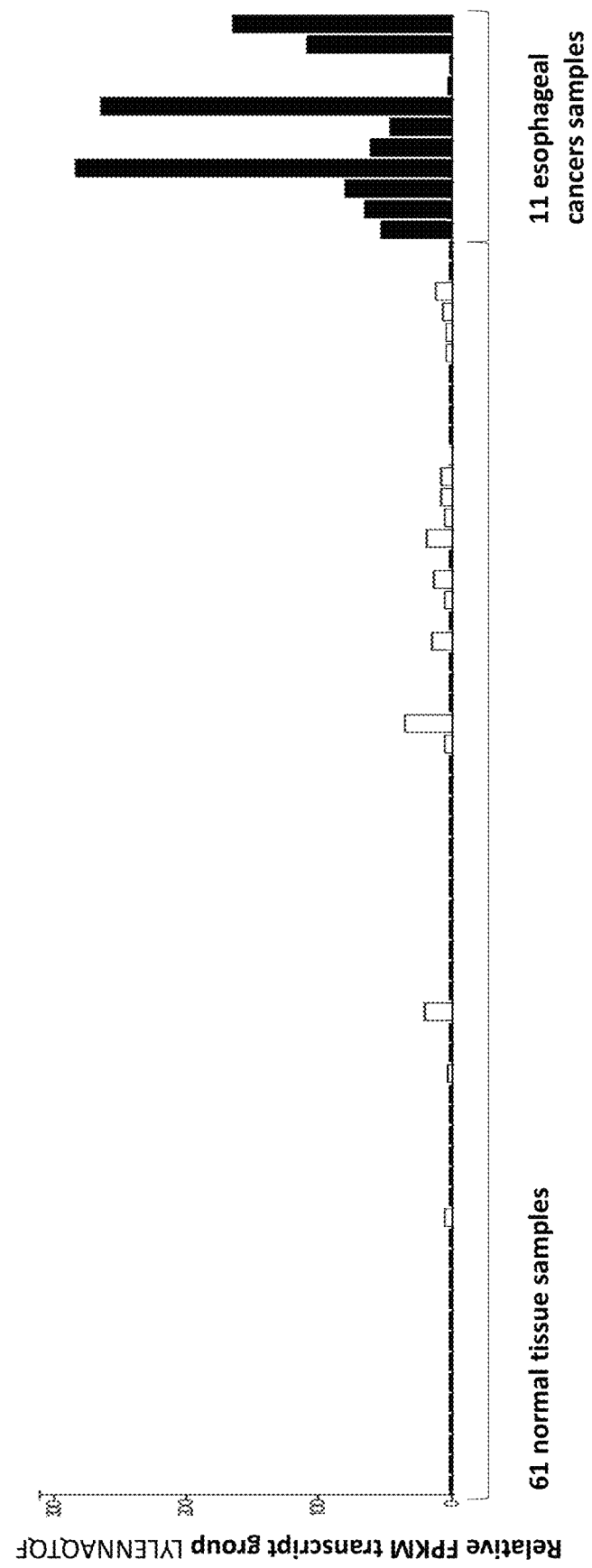
Figure 4A:
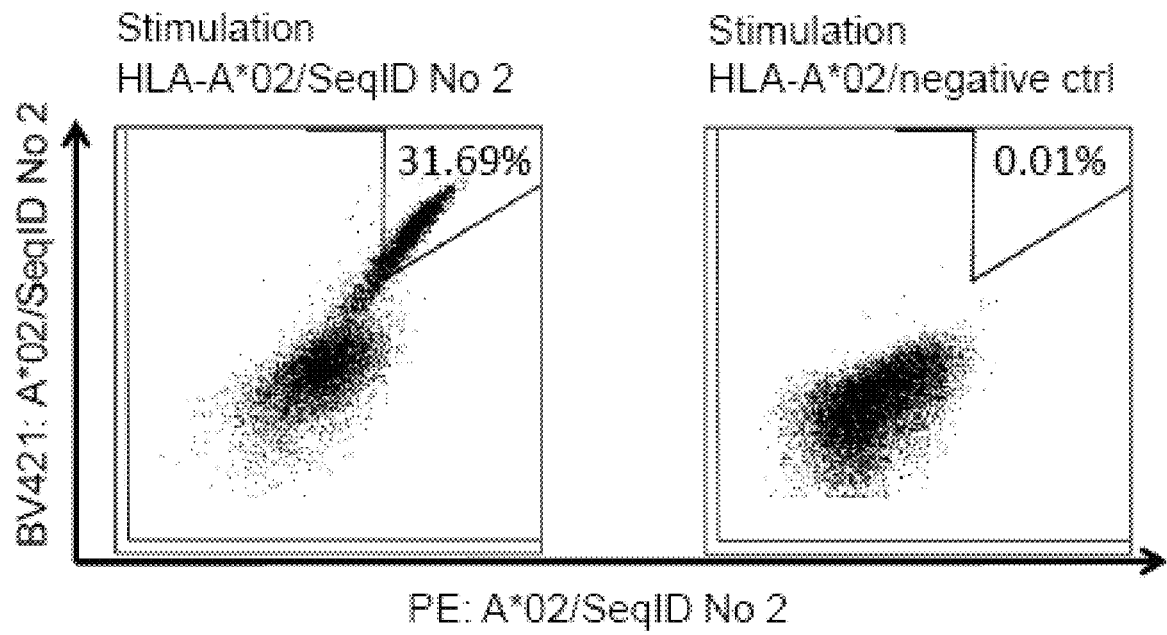
FIGS. 4A-4C show exemplary results of peptide-specific in vitro CD8+ T cell responses of a healthy HLA-A*02+ donor. CD8+ T cells were primed using artificial APCs coated with anti-CD28 mAb and HLA-A*02 in complex with SEQ ID NO: 2 peptide (FIG. 4A, left panel), SEQ ID NO: 9 peptide (FIG. 4B, left panel) and SEQ ID NO: 331 peptide (FIG. 4C, left panel), respectively. After three cycles of stimulation, the detection of peptide-reactive cells was performed by 2D multimer staining with A*02/SEQ ID NO: 2 (FIG. 4A), A*02/SEQ ID NO: 9 (FIG. 4B) or A*02/SEQ ID NO: 331 (FIG. 4C). Right panels (FIGS. 4A, 4B and 4C) show control staining of cells stimulated with irrelevant A*02/peptide complexes. Viable singlet cells were gated for CD8+ lymphocytes. Boolean gates helped excluding false-positive events detected with multimers specific for different peptides. Frequencies of specific multimer+ cells among CD8+ lymphocytes are indicated.
Figure 4B:
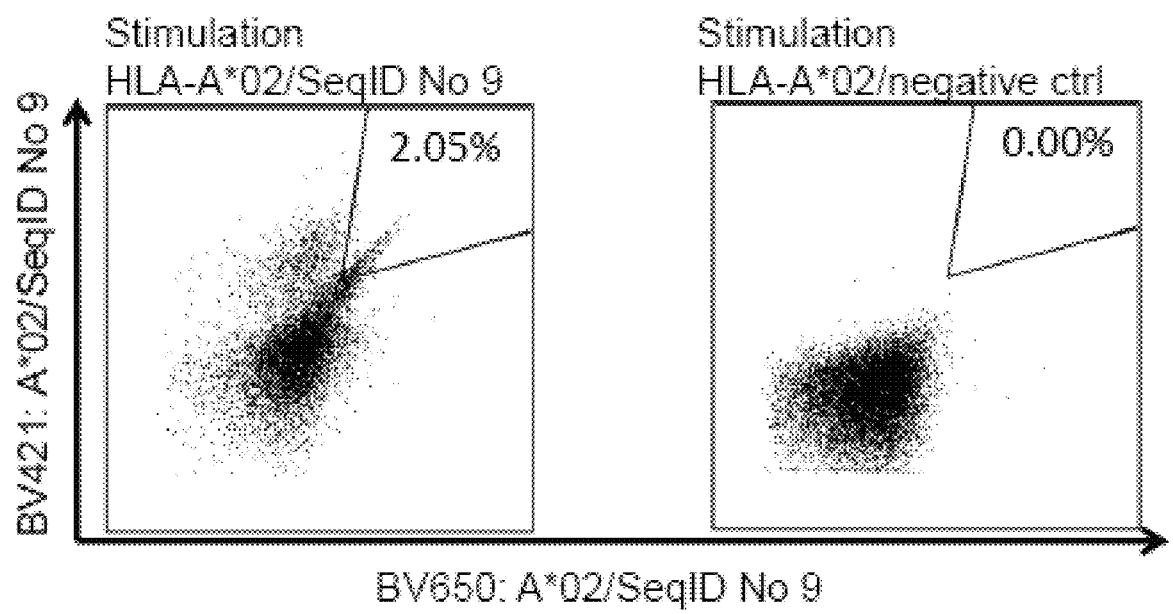
Figure 4C:
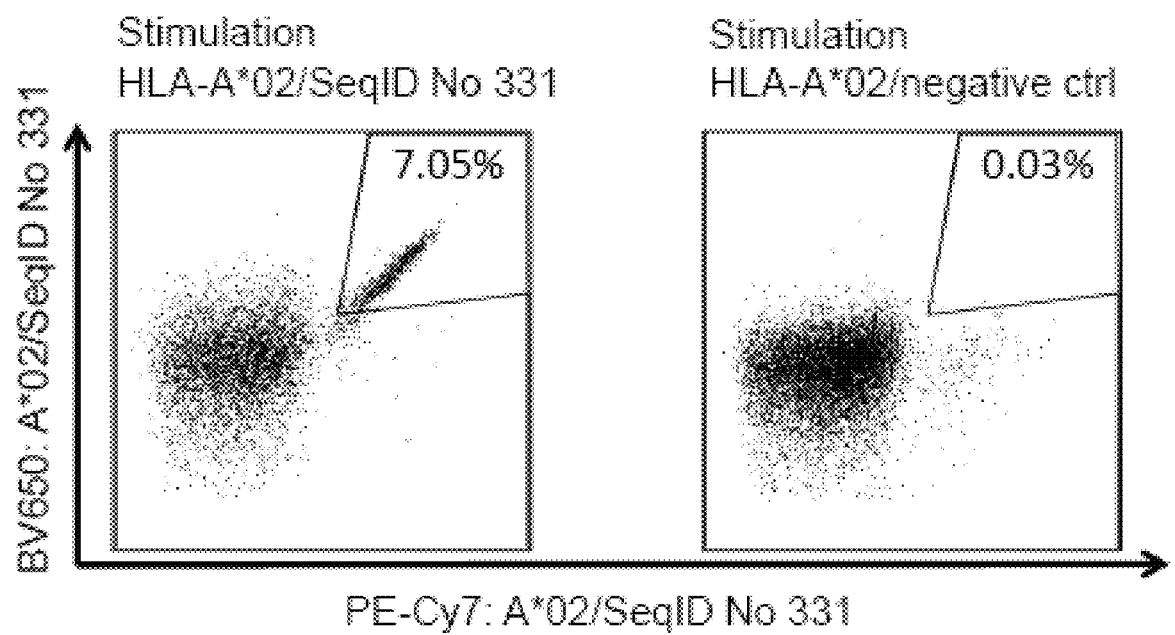

Identification and Quantitation of Tumor Associated Peptides Presented on the Cell Surface Tissue Samples Patients' tumor tissues were obtained under written informed consents of all patients had been given before surgery or autopsy. Tissues were shock-frozen immediately after excision and stored until isolation of TUMAPs at −70° C. or below.

Peptides were selected if two conditions were true: (1) Its underlying transcript(s) and/or exon(s) are expressed at very low levels, i.e. the median reads per kilobase per million reads (RPKM) was required to be less than two, and the 75% quartile was required to be less than 5 for the following organs: brain, blood vessel, heart, liver, lung, blood. In addition, the median RPKM was required to be less than 10 for the following organs: urinary bladder, salivary gland, stomach, adrenal gland, colon, small intestine, spleen, bone marrow, pancreas, muscle, adipose tissue, skin, esophagus, kidney, thyroid gland, pituitary gland, nerve. (2) The peptide was tumor-associated, i.e. found specifically or on tumors or over-expressed compared to a baseline of normal tissues (cf. Example 1).

Sample numbers for HLA-A*02 TUMAP selection were: for pancreatic cancer N=16, for renal cancer N=20, for colorectal cancer N=28, for esophageal carcinoma including cancer of the gastric-esophageal junction N=15, for prostate tumors N=35, for hepatocellular carcinoma N=16, for non-small cell lung cancer N=88, for gastric cancer N=29, for breast cancer N=9, for melanoma N=3, for ovarian cancer N=20, for chronic lymphocytic leukemia N=13 (of 12 donors), for urinary bladder cancer N=5, for testis cancer N=1, for small-cell lung cancer N=18 (of 13 donors), for gallbladder cancer and cholangiocarcinoma N=3, for acute myeloid leukemia N=5 (of 4 donors), for glioblastoma N=40, and for uterine cancer N=5.

Sample numbers for HLA-A*24 TUMAP selection were: for gastric cancer N=44, for prostate tumors N=37, for non-small cell lung cancer N=88, for hepatocellular carcinoma N=15, for renal cancer N=2, for colorectal cancer N=1, and for glioblastoma N=17.

Isolation of HLA Peptides from Tissue Samples

HLA peptide pools from shock-frozen tissue samples were obtained by immune precipitation from solid tissues according to published protocols (Falk et al., 1991; Seeger et al., 1999) with minor modifications using the HLA-A*02-specific antibody BB7.2, the HLA-A, -B, -C-specific antibody W6/32, the HLA class II-specific antibody L243, CNBr-activated sepharose, acid treatment, and ultrafiltration.

Mass Spectrometry Analyses

The HLA peptide pools as obtained were separated according to their hydrophobicity by reversed-phase chromatography (nanoAcquity UPLC system, Waters) and the eluting peptides were analyzed in LTQ-velos and fusion hybrid mass spectrometers (ThermoElectron) equipped with an ESI source. Peptide pools were loaded directly onto the analytical fused-silica micro-capillary column (75 µm i.d.× 250 mm) packed with 1.7 µm C18 reversed-phase material (Waters) applying a flow rate of 400 nL per minute. Subsequently, the peptides were separated using a two-step 180 minute-binary gradient from 10% to 33% B at a flow rate of 300 nL per minute. The gradient was composed of Solvent A (0.1% formic acid in water) and solvent B (0.1% formic acid in acetonitrile). A gold coated glass capillary (PicoTip, New Objective) was used for introduction into the nanoESI source. The LTQ-Orbitrap mass spectrometers were operated in the data-dependent mode using a TOP5 strategy. In brief, a scan cycle was initiated with a full scan of high mass accuracy in the orbitrap (R=30 000), which was followed by MS/MS scans also in the orbitrap (R=7500) on the 5 most abundant precursor ions with dynamic exclusion of previously selected ions. Tandem mass spectra were interpreted by SEQUEST and additional manual control. The identified peptide sequence was assured by comparison of the generated natural peptide fragmentation pattern with the fragmentation pattern of a synthetic sequence-identical reference peptide.

Label-free relative LC-MS quantitation was performed by ion counting i.e. by extraction and analysis of LC-MS features (Mueller et al., 2007). The method assumes that the peptide's LC-MS signal area correlates with its abundance in the sample. Extracted features were further processed by charge state deconvolution and retention time alignment (Mueller et al., 2008; Sturm et al., 2008). Finally, all LC-MS features were cross-referenced with the sequence identification results to combine quantitative data of different samples and tissues to peptide presentation profiles. The quantitative data were normalized in a two-tier fashion according to central tendency to account for variation within technical and biological replicates. Thus each identified peptide can be associated with quantitative data allowing relative quantification between samples and tissues. In addition, all quantitative data acquired for peptide candidates was inspected manually to assure data consistency and to verify the accuracy of the automated analysis. For each peptide a presentation profile was calculated showing the mean sample presentation as well as replicate variations. The profiles juxtapose different cancer samples to a baseline of normal tissue samples. Presentation profiles of exemplary over-presented peptides are shown in FIGS. 1A-1Z.

Table 8 (A and B) and 9 (A and B) show the presentation on various cancer entities for selected peptides, and thus the particular relevance of the peptides as mentioned for the diagnosis and/or treatment of the cancers as indicated (e.g. peptide SEQ ID No. 1 for urinary bladder cancer, esophageal cancer, including cancer of the gastric-esophageal junction, hepatocellular carcinoma, non-small cell lung cancer, and pancreatic cancer, peptide SEQ ID No. 2 for renal cancer, esophageal cancer, including cancer of the gastric-esophageal, glioblastoma, . . . etc.).

TABLE 8A

Overview of presentation of selected HLA-A*02-binding tumor-associated peptides of the present invention across entities. GB = glioblastoma, BRCA = breast cancer, CRC = colorectal cancer, RCC = renal cell carcinoma, CLL = chronic lymphocytic leukemia, HCC = hepatocellular carcinoma, NSCLC = non-small cell lung cancer, SCLC = small cell lung cancer, NHL = non-Hodgkin lymphoma (8 samples), AML = acute myeloid leukemia, OC = ovarian cancer, PC = pancreatic cancer, cIPC = pancreatic cancer cell lines, PCA = prostate cancer and benign prostate hyperplasia, OSCAR = esophageal cancer, including cancer of the gastric-esophageal junction, GBC_CCC = gallbladder adenocarcinoma and cholangiocarcinoma, MEL = melanoma, GC = gastric cancer, TC = testis cancer, UBC = urinary bladder cancer, UEC = uterine cancer.

| SEQ ID No. | Sequence | Peptide Presentation on cancer entities |
|---|---|---|
| 1 | HLYNNEEQV | UBC, OSCAR, HCC, NSCLC, clPC |
| 2 | ALYGKLLKL | RCC, OSCAR, GB, BRCA, CLL, UBC, HCC, SCLC, NSCLC, CRC, OC, GC, NHL |
| 4 | ELAEIVFKV | CRC, CLL, NSCLC, GB |
| 5 | SLFGQEVYC | HCC, GB, CRC |
| 6 | FLDPAQRDL | UBC, NSCLC, GB, AML, cIPC |
| 7 | AAAAKVPEV | NSCLC, GB, CRC |
| 8 | KLGPFLLNA | GC, GB, cIPC, NSCLC |
| 9 | FLGDYVENL | CLL, CRC, UBC |

TABLE 8A-continued

Overview of presentation of selected HLA-A*02-binding tumor-associated peptides of the present invention across entities. GB = glioblastoma, BRCA = breast cancer, CRC = colorectal cancer, RCC = renal cell carcinoma, CLL = chronic lymphocytic leukemia, HCC = hepatocellular carcinoma, NSCLC = non-small cell lung cancer, SCLC = small cell lung cancer, NHL = non-Hodgkin lymphoma (8 samples), AML = acute myeloid leukemia, OC = ovarian cancer, PC = pancreatic cancer, cIPC = pancreatic cancer cell lines, PCA = prostate cancer and benign prostate hyperplasia, OSCAR = esophageal cancer, including cancer of the gastric-esophageal junction, GBC_CCC = gallbladder adenocarcinoma and cholangiocarcinoma, MEL = melanoma, GC = gastric cancer, TC = testis cancer, UBC = urinary bladder cancer, UEC = uterine cancer.

| SEQ ID No. | Sequence | Peptide Presentation on cancer entities |
|---|---|---|
| 10 | KTLDVFNIIL | CLL, GC, GBC_CCC, OSCAR |
| 11 | GVLKVFLENV | HCC, NSCLC, GC, OC, OSCAR |
| 12 | GLIYEETRGV | GC, OSCAR, NSCLC, NHL |
| 13 | VLRDNIQGI | NSCLC, GBC_CCC, OC, GC, BRCA, OSCAR, CRC, GB, UEC, CLL, RCC, UBC, HCC, MEL, SCLC, NHL |
| 15 | ALGDYVHAC | HCC, GC |
| 16 | PLWGKVFYL | GBC_CCC, NSCLC, GB, cIPC, CRC |
| 17 | ILHEHHIFL | RCC, NSCLC |
| 19 | TLLPTVLTL | RCC, UBC, SCLC |
| 20 | ALDGHLYAI | RCC, UBC, GC |
| 21 | SLYHRVLLY | RCC, OSCAR, NSCLC |
| 22 | MLSDLTLQL | CRC, PCA, RCC, NSCLC, BRCA, GC, SCLC, PC, OSCAR |
| 23 | AQTVVVIKA | GC |
| 24 | FLWNGEDSAL | PC, CRC |
| 25 | IQADDFRTL | GC |
| 26 | KVDGVVIQL | OSCAR, GC |
| 27 | KVFGDLDQV | OSCAR, GC |
| 29 | TLCNKTFTA | PCA, GB |
| 30 | TVIDECTRI | GC |
| 31 | ALSDETKNNWEV | AML, CLL |
| 32 | ILADEAFFSV | CLL, PC, GB, UBC, PCA, CRC, SCLC, HCC, RCC, OC, NSCLC, MEL, OSCAR, cIPC, GC, BRCA, NHL |
| 34 | LLPKKTESHHKT | CRC, HCC, NSCLC, GB |
| 35 | YVLPKLYVKL | CLL, CRC, NSCLC, GBC_CCC, UBC, OSCAR |
| 36 | KLYGIEIEV | NSCLC, GB, RCC |
| 37 | ALINDILGELVKL | cIPC, CRC, RCC, HCC |
| 38 | KMQEDLVTL | NSCLC, RCC, OC, GC, GBC_CCC, OSCAR, cIPC, GB, BRCA, PCA, PC, UEC, HCC, CRC, SCLC, NHL |
| 39 | ALMAVVSGL | OSCAR, GBC_CCC, CLL, BRCA, HCC, UBC, NSCLC, OC, GC, MEL |
| 40 | SLLALPQDLQA | PCA, NSCLC, CRC, UBC, OC |
| 41 | FVLPLVVTL | OC, OSCAR, CLL, PCA, SCLC, NSCLC, NHL |
| 42 | VLSPFILTL | NSCLC, RCC, BRCA, UBC, OC, NHL |
| 43 | LLWAGPVTA | CLL, HCC, CRC, NSCLC, RCC, UBC, NHL, TC |
| 44 | GLLWQIIKV | CRC, NSCLC, GC |
| 45 | VLGPTPELV | CRC, SCLC, GC, cIPC, PC |
| 46 | SLAKHGIVAL | PC, NSCLC, CRC, RCC, OC, cIPC, PCA, NHL |
| 47 | GLYQAQVNL | NSCLC, SCLC |
| 48 | TLDHKPVTV | OC, PCA, NSCLC |
| 49 | LLDESKLTL | UBC, OC, PCA, NSCLC, RCC |
| 50 | EYALLYHTL | CRC, GC |
| 51 | LLLDGDFTL | SCLC, HCC |
| 52 | ELLSSIFFL | UBC, NSCLC, CRC, RCC |
| 53 | SLLSHVIVA | cIPC, RCC, GBC_CCC, UBC, NSCLC |
| 54 | FINPKGNWLL | UBC, NSCLC, cIPC |
| 55 | IASAIVNEL | BRCA, GC |
| 56 | KILDLTRVL | CRC, NSCLC |
| 57 | VLISSTVRL | cIPC, RCC, CLL, NHL |
| 58 | ALDDSLTSL | cIPC, PC, GB |
| 59 | ALTKILAEL | UBC, NSCLC |
| 60 | FLIDTSASM | UBC, SCLC, RCC |
| 61 | HLPDFVKQL | BRCA, CLL, GBC_CCC |
| 62 | SLFNQEVQI | CLL, NHL |
| 63 | TLSSERDFAL | NSCLC, GC |
| 66 | FITDFYTTV | GB |
| 67 | GVIETVTSL | NSCLC, GC, CRC |

TABLE 8A-continued

Overview of presentation of selected HLA-A*02-binding tumor-associated peptides of the present invention across entities. GB = glioblastoma, BRCA = breast cancer, CRC = colorectal cancer, RCC = renal cell carcinoma, CLL = chronic lymphocytic leukemia, HCC = hepatocellular carcinoma, NSCLC = non-small cell lung cancer, SCLC = small cell lung cancer, NHL = non-Hodgkin lymphoma (8 samples), AML = acute myeloid leukemia, OC = ovarian cancer, PC = pancreatic cancer, cIPC = pancreatic cancer cell lines, PCA = prostate cancer and benign prostate hyperplasia, OSCAR = esophageal cancer, including cancer of the gastric-esophageal junction, GBC_CCC = gallbladder adenocarcinoma and cholangiocarcinoma, MEL = melanoma, GC = gastric cancer, TC = testis cancer, UBC = urinary bladder cancer, UEC = uterine cancer.

| SEQ ID No. | Sequence | Peptide Presentation on cancer entities |
|---|---|---|
| 68 | ALYGFFFKI | UBC |
| 69 | GIYDGILHSI | UEC, GB |
| 70 | GLFSQHFNL | HCC, NSCLC |
| 71 | GLITVDIAL | SCLC, PCA |
| 72 | GMIGFQVLL | UBC, OC, CLL, GB, GBC_CCC |
| 74 | ILDETLENV | UBC, SCLC, NHL |
| 76 | ILLDESNFNHFL | NSCLC |
| 77 | IVLSTIASV | cIPC, CRC, PCA |
| 81 | VLFLGKLLV | CRC, UBC |
| 82 | VLLRVLIL | NSCLC, TC |
| 83 | ELLEYLPQL | PC, GBC_CCC |
| 84 | FLEEEITRV | CRC, GC |
| 85 | STLDGSLHAV | OSCAR, PCA, GC |
| 87 | YLTEVFLHVV | CLL, NHL |
| 89 | YLVAHNLLL | RCC |
| 90 | GAVAEEVLSSI | GB |
| 92 | LLRGPPVARA | cIPC, PC, RCC, UBC, OSCAR |
| 93 | SLLTQPIFL | RCC, HCC |
| 321 | SLWFKPEEL | GC, BRCA, CLL, PC, GB, UBC, PCA, CRC, SCLC, HCC, MEL, OC, NSCLC, GBC_CCC, OSCAR, cIPC, NHL |
| 322 | ALVSGGVAQA | GBC_CCC, OSCAR, BRCA, CLL, UBC, HCC, PC, SCLC, NSCLC, CRC, OC, NHL |
| 323 | ILSVVNSQL | CRC, GC, BRCA, OC, CLL, NSCLC, NHL |
| 324 | AIFDFCPSV | NSCLC, CRC, GC, MEL, GB, OSCAR, CLL |
| 325 | RLLPKVQEV | OSCAR, NSCLC, CRC, SCLC, OC |
| 326 | SLLPLVWKI | NSCLC, CRC, GB, RCC, MEL, CLL, TC |
| 327 | SIGDIFLKY | GC, GB, CRC, RCC, NSCLC |
| 328 | SVDSAPAAV | SCLC, OC, PC, OSCAR, RCC, NSCLC, UBC |
| 329 | FAWEPSFRDQV | SCLC, HCC |
| 330 | FLWPKEVEL | NSCLC, BRCA, SCLC, OC, CLL, NHL |
| 331 | AIWKELISL | GB, CRC |
| 332 | AVTKYTSAK | CLL, NSCLC, MEL, NHL |
| 333 | GTFLEGVAK | RCC, CLL, HCC |
| 334 | GRADALRVL | BRCA, SCLC, CLL |
| 335 | VLLAAGPSAA | UBC, CLL, NSCLC, GC, cIPC |
| 336 | GLMDGSPHFL | PC, NSCLC |
| 337 | KVLGKIEKV | RCC, CRC |
| 339 | VLGPGPPPL | NSCLC, cIPC, CLL, NHL |
| 340 | SVAKTILKR | NSCLC, OSCAR |

Table 8B shows the presentation on additional cancer entities for selected peptides, and thus the particular relevance of the peptides as mentioned for the diagnosis and/or treatment of the cancers as indicated.

TABLE 8B

Overview of presentation of selected HLA-A*02 peptides across entities. GB = glioblastoma, BRCA = breast cancer, CRC = colorectal cancer, RCC = renal cell carcinoma, CLL = chronic lymphocytic leukemia, HCC = hepatocellular carcinoma, NSCLC = non-small cell lung cancer, SCLC = small cell lung cancer, NHL = non-Hodgkin lymphoma, AML = acute myeloid leukemia, OC = ovarian cancer, PC = pancreatic cancer, BPH = prostate cancer and benign prostate hyperplasia, OSCAR = esophageal cancer, including cancer of the gastric-oesophageal junction, GBC_CCC = gallbladder adenocarcinoma and cholangiocarcinoma, MEL = melanoma, GC = gastric cancer, UBC = urinary bladder cancer, UTC = uterine cancer, HNSCC = head and neck squamous cell carcinoma.

| SEQ ID No. | Sequence | Peptide Presentation on cancer entities |
|---|---|---|
| 1 | HLYNNEEQV | GBC_CCC |
| 2 | ALYGKLLKL | cIPC, UTC, PCA, MEL, AML |
| 3 | TLLGKQVTL | CLL, NSCLC, NHL, AML |

TABLE 8B-continued

Overview of presentation of selected HLA-A*02 peptides across entities. GB = glioblastoma, BRCA = breast cancer, CRC = colorectal cancer, RCC = renal cell carcinoma, CLL = chronic lymphocytic leukemia, HCC = hepatocellular carcinoma, NSCLC = non-small cell lung cancer, SCLC = small cell lung cancer, NHL = non-Hodgkin lymphoma, AML = acute myeloid leukemia, OC = ovarian cancer, PC = pancreatic cancer, BPH = prostate cancer and benign prostate hyperplasia, OSCAR = esophageal cancer, including cancer of the gastric-oesophageal junction, GBC_CCC = gallbladder adenocarcinoma and cholangiocarcinoma, MEL = melanoma, GC = gastric cancer, UBC = urinary bladder cancer, UTC = uterine cancer, HNSCC = head and neck squamous cell carcinoma.

| SEQ ID No. | Sequence | Peptide Presentation on cancer entities |
|---|---|---|
| 5 | SLFGQEVYC | GBC_CCC, PCA |
| 6 | FLDPAQRDL | MEL |
| 7 | AAAAKVPEV | MEL, HNSCC, NHL |
| 8 | KLGPFLLNA | UTC, HCC |
| 9 | FLGDYVENL | UTC, AML, OC, cIPC |
| 12 | GLIYEETRGV | AML, UTC, HNSCC |
| 13 | VLRDNIQGI | AML, HNSCC |
| 17 | ILHEHHIFL | UTC |
| 18 | YVLNEEDLQKV | UTC, NSCLC |
| 19 | TLLPTVLTL | GBC_CCC, BRCA, UTC |
| 22 | MLSDLTLQL | MEL |
| 24 | FLWNGEDSAL | NSCLC, GC, UTC |
| 28 | TLYSMDLMKV | HNSCC, RCC |
| 32 | ILADEAFFSV | HNSCC, UTC, AML, GBC_CCC |
| 33 | LLLPLLPPLSPSLG | MEL, NSCLC, GBC_CCC, GC, cIPC, SCLC, GB, PC, MCC, CRC, HCC |
| 34 | LLPKKTESHHKT | UTC |
| 35 | YVLPKLYVKL | HNSCC, NHL, AML |
| 36 | KLYGIEIEV | UTC |
| 37 | ALINDILGELVKL | MEL, UTC |
| 38 | KMQEDLVTL | MEL, AML |
| 39 | ALMAVVSGL | HNSCC, NHL, UTC, AML |
| 40 | SLLALPQDLQA | GBC_CCC, BRCA, UTC |
| 41 | FVLPLVVTL | AML, CRC, BRCA, HNSCC, UTC |
| 42 | VLSPFILTL | AML, CLL, UTC |
| 43 | LLWAGPVTA | HNSCC |
| 45 | VLGPTPELV | OSCAR, GBC_CCC, BRCA |
| 46 | SLAKHGIVAL | UBC, HNSCC, GB, CLL, MEL, UTC, HCC |
| 47 | GLYQAQVNL | OSCAR |
| 50 | EYALLYHTL | GBC_CCC |
| 51 | LLLDGDFTL | OSCAR |
| 53 | SLLSHVIVA | HCC, AML, OC, OSCAR, HNSCC, MEL, CLL, NHL, BRCA |
| 54 | FINPKGNWLL | UTC, HNSCC |
| 55 | IASAIVNEL | HCC, GBC_CCC |
| 56 | KILDLTRVL | GBC_CCC |
| 57 | VLISSTVRL | MEL |
| 59 | ALTKILAEL | HCC |
| 60 | FLIDTSASM | AML, CLL, BRCA, HNSCC, UTC, NHL |
| 61 | HLPDFVKQL | MEL, AML |
| 64 | GLSSSSYEL | GBC_CCC, HCC |
| 65 | KLDGICWQV | GBC_CCC, HCC |
| 66 | FITDFYTTV | MEL, UBC, HCC, HNSCC, CRC |
| 67 | GVIETVTSL | AML |
| 70 | GLFSQHFNL | BRCA, UTC, HNSCC, UBC, AML, OSCAR, cIPC |
| 71 | GLITVDIAL | AML, MEL, UTC |
| 72 | GMIGFQVLL | HNSCC, AML |
| 73 | GVPDTIATL | GC |
| 74 | ILDETLENV | AML, BRCA |
| 75 | ILDNVKNLL | AML |
| 77 | IVLSTIASV | AML |
| 78 | LLWGHPRVA | NSCLC |
| 79 | SLVPLQILL | HCC |
| 80 | TLDEYLTYL | HCC |
| 81 | VLFLGKLLV | HNSCC |
| 86 | LLVTSLVVV | HCC, GBC_CCC |
| 88 | ILLNTEDLASL | RCC |
| 91 | SSLEPQIQPV | MEL, CLL |
| 93 | SLLTQPIFL | GBC_CCC |

TABLE 8B-continued

Overview of presentation of selected HLA-A*02 peptides across entities. GB = glioblastoma, BRCA = breast cancer, CRC = colorectal cancer, RCC = renal cell carcinoma, CLL = chronic lymphocytic leukemia, HCC = hepatocellular carcinoma, NSCLC = non-small cell lung cancer, SCLC = small cell lung cancer, NHL = non-Hodgkin lymphoma, AML = acute myeloid leukemia, OC = ovarian cancer, PC = pancreatic cancer, BPH = prostate cancer and benign prostate hyperplasia, OSCAR = esophageal cancer, including cancer of the gastric-oesophageal junction, GBC_CCC = gallbladder adenocarcinoma and cholangiocarcinoma, MEL = melanoma, GC = gastric cancer, UBC = urinary bladder cancer, UTC = uterine cancer, HNSCC = head and neck squamous cell carcinoma.

| SEQ ID No. | Sequence | Peptide Presentation on cancer entities |
|---|---|---|
| 321 | SLWFKPEEL | UTC, HNSCC, AML |
| 322 | ALVSGGVAQA | AML, GC, cIPC, UTC, MEL |
| 323 | ILSVVNSQL | MEL, GBC_CCC, AML, OSCAR |
| 324 | AIFDFCPSV | BRCA, NHL, UTC, AML, HNSCC |
| 325 | RLLPKVQEV | AML, BRCA, UBC, GC |
| 326 | SLLPLVWKI | AML |
| 327 | SIGDIFLKY | MEL, AML |
| 328 | SVDSAPAAV | NHL, BRCA, AML, UTC, CLL, HNSCC, MEL |
| 329 | FAWEPSFRDQV | GBC_CCC |
| 330 | FLWPKEVEL | AML |
| 331 | AIWKELISL | MEL, CLL, NSCLC |
| 333 | GTFLEGVAK | MEL, NSCLC |
| 334 | GRADALRVL | MEL, GBC_CCC, AML |
| 335 | VLLAAGPSAA | AML, CRC, UTC, NHL |
| 336 | GLMDGSPHFL | MEL |
| 338 | LLYDGKLSSA | CRC, UBC, OC |
| 339 | VLGPGPPPL | MEL, GB, UTC, AML, HCC |
| 340 | SVAKTILKR | NHL |

TABLE 9A

Overview of presentation of selected HLA-A*24-binding tumor-associated peptides of the present invention across entities. GB = glioblastoma, HCC = hepatocellular carcinoma, NSCLC = non-small cell lung cancer, PCA = prostate cancer, GC = gastric cancer, CRC = colorectal cancer, RCC = renal cell carcinoma.

| SEQ ID NO. | Sequence | ENTITIES |
|---|---|---|
| 96 | LYSPVPFTL | HCC, NSCLC, GC, GB |
| 97 | TYTFLKETF | PCA, HCC, NSCLC, GB |
| 98 | VFPRLHNVLF | HCC, NSCLC, GC |
| 99 | QYILAVPVL | NSCLC, GC, GB, PCA |
| 100 | VYIESRIGTSTSF | GB, HCC, NSCLC, GC |
| 101 | IYIPVLPPHL | HCC, NSCLC |
| 102 | VYPFENFEF | GC, NSCLC |
| 103 | NYIPVKNGKQF | PCA, HCC, NSCLC, GB |
| 104 | SYLTWHQQI | PCA, HCC, NSCLC |
| 105 | IYNETITDLL | GC, GB, HCC, NSCLC |
| 106 | IYNETVRDLL | GC, GB, NSCLC |
| 107 | KYFPYLVVI | HCC, NSCLC, GC |
| 109 | LFITGGQFF | HCC, NSCLC, GC |
| 110 | SYPKIIEEF | GB, HCC, NSCLC, GC |
| 111 | VYVQILQKL | GC, HCC, NSCLC |
| 112 | IYNFVESKL | NSCLC, GC |
| 113 | IYSFHTLSF | NSCLC, GC, GB |
| 114 | QYLDGTWSL | NSCLC, GC, GB |
| 115 | RYLNKSFVL | NSCLC, GC, GB, PCA, HCC |
| 116 | AYVIAVHLF | GB, PCA, HCC, NSCLC |
| 117 | IYLSDLTYI | HCC, NSCLC, GC, PCA |
| 118 | KYLNSVQYI | HCC, NSCLC, GC, GB, PCA |
| 119 | VYRVYVTTF | NSCLC, GC |
| 120 | GYIEHFSLW | HCC, NSCLC, GC |
| 121 | RYGLPAAWSTF | HCC, NSCLC, GC |
| 122 | EYQARIPEF | NSCLC, GC, GB, PCA, HCC |
| 123 | VYTPVLEHL | NSCLC, GC, GB, HCC |
| 124 | TYKDYVDLF | GC, RCC, GB, PCA, HCC, NSCLC |
| 125 | VFSRDFGLLVF | GC, HCC, NSCLC |
| 126 | PYDPALGSPSRLF | NSCLC, GC, PCA, HCC |
| 127 | QYFTGNPLF | NSCLC, GC, GB, RCC, PCA |
| 128 | VYPFDWQYI | GB, PCA, HCC, NSCLC, GC |
| 129 | KYIDYLMTW | NSCLC, GC, GB, PCA, HCC |
| 130 | VYAHIYHQHF | NSCLC, GC, PCA, HCC |
| 131 | EYLDRIGQLFF | NSCLC, GC, RCC, GB, PCA, HCC |
| 132 | RYPALFPVL | HCC, NSCLC, GC, PCA |
| 133 | KYLEDMKTYF | HCC, NSCLC, GC, GB |

TABLE 9A-continued

Overview of presentation of selected HLA-A*24-binding tumor-associated peptides of the present invention across entities. GB = glioblastoma, HCC = hepatocellular carcinoma, NSCLC = non-small cell lung cancer, PCA = prostate cancer, GC = gastric cancer, CRC = colorectal cancer, RCC = renal cell carcinoma.

| SEQ ID NO. | Sequence | ENTITIES |
| --- | --- | --- |
| 134 | AYIPTPIYF | PCA, NSCLC, GB |
| 135 | VYEAMVPLF | GC, NSCLC |
| 136 | IYPEWPVVFF | GC |
| 137 | EYLHNCSYF | GC, PCA, HCC, NSCLC |
| 138 | VYNAVSTSF | NSCLC, GC |
| 139 | IFGIFPNQF | PCA, NSCLC |
| 142 | VYVDDIYVI | NSCLC, GC |
| 143 | KYIFQLNEI | GB, NSCLC |
| 144 | VFASLPGFLF | NSCLC, GC |
| 145 | VYALKVRTI | NSCLC |
| 147 | LYLAFPLAF | NSCLC, GC, PCA, HCC |
| 148 | SYGTVSQIF | PCA, HCC, NSCLC, GC, GB |
| 149 | SYGTVSQI | HCC, NSCLC, GB |
| 150 | IYITRQFVQF | PCA, HCC, NSCLC, GB |
| 151 | AYISGLDVF | HCC, NSCLC, PCA |
| 153 | VYVPFGGKSMITF | NSCLC |
| 154 | VYGVPTPHF | GB, NSCLC |
| 155 | IYKWITDNF | HCC, NSCLC, GC, GB |
| 156 | YYMELTKLLL | NSCLC, GC, HCC |
| 157 | DYIPASGFALF | NSCLC, GB |
| 158 | IYEETRGVLKVF | HCC, NSCLC, GC |
| 159 | IYEETRGVL | HCC, NSCLC |
| 160 | RYGDGGSSF | PCA, NSCLC, GC |
| 161 | KYPDIVQQF | PCA, HCC, NSCLC, GC |
| 162 | KYTSYILAF | NSCLC, GC, PCA, HCC |
| 163 | RYLTISNLQF | NSCLC |
| 165 | EYFTPLLSGQF | NSCLC |
| 166 | FYTLPFHLI | HCC, NSCLC |
| 168 | RYLEAALRL | NSCLC, GC, GB, PCA, HCC |
| 169 | NYITGKGDVF | NSCLC, PCA |
| 170 | QYPFHVPLL | GC, PCA, HCC, NSCLC |
| 174 | VYEKNGYIYF | NSCLC, GB |
| 175 | YYTQYSQTI | GB, NSCLC |
| 176 | FYINGQYQF | GB, PCA, HCC, NSCLC, GC |
| 177 | VYFKAGLDVF | PCA, NSCLC |
| 178 | NYSSAVQKF | PCA, HCC, NSCLC, GB |
| 179 | TYIPVGLGRLL | NSCLC, GC |
| 180 | KYLQVVGMF | NSCLC, GB |
| 182 | AYAQLGYLLF | NSCLC |
| 183 | PYLQDVPRI | NSCLC, GB |
| 186 | VFTTSSNIF | NSCLC, GB |
| 187 | AYAANVHYL | NSCLC |
| 188 | GYKTFFNEF | NSCLC |
| 192 | RYSTFSEIF | HCC, NSCLC, GC |
| 194 | VYQSLSNSL | NSCLC |
| 195 | AYIKGGWIL | RCC, HCC, NSCLC, GC |
| 196 | GYIRGSWQF | NSCLC, GC |
| 197 | IFTDIFHYL | HCC, NSCLC, GC, GB |
| 199 | SYLNHLNNL | NSCLC |
| 201 | GYNPNRVFF | GB, NSCLC |
| 202 | RYVEGIVSL | NSCLC |
| 204 | EYLSTCSKL | NSCLC, HCC |
| 206 | NYLDVATFL | NSCLC, GC, GB, PCA, HCC |
| 207 | LYSDAFKFIVF | NSCLC |
| 209 | AFIETPIPLF | NSCLC |
| 210 | IYAGVGEFSF | NSCLC, GC |
| 215 | SYVASFFLL | GC, NSCLC |
| 217 | IYISNSIYF | NSCLC, GC |
| 221 | KYIGNLDLL | NSCLC, GB |
| 223 | TFITQSPLL | NSCLC |
| 225 | TYTNTLERL | NSCLC |
| 226 | MYLKLVQLF | HCC, GC |
| 228 | IYQYVADNF | NSCLC |
| 229 | IYQFVADSF | NSCLC |
| 232 | YYLSDSPLL | NSCLC, GC |
| 234 | SYLPAIWLL | GC |
| 235 | VYKDSIYYI | GB, PCA, HCC, NSCLC, GC |
| 236 | VYLPKIPSW | HCC, NSCLC |
| 238 | SYLEKVRQL | NSCLC |

TABLE 9A-continued

Overview of presentation of selected HLA-A*24-binding tumor-associated peptides of the present invention across entities. GB = glioblastoma, HCC = hepatocellular carcinoma, NSCLC = non-small cell lung cancer, PCA = prostate cancer, GC = gastric cancer, CRC = colorectal cancer, RCC = renal cell carcinoma.

| SEQ ID NO. | Sequence | ENTITIES |
|---|---|---|
| 240 | YYFFVQEKI | HCC, NSCLC |
| 243 | SYLELANTL | PCA, NSCLC |
| 248 | AFPTFSVQL | NSCLC |
| 249 | RYHPTTCTI | NSCLC |
| 250 | KYPDIASPTF | HCC |
| 251 | VYTKALSSL | NSCLC, HCC |
| 252 | AFGQETNVPLNNF | HCC |
| 253 | IYGFFNENF | HCC |
| 254 | KYLESSATF | NSCLC |
| 255 | VYQKIILKF | HCC |
| 257 | IFIDNSTQPLHF | HCC |
| 259 | YFIKSPPSQLF | NSCLC, GC |
| 260 | VYMNVMTRL | NSCLC |
| 261 | GYIKLINFI | GC |
| 262 | VYSSQFETI | GB |
| 264 | LYTETRLQF | NSCLC |
| 265 | SYLNEAFSF | PCA |
| 266 | KYTDWTEFL | HCC, NSCLC, GC, GB, PCA |
| 268 | IFITKALQI | GC |
| 269 | QYPYLQAFF | NSCLC |
| 271 | RFLMKSYSF | HCC |
| 274 | KQLDIANYELF | NSCLC, GB, HCC |
| 275 | KYGTLDVTF | NSCLC |
| 276 | QYLDVLHAL | GC, RCC |
| 277 | FYTFPFQQL | GC, RCC, PCA, HCC, NSCLC |
| 280 | TYNPNLQDKL | HCC |
| 281 | NYSPGLVSLIL | NSCLC |
| 284 | DYLKDPVTI | NSCLC |
| 285 | VYVGDALLHAI | PCA |
| 286 | SYGTILSHI | NSCLC |
| 288 | VYPDTVALTF | NSCLC, GC |
| 289 | FFHEGQYVF | GC |
| 290 | KYGDFKLLEF | PCA, GB |
| 295 | SYLVIHERI | NSCLC, GC |
| 296 | SYQVIFQHF | NSCLC, GC |
| 297 | TYIDTRTVF | PCA, HCC, NSCLC, GC |
| 298 | AYKSEVVYF | NSCLC, GB |
| 299 | KYQYVLNEF | NSCLC, GC, GB |
| 300 | TYPSQLPSL | CRC, GC |
| 301 | KFDDVTMLF | NSCLC, GC, HCC |
| 303 | LYSVIKEDF | GB, PCA, HCC, NSCLC, GC |
| 304 | EYNEVANLF | HCC, NSCLC, GC, RCC, GB, PCA |
| 305 | NYENKQYLF | NSCLC, GB, HCC |
| 306 | VYPAEQPQI | NSCLC |
| 307 | GYAFTLPLF | NSCLC, GC |
| 308 | TFDGHGVFF | NSCLC, GC |
| 309 | KYYRQTLLF | PCA, HCC, NSCLC, GC, GB |
| 310 | IYAPTLLVF | GC, GB, RCC, HCC, NSCLC |
| 311 | EYLQNLNHI | PCA |
| 312 | SYTSVLSRL | PCA, HCC, NSCLC |
| 313 | KYTHFIQSF | NSCLC, GC, RCC, GB, PCA, HCC |
| 314 | RYFKGDYSI | GB, HCC |
| 315 | FYIPHVPVSF | HCC, NSCLC |
| 316 | VYFEGSDFKF | GB, PCA, HCC, NSCLC |
| 317 | VFDTSIAQLF | GB, RCC, HCC, NSCLC, GC |
| 318 | TYSNSAFQYF | GC, RCC, PCA, HCC, NSCLC |
| 319 | KYSDVKNLI | PCA, HCC, NSCLC, GB |
| 320 | KFILALKVLF | HCC, NSCLC |
| 341 | SYLTQHQRI | PCA, NSCLC |
| 343 | NYLGGTSTI | PCA, HCC, GB |
| 344 | EYNSDLHQF | GB, RCC, HCC, NSCLC, GC |
| 345 | EYNSDLHQFF | GB, NSCLC |
| 346 | IYVIPQPHF | NSCLC, GC, GB, HCC |
| 347 | VYAEVNSL | GB, NSCLC, GC |
| 348 | IYLEHTESI | GC, HCC, NSCLC |
| 349 | QYSIISNVF | GC, HCC, NSCLC |
| 350 | KYGNFIDKL | NSCLC, GC, HCC |
| 351 | IFHEVPLKF | HCC, NSCLC |
| 352 | QYGGDLTNTF | NSCLC, GB |

TABLE 9A-continued

Overview of presentation of selected HLA-A*24-binding tumor-associated peptides of the present invention across entities. GB = glioblastoma, HCC = hepatocellular carcinoma, NSCLC = non-small cell lung cancer, PCA = prostate cancer, GC = gastric cancer, CRC = colorectal cancer, RCC = renal cell carcinoma.

| SEQ ID NO. | Sequence | ENTITIES |
| --- | --- | --- |
| 353 | TYGKIDLGF | HCC, NSCLC, GC, GB |
| 354 | VYNEQIRDLL | NSCLC, GC, GB |
| 355 | IYVTGGHLF | HCC, NSCLC, GC, RCC, GB, PCA |
| 356 | NYMPGQLTI | RCC, NSCLC, GC |
| 357 | QFITSTNTF | NSCLC |
| 358 | YYSEVPVKL | NSCLC, GB |
| 359 | NYGVLHVTF | RCC, HCC, NSCLC |
| 360 | VFSPDGHLF | GB, PCA, HCC, NSCLC |
| 361 | TYADIGGLDNQI | PCA, NSCLC, GC, GB, RCC |
| 362 | VYNYAEQTL | GC, GB, NSCLC |
| 363 | SYAELGTTI | GB, NSCLC, GC |
| 365 | VFIDHPVHL | NSCLC, GB |
| 366 | QYLELAHSL | HCC, NSCLC, GC |
| 367 | LYQDHMQYI | HCC, NSCLC, GC, GB, PCA |
| 368 | KYQNVKHNL | NSCLC, HCC |
| 369 | VYTHEVVTL | NSCLC |
| 370 | RFIGIPNQF | PCA |
| 371 | AYSHLRYVF | GB, PCA, HCC, NSCLC |
| 373 | GYISNGELF | PCA, HCC |
| 375 | KYTDYILKI | NSCLC |
| 376 | VYTPVASRQSL | HCC, NSCLC, GC, GB, PCA |
| 377 | QYTPHSHQF | HCC, NSCLC |
| 378 | VYIAELEKI | HCC, NSCLC |
| 380 | VYTGIDHHW | NSCLC, GC, RCC, GB, PCA, HCC |
| 382 | AYLPPLQQVF | PCA, HCC, NSCLC, GC, RCC, GB |
| 383 | RYKPGEPITF | GB, PCA, HCC, NSCLC |
| 384 | RYFDVGLHNF | GC, GB, PCA, HCC, NSCLC |
| 385 | QYIEELQKF | NSCLC, HCC |
| 386 | TFSDVEAHF | HCC, NSCLC, GC, GB |
| 387 | KYTEKLEEI | HCC, NSCLC, GB, PCA |
| 388 | IYGEKTYAF | HCC, NSCLC, GC, GB, PCA |
| 389 | EYLPEFLHTF | NSCLC |
| 390 | RYLWATVTI | GC, HCC, NSCLC |
| 391 | LYQILQGIVF | NSCLC, GC, GB, RCC, HCC |
| 392 | RYLDSLKAIVF | NSCLC, GC, RCC, HCC |
| 393 | KYIEAIQWI | HCC, NSCLC |
| 394 | FYQPKIQQF | GB, PCA, HCC, NSCLC, GC |
| 395 | LYINKANIW | NSCLC, GC, HCC |
| 396 | YYHFIFTTL | GB |
| 397 | IYNGKLFDL | GB, NSCLC, GC |
| 398 | IYNGKLFDLL | CRC, GC, RCC, GB, PCA, HCC, NSCLC |
| 399 | SYIDVLPEF | HCC, NSCLC, GC, RCC, GB, PCA |
| 400 | KYLEKYYNL | NSCLC |
| 401 | VFMKDGFFYF | NSCLC, GC, PCA |
| 402 | VWSDVTPLTF | NSCLC, CRC, GC, RCC, GB, PCA, HCC |
| 403 | TYKYVDINTF | NSCLC, GC |
| 404 | RYLEKFYGL | NSCLC, GC, HCC |
| 405 | NYPKSIHSF | NSCLC |
| 406 | TYSEKTTLF | NSCLC, GC |
| 407 | VYGIRLEHF | HCC, NSCLC, GC, GB |
| 408 | QYASRFVQL | GC, GB, HCC, NSCLC |
| 409 | YFISHVLAF | GC, NSCLC |
| 410 | RFLSGIINF | NSCLC, GC, GB, HCC |
| 411 | VYIGHTSTI | NSCLC |
| 412 | SYNPLWLRI | GB, RCC, HCC, NSCLC, GC |
| 413 | NYLLYVSNF | HCC, NSCLC, GC |
| 414 | MYPYIYHVL | HCC, NSCLC, GC, GB, PCA |
| 415 | SYQKVIELF | PCA, HCC, NSCLC, CRC, GC, RCC, GB |
| 416 | AYSDGHFLF | NSCLC, GC, RCC, GB, PCA, HCC |
| 417 | VYKVVGNLL | GB, RCC, HCC, NSCLC, GC |

Table 9B show the presentation on additional cancer entities for selected peptides, and thus the particular relevance of the peptides as mentioned for the diagnosis and/or treatment of the cancers as indicated.

TABLE 9B

Overview of presentation of selected HLA-A*24 peptides across cancer entities.
GB = glioblastoma, CRC = colorectal cancer, RCC = renal cell carcinoma, HCC = hepatocellular carcinoma, NSCLC = non-small cell king cancer, PCA = prostate cancer and benign prostate hyperplasia, GC = gastric cancer.

| SEQ ID No. | Sequence | Peptide Presentation on cancer entities |
|---|---|---|
| 50 | EYALLYHTL | PCA, HCC, NSCLC, CRC, GC, RCC |
| 104 | SYLTWHQQI | GB |
| 108 | PYLVVIHTL | NSCLC |
| 110 | SYPKIIEEF | PCA |
| 132 | RYPALFPVL | RCC |
| 135 | VYEAMVPLF | HCC |
| 140 | RYLINSYDF | NSCLC |
| 141 | SYNGHLTIWF | GB |
| 146 | NYYERIHAL | NSCLC |
| 148 | SYGTVSQIF | CRC |
| 152 | KFFDDLGDELLF | NSCLC |
| 155 | IYKWITDNF | PCA |
| 164 | HYVPATKVF | NSCLC |
| 167 | RYGFYYVEF | GB |
| 171 | NYEDHFPLL | NSCLC |
| 172 | VFIFKGNEF | NSCLC |
| 173 | QYLEKYYNL | NSCLC |
| 181 | VYPPYLNYL | PCA |
| 184 | IYSVGAFENF | NSCLC |
| 185 | QYLVHVNDL | GB |
| 189 | AYFKQSSVF | NSCLC |
| 190 | LYSELTETL | NSCLC |
| 191 | TYPDGTYTGRIF | NSCLC |
| 193 | LYLENNAQTQF | NSCLC |
| 198 | DYVGFTLKI | NSCLC |
| 200 | VFIHHLPQF | HCC |
| 203 | VYNVEVKNAEF | NSCLC |
| 204 | EYLSTCSKL | PCA |
| 205 | VYPVVLNQI | NSCLC |
| 208 | TYLEKIDGF | NSCLC |
| 211 | VFKSEGAYF | NSCLC |
| 212 | SYAPPSEDLF | NSCLC |
| 213 | SYAPPSEDLFL | NSCLC |
| 214 | KYLMELTLI | NSCLC |
| 216 | FYVNVKEQF | NSCLC |
| 218 | LYSELNKWSF | NSCLC |
| 219 | SYLKAVFNL | NSCLC |
| 220 | SYSEIKDFL | NSCLC |
| 222 | HYSTLVHMF | NSCLC |
| 224 | PYFFANQEF | HCC |
| 227 | IYRFITERF | NSCLC |
| 230 | TYGMVMVTF | NSCLC |
| 231 | AFADVSVKF | NSCLC |
| 233 | QYLTAAALHNL | NSCLC |
| 237 | KYVGQLAVL | HCC |
| 239 | VYAIFRILL | GC |
| 241 | SYVKVLHHL | HCC |
| 242 | VYGEPRELL | HCC |
| 244 | VHFEDTGKTLLF | NSCLC |
| 245 | LYPQLFVVL | GC |
| 246 | KYLSVQLTL | NSCLC |
| 247 | SFTKTSPNF | HCC |
| 256 | VFGKSAYLF | NSCLC |
| 258 | AYAQLGYLL | NSCLC |
| 263 | RYILENHDF | HCC |
| 267 | SFLNIEKTEILF | HCC |
| 270 | YYSQESKVLYL | HCC |
| 272 | RYVFPLPYL | NSCLC |
| 273 | IYGEKLQFIF | NSCLC |
| 278 | KYVNLVMYF | NSCLC |
| 279 | VWLPASVLF | NSCLC |
| 282 | NYLVDPVTI | NSCLC |
| 283 | EYQEIFQQL | NSCLC |
| 287 | IYNPNLLTASKF | NSCLC |
| 291 | YYLGSGRETF | NSCLC, GB, PCA, HCC |
| 292 | FYPQIINTF | NSCLC |
| 293 | VYPHFSTTNLI | HCC |
| 294 | RFPVQGTVTF | PCA |
| 302 | LYLPVHYGF | NSCLC |

TABLE 9B-continued

Overview of presentation of selected HLA-A*24
peptides across cancer entities.
GB = glioblastoma, CRC = colorectal cancer,
RCC = renal cell carcinoma, HCC = hepatocellular
carcinoma, NSCLC = non-small cell king cancer,
PCA = prostate cancer and benign prostate
hyperplasia, GC = gastric cancer.

| SEQ ID No. | Sequence | Peptide Presentation on cancer entities |
|---|---|---|
| 342 | NYAFLHRTL | NSCLC |
| 344 | EYNSDLHQF | PCA |
| 348 | IYLEHTESI | GB |
| 350 | KYGNFIDKL | PCA |
| 364 | KYLNENQLSQL | NSCLC |
| 372 | VYVIEPHSMEF | NSCLC |
| 374 | VFLPRVTEL | NSCLC |
| 379 | VFIAQGYTL | NSCLC |
| 381 | KYPASSSVF | RCC, NSCLC |

Example 2

Expression Profiling of Genes Encoding the Peptides of the Invention

Over-presentation or specific presentation of a peptide on tumor cells compared to normal cells is sufficient for its usefulness in immunotherapy, and some peptides are tumor-specific despite their source protein occurring also in normal tissues. Still, mRNA expression profiling adds an additional level of safety in selection of peptide targets for immuno-therapies. Especially for therapeutic options with high safety risks, such as affinity-matured TCRs, the ideal target peptide will be derived from a protein that is unique to the tumor and not found on normal tissues, and a high tumor-to-normal ratio of gene expression indicates a therapeutic window. Moreover, over-expression of source genes in tumor entities that were not yet analyzed for peptide presentation indicates that a certain peptide may be of importance in the respective entity.

For HLA class I-binding peptides of this invention, normal tissue expression of all source genes was shown to be minimal based on a database of RNASeq data covering around 3000 normal tissue samples (Lonsdale, 2013). In addition, gene expression data from tumors vs normal tissues were analyzed to assess target coverage in various tumor entities.

RNA Sources and Preparation

Surgically removed tissue specimens were provided as indicated above (see Example 1) after written informed consent had been obtained from each patient. Tumor tissue specimens were snap-frozen immediately after surgery and later homogenized with mortar and pestle under liquid nitrogen. Total RNA was prepared from these samples using TRI Reagent (Ambion, Darmstadt, Germany) followed by a cleanup with RNeasy (QIAGEN, Hilden, Germany); both methods were performed according to the manufacturer's protocol.

Total RNA from healthy human tissues for RNASeq experiments was obtained from: Asterand (Detroit, MI, USA and Royston, Herts, UK); Bio-Options Inc. (Brea, CA, USA); ProteoGenex Inc. (Culver City, CA, USA); Geneticist Inc. (Glendale, CA, USA); Istituto Nazionale Tumori "Pascale" (Naples, Italy); University Hospital of Heidelberg (Heidelberg, Germany); BioCat GmbH (Heidelberg, Germany), BioServe (Beltsville, MD, USA), Capital BioScience Inc. (Rockville, MD, USA).

Total RNA from tumor tissues for RNASeq experiments was obtained from: Asterand (Detroit, MI, USA & Royston, Herts, UK), Bio-Options Inc. (Brea, CA, USA), BioServe (Beltsville, MD, USA), Geneticist Inc. (Glendale, CA, USA), ProteoGenex Inc. (Culver City, CA, USA), Tissue Solutions Ltd (Glasgow, UK), University Hospital Bonn (Bonn, Germany), University Hospital Heidelberg (Heidelberg, Germany), University Hospital Tübingen (Tübingen, Germany) Quality and quantity of all RNA samples were assessed on an Agilent 2100 Bioanalyzer (Agilent, Waldbronn, Germany) using the RNA 6000 Pico LabChip Kit (Agilent).

RNAseq Experiments

Gene expression analysis of tumor and normal tissue RNA samples was performed by next generation sequencing (RNAseq) by CeGaT (Tübingen, Germany). Briefly, sequencing libraries are prepared using the Illumina HiSeq v4 reagent kit according to the provider's protocol (Illumina Inc, San Diego, CA, USA), which includes RNA fragmentation, cDNA conversion and addition of sequencing adaptors. Libraries derived from multiple samples are mixed equimolar and sequenced on the Illumina HiSeq 2500 sequencer according to the manufacturer's instructions, generating 50 bp single end reads. Processed reads are mapped to the human genome (GRCh38) using the STAR software. Expression data are provided on transcript level as RPKM (Reads Per Kilobase per Million mapped reads, generated by the software Cufflinks) and on exon level (total reads, generated by the software Bedtools), based on annotations of the ensembl sequence database (Ensembl77). Exon reads are normalized for exon length and alignment size to obtain RPKM values.

Exemplary expression profiles of source genes of the present invention that are highly over-expressed or exclusively expressed in different cancers are shown in FIGS. 2A-2D. Expression scores for further exemplary targets are shown in Table 10 (A and B), based on in-house RNASeq analyses. Expression data for other entities and further exemplary peptides are summarized in Table 11, based on data generated by the TCGA Research Network: cancergenome.nih.gov/.

TABLE 10A

Target coverage within various tumor entities, for expression of source genes of selected peptides. Over-expression was defined as more than 1.5-fold higher expression on a tumor compared to the relevant normal tissue that showed highest expression of the gene, <19% over-expression = I, 20-49% = II, 50-69% = III; >70% = IV; If a peptide could be derived from several source genes, the gene with minimal coverage was decisive. The baseline included the following relevant normal tissues: adipose tissue, adrenal gland, artery, bone marrow, brain, cartilage, colon, esophagus, gallbladder, heart, kidney, liver, lung, lymph node, pancreas, pituitary, rectum, skeletal muscle, skin, small intestine, spleen, stomach, thymus, thyroid gland, trachea, urinary bladder and vein. In case expression data for several samples of the same tissue type were available, the arithmetic mean of all respective samples was used for the calculation.

| SEQ ID NO. | Sequence | AML (N = 7) | BRCA (N = 10) | CLL (N = 10) | CRC (N = 20) | GB (N = 24) | HCC (N = 15) | pNSCLC (N = 11) | OC (N = 12) | OSCAR (N = 11) | PC (N = 26) | RCC (N = 10) | SCLC (N = 10) |
|---|---|---|---|---|---|---|---|---|---|---|---|---|---|
| 2 | ALYGKLLKL | I | II | I | I | I | I | I | I | I | I | I | I |
| 3 | TLLGKQVTL | I | II | I | I | I | I | I | I | I | I | I | I |
| 5 | SLFGQEVYC | I | I | I | I | I | II | I | I | I | I | I | I |
| 9 | FLGDYVENL | I | I | IV | I | III | I | I | II | I | I | I | II |
| 10 | KTLDVFNIIL | I | I | IV | I | III | I | I | II | I | I | I | II |
| 11 | GVLKVFLENV | I | II | I | I | I | I | I | I | I | I | I | I |
| 12 | GLIYETRGV | I | II | I | I | I | I | I | I | I | I | I | I |
| 13 | VLRDNIQGI | I | II | I | I | I | I | I | I | I | I | I | I |
| 14 | LLDHLSFINKI | I | I | III | I | I | I | I | I | I | I | I | III |
| 16 | HLYNNEEQV | I | I | I | I | I | IV | I | II | II | I | I | I |
| 17 | ILHEHHIFL | I | I | I | II | I | II | II | II | I | II | IB | I |
| 18 | YVLNEEDLQKV | I | I | I | II | I | II | II | II | I | II | IV | I |
| 19 | TLLPTVLTL | I | I | I | I | I | I | I | I | I | I | IV | I |
| 20 | ALDGHLYAI | I | I | I | I | I | I | I | I | I | I | II | I |
| 27 | KVFGDLDQV | I | I | I | I | I | I | I | I | I | I | II | I |
| 28 | TLYSMDLMKV | I | I | I | I | III | I | I | I | I | I | I | I |
| 31 | ALSDETKNNWEV | I | III | I | II | III | I | III | III | II | I | I | IV |
| 32 | ILADEAFFSV | I | III | I | II | III | I | III | III | II | I | I | IV |

TABLE 10A-continued

Target coverage within various tumor entities, for expression of source genes of selected peptides. Over-expression was defined as more than 1.5-fold higher expression on a tumor compared to the relevant normal tissue that showed highest expression of the gene, <19% over-expression = I, 20-49% = II, 50-69% = III; >70% = IV; If a peptide could be derived from several source genes, the gene with minimal coverage was decisive. The baseline included the following relevant normal tissues: adipose tissue, adrenal gland, artery, bone marrow, brain, cartilage, colon, esophagus, gallbladder, heart, kidney, liver, lung, lymph node, pancreas, pituitary, rectum, skeletal muscle, skin, small intestine, spleen, stomach, thymus, thyroid gland, trachea, urinary bladder and vein. In case expression data for several samples of the same tissue type were available, the arithmetic mean of all respective samples was used for the calculation.

| SEQ ID NO | Sequence | AML (N = 7) | BRCA (N = 10) | CLL (N = 10) | CRC (N = 20) | GB (N = 24) | HCC (N = 15) | pNSCLC (N = 11) | OC (N = 12) | OSCAR (N = 11) | PC (N = 26) | RCC (N = 10) | SCLC (N = 10) |
|---|---|---|---|---|---|---|---|---|---|---|---|---|---|
| 33 | LLLPLLPPLSPSLG | I | I | I | I | I | I | I | I | I | I | I | II |
| 36 | KLYGIEIEV | I | I | I | I | I | I | I | I | I | I | I | I |
| 39 | ALMAVVSGL | I | I | IV | I | II | I | I | I | I | I | I | I |
| 42 | VLSPFILTL | I | I | I | I | I | I | I | I | I | I | I | I |
| 44 | GLLWQIIKV | I | I | I | III | I | I | I | I | II | II | I | I |
| 45 | VLGPTPELV | I | I | I | I | I | I | I | I | I | I | I | I |
| 46 | SLAKHGIVAL | I | II | I | I | I | I | I | I | I | I | I | I |
| 47 | GLYQAQVNL | I | I | I | II | II | II | III | I | IV | II | I | II |
| 49 | LLDESKLTL | I | I | I | I | I | I | I | I | I | I | III | I |
| 50 | EYALLYHTL | I | I | I | II | I | I | I | I | I | I | II | I |
| 51 | LLLDGDFTL | I | I | I | I | I | III | I | I | I | I | I | I |
| 52 | ELLSSIFFL | I | II | I | I | I | I | I | II | I | II | II | II |
| 53 | SLLSHVIVA | I | I | I | II | I | I | II | II | II | I | I | II |
| 54 | FINPKGNWLL | I | I | I | I | I | I | II | II | I | II | I | II |
| 55 | IASAIVNEL | I | II | II | I | II | I | II | II | I | I | I | II |
| 59 | ALTKILAEL | I | I | I | I | I | I | I | I | I | I | I | II |
| 63 | TLSSERDFAL | I | I | I | I | I | III | I | I | I | I | II | I |
| 64 | GLSSSSYEL | I | I | I | I | I | III | I | I | I | I | I | I |
| 65 | KLDGICWQV | I | I | I | I | I | II | I | I | I | I | I | I |

TABLE 10A-continued

Target coverage within various tumor entities, for expression of source genes of selected peptides. Over-expression was defined as more than 1.5-fold higher expression on a tumor compared to the relevant normal tissue that showed highest expression of the gene, <19% over-expression = I, 20-49% = II, 50-69% = III; >70% = IV; If a peptide could be derived from several source genes, the gene with minimal coverage was decisive. The baseline included the following relevant normal tissues: adipose tissue, adrenal gland, artery, bone marrow, brain, cartilage, colon, esophagus, gallbladder, heart, kidney, liver, lung, lymph node, pancreas, pituitary, rectum, skeletal muscle, skin, small intestine, spleen, stomach, thymus, thyroid gland, trachea, urinary bladder and vein. In case expression data for several samples of the same tissue type were available, the arithmetic mean of all respective samples was used for the calculation.

| SEQ ID NO | Sequence | AML (N = 7) | BRCA (N = 10) | CLL (N = 10) | CRC (N = 20) | GB (N = 24) | HCC (N = 15) | pNSCLC (N = 11) | OC (N = 12) | OSCAR (N = 11) | PC (N = 26) | RCC (N = 10) | SCLC (N = 10) |
|---|---|---|---|---|---|---|---|---|---|---|---|---|---|
| 67 | GVIETVTSL | IV | I | I | I | I | I | I | I | I | I | I | I |
| 69 | GIYDGILHSI | I | I | I | II | II | II | II | II | II | II | I | II |
| 70 | GLFSQHFNL | III | I | I | I | I | I | I | I | II | I | I | I |
| 73 | GVPDTIATL | I | I | I | II | I | I | I | I | I | I | I | I |
| 75 | ILDNVKNLL | IV | I | I | I | I | I | I | I | I | I | I | I |
| 78 | LLWGHPRVA | I | IV | I | II | I | II | III | III | IV | III | I | I |
| 79 | SLVPLQILL | I | I | I | I | I | I | I | I | I | I | I | I |
| 80 | TLDEYLTYL | I | I | I | I | I | II | I | II | I | I | I | I |
| 81 | VLFLGKLLV | I | I | II | II | III | II | I | II | II | II | II | IV |
| 84 | FLEEEITRV | I | I | I | I | I | I | I | I | I | I | I | II |
| 86 | LLVTSLVVV | I | I | I | I | I | I | I | I | III | I | I | I |
| 88 | ILLNTEDLASL | I | I | II | I | I | II | I | II | III | II | II | II |
| 91 | SSLEPQIQPV | I | II | II | I | II | I | I | I | III | I | I | I |
| 322 | ALVSGGVAQA | I | III | IV | I | I | I | I | III | III | II | I | I |
| 323 | ILSVVNSQL | I | I | IV | I | I | I | I | I | I | I | I | I |
| 324 | AIFDFCPSV | I | I | I | I | I | I | I | I | I | I | I | I |
| 325 | RLLPKVQEV | I | I | I | I | II | I | I | I | I | I | I | I |
| 327 | SIGDIFLKY | I | II | I | III | II | II | IV | III | III | II | I | IV |
| 328 | SVDSAPAAV | I | I | I | I | I | II | I | I | I | I | I | II |

TABLE 10A-continued

Target coverage within various tumor entities, for expression of source genes of selected peptides. Over-expression was defined as more than 1.5-fold higher expression on a tumor compared to the relevant normal tissue that showed highest expression of the gene, <19% over-expression = I, 20-49% = II, 50-69% = III; >70% = IV; If a peptide could be derived from several source genes, the gene with minimal coverage was decisive. The baseline included the following relevant normal tissues: adipose tissue, adrenal gland, artery, bone marrow, brain, cartilage, colon, esophagus, gallbladder, heart, kidney, liver, lung, lymph node, pancreas, pituitary, rectum, skeletal muscle, skin, small intestine, spleen, stomach, thymus, thyroid gland, trachea, urinary bladder and vein. In case expression data for several samples of the same tissue type were available, the arithmetic mean of all respective samples was used for the calculation.

| SEQ ID NO | Sequence | AML (N = 7) | BRCA (N = 10) | CLL (N = 10) | CRC (N = 20) | GB (N = 24) | HCC (N = 15) | pNSCLC (N = 11) | OC (N = 12) | OSCAR (N = 11) | PC (N = 26) | RCC (N = 10) | SCLC (N = 10) |
|---|---|---|---|---|---|---|---|---|---|---|---|---|---|
| 329 | FAWEPSFRDQV | I | I | I | I | I | III | I | I | I | I | I | I |
| 331 | AIWKELISL | I | I | I | I | II | I | I | I | I | I | I | III |
| 332 | AVTKYTSAK | I | II | I | I | I | II | I | I | I | I | I | II |
| 334 | GRADALRVL | I | I | IV | I | I | I | I | I | I | I | I | I |
| 335 | VLLAAGPSAA | I | I | II | I | I | I | I | I | I | I | I | II |
| 336 | GLMDGSPHFL | I | II | I | I | I | I | I | I | I | I | I | I |
| 337 | KVLGKIEKV | I | II | I | I | I | I | I | I | I | I | I | II |
| 338 | LLYDGKLSSA | I | II | I | I | I | I | I | I | I | I | I | II |
| 96 | YYTQYSQTI | I | IV | I | II | I | I | III | III | IV | III | I | I |
| 98 | VFPPRLHNVLF | I | I | I | I | I | I | I | I | I | I | I | I |
| 100 | VYIESRIGTSTSF | I | II | I | I | I | I | I | II | II | I | I | I |
| 101 | IYIPVLPPHL | I | IV | I | I | I | I | IV | III | III | I | I | II |
| 103 | NYIPVKNGKQF | I | I | III | I | I | I | I | I | I | I | I | I |
| 106 | IYNETVRDLL | I | I | I | I | I | I | I | II | III | I | I | I |
| 107 | KYFPYLVVI | I | II | I | I | I | I | I | II | III | I | II | I |
| 108 | PYLVVIHTL | I | II | I | I | I | I | I | II | III | I | II | I |
| 110 | SYPKIIEEF | I | I | III | I | II | I | I | I | I | I | I | I |
| 113 | IYSFHTLSF | I | I | I | I | II | I | I | I | I | I | I | III |
| 114 | QYLDGTWSL | I | IV | I | II | II | I | IV | II | IV | III | I | II |

TABLE 10A-continued

Target coverage within various tumor entities, for expression of source genes of selected peptides. Over-expression was defined as more than 1.5-fold higher expression on a tumor compared to the relevant normal tissue that showed highest expression of the gene, <19% over-expression = I, 20-49% = II, 50-69% = III; >70% = IV; If a peptide could be derived from several source genes, the gene with minimal coverage was decisive. The baseline included the following relevant normal tissues: adipose tissue, adrenal gland, artery, bone marrow, brain, cartilage, colon, esophagus, gallbladder, heart, kidney, liver, lung, lymph node, pancreas, pituitary, rectum, skeletal muscle, skin, small intestine, spleen, stomach, thymus, thyroid gland, trachea, urinary bladder and vein. In case expression data for several samples of the same tissue type were available, the arithmetic mean of all respective samples was used for the calculation.

| SEQ ID NO. | Sequence | AML (N = 7) | BRCA (N = 10) | CLL (N = 10) | CRC (N = 20) | GB (N = 24) | HCC (N = 15) | pNSCLC (N = 11) | OC (N = 12) | OSCAR (N = 11) | PC (N = 26) | RCC (N = 10) | SCLC (N = 10) |
|---|---|---|---|---|---|---|---|---|---|---|---|---|---|
| 115 | RYLNKSFVL | I | II | I | II | I | I | I | III | I | I | I | II |
| 117 | IYLSDLTYI | I | I | IV | I | I | I | I | I | I | I | I | I |
| 118 | KYLNSVQYI | I | I | IV | I | I | I | I | I | I | I | I | I |
| 119 | VYRVVVTTF | I | I | I | I | I | I | II | I | II | I | I | I |
| 121 | RYGLPAAWSTF | I | I | IV | I | I | I | I | I | I | I | I | I |
| 123 | VYTPVLEHL | I | III | I | II | III | I | III | III | II | I | I | IV |
| 124 | TYKDYVDLF | I | III | I | II | III | I | III | III | II | I | I | IV |
| 125 | VFSRDFGLLVF | I | III | I | II | III | I | III | III | II | I | I | IV |
| 126 | PYDPALGSPSRLF | I | I | I | II | I | III | I | II | I | I | I | I |
| 127 | QYFTGNPLF | I | I | I | I | I | I | I | I | I | I | I | II |
| 132 | RYPALFPVL | I | I | I | I | I | I | II | II | I | I | I | I |
| 135 | VYEAMVPLF | I | I | I | I | I | I | III | I | I | I | I | II |
| 138 | VYNAVSTSF | I | I | I | I | I | I | III | I | I | I | I | II |
| 139 | IFGIFPNQF | IV | I | I | I | I | I | I | II | I | I | I | I |
| 140 | RYLINSYDF | I | I | I | I | I | I | II | I | I | I | I | I |
| 141 | SYNGHLTIWF | I | I | I | I | III | I | II | II | I | I | I | I |
| 146 | NYYERIHAL | III | I | IV | I | II | I | I | I | I | I | I | I |
| 147 | LYLAFPLAF | I | II | I | I | I | I | I | I | I | I | I | I |
| 151 | AYISGLDVF | I | I | I | I | I | I | I | I | IV | I | I | II |

TABLE 10A-continued

Target coverage within various tumor entities, for expression of source genes of selected peptides. Over-expression was defined as more than 1.5-fold higher expression on a tumor compared to the relevant normal tissue that showed highest expression of the gene, <19% over-expression = I, 20-49% = II, 50-69% = III; >70% = IV; If a peptide could be derived from several source genes, the gene with minimal coverage was decisive. The baseline included the following relevant normal tissues: adipose tissue, adrenal gland, artery, bone marrow, brain, cartilage, colon, esophagus, gallbladder, heart, kidney, liver, lung, lymph node, pancreas, pituitary, rectum, skeletal muscle, skin, small intestine, spleen, stomach, thymus, thyroid gland, trachea, urinary bladder and vein. In case expression data for several samples of the same tissue type were available, the arithmetic mean of all respective samples was used for the calculation.

| SEQ ID NO | Sequence | AML (N = 7) | BRCA (N = 10) | CLL (N = 10) | CRC (N = 20) | GB (N = 24) | HCC (N = 15) | pNSCLC (N = 11) | OC (N = 12) | OSCAR (N = 11) | PC (N = 26) | RCC (N = 10) | SCLC (N = 10) |
|---|---|---|---|---|---|---|---|---|---|---|---|---|---|
| 152 | KFFDDLGDELLF | I | I | I | I | I | I | II | I | II | I | I | II |
| 156 | YYMELTKLLL | I | I | I | I | I | I | I | I | II | I | I | IV |
| 157 | DYIPASGFALF | I | I | I | I | II | I | I | I | I | I | I | I |
| 158 | IYEETRGVLKVF | I | II | I | I | I | I | I | II | I | I | I | I |
| 159 | IYEETRGVL | I | II | I | I | I | I | I | I | I | I | I | I |
| 162 | KYTSYILAF | I | I | I | I | I | I | I | II | III | I | II | II |
| 164 | HYVPATKVF | I | II | I | I | I | I | IV | IV | II | I | II | I |
| 167 | RYGFYYVEF | I | I | I | I | IV | I | III | II | III | I | I | I |
| 171 | NYEDHPPLL | I | I | I | I | I | I | I | II | II | I | I | II |
| 172 | VFIFKGNEF | I | I | I | I | I | I | II | I | II | I | I | II |
| 173 | QYLEKYYNL | I | II | I | I | I | I | I | I | II | I | I | I |
| 174 | VYEKNGYIYF | I | II | I | I | I | I | III | I | III | I | I | I |
| 175 | LYSPVPFTL | I | I | I | I | I | I | II | I | II | I | I | I |
| 176 | FYINGQYQF | III | I | III | II | II | I | II | I | II | I | I | II |
| 177 | VYFKAGLDVF | I | II | I | I | I | I | I | II | I | I | I | I |
| 178 | NYSSAVQKF | I | I | I | I | III | I | I | III | I | I | I | I |
| 179 | TYIPVGLGRLL | I | I | I | I | I | I | I | I | II | I | I | II |
| 181 | VYPPYLNYL | I | II | I | I | I | I | I | I | I | I | I | I |
| 182 | AYAQLGYLLF | I | I | I | I | I | I | I | I | I | I | I | II |

TABLE 10A-continued

Target coverage within various tumor entities, for expression of source genes of selected peptides. Over-expression was defined as more than 1.5-fold higher expression on a tumor compared to the relevant normal tissue that showed highest expression of the gene, <19% over-expression = I, 20-49% = II, 50-69% = III; >70% = IV; If a peptide could be derived from several source genes, the gene with minimal coverage was decisive. The baseline included the following relevant normal tissues: adipose tissue, adrenal gland, artery, bone marrow, brain, cartilage, colon, esophagus, gallbladder, heart, kidney, liver, lung, lymph node, pancreas, pituitary, rectum, skeletal muscle, skin, small intestine, spleen, stomach, thymus, thyroid gland, trachea, urinary bladder and vein. In case expression data for several samples of the same tissue type were available, the arithmetic mean of all respective samples was used for the calculation.

| SEQ ID NO | Sequence | AML (N = 7) | BRCA (N = 10) | CLL (N = 10) | CRC (N = 20) | GB (N = 24) | HCC (N = 15) | pNSCLC (N = 11) | OC (N = 12) | OSCAR (N = 11) | PC (N = 26) | RCC (N = 10) | SCLC (N = 10) |
|---|---|---|---|---|---|---|---|---|---|---|---|---|---|
| 184 | IYSVGAFENF | I | II | I | I | I | I | I | I | I | I | I | II |
| 185 | QYLVHVNDL | I | I | I | I | II | I | I | I | I | I | II | II |
| 189 | AYFKQSSVF | II | I | II | I | I | I | I | I | I | I | I | I |
| 190 | LYSELTETL | IV | III | IV | I | II | I | IV | I | I | II | I | IV |
| 191 | TYPDGTYTGRIF | I | I | II | I | I | I | I | I | I | I | I | I |
| 193 | LYLENNAQTQF | I | I | I | I | I | I | II | I | IV | I | I | I |
| 195 | AYIKGGWIL | I | I | I | I | I | II | I | I | I | I | I | I |
| 198 | DYVGFTLKI | I | I | I | I | III | I | I | I | I | I | I | I |
| 203 | VYNVEVKNAEF | I | I | I | I | I | I | I | I | I | I | I | II |
| 204 | EYLSTCSKL | II | II | I | I | I | I | I | II | I | I | I | III |
| 205 | VYPVVLNQI | I | I | I | I | I | I | I | I | I | I | I | II |
| 206 | NYLDVATFL | I | I | I | I | II | I | II | I | II | II | I | II |
| 208 | TYLEKIDGF | I | I | I | I | I | I | I | I | I | I | I | I |
| 210 | IYAGVGEFSF | I | I | I | I | I | I | I | I | I | I | I | II |
| 211 | VFKSEGAYF | I | II | I | I | I | I | I | I | I | I | I | I |
| 212 | SYAPPSEDLF | I | II | I | I | I | I | I | I | I | I | I | I |
| 213 | SYAPPSEDLFL | I | I | I | I | I | I | I | I | I | I | I | I |
| 214 | KYLMELTLI | I | I | I | I | I | I | I | I | I | I | I | I |
| 216 | FYVNVKEQF | I | I | I | I | I | I | I | I | I | I | I | II |

TABLE 10A-continued

Target coverage within various tumor entities, for expression of source genes of selected peptides. Over-expression was defined as more than 1.5-fold higher expression on a tumor compared to the relevant normal tissue that showed highest expression of the gene, <19% over-expression = I, 20-49% = II, 50-69% = III; >70% = IV; If a peptide could be derived from several source genes, the gene with minimal coverage was decisive. The baseline included the following relevant normal tissues: adipose tissue, adrenal gland, artery, bone marrow, brain, cartilage, colon, esophagus, gallbladder, heart, kidney, liver, lung, lymph node, pancreas, pituitary, rectum, skeletal muscle, skin, small intestine, spleen, stomach, thymus, thyroid gland, trachea, urinary bladder and vein. In case expression data for several samples of the same tissue type were available, the arithmetic mean of all respective samples was used for the calculation.

| SEQ ID NO | Sequence | AML (N = 7) | BRCA (N = 10) | CLL (N = 10) | CRC (N = 20) | GB (N = 24) | HCC (N = 15) | pNSCLC (N = 11) | OC (N = 12) | OSCAR (N = 11) | PC (N = 26) | RCC (N = 10) | SCLC (N = 10) |
|---|---|---|---|---|---|---|---|---|---|---|---|---|---|
| 218 | LYSELNKWSF | I | I | I | I | I | I | I | I | I | I | I | I |
| 219 | SYLKAVFNL | I | III | I | I | I | I | II | I | I | I | I | I |
| 220 | SYSEIKDFL | I | I | IV | I | I | I | I | I | I | I | I | I |
| 221 | KYIGNLDLL | I | I | I | I | I | I | I | I | I | I | II | I |
| 222 | HYSTIVHMF | I | I | I | I | I | I | I | I | I | I | II | I |
| 224 | PYFFANQEF | II | I | I | I | I | I | I | I | I | I | I | I |
| 226 | MYLKLVQLF | I | I | I | I | I | I | I | I | I | I | I | I |
| 227 | IYRFITERF | I | I | I | I | I | I | I | I | I | I | I | II |
| 230 | TYGMVMVTF | I | I | I | I | II | I | I | I | I | I | I | I |
| 231 | AFADVSVKF | I | I | I | I | II | I | I | I | I | I | I | I |
| 233 | QYLTAAALHNL | I | I | I | I | I | I | I | I | I | I | I | I |
| 235 | VYKDSIYYI | II | I | IV | I | I | I | I | I | I | I | I | I |
| 236 | VYLPKIPSW | I | I | I | I | I | I | I | I | I | I | I | I |
| 237 | KYVGQLAVL | I | I | I | I | I | II | I | I | I | I | I | II |
| 239 | VYAIFRILL | I | II | I | I | I | I | I | I | I | I | I | II |
| 240 | YYFFVQEKI | I | I | I | I | II | I | I | I | I | I | I | I |
| 241 | SYVKVLHHL | I | I | I | I | I | II | I | I | I | I | I | II |
| 242 | VYGEPRELL | I | II | I | I | I | I | I | I | II | I | I | II |
| 243 | SYLELANTL | I | I | I | I | I | I | I | I | I | I | I | I |

TABLE 10A-continued

Target coverage within various tumor entities, for expression of source genes of selected peptides. Over-expression was defined as more than 1.5-fold higher expression on a tumor compared to the relevant normal tissue that showed highest expression of the gene, <19% over-expression = I, 20-49% = II, 50-69% = III; >70% = IV; If a peptide could be derived from several source genes, the gene with minimal coverage was decisive. The baseline included the following relevant normal tissues: adipose tissue, adrenal gland, artery, bone marrow, brain, cartilage, colon, esophagus, gallbladder, heart, kidney, liver, lung, lymph node, pancreas, pituitary, rectum, skeletal muscle, skin, small intestine, spleen, stomach, thymus, thyroid gland, trachea, urinary bladder and vein. In case expression data for several samples of the same tissue type were available, the arithmetic mean of all respective samples was used for the calculation.

| SEQ ID NO | Sequence | AML (N = 7) | BRCA (N = 10) | CLL (N = 10) | CRC (N = 20) | GB (N = 24) | HCC (N = 15) | pNSCLC (N = 11) | OC (N = 12) | OSCAR (N = 11) | PC (N = 26) | RCC (N = 10) | SCLC (N = 10) |
|---|---|---|---|---|---|---|---|---|---|---|---|---|---|
| 244 | VHFEDTGKTLLF | I | II | I | I | I | I | I | I | III | I | I | I |
| 245 | LYPQLFVVL | I | I | I | I | I | I | II | II | I | I | I | I |
| 246 | KYLSVQLTL | I | I | I | I | I | I | I | I | I | I | I | II |
| 247 | SFTKTSPNF | I | I | I | II | I | I | I | I | I | I | I | I |
| 251 | VYTKALSSL | I | I | I | I | I | I | I | I | I | I | I | III |
| 256 | VFGKSAYLF | II | I | I | I | I | I | I | I | I | I | I | I |
| 258 | AYAQLGYLL | I | I | I | I | I | I | I | I | I | I | I | II |
| 263 | RYILENHDF | I | I | I | I | I | II | I | I | I | I | I | I |
| 267 | SFLNIEKTEILF | I | I | I | I | I | III | I | I | I | I | I | II |
| 270 | YYSQRSKVLYL | I | II | II | I | II | I | I | III | II | II | I | II |
| 272 | RYVFPLPYL | I | I | I | II | I | II | I | I | I | I | I | I |
| 273 | IYGEKLQFIF | I | I | I | I | II | I | I | II | I | I | I | II |
| 274 | KQLDIANYELF | I | III | I | I | I | I | I | II | I | I | I | II |
| 276 | QYLDVLHAL | I | II | I | I | I | I | I | II | II | I | II | II |
| 277 | FYTPFPQQL | I | I | I | I | I | I | I | II | I | I | I | II |
| 278 | KYVNLVMYF | I | I | I | I | I | I | I | I | I | I | I | I |
| 279 | VWLPASVLF | I | II | I | I | II | I | I | I | I | I | I | II |
| 282 | NYLVDPVTI | I | II | I | I | I | I | I | III | I | I | I | I |
| 283 | EYQEIFQQL | I | I | I | I | I | I | I | III | I | I | I | I |

TABLE 10A-continued

Target coverage within various tumor entities, for expression of source genes of selected peptides. Over-expression was defined as more than 1.5-fold higher expression on a tumor compared to the relevant normal tissue that showed highest expression of the gene, <19% over-expression = I, 20-49% = II, 50-69% = III; >70% = IV; If a peptide could be derived from several source genes, the gene with minimal coverage was decisive. The baseline included the following relevant normal tissues: adipose tissue, adrenal gland, artery, bone marrow, brain, cartilage, colon, esophagus, gallbladder, heart, kidney, liver, lung, lymph node, pancreas, pituitary, rectum, skeletal muscle, skin, small intestine, spleen, stomach, thymus, thyroid gland, trachea, urinary bladder and vein. In case expression data for several samples of the same tissue type were available, the arithmetic mean of all respective samples was used for the calculation.

| SEQ ID NO | Sequence | AML (N=7) | BRCA (N=10) | CLL (N=10) | CRC (N=20) | GB (N=24) | HCC (N=15) | pNSCLC (N=11) | OC (N=12) | OSCAR (N=11) | PC (N=26) | RCC (N=10) | SCLC (N=10) |
|---|---|---|---|---|---|---|---|---|---|---|---|---|---|
| 287 | IYNPNLLTASKF | I | III | I | I | I | I | I | III | III | I | I | I |
| 291 | YYLGSGRETF | I | I | I | I | II | I | II | II | III | I | I | II |
| 292 | FYPQIINTF | I | I | I | I | II | I | I | I | I | I | I | I |
| 293 | VYPHFSTTNLI | I | I | I | I | II | I | I | I | I | I | I | I |
| 294 | RFPVQGTVTF | I | IV | I | I | I | I | I | II | I | I | I | I |
| 295 | SYLVIHERI | I | I | II | I | I | I | I | III | I | I | I | II |
| 300 | TYPSQLPSL | I | I | I | II | II | I | I | I | I | I | I | I |
| 302 | LYLPVHYGF | I | I | I | II | I | I | I | I | I | I | I | II |
| 304 | EYNEVANLF | I | I | I | I | II | I | I | I | I | I | I | II |
| 307 | GYAFTLPLF | I | II | I | II | II | I | II | I | I | I | II | II |
| 308 | TFDGHGVFF | I | I | I | II | I | I | I | I | II | I | I | I |
| 309 | KYYRQTLLF | I | I | II | I | II | I | III | I | IV | I | II | II |
| 310 | IYAPTLLVF | I | II | II | I | II | I | I | I | I | I | I | II |
| 314 | RYFKGDYSI | I | I | I | I | II | I | II | I | I | I | I | I |
| 315 | FYIPHVPVSF | I | I | I | I | I | II | I | I | I | I | I | II |
| 320 | KFILALKVLF | I | I | I | I | I | I | I | I | I | I | I | II |
| 342 | NYAFLHRTL | II | II | I | I | I | II | I | II | III | I | I | I |
| 343 | NYLGGTSTI | I | I | I | I | I | II | I | I | I | I | I | II |
| 344 | EYNSDLHQF | I | I | I | I | I | I | I | I | I | I | I | II |

TABLE 10A-continued

Target coverage within various tumor entities, for expression of source genes of selected peptides. Over-expression was defined as more than 1.5-fold higher expression on a tumor compared to the relevant normal tissue that showed highest expression of the gene, <19% over-expression = I, 20-49% = II, 50-69% = III; >70% = IV; If a peptide could be derived from several source genes, the gene with minimal coverage was decisive. The baseline included the following relevant normal tissues: adipose tissue, adrenal gland, artery, bone marrow, brain, cartilage, colon, esophagus, gallbladder, heart, kidney, liver, lung, lymph node, pancreas, pituitary, rectum, skeletal muscle, skin, small intestine, spleen, stomach, thymus, thyroid gland, trachea, urinary bladder and vein. In case expression data for several samples of the same tissue type were available, the arithmetic mean of all respective samples was used for the calculation.

| SEQ ID NO | Sequence | AML (N = 7) | BRCA (N = 10) | CLL (N = 10) | CRC (N = 20) | GB (N = 24) | HCC (N = 15) | pNSCLC (N = 11) | OC (N = 12) | OSCAR (N = 11) | PC (N = 26) | RCC (N = 10) | SCLC (N = 10) |
|---|---|---|---|---|---|---|---|---|---|---|---|---|---|
| 345 | EYNSDLHQFF | I | I | I | I | I | I | I | I | I | I | I | II |
| 348 | IYLEHTESI | I | I | II | I | I | I | I | I | I | I | I | I |
| 350 | KYGNFIDKL | I | I | I | I | I | I | I | II | I | I | I | I |
| 351 | IFHEVPLKF | I | I | I | I | I | I | I | I | I | I | I | II |
| 352 | QYGGDLTNTF | I | I | I | I | I | I | II | I | I | II | I | I |
| 353 | TYGKIDLGF | I | I | I | I | I | I | I | I | I | I | I | II |
| 354 | VYNEQIRDLL | I | I | I | I | I | I | I | I | I | I | I | II |
| 355 | IYVTGGHLF | I | I | I | II | I | I | I | I | II | I | II | I |
| 356 | NYMPGQLT | I | I | I | I | I | I | II | II | I | II | I | I |
| 358 | YYSEVPVKL | I | IV | I | I | I | I | I | III | IV | I | II | I |
| 359 | NYGVLHVTF | II | I | II | II | II | III | I | I | I | I | II | II |
| 360 | VFSPDGHLF | I | II | I | I | I | I | I | I | I | I | I | I |
| 361 | TYADIGGLDNQI | II | I | I | I | II | I | II | I | II | I | I | I |
| 363 | SYAELGTTI | I | I | I | I | II | I | I | I | I | I | I | I |
| 364 | KYLNENQLSQL | I | I | I | I | I | I | III | I | II | I | I | III |
| 365 | VFIDHPVHL | I | I | I | I | I | I | I | I | I | I | I | II |
| 366 | QYLELAHSL | I | I | I | I | I | I | I | II | I | I | I | II |
| 367 | LYQDHMQYI | I | I | I | I | I | I | I | I | II | I | I | I |
| 368 | KYQNVKHNL | I | I | I | I | I | I | I | I | I | I | I | III |

TABLE 10A-continued

Target coverage within various tumor entities, for expression of source genes of selected peptides. Over-expression was defined as more than 1.5-fold higher expression on a tumor compared to the relevant normal tissue that showed highest expression of the gene, <19% over-expression = I, 20-49% = II, 50-69% = III; >70% = IV; If a peptide could be derived from several source genes, the gene with minimal coverage was decisive. The baseline included the following relevant normal tissues: adipose tissue, adrenal gland, artery, bone marrow, brain, cartilage, colon, esophagus, gallbladder, heart, kidney, liver, lung, lymph node, pancreas, pituitary, rectum, skeletal muscle, skin, small intestine, spleen, stomach, thymus, thyroid gland, trachea, urinary bladder and vein. In case expression data for several samples of the same tissue type were available, the arithmetic mean of all respective samples was used for the calculation.

| SEQ ID NO. | Sequence | AML (N = 7) | BRCA (N = 10) | CLL (N = 10) | CRC (N = 20) | GB (N = 24) | HCC (N = 15) | pNSCLC (N = 11) | OC (N = 12) | OSCAR (N = 11) | PC (N = 26) | RCC (N = 10) | SCLC (N = 10) |
|---|---|---|---|---|---|---|---|---|---|---|---|---|---|
| 371 | AYSHLRYVF | I | I | I | IV | III | I | IV | II | IV | III | III | II |
| 372 | VYVIEPHSMEF | I | I | II | I | I | I | I | I | I | I | I | II |
| 374 | VFLPRVTEL | I | III | I | II | III | I | III | III | II | I | I | IV |
| 376 | VYTPVASRQSL | I | I | I | I | II | I | II | I | I | I | I | II |
| 377 | QYTPHSHQF | I | I | I | I | I | I | I | I | I | I | I | II |
| 378 | VYIAELEKI | I | II | I | I | I | I | I | I | I | I | I | II |
| 379 | VFIAQGYTL | I | I | I | II | I | I | II | I | II | I | II | II |
| 380 | VYTGIDHHW | I | II | I | I | I | I | II | III | IV | I | I | III |
| 381 | KYPASSVF | I | I | I | I | I | I | I | I | I | I | III | I |
| 382 | AYLPPLQQVF | I | I | I | I | I | I | I | II | I | I | I | II |
| 383 | RYKPGEPITF | II | IV | I | II | I | I | IV | II | II | I | I | II |
| 385 | QYIEELQKF | I | I | IV | I | I | I | I | I | I | I | I | I |
| 386 | TFSDVEAHF | I | I | I | I | I | I | I | I | I | I | I | II |
| 387 | KYTEKLEEI | I | I | I | I | IV | I | I | II | I | I | I | III |

TABLE 10B

Target coverage for source genes of selected peptides. Over-expression was defined as more than 1.54-fold higher expression on a tumor compared to the relevant normal tissue that showed highest expression of the gene. <19% over-expression = I, 20-49% = II, 50-69% = III, >70% = IV. If a peptide could be derived from several source genes, the gene with minimal coverage was decisive. The baseline included the following relevant normal tissues: adipose tissue, adrenal gland, artery, bone marrow, brain, cartilage, colon, esophagus, gallbladder, heart, kidney, liver, lung, lymph node, pancreas, pituitary, rectum, skeletal muscle, skin, small intestine, spleen, stomach, thymus, thyroid gland, trachea, urinary bladder and vein. In case expression data for several samples of the same tissue type were available, the arithmetic mean of all respective samples was used for the calculation. NHL = non-Hodgkin lymphoma, PCA = prostate cancer and benign prostate hyperplasia, GC = gastric cancer, GBCSCC = gallbladder adenocarcinoma and cholangiocarcinoma, MEL = melanoma, UBC = urinary bladder cancer, UTC = uterine cancer, HNSCC = head and neck small cell carcinoma.

| SEQ ID NO. | Sequence | NHL (N = 10) | PCA (N = 10) | GC (N = 11) | GBC_CCC (N = 10) | MEL (N = 10) | UBC (N = 10) | UTC (N = 10) | HNSCC (N = 10) |
|---|---|---|---|---|---|---|---|---|---|
| 2 | ALYGKLLKL | I | I | I | I | I | I | I | I |
| 3 | TLLGKQVTL | I | I | I | I | I | I | I | I |
| 4 | ELAEIVFKV | I | I | I | I | I | I | I | II |
| 9 | FLGDYVENL | I | I | I | I | I | I | I | I |
| 12 | GLIYEETRGV | II | II | I | I | II | I | I | I |
| 13 | VLRDNIQGI | II | II | I | I | II | I | I | I |
| 19 | TLLPTVLTL | I | I | I | I | I | III | I | I |
| 32 | ILADEAFFSV | II | I | I | I | II | I | I | I |
| 34 | LLPKKTESHHKT | II | I | I | I | I | I | I | I |
| 35 | YVLPKLYVKL | I | I | I | I | I | I | I | I |
| 36 | ALINDILGELVKL | I | I | I | I | I | I | I | I |
| 39 | ALMAVVSGL | II | I | I | I | I | I | I | I |
| 41 | FVLPLVVTL | I | I | I | I | I | I | I | I |
| 42 | VLSPFILTL | I | I | I | II | I | II | I | II |
| 45 | VLGPTPELV | I | I | II | II | I | I | I | I |
| 46 | SLAKHGIVAL | I | I | I | I | I | I | II | I |
| 47 | GLYQAQVNL | I | I | I | II | IV | II | I | II |
| 51 | LLLDGDFTL | I | I | I | I | I | I | I | I |
| 53 | SLLSHVIVA | III | I | I | II | I | I | II | I |
| 55 | IASAIVNEL | II | I | I | II | I | I | I | I |
| 60 | FLIDTSASM | I | I | I | I | I | I | I | I |
| 61 | HLPDFVKQL | I | I | I | I | I | I | I | I |
| 70 | GLFSQHFNL | I | I | I | II | I | II | III | II |
| 96 | YYTQYSQTI | I | I | I | II | I | I | I | II |
| 98 | VFPRLHNVLF | I | I | I | I | I | I | I | I |
| 99 | QYILAVPVL | I | I | I | I | I | I | I | I |
| 100 | VYIESRIGTSTSF | I | I | I | I | II | I | I | I |
| 101 | IYIPVILPPHL | III | III | I | III | I | II | III | III |
| 103 | NYIPVKNGKQF | I | I | I | I | I | I | I | I |
| 104 | SYLTWHQQI | I | I | I | I | I | I | I | I |
| 105 | IYNETITDLL | I | I | I | I | I | I | I | I |

TABLE 10B-continued

Target coverage for source genes of selected peptides. Over-expression was defined as more than 1.54-fold higher expression on a tumor compared to the relevant normal tissue that showed highest expression of the gene. <19% over-expression = I, 20-49% = II, 50-69% = III, >70% = IV. If a peptide could be derived from several source genes, the gene with minimal coverage was decisive. The baseline included the following relevant normal tissues: adipose tissue, adrenal gland, artery, bone marrow, brain, cartilage, colon, esophagus, gallbladder, heart, kidney, liver, lung, lymph node, pancreas, pituitary, rectum, skeletal muscle, skin, small intestine, spleen, stomach, thymus, thyroid gland, trachea, urinary bladder and vein. In case expression data for several samples of the same tissue type were available, the arithmetic mean of all respective samples was used for the calculation. NHL = non-Hodgkin lymphoma, PCA = prostate cancer and benign prostate hyperplasia, GC = gastric cancer, GBCSCC = gallbladder adenocarcinoma and cholangiocarcinoma, MEL = melanoma, UBC = urinary bladder cancer, UTC = uterine cancer, HNSCC = head and neck small cell carcinoma.

| SEQ ID NO. | Sequence | NHL (N = 10) | PCA (N = 10) | GC (N = 11) | GBC_CCC (N = 10) | MEL (N = 10) | UBC (N = 10) | UTC (N = 10) | HNSCC (N = 10) |
|---|---|---|---|---|---|---|---|---|---|
| 110 | SYPKIIEEF | II | I | I | I | I | I | I | I |
| 113 | IYSFHTLSF | I | I | I | I | I | I | I | II |
| 114 | QYLDGTWSL | II | I | II | IV | II | III | IV | III |
| 116 | AYVIAVHLF | I | I | I | I | I | I | I | I |
| 117 | IYLSDLTYI | II | I | I | I | I | I | I | I |
| 118 | KYLNSVQYI | II | I | I | I | I | I | I | I |
| 119 | VYRVYVTTF | I | I | I | I | I | I | II | I |
| 121 | RYGLPAAWSTF | I | I | I | I | I | I | I | I |
| 123 | VYTPVLEHL | II | I | I | I | II | I | I | I |
| 124 | TYKDYVDLF | II | I | I | I | II | I | I | I |
| 126 | PYDPALGSPSRLF | I | II | II | II | I | I | III | I |
| 127 | QYFTGNPLF | I | I | I | I | I | I | I | I |
| 128 | VYPFDWQYI | I | I | I | I | I | I | I | I |
| 132 | RYPALFPVL | I | I | I | I | I | I | I | I |
| 135 | VYEAMVPLF | I | I | I | I | I | I | I | I |
| 144 | VFASLPGFLF | III | I | I | I | I | I | I | I |
| 145 | VYALKVRTI | II | I | I | II | II | II | I | II |
| 147 | LYLAFPLAF | I | I | I | I | I | I | I | I |
| 150 | IYITRQFVQF | I | I | I | I | II | I | I | I |
| 151 | AYISGLDVF | I | I | I | I | I | I | I | III |
| 155 | IYKWITDNF | I | I | I | I | I | I | II | I |
| 156 | YYMELTKLLL | II | I | I | II | I | I | I | I |
| 158 | IYEETRGVLKVF | II | II | I | I | II | I | I | I |
| 161 | KYPDIVQQF | II | I | I | I | I | I | I | I |
| 162 | KYTSYILAF | II | I | I | II | I | I | I | I |
| 163 | RYLTISNLQF | I | I | I | I | I | I | I | I |
| 165 | EYFTPLLSGQF | I | I | I | I | I | I | I | I |
| 166 | FYTLPFHLI | I | I | I | I | I | I | I | I |
| 168 | RYLEAALRL | I | I | I | I | II | I | I | I |
| 170 | QYPFHVPLL | III | I | I | I | I | I | I | I |

TABLE 10B-continued

Target coverage for source genes of selected peptides. Over-expression was defined as more than 1.54-fold higher expression on a tumor compared to the relevant normal tissue that showed highest expression of the gene. <19% over-expression = I, 20-49% = II, 50-69% = III, >70% = IV. If a peptide could be derived from several source genes, the gene with minimal coverage was decisive. The baseline included the following relevant normal tissues: adipose tissue, adrenal gland, artery, bone marrow, brain, cartilage, colon, esophagus, gallbladder, heart, kidney, liver, lung, lymph node, pancreas, pituitary, rectum, skeletal muscle, skin, small intestine, spleen, stomach, thymus, thyroid gland, trachea, urinary bladder and vein. In case expression data for several samples of the same tissue type were available, the arithmetic mean of all respective samples was used for the calculation. NHL = non-Hodgkin lymphoma, PCA = prostate cancer and benign prostate hyperplasia, GC = gastric cancer, GBCSCC = gallbladder adenocarcinoma and cholangiocarcinoma, MEL = melanoma, UBC = urinary bladder cancer, UTC = uterine cancer, HNSCC = head and neck small cell carcinoma.

| SEQ ID NO. | Sequence | NHL (N = 10) | PCA (N = 10) | GC (N = 11) | GBC_CCC (N = 10) | MEL (N = 10) | UBC (N = 10) | UTC (N = 10) | HNSCC (N = 10) |
|---|---|---|---|---|---|---|---|---|---|
| 171 | NYEDHFPLL | I | I | II | I | IV | II | I | II |
| 172 | VFIFKGNEF | I | I | I | I | I | I | I | I |
| 175 | LYSPVPFTL | I | I | I | II | I | I | I | II |
| 176 | FYINGQYQF | I | II | I | I | I | I | I | II |
| 177 | VYFKAGLDVF | I | III | I | II | I | II | II | I |
| 178 | NYSSAVQKF | I | III | I | I | II | I | I | I |
| 179 | TYIPVGLGRLL | I | I | I | I | I | I | III | II |
| 180 | KYLQVVGMF | I | I | I | I | I | I | I | I |
| 191 | TYPDGTYTGRIF | II | I | I | I | I | I | I | I |
| 195 | AYIKGGWIL | I | I | I | I | I | I | I | I |
| 197 | IFTDIFHYL | I | I | I | I | I | I | I | I |
| 204 | EYLSTCSKL | II | II | I | I | I | I | IV | II |
| 206 | NYLDVATFL | I | I | I | I | I | I | II | I |
| 235 | VYKDSIYYI | IV | I | I | I | I | I | I | I |
| 277 | FYTFPFQQL | I | I | I | I | I | I | I | II |
| 291 | YYLGSGRETF | I | I | I | II | II | II | III | III |
| 296 | SYQVIFQHF | I | I | I | I | I | I | I | II |
| 297 | TYIDTRTVF | I | I | I | I | I | I | III | I |
| 304 | EYNEVANLF | I | III | I | I | I | I | I | I |
| 307 | GYAFTLPLF | I | II | I | I | I | I | II | I |
| 309 | KYYRQTLLF | I | I | I | I | I | I | II | I |
| 312 | SYTSVLSRL | II | I | I | I | II | I | I | I |
| 316 | VYFEGSDFKF | II | I | I | I | I | I | I | I |
| 317 | VFDTSIAQLF | I | I | I | I | I | I | I | I |
| 318 | TYSNSAFQYF | I | I | I | I | I | I | I | I |
| 319 | KYSDVKNLI | I | I | I | I | I | I | I | I |
| 326 | SLLPLVWKI | I | I | I | I | I | I | I | I |
| 327 | SIGDIFLKY | I | I | II | III | I | I | III | II |
| 328 | SVDSAPAAV | II | I | I | I | I | I | I | I |
| 330 | FLWPKEVEL | II | I | I | I | I | I | I | I |
| 331 | AIWKELISL | I | I | I | I | I | I | I | II |

TABLE 10B-continued

Target coverage for source genes of selected peptides. Over-expression was
defined as more than 1.54-fold higher expression on a tumor compared to the relevant normal
tissue that showed highest expression of the gene. <19% over-expression = I, 20-49% = II,
50-69% = III, >70% = IV. If a peptide could be derived from several source genes, the gene
with minimal coverage was decisive. The baseline included the following relevant normal
tissues: adipose tissue, adrenal gland, artery, bone marrow, brain, cartilage, colon,
esophagus, gallbladder, heart, kidney, liver, lung, lymph node, pancreas, pituitary, rectum,
skeletal muscle, skin, small intestine, spleen, stomach, thymus, thyroid gland, trachea,
urinary bladder and vein. In case expression data for several samples of the same tissue
type were available, the arithmetic mean of all respective samples was used for the
calculation. NHL = non-Hodgkin lymphoma, PCA = prostate cancer and benign prostate
hyperplasia, GC = gastric cancer, GBCSCC = gallbladder adenocarcinoma and
cholangiocarcinoma, MEL = melanoma, UBC = urinary bladder cancer, UTC = uterine
cancer, HNSCC = head and neck small cell carcinoma.

| SEQ ID NO. | Sequence | NHL (N = 10) | PCA (N = 10) | GC (N = 11) | GBC_CCC (N = 10) | MEL (N = 10) | UBC (N = 10) | UTC (N = 10) | HNSCC (N = 10) |
|---|---|---|---|---|---|---|---|---|---|
| 332 | AVTKYTSAK | I | I | I | I | I | I | I | I |
| 333 | GTFLEGVAK | I | I | I | I | I | I | I | I |
| 334 | GRADALRVL | I | I | I | I | I | I | I | I |
| 335 | VLLAAGPSAA | III | I | I | I | I | I | I | I |
| 342 | NYAFLHRTL | I | I | I | I | I | II | I | I |
| 343 | NYLGGTSTI | I | IV | I | I | I | I | II | I |
| 344 | EYNSDLHQF | II | I | I | I | I | I | I | I |
| 345 | EYNSDLHQFF | II | I | I | I | I | I | I | I |
| 347 | VYAEVNSL | I | I | I | I | I | I | I | I |
| 348 | IYLEHTESI | I | I | I | I | I | I | I | I |
| 350 | KYGNFIDKL | I | I | I | I | I | I | I | I |
| 352 | QYGGDLTNTF | I | I | I | II | I | II | I | I |
| 353 | TYGKIDLGF | II | I | I | I | I | I | I | I |
| 354 | VYNEQIRDLL | I | I | I | I | I | I | I | I |
| 355 | IYVTGGHLF | I | I | I | II | I | II | I | II |
| 356 | NYMPGQLTI | I | I | II | II | I | I | I | I |
| 359 | NYGVLHVTF | IV | I | I | I | II | I | I | I |
| 360 | VFSPDGHLF | II | I | I | I | I | I | I | I |
| 361 | TYADIGGLDNQI | I | I | I | I | I | I | I | I |
| 362 | VYNYAEQTL | I | I | I | I | I | I | I | I |
| 363 | SYAELGTTI | I | I | I | I | I | I | I | I |
| 365 | VFIDHPVHL | I | I | I | I | I | I | I | I |
| 366 | QYLELAHSL | I | I | I | I | I | I | I | I |
| 367 | LYQDHMQYI | I | I | I | I | I | I | I | I |
| 371 | AYSHLRYVF | I | I | III | II | I | IV | I | II |
| 376 | VYTPVASRQSL | II | I | I | II | I | II | I | I |
| 380 | VYTGIDHHW | II | I | I | II | I | I | I | II |
| 383 | RYKPGEPITF | II | III | I | III | I | II | III | II |
| 386 | TFSDVEAHF | II | I | I | I | I | I | I | I |
| 387 | KYTEKLEEI | I | I | I | I | I | I | I | I |

TABLE 8

Target coverage within various tumor entities, for expression of source genes of selected peptides. A gene was considered over-expressed if its expression level in a tumor sample was more than 2-fold above the highest 75% percentile of expression levels determined from samples of the following normal organs (adjacent to tumors): rectum (n = 10), esophagus (n = 11), bladder (n = 19), kidney (n = 129), stomach (n = 35), colon (n = 41), head and neck (n = 43), liver (n = 50), lung (n = 51), thyroid (n = 59). Over-expression categories are indicated as "A" (>=50% of tumors above the cutoff), "B" (>=20% of tumors above the cutoff, but <50%), and "C" (>=5% of tumors above the cutoff, but <20%). ACC = Adrenocortical carcinoma (N = 79), BLCA = Bladder urothelial carcinoma (N = 408), LGG = Lower grade glioma (N = 534), CESC = Cervical squamous cell carcinoma and endocervical adenocarcinoma (N = 307), STAD = Stomach adenocarcinoma (N = 415), CHOL = Cholangiocarcinoma (N = 36), MESO = Mesothelioma (N = 87), KICH = Kidney chromophobe (N = 66), PRAD = Prostate adenocarcinoma (N = 498), DLBC = Lymphoid neoplasm diffuse large B-cell lymphoma (N = 48), PCPG = Pheochromocytoma and paraganglioma (N = 184), KIRP = Kidney renal papillary cell carcinoma (N = 291), SKCM = Skin cutaneous melanoma (N = 473), SARC = Sarcoma (N = 263), THCA = Thyroid carcinoma (N = 513), THYM = Thymoma (N = 120), UCS = Uterine carcinosarcoma (N = 57), UCEC = Uterine corpus endometrial carcinoma (N = 546), UVM = Uveal melanoma (N = 80), TGCT = Testicular germ cell tumors (N = 156), HNSC = Head and neck squamous cell carcinoma (N = 521).

| SEQ ID NO. | ACC (N = 79) | BLCA (N = 408) | CESC (N = 307) | CHOL (N = 36) | DLBC (N = 48) | HNSC (N = 521) | KICH (N = 66) | KIRP (N = 291) | LGG (N = 534) | MESO (N = 87) | PCPG (N = 184) | PRAD (N = 498) | SARC (N = 263) | SKCM (N = 473) | STAD (N = 415) | TGCT (N = 156) | THCA (N = 513) | THYM (N = 120) | UCEC (N = 546) | UCS (N = 57) | UVM (N = 80) |
|---|---|---|---|---|---|---|---|---|---|---|---|---|---|---|---|---|---|---|---|---|---|
| 16 | | C | C | C | | C | | C | | | | | | | | | | | | | |
| 2 | | | C | | | | | | | | | | | | | C | | | | C | |
| 3 | | | | | | | | | | | | | | | | | | | | | |
| 4 | | B | | | B | B | | | | | | | | | | A | | | | | |
| 5 | | | | | | | | | | | | | | | | | | | | | |
| 6 | C | | | | | | | | | | | | | | | | | | | | |
| 8 | | | | | | | | C | C | | | C | | | | | | | | | |
| 9 | | | | | | | | | | | | | | | | | | | | | |
| 10 | | | | | | | | | | | | | | | | | | | | | |
| 11 | | B | B | B | A | C | C | | C | C | B | A | C | B | B | B | C | A | A | B | C |
| 12 | | B | B | B | A | C | C | | C | C | B | A | C | B | B | B | C | A | A | B | C |
| 13 | | B | B | B | A | C | C | | C | C | B | A | C | B | B | B | C | A | A | B | C |
| 1 | | C | B | | B | C | | | | C | | | C | C | C | A | A | B | C | B | B |
| 17 | | | | | | | B | B | | C | | | | | | | | | | | |
| 18 | | | | | | | B | A | | C | | | | | | | | A | | | |
| 21 | | | | | | | | | | | | B | | | | | | | | | B |
| 22 | | | | | | | | | | | | B | | | | | | | | | B |
| 24 | | C | | | | | | | | | | | | | C | | | | C | | |
| 27 | | | | | | | | | | | | | C | | | | | | | | |
| 28 | | | | | | | | | | | | | C | | | | | | | | |
| 29 | | | | | | | | | | | | | | | C | | | | | | |
| 30 | | | C | | | B | | | | | | | C | | B | B | | | B | B | C |
| 31 | | C | C | | | B | | | | | | | C | C | B | B | | | B | B | C |
| 32 | | C | C | | | | | | | | | | C | C | B | B | | | B | C | |
| 34 | | C | | B | | | | | | | | | | | C | | | | | | |
| 35 | | | | | | | | | | | | | | | | | | | | | |
| 36 | | | | C | | | | C | B | C | | | C | | | | | | | | |
| 37 | | | | | | | | | | | | | | | | | | | | | |
| 38 | | | | | | | | | | | C | | | | | | | | | | |
| 39 | | | | C | B | C | B | | | C | | | | | C | | | | | | |
| 40 | | C | C | A | | B | | | | | | | C | C | C | A | A | C | B | A | |
| 42 | | A | A | | | B | | | | | | | | C | C | | C | A | C | | |
| 45 | | | | | | | | | | | | | | | B | | | | | | |
| 47 | | C | C | C | C | B | | | | C | | | | B | C | | | | | | |
| 48 | | | | | | | | | | | | | | | | C | | | | C | |
| 49 | C | | | | | | | | | | | | | | | | | | | C | |

TABLE 8-continued

Target coverage within various tumor entities, for expression of source genes of selected peptides. A gene was considered over-expressed if its expression level in a tumor sample was more than 2-fold above the highest 75% percentile of expression levels determined from samples of the following normal organs (adjacent to tumors): rectum (n = 10), esophagus (n = 11), bladder (n = 19), kidney (n = 35), colon (n = 41), head and neck (n = 43), liver (n = 50), lung (n = 51), thyroid (n = 59), lung (n = 59). Over-expression categories are indicated as "A" (>=50% of tumors above the cutoff), "B" (>=20% of tumors above the cutoff, but <50%), and "C" (>=5% of tumors above the cutoff, but <20%). ACC = Adrenocortical carcinoma (N = 79), BLCA = Bladder urothelial carcinoma (N = 408), LGG = Lower grade glioma (N = 534), CESC = Cervical squamous cell carcinoma and endocervical adenocarcinoma (N = 307), STAD = Stomach adenocarcinoma (N = 415), CHOL = Cholangiocarcinoma (N = 36), MESO = Mesothelioma (N = 87), KICH = Kidney chromophobe (N = 66), PRAD = Prostate adenocarcinoma (N = 498), DLBC = Lymphoid neoplasm diffuse large B-cell lymphoma (N = 48), PCPG = Pheochromocytoma and paraganglioma (N = 184), KIRP = Kidney renal papillary cell carcinoma (N = 291), SKCM = Skin cutaneous melanoma (N = 473), SARC = Sarcoma (N = 263), THCA = Thyroid carcinoma (N = 513), THYM = Thymoma (N = 120), UCS = Uterine carcinosarcoma (N = 57), UCEC = Uterine corpus endometrial carcinoma (N = 546), UVM = Uveal melanoma (N = 80), TGCT = Testicular germ cell tumors (N = 156), HNSC = Head and neck squamous cell carcinoma (N = 521)

| SEQ ID NO. | ACC (N = 79) | BLCA (N = 408) | CESC (N = 307) | CHOL (N = 36) | DLBC (N = 48) | HNSC (N = 521) | KICH (N = 66) | KIRP (N = 291) | LGG (N = 534) | MESO (N = 87) | PCPG (N = 184) | PRAD (N = 498) | SARC (N = 263) | SKCM (N = 473) | STAD (N = 415) | TGCT (N = 156) | THCA (N = 513) | THYM (N = 120) | UCEC (N = 546) | UCS (N = 57) | UVM (N = 80) |
|---|---|---|---|---|---|---|---|---|---|---|---|---|---|---|---|---|---|---|---|---|---|
| 51 | | | | | | | | | | | | | | | | | | | | | |
| 52 | | | | | | | | | | | | | | | | | | | | | |
| 53 | | | | C | | | | | | | | | | | | | | | | | |
| 54 | | C | C | C | | | | | | | | | | | | | | C | | | |
| 55 | | C | C | | | C | | | | | | | | | | | | C | | | |
| 56 | | | | | | | | | | | | | | | | C | | | | | |
| 58 | C | | | | | | | | | | | | | | | | | | B | C | |
| 60 | | | | | B | | | | | C | C | | | C | | | | | | | |
| 61 | | | | | B | | | | | | | | | | | | | | | | |
| 62 | | | | | | | | | | | | | | C | | C | | | | | |
| 63 | | | | C | | | | | | | | | | | | | | | | | |
| 64 | | | | | | | | | | | | | | | | | | | | | |
| 65 | | | | | | | | | | | | | | | | | | | | | |
| 66 | | | | | | C | | | B | | A | C | C B | | | | | | | | |
| 67 | | | | | | | B | | | | | | | | | | | | | | |
| 68 | | C | | | | | | | | | | | | | | | | | | | |
| 69 | | | | | | | | | | | | | | | | | | | | | |
| 70 | | B | B | C | | B | | B | B | | | B | C | C | C | C A | | B | A A | A C | |
| 72 | C | C | | | | | | | | | C | | C | C | | B | | C | C | C | |
| 74 | | | | | A | | | | | | | | | | | A | | A B | | | |
| 75 | | | | | | | | | | | | | | | | | | B | | | |
| 76 | | | | | | C | | | | | | | | | | | | | | | |
| 78 | | | | | | C C | | | | B | | | B | | B | C | C | C | C | C | |
| 79 | C | | | | | | | | | | | | | | | | | | | | |
| 80 | | | | | | | | | | | | | | | | | | | | | |
| 81 | | C | C | | | C | | C | C | | | C | | | C | | | C | C | | |
| 84 | | | | | | | | | | | A | | | | | | | | | | |
| 86 | | | | | C | | | | | | | C | | | | | | | | | |
| 87 | | | | | | | | | | | A | | | | | | | | | | |
| 88 | | | | | | | | | | | | | | | | | | | B | | |
| 90 | C | | | | | | | | | | | | B | A | | | | | | | A |
| 91 | | | C | | | C | | C | A | | | | C | C | | C | | | C | C | |
| 92 | B | B | C | | B | B | | C | | B | B | | B | B | B | C | | B | C B | B | B |
| 321 | | | | | B | | | | | | | | | | | | | | | | |
| 323 | | C | B | C | C | B | | | A | C | | | | | B | | | C | B | B | |
| 325 | | | | | | B | | | | | | | | A C | | C | C | | | C | C |
| 326 | | | | | | | | | | | | | | | | | | | | | |
| 327 | | B | A | C | A | A | | | | | | | B | | A | A | C | C | B | B | C |

TABLE 8-continued

Target coverage within various tumor entities, for expression of source genes of selected peptides. A gene was considered over-expressed if its expression level in a tumor sample was more than 2-fold above the highest 75% percentile of expression levels determined from samples of the following normal organs (adjacent to tumors): rectum (n = 10), esophagus (n = 11), bladder (n = 19), kidney (n = 35), colon (n = 41), head and neck (n = 43), liver (n = 50), lung (n = 51), thyroid (n = 59), lung (n = 59). Over-expression categories are indicated as "A" (>=50% of tumors above the cutoff), "B" (>=20% of tumors above the cutoff, but <50%), and "C" (>=5% of tumors above the cutoff, but <20%). ACC = Adrenocortical carcinoma (N = 79), BLCA = Bladder urothelial carcinoma (N = 408), LGG = Lower grade glioma (N = 534), CESC = Cervical squamous cell carcinoma and endocervical adenocarcinoma (N = 307), STAD = Stomach adenocarcinoma (N = 415), CHOL = Cholangiocarcinoma (N = 36), MESO = Mesothelioma (N = 87), KICH = Kidney chromophobe (N = 66), PRAD = Prostate adenocarcinoma (N = 498), DLBC = Lymphoid neoplasm diffuse large B-cell lymphoma (N = 48), PCPG = Pheochromocytoma and paraganglioma (N = 184), KIRP = Kidney renal papillary cell carcinoma (N = 291), SKCM = Skin cutaneous melanoma (N = 473), SARC = Sarcoma (N = 263), THCA = Thyroid carcinoma (N = 513), THYM = Thymoma (N = 120), UCS = Uterine carcinosarcoma (N = 57), UCEC = Uterine corpus endometrial carcinoma (N = 546), UVM = Uveal melanoma (N = 80), TGCT = Testicular germ cell tumors (N = 156), HNSC = Head and neck squamous cell carcinoma (N = 521)

| SEQ ID NO. | ACC (N = 79) | BLCA (N = 408) | CESC (N = 307) | CHOL (N = 36) | DLBC (N = 48) | HNSC (N = 521) | KICH (N = 66) | KIRP (N = 291) | LGG (N = 534) | MESO (N = 87) | PCPG (N = 184) | PRAD (N = 498) | SARC (N = 263) | SKCM (N = 473) | STAD (N = 415) | TGCT (N = 156) | THCA (N = 513) | THYM (N = 120) | UCEC (N = 546) | UCS (N = 57) | UVM (N = 80) |
|---|---|---|---|---|---|---|---|---|---|---|---|---|---|---|---|---|---|---|---|---|---|
| 328 | C | C | B | | C | C | | | | | | | C | | B | A | | C | C | B | |
| 329 | | C | C | C | A | | | | C | C | A | | | C | C | | | A | C | C | |
| 330 | | | | | | | | | | | | | | | | | | | | | |
| 331 | | | | | | | | | | | | | | | | A | | B | A | | |
| 332 | C | B | A | B | B | B | C | | | B | | A | B | B | B | A | C | C | A | B | |
| 334 | | | A | | A | | | | | | | | C | C | B | C | | C | | | B |
| 335 | | B | A | C | A | C | | | | C | | C | C | B | B | C | | A | B | C | |
| 336 | | | | | | | | | | | | | | | | | | | | | |
| 340 | | | | | | | | | | | | | | | | | | | | | |
| 175 | | C | C | | B | B | B | | | | | | | | C | | | | | | |
| 97 | | | | | | | | | | | | | | | | C | | B | | | |
| 98 | | | | | | C | | | | | | | | B | C | B | | | B | | |
| 100 | C | B | A | | C | B | | | | B | | | B | B | B | A | | B | B | A | |
| 101 | | | | | C | | | | | | | | | | | | | | | | |
| 103 | | | | | | | | | | | | | | | | | | | | | |
| 104 | | | | | | | | | | | | | | | | | | | | | |
| 105 | | B | A | | B | B | | | | | | | B | C | A | B | | B | C | B | |
| 106 | | B | A | | A | B | | | | | | | B | B | C | A | | A | B | A | |
| 107 | | | C | | | B | | | | | | | C | | | | | | | | |
| 108 | | | C | | | B | | | | | | | C | | | | | | | | |
| 110 | | B | A | | A | C | | | | | | | C | B | C | A | | B | B | B | |
| 111 | | C | A | | B | B | | | | | | | C | C | C | A | | B | C | | |
| 112 | | C | A | | B | B | | | | | | | C | C | C | A | | B | C | | |
| 113 | | | | | | | | | | | | | | | | B | | | | | |
| 114 | | C | | | C | C | | | | C | | | B | B | B | C | | C | C | C | C |
| 115 | | | | | | | | | B | | | | | | C | | | B | | | |
| 116 | | | | | B | | | | B | | A | B | C | | | B | A | | | | |
| 117 | | | | C | B | | | | | | | | | | C | | | | | | |
| 118 | | | | C | B | | | | | | | | | | C | | | | | | |
| 119 | | C | | | | | | | | | | | | | | | | C | | | |
| 121 | | | | | A | | | | | | | | | | | | | | | | |
| 122 | | | | | | | | | | | | | | | | | | | B | | |
| 123 | | C | C | | | B | | | | | | | C | C | B | B | | B | B | B | C |
| 124 | | C | C | | | B | | | | | | | C | C | B | B | | B | C | B | C |
| 125 | | C | C | | | B | | | | | | | C | C | B | B | | B | C | B | C |
| 126 | | | | | | | | | | | | B | | | | | | | | | |
| 127 | | | | | | | | | | | | B | | | | | | | | C | |
| 128 | | | | | C | | | | | | | | | | | C | | | | | |

TABLE 8-continued

Target coverage within various tumor entities, for expression of source genes of selected peptides. A gene was considered over-expressed if its expression level in a tumor sample was more than 2-fold above the highest 75% percentile of expression levels determined from samples of the following normal organs (adjacent to tumors): rectum (n = 10), esophagus (n = 11), bladder (n = 19), kidney (n = 35), colon (n = 41), head and neck (n = 43), liver (n = 50), lung (n = 51), thyroid (n = 59), lung (n = 59). Over-expression categories are indicated as "A" (>=50% of tumors above the cutoff), "B" (>=20% of tumors above the cutoff, but <50%), and "C" (>=5% of tumors above the cutoff, but <20%). ACC = Adrenocortical carcinoma (N = 79), BLCA = Bladder urothelial carcinoma (N = 408), LGG = Lower grade glioma (N = 534), CESC = Cervical squamous cell carcinoma and endocervical adenocarcinoma (N = 307), STAD = Stomach adenocarcinoma (N = 415), CHOL = Cholangiocarcinoma (N = 36), MESO = Mesothelioma (N = 87), KICH = Kidney chromophobe (N = 66), PRAD = Prostate adenocarcinoma (N = 498), DLBC = Lymphoid neoplasm diffuse large B-cell lymphoma (N = 48), PCPG = Pheochromocytoma and paraganglioma (N = 184), KIRP = Kidney renal papillary cell carcinoma (N = 291), SKCM = Skin cutaneous melanoma (N = 473), SARC = Sarcoma (N = 263), THCA = Thyroid carcinoma (N = 513), THYM = Thymoma (N = 120), UCS = Uterine carcinosarcoma (N = 57), UCEC = Uterine corpus endometrial carcinoma (N = 546), UVM = Uveal melanoma (N = 80), TGCT = Testicular germ cell tumors (N = 156), HNSC = Head and neck squamous cell carcinoma (N = 521)

| SEQ ID NO. | ACC (N = 79) | BLCA (N = 408) | CESC (N = 307) | CHOL (N = 36) | DLBC (N = 48) | HNSC (N = 521) | KICH (N = 66) | KIRP (N = 291) | LGG (N = 534) | MESO (N = 87) | PCPG (N = 184) | PRAD (N = 498) | SARC (N = 263) | SKCM (N = 473) | STAD (N = 415) | TGCT (N = 156) | THCA (N = 513) | THYM (N = 120) | UCEC (N = 546) | UCS (N = 57) | UVM (N = 80) |
|---|---|---|---|---|---|---|---|---|---|---|---|---|---|---|---|---|---|---|---|---|---|
| 129 | | | | | | | | | | | | | | | | | | | | | |
| 130 | B | | | | B | B | | | | | | | | | C | | | | | | |
| 131 | | | | | B | | B | | | | | | | | C | | | | | | |
| 132 | | | | | | | | | | | | | | | | | | | | | |
| 133 | | | | | | C | | | | | | | | | C | | | | | | |
| 134 | | | | | | | | | | | | B | C | C | | B | | A | C | B | B |
| 135 | | | C | | B | C | C | | C | | | | | | C | C | | | | | |
| 136 | | B | A | C | | | | | | | | | | | | | | | | | |
| 137 | | | | | | | | | | | | | | | | | | | | | |
| 138 | B | | | | B | B | B | | | | | | C | C | A | A | | B | C | B | |
| 139 | | | | | | | | | | | C | | B | | | | | | | | |
| 140 | | | | | | | | | | | | | | | | | | | | | |
| 141 | | C | B | | | | | | C | | | | | | | | | | | | |
| 142 | | | | | B | B | | | | | | | B | C | A | A | | C | C | | |
| 143 | | | | | C | | | | | | | | | | C | | | B | | | |
| 144 | | | | | C | C | C | | | | | | | | C | C | | | | | |
| 145 | | | | | B | | | | | | | | | | C | | | | | | |
| 146 | | | | | | | | | | | | | | | | | | | | | |
| 147 | | | | | | | | | | C | | | | | | | | | | | |
| 148 | | | | | | | | | | C | | | | | | | | | | | |
| 149 | | | | | | | | | | | | | | C | | | | | | | |
| 150 | | | | | | | | | | | | | | | | | A | | | | |
| 151 | | | C | | A | A | | | B | | | | | | | | | | | | |
| 152 | | | C | | A | A | | | B | | | | | | | | | | | | |
| 153 | | | | | | | | | | | | | | | | | | | | | |
| 155 | C | C | C | | | B | | | | | | | | | | B | | B | B | C | |
| 156 | B | | A | | A | | | | | | C | | C | | B | B | | C | C | C | |
| 157 | C | B | B | B | A | C | C | | B | | B | A | C | B | B | B | C | A | A | B | C |
| 158 | | B | B | B | A | C | C | | C | | B | A | C | B | B | B | | A | A | B | C |
| 159 | | | | | C | | | | | | | | | | C | | | B | | | |
| 161 | | | | | | | | | | | | | | | | | | | | | |
| 162 | | C | B | | A | C | | | | | | | C | B | C | B | | B | C | | |
| 164 | | B | B | C | A | B | | B | | | | | B | B | B | A | C | C | A | B | |
| 165 | | | | | | | | | | | | | | | C | | | | | | |
| 166 | | | | | | | | | | | | | | | C | | | | | | |
| 167 | | C | | | | | | | | | | | C | B | C | | | | | | |
| 168 | | | | | | | | | | | | | | | C | C | | C | C | A | |
| 169 | | | C | | | | | | | | | | | | | | | | | | |
| 170 | | | C | | A | C | | | | | | | C | | C | B | | B | | | |

TABLE 8-continued

Target coverage within various tumor entities, for expression of source genes of selected peptides. A gene was considered over-expressed if its expression level in a tumor sample was more than 2-fold above the highest 75% percentile of expression levels determined from samples of the following normal organs (adjacent to tumors): rectum (n = 10), esophagus (n = 11), bladder (n = 19), kidney (n = 19), stomach (n = 35), colon (n = 41), head and neck (n = 43), liver (n = 50), lung (n = 51), thyroid (n = 59), lung (n = 59). Over-expression categories are indicated as "A" (>=50% of tumors above the cutoff), "B" (>=20% of tumors above the cutoff, but <50%), and "C" (>=5% of tumors above the cutoff, but <20%). ACC = Adrenocortical carcinoma (N = 79), BLCA = Bladder urothelial carcinoma (N = 408), LGG = Lower grade glioma (N = 534), CESC = Cervical squamous cell carcinoma and endocervical adenocarcinoma (N = 307), STAD = Stomach adenocarcinoma (N = 415), CHOL = Cholangiocarcinoma (N = 36), MESO = Mesothelioma (N = 87), KICH = Kidney chromophobe (N = 66), PRAD = Prostate adenocarcinoma (N = 498), DLBC = Lymphoid neoplasm diffuse large B-cell lymphoma (N = 48), PCPG = Pheochromocytoma and paraganglioma (N = 184), KIRP = Kidney renal papillary cell carcinoma (N = 291), SKCM = Skin cutaneous melanoma (N = 473), SARC = Sarcoma (N = 263), THCA = Thyroid carcinoma (N = 513), THYM = Thymoma (N = 120), UCS = Uterine carcinosarcoma (N = 57), UCEC = Uterine corpus endometrial carcinoma (N = 546), UVM = Uveal melanoma (N = 80), TGCT = Testicular germ cell tumors (N = 156), HNSC = Head and neck squamous cell carcinoma (N = 521)

| SEQ ID NO. | ACC (N = 79) | BLCA (N = 408) | CESC (N = 307) | CHOL (N = 36) | DLBC (N = 48) | HNSC (N = 521) | KICH (N = 66) | KIRP (N = 291) | LGG (N = 534) | MESO (N = 87) | PCPG (N = 184) | PRAD (N = 498) | SARC (N = 263) | SKCM (N = 473) | STAD (N = 415) | TGCT (N = 156) | THCA (N = 513) | THYM (N = 120) | UCEC (N = 546) | UCS (N = 57) | UVM (N = 80) |
|---|---|---|---|---|---|---|---|---|---|---|---|---|---|---|---|---|---|---|---|---|---|
| 171 | | B | C | | | C | | | | | | | | | | C | | | C | C | |
| 172 | | C | B | | | A | | | | | | | | | | | | | C | C | |
| 173 | | C | B | | | A | | | | | | | | | | | | | C | C | |
| 174 | | B | B | | C | A | | | | | | | | | | | | C | C | C | |
| 96 | C | | | | | C | | | | | | | | B | | C | | C | | | |
| 176 | | | | | | | | | | | | | | | | | | | | | |
| 177 | | | | | | | | | | | | B | | | | | | | | | |
| 178 | | | | | | | | | A | | | C | | | | | | | | | |
| 180 | C | C | | A | | | B | | B | A | C | | B | | C | C | | | C | | |
| 181 | | | | | | | B | C | | | | | C | | B | | | | A | | |
| 182 | | | | | | | | | | | | | C | | | | | | C | | |
| 183 | | | | | | | | | | | | | | | | | C | | | | |
| 184 | | | | | | | | C | | | | | | | | | | | C | | |
| 185 | C | | | | | | | | | C | | | C | | | | | | C | | |
| 186 | | | | | | | | | | | | | C | C | | | | | | | |
| 187 | C | C | C | B | | C | | | A | B | | C | C | | C | C | | C | C | | |
| 188 | | | B | | | B | | | | | | | | | B | B | | | | | |
| 189 | | | | | | | | | | | | | | | | | | | | | |
| 190 | | | | | | | | | | | | | | | | | | | | | |
| 191 | | | | | A | | | | | | | | | | | C | | | | | |
| 192 | | | | | | | | | B | | | | C | C | | C | | | C | B | C |
| 193 | | B | C | | A | B | | | | | | | C | B | C | A | | | | | |
| 194 | | B | A | C | | B | | | C | B | | | B | | B | A | | A | B | B | |
| 195 | | | | | | | | | | | | | | | | | | | | | |
| 196 | | | | | | | | | | | | | | | | | | | | | |
| 197 | | | | | | | | | C | | | | | | C | | | | | | |
| 198 | | | | | | B | | | | | | | | | | | | | | | |
| 199 | | C | B | | | | C | | | | | | | | | C | C | C | C | | |
| 200 | | | | | | | | | | | | A | | | | | | | | | |
| 202 | C | C | A | | C | C | | | C | C | C | | B | C | C | A | | C | C | B | C |
| 203 | | | | | | | | | | | | | | | C | | | | | | |
| 204 | | | | | | | | C | | | | | | | | | | | | C | |
| 205 | | | | | | | | | | | | | | | | | | | | | |
| 206 | | | C | | | C | C | C | C | | | | | | | A | | | | | |
| 207 | | | | | | C | | C | | | | | | B | C | C | | | A | | |
| 208 | | | | | | C | | | | | | | | B | B | | | | B | | C |
| 209 | | | | | | | | | | | | | | | | | | | | | |
| 210 | | B | A | | | B | | | C | | | | B | B | B | A | | B | B | B | |

TABLE 8-continued

Target coverage within various tumor entities, for expression of source genes of selected peptides. A gene was considered over-expressed if its expression level in a tumor sample was more than 2-fold above the highest 75% percentile of expression levels determined from samples of the following normal organs (adjacent to tumors): rectum (n = 10), esophagus (n = 11), bladder (n = 19), kidney (n = 129), stomach (n = 35), colon (n = 41), head and neck (n = 43), liver (n = 50), lung (n = 51), thyroid (n = 59), lung (n = 59). Over-expression categories are indicated as "A" (>=50% of tumors above the cutoff), "B" (>=20% of tumors above the cutoff, but <50%), and "C" (>=5% of tumors above the cutoff, but <20%). ACC = Adrenocortical carcinoma (N = 79), BLCA = Bladder urothelial carcinoma (N = 408), LGG = Lower grade glioma (N = 534), CESC = Cervical squamous cell carcinoma and endocervical adenocarcinoma (N = 307), STAD = Stomach adenocarcinoma (N = 415), CHOL = Cholangiocarcinoma (N = 36), MESO = Mesothelioma (N = 87), KICH = Kidney chromophobe (N = 66), PRAD = Prostate adenocarcinoma (N = 498), DLBC = Lymphoid neoplasm diffuse large B-cell lymphoma (N = 48), PCPG = Pheochromocytoma and paraganglioma (N = 184), KIRP = Kidney renal papillary cell carcinoma (N = 291), SKCM = Skin cutaneous melanoma (N = 473), SARC = Sarcoma (N = 263), THCA = Thyroid carcinoma (N = 513), THYM = Thymoma (N = 120), UCS = Uterine carcinosarcoma (N = 57), UCEC = Uterine corpus endometrial carcinoma (N = 546), UVM = Uveal melanoma (N = 80), TGCT = Testicular germ cell tumors (N = 156), HNSC = Head and neck squamous cell carcinoma (N = 521)

| SEQ ID NO. | ACC (N = 79) | BLCA (N = 408) | CESC (N = 307) | CHOL (N = 36) | DLBC (N = 48) | HNSC (N = 521) | KICH (N = 66) | KIRP (N = 291) | LGG (N = 534) | MESO (N = 87) | PCPG (N = 184) | PRAD (N = 498) | SARC (N = 263) | SKCM (N = 473) | STAD (N = 415) | TGCT (N = 156) | THCA (N = 513) | THYM (N = 120) | UCEC (N = 546) | UCS (N = 57) | UVM (N = 80) |
|---|---|---|---|---|---|---|---|---|---|---|---|---|---|---|---|---|---|---|---|---|---|
| 211 | B |   | A |   | B | C |   |   | C | C |   |   | A | B | B | A |   | B | B |   | A |
| 212 |   | B | A |   | B | B |   |   |   |   |   |   | B | C | B |   |   | A | C | B |   |
| 213 |   | B | A |   | B | B |   |   |   | C |   |   | B | C | C | A | C | B | C | B |   |
| 214 |   |   |   |   |   |   |   |   |   |   |   |   |   | C |   | B |   |   |   |   |   |
| 216 | C | C | C |   |   |   |   |   |   |   |   |   |   |   |   |   |   |   |   |   |   |
| 217 |   | C |   |   |   |   |   | C |   |   |   |   |   |   |   |   |   |   |   |   |   |
| 218 |   |   | C |   |   |   |   |   |   |   |   |   |   |   |   |   |   |   |   |   |   |
| 219 | B |   |   |   |   |   |   |   |   |   |   |   |   |   |   |   |   |   |   |   |   |
| 220 | B |   |   |   |   |   |   |   |   |   |   |   |   |   |   |   |   |   | C |   | C |
| 221 |   |   |   |   |   |   |   |   |   |   |   |   |   |   | C |   |   | B | C |   |   |
| 222 |   |   |   |   |   |   |   |   |   |   |   |   |   |   |   |   |   |   | C |   |   |
| 223 |   |   |   |   |   |   |   |   |   |   |   | C |   |   |   |   |   |   |   |   |   |
| 224 |   |   |   |   |   |   |   |   |   |   |   |   |   |   |   | B |   |   |   |   |   |
| 225 | C |   |   |   |   |   |   |   | C |   |   |   | C |   |   | C |   |   |   | C |   |
| 226 | C | B | A | C | A | B |   |   |   | C |   |   | B | B | A | A |   | C | B | B |   |
| 227 |   |   | C |   |   |   |   |   |   |   |   |   |   |   |   | C |   |   |   | C |   |
| 228 |   |   |   |   |   |   | A |   |   |   |   |   |   |   |   |   |   |   |   |   |   |
| 229 |   |   |   |   |   | C |   |   |   |   |   |   |   |   |   | A |   |   |   |   |   |
| 230 | B |   |   |   |   |   |   |   | B |   | C |   |   |   |   |   |   | C |   |   |   |
| 231 | B |   |   |   |   |   |   |   | B |   | C |   |   |   |   |   |   | C |   |   |   |
| 232 | C | B | A | C | A | B |   |   | C | C |   |   | B | A | B | A |   | A | B | A |   |
| 233 |   | B | C |   |   | B |   |   |   |   |   |   |   | B | C | C |   |   |   |   |   |
| 234 |   | C | C |   |   |   |   |   |   |   |   |   |   | C |   | B |   |   |   |   |   |
| 235 |   |   |   |   | A |   |   |   |   |   |   |   |   |   |   |   |   |   |   |   |   |
| 236 |   |   |   |   |   |   |   |   |   |   |   |   |   |   |   |   |   |   | C |   |   |
| 237 | C | A | A | C | A | A |   |   | C | B |   |   | B | A | A | A |   | A | B | A |   |
| 238 |   | C | C |   |   | B |   |   | C | C |   |   | C |   |   |   |   | B |   |   |   |
| 240 |   |   |   |   |   |   |   | C |   |   |   |   |   |   |   |   |   |   |   |   |   |
| 241 | C | B | C |   |   | C |   |   |   |   |   |   | C | C | B | B |   |   | C | C |   |
| 242 | C | C |   |   |   | C |   |   |   | C | C |   | C | A | C | C |   |   |   | C |   |
| 243 |   | C |   |   |   | A |   |   |   |   |   |   |   | B |   | B |   |   |   |   |   |
| 244 |   | B | B |   |   |   |   |   |   |   |   |   | B | C |   |   |   |   |   |   |   |
| 247 |   | C | C |   | C |   |   |   |   | C |   |   |   |   | C | C |   | C | C | C | C |
| 249 |   |   |   |   |   | C |   |   |   |   |   |   |   |   |   |   |   |   |   |   |   |
| 250 | C | B | B |   |   | B |   |   | A | C | C |   | B | B | B | B |   | C |   | B |   |
| 251 | C | C | A |   | A |   |   |   | C | C | B |   | A | B |   | A | C | A | B | B |   |
| 253 |   |   |   |   |   |   |   |   |   | B |   |   | C |   |   | C | C |   |   | A |   |
| 255 |   |   |   |   |   |   |   |   |   |   |   |   |   | C |   | B |   |   |   |   |   |

TABLE 8-continued

Target coverage within various tumor entities, for expression of source genes of selected peptides. A gene was considered over-expressed if its expression level in a tumor sample was more than 2-fold above the highest 75% percentile of expression levels determined from samples of the following normal organs (adjacent to tumors): rectum (n = 10), esophagus (n = 11), bladder (n = 19), kidney (n = 35), colon (n = 41), head and neck (n = 43), liver (n = 50), lung (n = 51), thyroid (n = 59), lung (n = 59). Over-expression categories are indicated as "A" (>=50% of tumors above the cutoff), "B" (>=20% of tumors above the cutoff, but <50%), and "C" (>=5% of tumors above the cutoff, but <20%). ACC = Adrenocortical carcinoma (N = 79), BLCA = Bladder urothelial carcinoma (N = 408), LGG = Lower grade glioma (N = 534), CESC = Cervical squamous cell carcinoma and endocervical adenocarcinoma (N = 307), STAD = Stomach adenocarcinoma (N = 415), CHOL = Cholangiocarcinoma (N = 36), MESO = Mesothelioma (N = 87), KICH = Kidney chromophobe (N = 66), PRAD = Prostate adenocarcinoma (N = 498), DLBC = Lymphoid neoplasm diffuse large B-cell lymphoma (N = 48), PCPG = Pheochromocytoma and paraganglioma (N = 184), KIRP = Kidney renal papillary cell carcinoma (N = 291), SKCM = Skin cutaneous melanoma (N = 473), SARC = Sarcoma (N = 263), THCA = Thyroid carcinoma (N = 513), THYM = Thymoma (N = 120), UCS = Uterine carcinosarcoma (N = 57), UCEC = Uterine corpus endometrial carcinoma (N = 546), UVM = Uveal melanoma (N = 80), TGCT = Testicular germ cell tumors (N = 156), HNSC = Head and neck squamous cell carcinoma (N = 521)

| SEQ ID NO. | ACC (N = 79) | BLCA (N = 408) | CESC (N = 307) | CHOL (N = 36) | DLBC (N = 48) | HNSC (N = 521) | KICH (N = 66) | KIRP (N = 291) | LGG (N = 534) | MESO (N = 87) | PCPG (N = 184) | PRAD (N = 498) | SARC (N = 263) | SKCM (N = 473) | STAD (N = 415) | TGCT (N = 156) | THCA (N = 513) | THYM (N = 120) | UCEC (N = 546) | UCS (N = 57) | UVM (N = 80) |
|---|---|---|---|---|---|---|---|---|---|---|---|---|---|---|---|---|---|---|---|---|---|
| 256 | | | | | | | | | | | | | | | | | | | C | | |
| 258 | | | | C | | | | | | | | | | | | | | | B | | |
| 259 | C | | C | | | | | | | | | | | | | | | | | | |
| 262 | | | | | | C | | | B | | | | | | B | | | | | | |
| 263 | | | | | | | | | | | | | | | | B | B | | | | |
| 264 | | C | A | | | | | | | | | | | | | | | | B | C | |
| 265 | | | | | | | | | | | | | | | | | | C | | | |
| 266 | | | | C | C | | | | | | | | | | C | | | | | | |
| 267 | | | | | | | | | | | | C | | | C | | | | | | |
| 269 | | C | A | | | C | | B | | C | | | B | | B | C | C | B | C | | |
| 270 | | | | A | | | | | | | | | | | C | A | | | | | |
| 271 | | | | | | | | | | | | | | C | | | | | | | |
| 272 | | | | | | | | | | | | B | | | | | | | | | |
| 273 | C | C | B | C | A | C | | C | | | | | C | C | C | A | | C | C | B | A |
| 274 | | | | | | | | | | C | | | C | | B | C | | A | C | | |
| 276 | | | | | | | | | | | | | | A | | C | | | C | C | |
| 277 | | C | | | C | | | | | | | | | | C | | | | C | | |
| 278 | | B | | | | | | | | | | C | | | C | | | | C | | |
| 279 | | | | | | C | | | | | | | | | | | | | | | |
| 282 | | | | | | | | | | | C | | | | | C | | C | C | | |
| 283 | | | | | | | | | | | C | | | | | C | | C | C | | |
| 284 | | | | | | | | | | | | | | | | C | | | | | |
| 285 | | | | | | | | | | | | | C | B | | C | | | C | | B |
| 286 | | | | | | | | | | | | | | | | | | | | | |
| 287 | | | | | | | | | | | | | | | | | | | | | |
| 288 | | C | B | | B | C | | | C | | | | B | C | B | A | | A | C | B | |
| 289 | | | C | | | | | | | | | | | | C | | | | | C | |
| 291 | | | C | | | C | | | C | | | | C | | | C | | | C | B | |
| 292 | | | | | | | | | C | | C | | C | | | | | | | B | |
| 293 | | | | | | | | | C | | C | | C | | | | | | | B | |
| 294 | C | | | | | | | | C | | | | B | | | | | | | B | |
| 295 | | | | | | | | | | | | | C | | | C | | | | | |
| 296 | | | C | | | C | | C | | C | | C | | | | B | | | | C | |
| 297 | | | | C | | | C | | | | | | C | | | | | | C | C | |
| 298 | | | | | | | | | A | | | | B | | | | | | | | |
| 300 | | | | | | | | | C | | A | | B | | | A | | | | B | |
| 301 | | | | | | | | | | | | | C | | | | | | | | |

TABLE 8-continued

Target coverage within various tumor entities, for expression of source genes of selected peptides. A gene was considered over-expressed if its expression level in a tumor sample was more than 2-fold above the highest 75% percentile of expression levels determined from samples of the following normal organs (adjacent to tumors): rectum (n = 10), esophagus (n = 11), bladder (n = 19), kidney (n = 129), stomach (n = 35), colon (n = 41), head and neck (n = 43), liver (n = 50), lung (n = 51), thyroid (n = 59), lung (n = 59). Over-expression categories are indicated as "A" (>=50% of tumors above the cutoff), "B" (>=20% of tumors above the cutoff, but <50%), and "C" (>=5% of tumors above the cutoff, but <20%). ACC = Adrenocortical carcinoma (N = 79), BLCA = Bladder urothelial carcinoma (N = 408), LGG = Lower grade glioma (N = 534), CESC = Cervical squamous cell carcinoma and endocervical adenocarcinoma (N = 307), STAD = Stomach adenocarcinoma (N = 415), CHOL = Cholangiocarcinoma (N = 36), MESO = Mesothelioma (N = 87), KICH = Kidney chromophobe (N = 66), PRAD = Prostate adenocarcinoma (N = 498), DLBC = Lymphoid neoplasm diffuse large B-cell lymphoma (N = 48), PCPG = Pheochromocytoma and paraganglioma (N = 184), KIRP = Kidney renal papillary cell carcinoma (N = 291), SKCM = Skin cutaneous melanoma (N = 473), SARC = Sarcoma (N = 263), THCA = Thyroid carcinoma (N = 513), THYM = Thymoma (N = 120), UCS = Uterine carcinosarcoma (N = 57), UCEC = Uterine corpus endometrial carcinoma (N = 546), UVM = Uveal melanoma (N = 80), TGCT = Testicular germ cell tumors (N = 156), HNSC = Head and neck squamous cell carcinoma (N = 521)

| SEQ ID NO. | ACC (N = 79) | BLCA (N = 408) | CESC (N = 307) | CHOL (N = 36) | DLBC (N = 48) | HNSC (N = 521) | KICH (N = 66) | KIRP (N = 291) | LGG (N = 534) | MESO (N = 87) | PCPG (N = 184) | PRAD (N = 498) | SARC (N = 263) | SKCM (N = 473) | STAD (N = 415) | TGCT (N = 156) | THCA (N = 513) | THYM (N = 120) | UCEC (N = 546) | UCS (N = 57) | UVM (N = 80) |
|---|---|---|---|---|---|---|---|---|---|---|---|---|---|---|---|---|---|---|---|---|---|
| 302 | | | | | | B | | | | | | | | | | | | | | | |
| 304 | | | | | | | | | | | | | | | | | | | | | |
| 305 | | C | B | C | C | A | | | | | | | | | | B | | | C | C | |
| 306 | C | C | C | C | B | | | | B | | | | | | | C | C | | C | C | |
| 307 | | | | B | | | | | | | | | | | | | | B | | C | |
| 309 | | | | | | | | | | | | | | | | | | | | | C |
| 312 | C | | | | | | | | | | | | | | | | | | | | |
| 313 | | | | | B | | | | | | | | | | | | | | | | |
| 314 | | | | C | | | | | | | | | | | | | | | | | |
| 315 | | | | | | | | | | | | | | | | | | | | | C |
| 316 | | | | | | | | | | | | | | | | C | | | | | |
| 317 | | | | | | | | | | | | | | | | B | | | | | |
| 319 | | | | | B | | | | | | | | | | | | | | | | |
| 320 | C | B | B | | B | B | | | B | | | | B | B | B | A | | C | C | A | |
| 341 | | | C | | B | C | | | | | | | C | | | | | | C | C | |
| 342 | | C | | | | | | C | | | | | | | | | | | | | |
| 343 | | | | | | | | | | | | B | | | | | | | | | |
| 344 | | B | B | | A | B | | | | C | | | B | B | A | A | | B | B | A | |
| 345 | | B | B | | A | B | | | | C | | | B | B | A | A | | C | B | A | |
| 346 | | C | B | | B | B | B | C | | | | | B | C | A | A | | | C | | |
| 347 | | | | | | | | | | | | | | | | | | | | | C |
| 348 | | B | A | | A | C | | | | C | | | C | B | C | A | | B | B | B | |
| 349 | | | | | | | C | | | | | | | | C | B | | | | | |
| 350 | | | | | | | | | | | | | | | C | C | | | | | |
| 351 | | | | | | | | | | | | | | | | | | | | | |
| 352 | | C | C | | C | C | | | | | | | | | C | | C | | | | |
| 353 | C | B | A | | A | A | | | C | B | | | B | B | A | A | | B | B | A | |
| 354 | C | B | A | | B | B | | | | B | | | B | B | A | A | | C | B | A | |
| 355 | | A | A | | B | B | | | | C | | | C | C | C | | | A | C | | |
| 356 | | | | | C | C | | | | | | | | | C | | | | | | |
| 357 | | C | B | | C | C | | | | | | | | | C | | | C | A | | |
| 358 | C | | C | | B | | | | | | | | B | C | | | C | | C | C | |
| 359 | C | | C | | C | C | | | | | | | C | C | | | | | C | C | |
| 360 | | | C | | | C | | | | | | | | | | | | C | | B | |
| 361 | | C | C | | | | | | B | | | | B | | | B | | | B | | |
| 363 | | C | | C | | C | | | | | | | | | | B | | | | C | |
| 364 | | B | A | | B | B | | C | C | | | | B | C | A | A | | | B | C | |
| 365 | | | | | | | | | C | | | | | | | | | | | C | |

TABLE 8-continued

Target coverage within various tumor entities, for expression of source genes of selected peptides. A gene was considered over-expressed if its expression level in a tumor sample was more than 2-fold above the highest 75% percentile of expression levels determined from samples of the following normal organs (adjacent to tumors): rectum (n = 10), esophagus (n = 11), bladder (n = 19), kidney (n = 35), colon (n = 41), head and neck (n = 43), liver (n = 50), lung (n = 51), thyroid (n = 59), lung (n = 59). Over-expression categories are indicated as "A" (>=50% of tumors above the cutoff), "B" (>=20% of tumors above the cutoff, but <50%), and "C" (>=5% of tumors above the cutoff, but <20%). ACC = Adrenocortical carcinoma (N = 79), BLCA = Bladder urothelial carcinoma (N = 408), LGG = Lower grade glioma (N = 534), CESC = Cervical squamous cell carcinoma and endocervical adenocarcinoma (N = 307), STAD = Stomach adenocarcinoma (N = 415), CHOL = Cholangiocarcinoma (N = 36), MESO = Mesothelioma (N = 87), KICH = Kidney chromophobe (N = 66), PRAD = Prostate adenocarcinoma (N = 498), DLBC = Lymphoid neoplasm diffuse large B-cell lymphoma (N = 48), PCPG = Pheochromocytoma and paraganglioma (N = 184), KIRP = Kidney renal papillary cell carcinoma (N = 291), SKCM = Skin cutaneous melanoma (N = 473), SARC = Sarcoma (N = 263), THCA = Thyroid carcinoma (N = 513), THYM = Thymoma (N = 120), UCS = Uterine carcinosarcoma (N = 57), UCEC = Uterine corpus endometrial carcinoma (N = 546), UVM = Uveal melanoma (N = 80), TGCT = Testicular germ cell tumors (N = 156), HNSC = Head and neck squamous cell carcinoma (N = 521)

| SEQ ID NO. | ACC (N = 79) | BLCA (N = 408) | CESC (N = 307) | CHOL (N = 36) | DLBC (N = 48) | HNSC (N = 521) | KICH (N = 66) | KIRP (N = 291) | LGG (N = 534) | MESO (N = 87) | PCPG (N = 184) | PRAD (N = 498) | SARC (N = 263) | SKCM (N = 473) | STAD (N = 415) | TGCT (N = 156) | THCA (N = 513) | THYM (N = 120) | UCEC (N = 546) | UCS (N = 57) | UVM (N = 80) |
|---|---|---|---|---|---|---|---|---|---|---|---|---|---|---|---|---|---|---|---|---|---|
| 366 | C |   | A |   |   |   |   |   |   |   |   |   | C | B | A |   |   | C | B | A | C |
| 367 |   | B | A |   | B | B |   |   |   |   |   |   | B | C | B |   |   | B | B | B |   |
| 368 |   |   |   |   |   |   |   |   |   |   |   |   | C |   | C | C |   |   |   |   |   |
| 369 | C | B | A | C | B | B |   |   |   |   |   |   | C | B | B | C |   | A | B | C |   |
| 370 |   |   |   |   |   |   |   | B |   |   |   |   |   |   |   |   |   |   |   |   |   |
| 371 |   | B | A |   | A |   |   |   |   |   |   |   |   | C | C | C |   |   | B |   |   |
| 372 |   | C | C | C |   | B |   |   | C | C |   | C |   | C | B |   |   |   |   | B |   |
| 373 |   |   |   |   |   |   |   |   |   |   |   |   |   |   |   |   |   |   |   |   |   |
| 374 |   | C | C |   | C |   |   |   |   | B |   |   |   | B | B | B |   |   |   |   | C |
| 375 |   |   |   |   |   |   |   |   |   | C |   |   |   |   |   |   |   |   |   |   |   |
| 376 |   | C | A |   |   | C |   |   |   |   |   |   | C |   | C | C |   |   | C | C |   |
| 377 | C |   |   |   |   |   |   |   |   |   |   |   |   |   |   |   |   |   |   |   |   |
| 378 |   | C |   |   |   | C |   |   |   |   |   |   | C | C | C |   |   |   | C | B | C |
| 379 |   |   |   |   |   | C |   |   |   |   |   |   |   |   |   |   |   |   |   |   |   |
| 380 |   | C |   |   |   | C |   |   |   |   |   |   | C | C |   | B |   |   |   |   |   |
| 382 |   |   |   |   |   |   |   |   |   |   |   |   |   |   |   | C |   |   |   |   |   |
| 383 |   |   |   |   |   |   |   |   |   |   |   |   |   |   |   |   |   |   |   |   |   |
| 385 |   |   | C | C |   |   |   |   |   |   |   |   |   |   | C |   |   |   |   |   |   |
| 386 |   |   |   |   | B |   |   |   |   |   |   |   | C |   |   | B |   |   |   |   |   |
| 387 |   |   |   |   | C | C |   |   | B | B | B |   | C |   | B | C |   |   |   |   |   |
| 388 |   |   |   |   |   |   |   |   |   |   |   |   |   |   |   |   |   |   |   |   |   |
| 389 |   | C |   |   |   | C |   |   |   |   |   |   |   |   |   |   |   |   |   |   |   |
| 390 | C | B | B |   | B | B |   |   |   | A |   |   | B | B | A | A |   | C | B | B |   |
| 391 | C | B | A | C | B | B |   |   |   |   |   |   | B | C | B | C |   | B | B | B |   |
| 392 | B | B | A |   | B | B |   |   |   | C |   | A | B | B | B | A |   | B | C | B |   |
| 393 |   |   |   |   |   |   |   |   |   |   |   |   |   |   |   |   |   |   |   |   |   |
| 394 |   | B | A |   | A | B |   |   | C | C |   |   | B | B | B | A | A | A | B | B |   |
| 395 |   |   |   |   |   |   |   |   | C | C |   |   | C | C | C | B |   |   |   |   | C |
| 396 |   |   |   |   |   |   |   |   | C | C | B |   | B | B | B |   |   |   |   |   | B |
| 397 |   | A | A | C | A | A |   | A |   |   |   |   | B | B | B | A |   | A | B | A |   |
| 398 |   | A | A | C | A | A |   |   |   |   |   |   | B | B | B | A |   | A | B | A |   |
| 399 |   |   |   |   |   |   | B |   |   |   |   |   |   |   |   |   |   |   |   |   |   |
| 400 |   | B | B |   | B | A |   |   |   | C |   |   | C | C | A |   |   | A | C |   |   |
| 401 |   | B | B |   | B | A |   |   |   | C |   |   | C | C | A |   |   | A | C |   |   |
| 402 | C | A | A | A | C | A | C | A | A | A |   | C | A | C | A |   | A | B | A | A |   |
| 403 |   | C | B |   | B | B |   |   |   |   |   |   | B | B | B | B |   | B | B |   |   |
| 404 |   | C | B |   | B | B |   |   |   |   |   |   | B | B | B | B |   |   |   |   |   |
| 405 |   | C | B |   | B | B |   |   |   |   |   |   | B | B | B | B |   |   |   |   |   |
| 406 |   | C | B | C | C | C |   |   |   | B |   |   |   | B | C |   |   |   | A | C |   |

TABLE 8-continued

Target coverage within various tumor entities, for expression of source genes of selected peptides. A gene was considered over-expressed if its expression level in a tumor sample was more than 2-fold above the highest 75% percentile of expression levels determined from samples of the following normal organs (adjacent to tumors): rectum (n = 10), esophagus (n = 11), bladder (n = 19), kidney (n = 35), colon (n = 41), head and neck (n = 43), liver (n = 50), lung (n = 51), thyroid (n = 59), lung (n = 59). Over-expression categories are indicated as "A" (>=50% of tumors above the cutoff), "B" (>=20% of tumors above the cutoff, but <50%), and "C" (>=5% of tumors above the cutoff, but <20%). ACC = Adrenocortical carcinoma (N = 79), BLCA = Bladder urothelial carcinoma (N = 408), LGG = Lower grade glioma (N = 534), CESC = Cervical squamous cell carcinoma and endocervical adenocarcinoma (N = 307), STAD = Stomach adenocarcinoma (N = 415), CHOL = Cholangiocarcinoma (N = 36), MESO = Mesothelioma (N = 87), KICH = Kidney chromophobe (N = 66), PRAD = Prostate adenocarcinoma (N = 498), DLBC = Lymphoid neoplasm diffuse large B-cell lymphoma (N = 48), PCPG = Pheochromocytoma and paraganglioma (N = 184), KIRP = Kidney renal papillary cell carcinoma (N = 291), SKCM = Skin cutaneous melanoma (N = 473), SARC = Sarcoma (N = 263), THCA = Thyroid carcinoma (N = 513), THYM = Thymoma (N = 120), UCS = Uterine carcinosarcoma (N = 57), UCEC = Uterine corpus endometrial carcinoma (N = 546), UVM = Uveal melanoma (N = 80), TGCT = Testicular germ cell tumors (N = 156), HNSC = Head and neck squamous cell carcinoma (N = 521)

| SEQ ID NO. | ACC (N = 79) | BLCA (N = 408) | CESC (N = 307) | CHOL (N = 36) | DLBC (N = 48) | HNSC (N = 521) | KICH (N = 66) | KIRP (N = 291) | LGG (N = 534) | MESO (N = 87) | PCPG (N = 184) | PRAD (N = 498) | SARC (N = 263) | SKCM (N = 473) | STAD (N = 415) | TGCT (N = 156) | THCA (N = 513) | THYM (N = 120) | UCEC (N = 546) | UCS (N = 57) | UVM (N = 80) |
|---|---|---|---|---|---|---|---|---|---|---|---|---|---|---|---|---|---|---|---|---|---|
| 407 | C | A | A | C | A | B | | | | C | | | B | B | B | A | | A | B | A | |
| 408 | | B | A | | B | B | | | | | | | B | C | B | A | | B | B | B | |
| 409 | | B | A | | B | B | | | | | | | C | C | B | B | | B | C | | |
| 410 | C | A | A | C | A | B | | | | C | | | B | B | B | A | | A | B | A | |
| 412 | C | B | A | C | B | B | | | | A | | | B | B | A | A | | B | C | B | |
| 413 | | | | | | | | | A | | | | | | | | | | | | |
| 414 | | | | | | | | | C | | | | | | | C | | | | | |
| 415 | C | C | B | | C | C | | | C | | | | C | B | B | C | | C | C | | |
| 416 | | | | | | | | | | | | | | | | | | | C | | |
| 417 | | B | A | B | | B | | | | C | | | B | B | A | A | | B | B | B | |

Example 3

In Vitro Immunogenicity for MHC Class I Presented Peptides

In order to obtain information regarding the immunogenicity of the TUMAPs of the present invention, the inventors performed investigations using an in vitro T-cell priming assay based on repeated stimulations of CD8+ T cells with artificial antigen presenting cells (aAPCs) loaded with peptide/MHC complexes and anti-CD28 antibody. This way the inventors could show immunogenicity for HLA-A*02:01 restricted TUMAPs of the invention, demonstrating that these peptides are T-cell epitopes against which CD8+ precursor T cells exist in humans (Table 9).

In Vitro Priming of CD8+ T Cells

In order to perform in vitro stimulations by artificial antigen presenting cells loaded with peptide-MHC complex (pMHC) and anti-CD28 antibody, the inventors first isolated CD8+ T cells from fresh HLA-A*02 leukapheresis products via positive selection using CD8 microbeads (Miltenyi Biotec, Bergisch-Gladbach, Germany) of healthy donors obtained from the University clinics Mannheim, Germany, after informed consent.

PBMCs and isolated CD8+ lymphocytes were incubated in T-cell medium (TCM) until use consisting of RPMI-Glutamax (Invitrogen, Karlsruhe, Germany) supplemented with 10% heat inactivated human AB serum (PAN-Biotech, Aidenbach, Germany), 100 U/ml Penicillin/100 µg/ml Streptomycin (Cambrex, Cologne, Germany), 1 mM sodium pyruvate (CC Pro, Oberdorla, Germany), 20 µg/ml Gentamycin (Cambrex). 2.5 ng/ml IL-7 (PromoCell, Heidelberg, Germany) and 10 U/ml IL-2 (Novartis Pharma, Nurnberg, Germany) were also added to the TCM at this step.

Generation of pMHC/anti-CD28 coated beads, T-cell stimulations and readout was performed in a highly defined in vitro system using four different pMHC molecules per stimulation condition and 8 different pMHC molecules per readout condition.

The purified co-stimulatory mouse IgG2a anti human CD28 Ab 9.3 (Jung et al., 1987) was chemically biotinylated using Sulfo-N-hydroxysuccinimidobiotin as recommended by the manufacturer (Perbio, Bonn, Germany). Beads used were 5.6 µm diameter streptavidin coated polystyrene particles (Bangs Laboratories, Illinois, USA).

pMHC used for positive and negative control stimulations were A*0201/MLA-001 (peptide ELAGIGILTV (SEQ ID NO. 418) from modified Melan-A/MART-1) and A*0201/DDX5-001 (YLLPAIVHI from DDX5, SEQ ID NO. 419), respectively.

800.000 beads/200 µl were coated in 96-well plates in the presence of 4×12.5 ng different biotin-pMHC, washed and 600 ng biotin anti-CD28 were added subsequently in a volume of 200 µl. Stimulations were initiated in 96-well plates by co-incubating 1×10$^6$ CD8+ T cells with 2×10$^5$ washed coated beads in 200 µl TCM supplemented with 5 ng/ml IL-12 (PromoCell) for 3 days at 37° C. Half of the medium was then exchanged by fresh TCM supplemented with 80 U/ml IL-2 and incubating was continued for 4 days at 37° C. This stimulation cycle was performed for a total of three times. For the pMHC multimer readout using 8 different pMHC molecules per condition, a two-dimensional combinatorial coding approach was used as previously described (Andersen et al., 2012) with minor modifications encompassing coupling to 5 different fluorochromes. Finally, multimeric analyses were performed by staining the cells with Live/dead near IR dye (Invitrogen, Karlsruhe, Germany), CD8-FITC antibody clone SK1 (BD, Heidelberg, Germany) and fluorescent pMHC multimers. For analysis, a BD LSRII SORP cytometer equipped with appropriate lasers and filters was used. Peptide specific cells were calculated as percentage of total CD8+ cells. Evaluation of multimeric analysis was done using the FlowJo software (Tree Star, Oregon, USA). In vitro priming of specific multimer+ CD8+ lymphocytes was detected by comparing to negative control stimulations Immunogenicity for a given antigen was detected if at least one evaluable in vitro stimulated well of one healthy donor was found to contain a specific CD8+ T-cell line after in vitro stimulation (i.e. this well contained at least 1% of specific multimer+ among CD8+ T-cells and the percentage of specific multimer+ cells was at least 10× the median of the negative control stimulations).

In Vitro Immunogenicity for Different Cancer Peptides

For tested HLA class I peptides, in vitro immunogenicity could be demonstrated by generation of peptide specific T-cell lines. Exemplary flow cytometry results after TUMAP-specific multimer staining for 2 peptides of the invention are shown in FIGS. 3A-3B together with corresponding negative controls. Results for 5 peptides from the invention are summarized in Table 12A. Exemplary flow cytometry results after TUMAP-specific multimer staining for 7 peptides of the invention are shown in FIGS. 4A-4C and FIGS. 5A-5D together with corresponding negative controls. Results for 74 peptides from the invention are summarized in Table 12B.

TABLE 9A in vitro immunogenicity of HLA class I peptides of the invention
Exemplary results of in vitro immunogenicity experiments conducted by the applicant for the peptides of the invention.
<20% = +; 20%-49% = ++;
50%-69% = +++; >=70% = ++++

| Seq ID | Sequence | wells |
|---|---|---|
| 393 | KYIEAIQWI | ++ |
| 399 | SYIDVLPEF | ++ |
| 400 | KYLEKYYNL | ++ |
| 407 | VYGIRLEHF | +++ |
| 414 | MYPYIYHVL | ++ |

TABLE 12B in vitro immunogenicity of HLA class I peptides of the invention
Exemplary results of in vitro immunogenicity experiments conducted by the applicant for the peptides of the invention. <20% = +; 20%-49% = ++; 50%-69% = +++; >=70% = ++++

| Seq ID | Sequence | Wells positive [%] |
|---|---|---|
| 2 | ALYGKLLKL | ++++ |
| 7 | AAAAKVPEV | + |
| 8 | KLGPFLLNA | +++ |
| 9 | FLGDYVENL | + |
| 17 | ILHEHHIFL | + |

TABLE 12B-continued in vitro immunogenicity of HLA class I
peptides of the invention
Exemplary results of in vitro immunogenicity
experiments conducted by the applicant for the
peptides of the invention. <20% = +;
20%-49% = ++; 50%-69% = +++;
>=70% = ++++

| Seq ID | Sequence | Wells positive [%] |
|---|---|---|
| 43 | LLWAGPVTA | ++++ |
| 322 | ALVSGGVAQA | + |
| 331 | AIWKELISL | ++ |
| 96 | YYTQYSQTI | + |
| 98 | VFPRLHNVLF | + |
| 99 | QYILAVPVL | +++ |
| 102 | VYPFENFEF | +++ |
| 103 | NYIPVKNGKQF | + |
| 104 | SYLTWHQQI | + |
| 105 | IYNETITDLL | + |
| 106 | IYNETVRDLL | + |
| 107 | KYFPYLVVI | ++ |
| 109 | LFITGGQFF | ++ |
| 110 | SYPKIIEEF | ++ |
| 111 | VYVQILQKL | + |
| 112 | IYNFVESKL | +++ |
| 114 | QYLDGTWSL | +++ |
| 115 | RYLNKSFVL | + |
| 119 | VYRVYVTTF | +++ |
| 120 | GYIEHFSLW | ++ |
| 122 | EYQARIPEF | ++ |
| 132 | RYPALFPVL | + |
| 137 | EYLHNCSYF | + |
| 139 | IFGIFPNQF | ++ |
| 140 | RYLINSYDF | +++ |
| 142 | VYVDDIYVI | ++++ |
| 144 | VFASLPGFLF | ++ |
| 155 | IYKWITDNF | ++ |
| 156 | YYMELTKLLL | + |
| 157 | DYIPASGFALF | + |
| 158 | IYEETRGVLKVF | + |
| 160 | RYGDGGSSF | + |
| 161 | KYPDIVQQF | + |
| 162 | KYTSYILAF | + |
| 163 | RYLTISNLQF | + |
| 164 | HYVPATKVF | + |
| 166 | FYTLPFHLI | ++++ |
| 167 | RYGFYYVEF | ++++ |
| 168 | RYLEAALRL | +++ |
| 170 | QYPFHVPLL | +++ |
| 171 | NYEDHFPLL | ++ |
| 172 | VFIFKGNEF | + |
| 174 | VYEKNGYIYF | ++++ |
| 175 | LYSPVPFTL | + |
| 177 | VYFKAGLDVF | + |
| 179 | TYIPVGLGRLL | +++ |
| 180 | KYLQVVGMF | + |
| 181 | VYPPYLNYL | ++++ |
| 182 | AYAQLGYLLF | +++ |
| 186 | VFTTSSNIF | + |
| 190 | LYSELTETL | ++++ |
| 277 | FYTFPFQQL | +++ |
| 344 | EYNSDLHQF | + |
| 345 | EYNSDLHQFF | ++ |
| 349 | QYSIISNVF | ++ |
| 350 | KYGNFIDKL | +++ |
| 351 | IFHEVPLKF | ++ |
| 353 | TYGKIDLGF | + |
| 354 | VYNEQIRDLL | + |
| 356 | NYMPGQLTI | + |
| 358 | YYSEVPVKL | ++++ |
| 359 | NYGVLHVTF | + |
| 360 | VFSPDGHLF | ++ |
| 363 | SYAELGTTI | + |
| 365 | VFIDHPVHL | + |
| 366 | QYLELAHSL | ++ |
| 367 | LYQDHMQYI | ++ |
| 371 | AYSHLRYVF | ++ |
| 380 | VYTGIDHHW | + |

Example 4

Synthesis of Peptides

All peptides were synthesized using standard and well-established solid phase peptide synthesis using the Fmoc-strategy. Identity and purity of each individual peptide have been determined by mass spectrometry and analytical RP-HPLC. The peptides were obtained as white to off-white lyophilizates (trifluoro acetate salt) in purities of >50%. All TUMAPs are preferably administered as trifluoro-acetate salts or acetate salts, other salt-forms are also possible.

Example 5

MHC Binding Assays

Candidate peptides for T cell based therapies according to the present invention were further tested for their MHC binding capacity (affinity). The individual peptide-MHC complexes were produced by UV-ligand exchange, where a UV-sensitive peptide is cleaved upon UV-irradiation, and exchanged with the peptide of interest as analyzed. Only peptide candidates that can effectively bind and stabilize the peptide-receptive MHC molecules prevent dissociation of the MHC complexes. To determine the yield of the exchange reaction, an ELISA was performed based on the detection of the light chain (β2m) of stabilized MHC complexes. The assay was performed as generally described in Rodenko et al. (Rodenko et al., 2006).

96 well MAXISorp plates (NUNC) were coated over night with 2 μg/ml streptavidin in PBS at room temperature, washed 4× and blocked for 1 h at 37° C. in 2% BSA containing blocking buffer. Refolded HLA-A*02:01/MLA-001 monomers served as standards, covering the range of 15-500 ng/ml. Peptide-MHC monomers of the UV-exchange reaction were diluted 100 fold in blocking buffer. Samples were incubated for 1 h at 37° C., washed four times, incubated with 2 μg/ml HRP conjugated anti-β2m for 1 h at 37° C., washed again and detected with TMB solution that is stopped with $NH_2SO_4$. Absorption was measured at 450 nm. Candidate peptides that show a high exchange yield (preferably higher than 50%, most preferred higher than 75%) are generally preferred for a generation and production of antibodies or fragments thereof, and/or T cell receptors or fragments thereof, as they show sufficient avidity to the MHC molecules and prevent dissociation of the MHC complexes.

TABLE 13

MHC class I binding scores.
Binding of HLA-class I restricted peptides to HLA-A*02 was ranged by peptide exchange yield:
<20% = +; 20%-49% = ++;
50%-75% = +++; >=75% = ++++

| Seq ID | Sequence | Peptide exchange |
|---|---|---|
| 1 | PLWGKVFYL | ++ |
| 2 | ALYGKLLKL | +++ |
| 3 | TLLGKQVTL | +++ |
| 4 | ELAEIVFKV | +++ |
| 5 | SLFGQEVYC | +++ |
| 6 | FLDPAQRDL | +++ |
| 7 | AAAKVPEV | +++ |
| 8 | KLGPFLLNA | +++ |
| 9 | FLGDYVENL | ++ |
| 10 | KTLDVFNIIL | ++ |
| 11 | GVLKVFLENV | ++ |
| 12 | GLIYEETRGV | ++ |
| 13 | VLRDNIQGI | +++ |
| 14 | LLDHLSFINKI | ++ |
| 16 | HLYNNEEQV | ++ |
| 17 | ILHEHHIFL | +++ |
| 18 | YVLNEEDLQKV | +++ |
| 19 | TLLPTVLTL | +++ |
| 20 | ALDGHLYAI | +++ |
| 21 | SLYHRVLLY | ++++ |
| 22 | MLSDLTLQL | ++++ |
| 23 | AQTVVVIKA | + |
| 24 | FLWNGEDSAL | +++ |
| 25 | IQADDFRTL | ++ |
| 26 | KVDGVVIQL | +++ |
| 27 | KVFGDLDQV | +++ |
| 28 | TLYSMDLMKV | +++ |
| 29 | TLCNKTFTA | +++ |
| 31 | ALSDETKNNWEV | ++++ |
| 32 | ILADEAFFSV | +++ |
| 33 | LLLPLLPPLSPSLG | +++ |
| 35 | YVLPKLYVKL | ++ |
| 36 | KLYGIEIEV | ++++ |
| 37 | ALINDILGELVKL | +++ |
| 38 | KMQEDLVTL | +++ |
| 39 | ALMAVVSGL | +++ |
| 40 | SLLALPQDLQA | +++ |
| 41 | FVLPLVVTL | +++ |
| 42 | VLSPFILTL | +++ |
| 43 | LLWAGPVTA | +++ |
| 44 | GLLWQIIKV | ++ |
| 45 | VLGPTPELV | +++ |
| 46 | SLAKHGIVAL | +++ |

TABLE 13-continued

MHC class I binding scores.
Binding of HLA-class I restricted peptides to
HLA-A*02 was ranged by peptide exchange yield:
<20% = +; 20%-49% = ++;
50%-75% = +++; >=75% = ++++

| Seq ID | Sequence | Peptide exchange |
|---|---|---|
| 47 | GLYQAQVNL | +++ |
| 48 | TLDHKPVTV | ++ |
| 49 | LLDESKLTL | +++ |
| 50 | EYALLYHTL | ++ |
| 51 | LLLDGDFTL | +++ |
| 52 | ELLSSIFFL | +++ |
| 53 | SLLSHVIVA | +++ |
| 54 | FINPKGNWLL | +++ |
| 55 | IASAIVNEL | ++ |
| 56 | KILDLTRVL | ++ |
| 57 | VLISSTVRL | ++ |
| 58 | ALDDSLTSL | ++ |
| 59 | ALTKILAEL | +++ |
| 60 | FLIDTSASM | ++ |
| 61 | HLPDFVKQL | ++ |
| 62 | SLFNQEVQ1 | +++ |
| 63 | TLSSERDFAL | + |
| 64 | GLSSSSYEL | ++ |
| 65 | KLDGICWQV | +++ |
| 66 | FITDFYTTV | +++ |
| 67 | GVIETVTSL | ++ |
| 69 | GIYDGILHSI | +++ |
| 70 | GLFSQHFNL | +++ |
| 71 | GLITVDIAL | +++ |
| 72 | GMIGFQVLL | +++ |
| 74 | ILDETLENV | ++ |
| 75 | ILDNVKNLL | +++ |
| 76 | ILLDESNFNHFL | +++ |
| 77 | IVLSTIASV | +++ |
| 78 | LLWGHPRVA | +++ |
| 79 | SLVPLQILL | ++++ |
| 80 | TLDEYLTYL | +++ |
| 81 | VLFLGKLLV | ++ |
| 82 | VLLRVLIL | ++ |
| 83 | ELLEYLPQL | +++ |
| 84 | FLEEEITRV | +++ |

TABLE 13-continued

MHC class I binding scores.
Binding of HLA-class I restricted peptides to
HLA-A*02 was ranged by peptide exchange yield:
<20% = +; 20%-49% = ++;
50%-75% = +++; >=75% = ++++

| Seq ID | Sequence | Peptide exchange |
|---|---|---|
| 85 | STLDGSLHAV | +++ |
| 87 | YLTEVFLHVV | +++ |
| 88 | ILLNTEDLASL | +++ |
| 89 | YLVAHNLLL | +++ |
| 90 | GAVAEEVLSSI | + |
| 91 | SSLEPQIQPV | + |
| 92 | LLRGPPVARA | ++ |
| 93 | SLLTQPIFL | +++ |
| 321 | SLWFKPEEL | +++ |
| 322 | ALVSGGVAQA | +++ |
| 323 | ILSVVNSQL | +++ |
| 324 | AIFDFCPSV | ++++ |
| 325 | RLLPKVQEV | ++ |
| 326 | SLLPLVWKI | +++ |
| 327 | SIGDIFLKY | +++ |
| 328 | SVDSAPAAV | ++ |
| 329 | FAWEPSFRDQV | ++ |
| 330 | FLWPKEVEL | +++ |
| 331 | AIWKELISL | +++ |
| 333 | GTFLEGVAK | +++ |
| 334 | GRADALRVL | +++ |
| 335 | VLLAAGPSAA | ++ |
| 336 | GLMDGSPHFL | ++ |
| 337 | KVLGKIEKV | +++ |
| 338 | LLYDGKLSSA | ++ |
| 339 | VLGPGPPPL | ++ |
| 340 | SVAKTILKR | ++ |

TABLE 14

MHC class I binding scores. Binding of
HLA-class I restricted peptides to HLA-
A*24 was ranged by peptide exchange yield:
<20% = +; 20%-49% = ++; 50%-75% =
+++; >=75% = ++++

| Seq ID | Sequence | Peptide exchange |
|---|---|---|
| 96 | YYTQYSQTI | ++++ |
| 97 | TYTFLKETF | ++++ |

TABLE 14-continued

MHC class I binding scores. Binding of HLA-class I restricted peptides to HLA-A*24 was ranged by peptide exchange yield: <20% = +; 20%-49% = ++; 50%-75% = +++; >=75% = ++++

| Seq ID | Sequence | Peptide exchange |
|---|---|---|
| 98 | VFPRLHNVLF | +++ |
| 99 | QYILAVPVL | ++++ |
| 100 | VYIESRIGTSTSF | +++ |
| 102 | VYPFENFEF | +++ |
| 103 | NYIPVKNGKQF | +++ |
| 104 | SYLTHQQI | ++++ |
| 105 | IYNETITDLL | +++ |
| 106 | IYNETVRDLL | +++ |
| 107 | KYFPYLVVI | +++ |
| 108 | PYLVVIHTL | +++ |
| 109 | LFITGGQFF | ++++ |
| 110 | SYPKIIEEF | +++ |
| 111 | VYVQILQKL | +++ |
| 112 | IYNFVESKL | +++ |
| 113 | IYSFHTLSF | +++ |
| 114 | QYLDGTWSL | ++++ |
| 115 | RYLNKSFVL | +++ |
| 116 | AYVIAVHLF | ++++ |
| 117 | IYLSDLTYI | +++ |
| 118 | KYLNSVQYI | +++ |
| 119 | VYRVYVTTF | +++ |
| 120 | GYIEHFSLW | ++++ |
| 121 | RYGLPAAWSTF | +++ |
| 122 | EYQARIPEF | +++ |
| 123 | VYTPVLEHL | ++ |
| 124 | TYKDYVDLF | + |
| 125 | VFSRDFGLLVF | +++ |
| 127 | QYFTGNPLF | +++ |
| 128 | VYPFDWQYI | ++++ |
| 129 | KYIDYLMTW | ++++ |
| 131 | EYLDRIGQLFF | +++ |
| 132 | RYPALFPVL | ++++ |
| 133 | KYLEDMKTYF | +++ |
| 134 | AYIPTPIYF | +++ |
| 135 | VYEAMVPLF | ++++ |
| 136 | IYPEWPVVFF | +++ |
| 137 | EYLHNCSYF | ++++ |
| 138 | VYNAVSTSF | ++ |
| 139 | IFGIFPNQF | +++ |
| 140 | RYLINSYDF | ++++ |
| 141 | SYNGHLTIWF | +++ |
| 142 | VYVDDIYVI | +++ |
| 143 | KYIFQLNEI | +++ |
| 144 | VFASLPGFLF | ++++ |
| 145 | VYALKVRTI | +++ |
| 146 | NYYERIHAL | +++ |
| 147 | LYLAFPLAF | +++ |
| 148 | SYGTVSQIF | ++++ |
| 149 | SYGTVSQI | ++++ |
| 152 | KFFDDLGDELLF | ++ |
| 153 | VYVPFGGKSMITF | ++++ |
| 154 | VYGVPTPHF | ++++ |
| 155 | IYKWITDNF | ++++ |
| 156 | YYMELTKLLL | ++++ |
| 157 | DYIPASGFALF | +++ |
| 158 | IYEETRGVLKVF | +++ |
| 159 | IYEETRGVL | +++ |
| 160 | RYGDGGSSF | +++ |
| 161 | KYPDIVQQF | +++ |
| 162 | KYTSYILAF | ++ |
| 163 | RYLTISNLQF | ++++ |
| 164 | HYVPATKVF | +++ |
| 165 | EYFTPLLSGQF | +++ |
| 166 | FYTLPFHLI | ++++ |
| 167 | RYGFYYVEF | +++ |
| 168 | RYLEAALRL | +++ |
| 169 | NYITGKGDVF | +++ |
| 170 | QYPFHVPLL | ++++ |
| 171 | NYEDHFPLL | +++ |
| 172 | VFIFKGNEF | ++++ |
| 173 | QYLEKYYNL | ++++ |
| 174 | VYEKNGYIYF | +++ |

TABLE 14-continued

MHC class I binding scores. Binding of HLA-class I restricted peptides to HLA-A*24 was ranged by peptide exchange yield: <20% = +; 20%-49% = ++; 50%-75% = +++; >=75% = ++++

| Seq ID | Sequence | Peptide exchange |
|---|---|---|
| 175 | LYSPVPFTL | +++ |
| 176 | FYINGQYQF | +++ |
| 177 | VYFKAGLDVF | +++ |
| 178 | NYSSAVQKF | +++ |
| 179 | TYIPVGLGRLL | +++ |
| 180 | KYLQVVGMF | +++ |
| 181 | VYPPYLNYL | +++ |
| 182 | AYAQLGYLLF | ++++ |
| 183 | PYLQDVPRI | +++ |
| 184 | IYSVGAFENF | ++++ |
| 185 | QYLVHVNDL | ++++ |
| 186 | VFTTSSNIF | ++++ |
| 187 | AYAANVHYL | ++++ |
| 188 | GYKTFFNEF | +++ |
| 190 | LYSELTETL | +++ |
| 191 | TYPDGTYTGRIF | +++ |
| 192 | RYSTFSEIF | +++ |
| 193 | LYLENNAQTQF | +++ |
| 194 | VYQSLSNSL | +++ |
| 195 | AYIKGGWIL | +++ |
| 196 | GYIRGSWQF | ++++ |
| 197 | IFTDIFHYL | ++++ |
| 198 | DYVGFTLKI | ++ |
| 199 | SYLNHLNNL | +++ |
| 200 | VFIHHLPQF | +++ |
| 201 | GYNPNRVFF | +++ |
| 202 | RYVEGIVSL | +++ |
| 204 | EYLSTCSKL | +++ |
| 205 | VYPVVLNQI | +++ |
| 206 | NYLDVATFL | ++++ |
| 207 | LYSDAFKFIVF | +++ |
| 208 | TYLEKIDGF | ++++ |
| 209 | AFIETPIPLF | ++++ |
| 210 | IYAGVGEFSF | ++++ |
| 211 | VFKSEGAYF | ++++ |
| 212 | SYAPPSEDLF | ++ |
| 213 | SYAPPSEDLFL | ++ |
| 214 | KYLMELTLI | +++ |
| 215 | SYVASFFLL | ++ |
| 216 | FYVNVKEQF | +++ |
| 217 | IYISNSIYF | ++++ |
| 218 | LYSELNKWSF | +++ |
| 219 | SYLKAVFNL | +++ |
| 220 | SYSEIKDFL | ++++ |
| 221 | KYIGNLDLL | ++++ |
| 223 | TFITQSPLL | ++++ |
| 224 | PYFFANQEF | +++ |
| 225 | TYTNTLERL | +++ |
| 226 | MYLKLVQLF | ++ |
| 227 | IYRFITERF | +++ |
| 228 | IYQYVADNF | +++ |
| 229 | IYQFVADSF | +++ |
| 230 | TYGMVMVTF | +++ |
| 231 | AFADVSVKF | ++++ |
| 232 | YYLSDSPLL | +++ |
| 233 | QYLTAAALHNL | +++ |
| 234 | SYLPAIWLL | +++ |
| 235 | VYKDSIYYI | +++ |
| 236 | VYLPKIPSW | +++ |
| 237 | KYVGQLAVL | +++ |
| 239 | VYAIFRILL | +++ |
| 240 | YYFFVQEKI | +++ |
| 241 | SYVKVLHHL | +++ |
| 242 | VYGEPRELL | +++ |
| 243 | SYLELANTL | +++ |
| 244 | VHFEDTGKTLLF | +++ |
| 245 | LYPQLFVVL | +++ |
| 246 | KYLSVQLTL | ++ |
| 247 | SFTKTSPNF | +++ |
| 248 | AFPTFSVQL | ++++ |
| 249 | RYHPTTCTI | ++++ |
| 250 | KYPDIASPTF | ++ |

TABLE 14-continued

MHC class I binding scores. Binding of HLA-class I restricted peptides to HLA-A*24 was ranged by peptide exchange yield: <20% = +; 20%-49% = ++; 50%-75% = +++; >=75% = ++++

| Seq ID | Sequence | Peptide exchange |
|---|---|---|
| 251 | VYTKALSSL | +++ |
| 252 | AFGQETNVPLNNF | ++++ |
| 253 | IYGFFNENF | +++ |
| 254 | KYLESSATF | +++ |
| 255 | VYQKIILKF | +++ |
| 256 | VFGKSAYLF | +++ |
| 257 | IFIDNSTQPLHF | +++ |
| 258 | AYAQLGYLL | +++ |
| 259 | YFIKSPPSQLF | ++ |
| 260 | VYMNVMTRL | ++++ |
| 261 | GYIKLINFI | ++++ |
| 262 | VYSSQFETI | ++++ |
| 263 | RYILENHDF | +++ |
| 264 | LYTETRLQF | ++++ |
| 265 | SYLNEAFSF | ++++ |
| 266 | KYTDWTEFL | +++ |
| 267 | SFLNIEKTEILF | ++ |
| 268 | IFITKALQI | ++ |
| 269 | QYPYLQAFF | +++ |
| 270 | YYSQESKVLYL | +++ |
| 271 | RFLMKSYSF | ++++ |
| 272 | RYVFPLPYL | ++++ |
| 273 | IYGEKLQFIF | +++ |
| 274 | KQLDIANYELF | ++++ |
| 275 | KYGTLDVTF | ++++ |
| 276 | QYLDVLHAL | ++++ |
| 277 | FYTFPFQQL | +++ |
| 279 | VWLPASVLF | +++ |
| 280 | TYNPNLQDKL | ++++ |
| 281 | NYSPGLVSLIL | +++ |
| 282 | NYLVDPVTI | +++ |
| 283 | EYQEIFQQL | +++ |
| 284 | DYLKDPVTI | +++ |
| 285 | VYVGDALLHAI | +++ |
| 286 | SYGTILSHI | ++++ |
| 287 | IYNPNLLTASKF | +++ |
| 288 | VYPDTVALTF | ++ |
| 289 | FFHEGQYVF | ++++ |
| 290 | KYGDFKLLEF | ++++ |
| 291 | YYLGSGRETF | +++ |
| 292 | FYPQIINTF | ++++ |
| 293 | VYPHFSTTNLI | ++++ |
| 294 | RFPVQGTVTF | +++ |
| 295 | SYLVIHERI | +++ |
| 296 | SYQVIFQHF | ++++ |
| 297 | TYIDTRTVF | ++++ |
| 298 | AYKSEVVYF | ++++ |
| 299 | KYQYVLNEF | +++ |
| 300 | TYPSQLPSL | +++ |
| 301 | KFDDVTMLF | ++++ |
| 302 | LYLPVHYGF | +++ |
| 303 | LYSVIKEDF | +++ |
| 304 | EYNEVANLF | +++ |
| 305 | NYENKQYLF | ++++ |
| 306 | VYPAEQPQI | +++ |
| 307 | GYAFTLPLF | +++ |
| 308 | TFDGHGVFF | +++ |
| 309 | KYYRQTLLF | ++ |
| 310 | IYAPTLLVF | +++ |
| 311 | EYLQNLNHI | ++++ |
| 312 | SYTSVLSRL | +++ |
| 313 | KYTHFIQSF | ++++ |
| 314 | RYFKGDYSI | +++ |
| 315 | FYIPHVPVSF | +++ |
| 316 | VYFEGSDFKF | +++ |
| 317 | VFDTSIAQLF | +++ |
| 318 | TYSNSAFQYF | +++ |
| 319 | KYSDVKNLI | ++++ |
| 341 | SYLTQHQRI | +++ |
| 342 | NYAFLHRTL | +++ |
| 343 | NYLGGTSTI | +++ |
| 344 | EYNSDLHQF | +++ |

TABLE 14-continued

MHC class I binding scores. Binding of HLA-class I restricted peptides to HLA-A*24 was ranged by peptide exchange yield: <20% = +; 20%-49% = ++; 50%-75% = +++; >=75% = ++++

| Seq ID | Sequence | Peptide exchange |
|---|---|---|
| 345 | EYNSDLHQFF | +++ |
| 347 | VYAEVNSL | +++ |
| 348 | IYLEHTESI | +++ |
| 349 | QYSIISNVF | +++ |
| 350 | KYGNFIDKL | +++ |
| 351 | IFHEVPLKF | +++ |
| 352 | QYGGDLTNTF | +++ |
| 353 | TYGKIDLGF | +++ |
| 354 | VYNEQIRDLL | +++ |
| 355 | IYVTGGHLF | +++ |
| 356 | NYMPGQLTI | ++++ |
| 357 | QFITSTNTF | ++++ |
| 358 | YYSEVPVKL | +++ |
| 359 | NYGVLHVTF | ++++ |
| 360 | VFSPDGHLF | +++ |
| 361 | TYADIGGLDNQI | +++ |
| 362 | VYNYAEQTL | ++ |
| 363 | SYAELGTTI | ++ |
| 364 | KYLNENQLSQL | +++ |
| 365 | VFIDHPVHL | ++++ |
| 366 | QYLELAHSL | +++ |
| 367 | LYQDHMQYI | ++ |
| 368 | KYQNVKHNL | +++ |
| 369 | VYTHEVVTL | +++ |
| 370 | RFIGIPNQF | +++ |
| 371 | AYSHLRYVF | ++ |
| 372 | VYVIEPHSMEF | +++ |
| 373 | GYISNGELF | +++ |
| 374 | VFLPRVTEL | ++ |
| 375 | KYTDYILKI | +++ |
| 376 | VYTPVASRQSL | +++ |
| 377 | QYTPHSHQF | +++ |
| 378 | VYIAELEKI | +++ |
| 379 | VFIAQGYTL | ++++ |
| 380 | VYTGIDHHW | ++++ |
| 381 | KYPASSSVF | +++ |
| 382 | AYLPPLQQVF | +++ |
| 383 | RYKPGEPITF | +++ |
| 384 | RYFDVGLHNF | +++ |
| 385 | QYIEELQKF | +++ |
| 386 | TFSDVEAHF | +++ |
| 387 | KYTEKLEEI | +++ |
| 388 | IYGEKTYAF | +++ |

Example 6

Absolute Quantitation of Tumor Associated Peptides Presented on the Cell Surface The generation of binders, such as antibodies and/or TCRs, is a laborious process, which may be conducted only for a number of selected targets. In the case of tumor-associated and -specific peptides, selection criteria include but are not restricted to exclusiveness of presentation and the density of peptide presented on the cell surface. In addition to the isolation and relative quantitation of peptides as described in Example 1, the inventors did analyze absolute peptide copies per cell as described. The quantitation of TUMAP copies per cell in solid tumor samples requires the absolute quantitation of the isolated TUMAP, the efficiency of TUMAP isolation, and the cell count of the tissue sample analyzed.

Peptide Quantitation by nanoLC-MS/MS

For an accurate quantitation of peptides by mass spectrometry, a calibration curve was generated for each peptide using the internal standard method. The internal standard is a double-isotope-labeled variant of each peptide, i.e. two isotope-labeled amino acids were included in TUMAP synthesis. It differs from the tumor-associated peptide only in its mass but shows no difference in other physicochemical properties (Anderson et al., 2012). The internal standard was spiked to each MS sample and all MS signals were normalized to the MS signal of the internal standard to level out potential technical variances between MS experiments.

The calibration curves were prepared in at least three different matrices, i.e. HLA peptide eluates from natural samples similar to the routine MS samples, and each preparation was measured in duplicate MS runs. For evaluation, MS signals were normalized to the signal of the internal standard and a calibration curve was calculated by logistic regression.

For the quantitation of tumor-associated peptides from tissue samples, the respective samples were also spiked with the internal standard, the MS signals were normalized to the internal standard and quantified using the peptide calibration curve.

Efficiency of Peptide/MHC Isolation

As for any protein purification process, the isolation of proteins from tissue samples is associated with a certain loss of the protein of interest. To determine the efficiency of TUMAP isolation, peptide/MHC complexes were generated for all TUMAPs selected for absolute quantitation. To be able to discriminate the spiked from the natural peptide/MHC complexes, single-isotope-labeled versions of the TUMAPs were used, i.e. one isotope-labeled amino acid was included in TUMAP synthesis. These complexes were spiked into the freshly prepared tissue lysates, i.e. at the earliest possible point of the TUMAP isolation procedure, and then captured like the natural peptide/MHC complexes in the following affinity purification. Measuring the recovery of the single-labeled TUMAPs therefore allows conclusions regarding the efficiency of isolation of individual natural TUMAPs.

The efficiency of isolation was analyzed in a low number of samples and was comparable among these tissue samples. In contrast, the isolation efficiency differs between individual peptides. This suggests that the isolation efficiency, although determined in only a limited number of tissue samples, may be extrapolated to any other tissue preparation. However, it is necessary to analyze each TUMAP individually as the isolation efficiency may not be extrapolated from one peptide to others.

Determination of the Cell Count in Solid, Frozen Tissue

In order to determine the cell count of the tissue samples subjected to absolute peptide quantitation, the inventors applied DNA content analysis. This method is applicable to a wide range of samples of different origin and, most importantly, frozen samples (Alcoser et al., 2011; Forsey and Chaudhuri, 2009; Silva et al., 2013). During the peptide isolation protocol, a tissue sample is processed to a homogenous lysate, from which a small lysate aliquot is taken. The aliquot is divided in three parts, from which DNA is isolated (QiaAmp DNA Mini Kit, Qiagen, Hilden, Germany). The total DNA content from each DNA isolation is quantified using a fluorescence-based DNA quantitation assay (Qubit dsDNA HS Assay Kit, Life Technologies, Darmstadt, Germany) in at least two replicates.

In order to calculate the cell number, a DNA standard curve from aliquots of single healthy blood cells, with a range of defined cell numbers, has been generated. The standard curve is used to calculate the total cell content from the total DNA content from each DNA isolation. The mean total cell count of the tissue sample used for peptide isolation is extrapolated considering the known volume of the lysate aliquots and the total lysate volume.

Peptide Copies Per Cell

With data of the aforementioned experiments, the inventors calculated the number of TUMAP copies per cell by dividing the total peptide amount by the total cell count of the sample, followed by division through isolation efficiency. Copy cell number for selected peptides is shown in Table 15.

REFERENCE LIST

Aalto, Y. et al., Leukemia 15 (2001): 1721-1728
Abaan, O. D. et al., Cancer Res 73 (2013): 4372-4382
Accardi, L. et al., Int. J Cancer 134 (2014): 2742-2747
Adams, D. J. et al., Mol. Cell Biol 25 (2005): 779-788
Agha-Hosseini, F. et al., Med. J Islam Repub. Iran 29 (2015): 218
Agostini, M. et al., Oncotarget. 6 (2015): 32561-32574
Akiyama, Y. et al., Oncol. Rep. 31 (2014): 1683-1690
Al-haidari, A. A. et al., Int. J Colorectal Dis. 28 (2013): 1479-1487
Alcoser, S. Y. et al., BMC. Biotechnol. 11 (2011): 124
Allison, J. P. et al., Science 270 (1995): 932-933
Alonso, C. N. et al., Leuk. Res. 36 (2012): 704-708
Amaro, A. et al., Cancer Metastasis Rev 33 (2014): 657-671
American Cancer Society, (2015),
Ammirante, M. et al., Nature 464 (2010): 302-305
Ampie, L. et al., Front Oncol. 5 (2015): 12
An, C. H. et al., Hum. Pathol. 43 (2012): 40-47
Andersen, R. S. et al., Nat. Protoc. 7 (2012): 891-902
Anderson, N. L. et al., J Proteome. Res 11 (2012): 1868-1878
Appay, V. et al., Eur. J Immunol. 36 (2006): 1805-1814
Arai, E. et al., Int. J Cancer 137 (2015): 2589-2606
Armitage, J. O., Blood 110 (2007): 29-36
Armstrong, C. M. et al., Am. J Clin Exp. Urol. 3 (2015): 64-76
Asahara, S. et al., J Transl. Med. 11 (2013): 291
Atcheson, E. et al., Biosci. Rep. 31 (2011): 371-379
Avigan, D. et al., Clin Cancer Res. 10 (2004): 4699-4708
Azevedo, R. et al., J Control Release 214 (2015): 40-61
Baek, J. M. et al., Biochem. Biophys. Res Commun. 461 (2015): 334-341
Baker, M. et al., PLoS. One. 8 (2013): e62516
Banchereau, J. et al., Cell 106 (2001): 271-274
Bankovic, J. et al., Lung Cancer 67 (2010): 151-159
Barlin, J. N. et al., Neoplasia. 17 (2015): 183-189
Batliner, J. et al., Mol Immunol. 48 (2011): 714-719
Battistella, M. et al., J Cutan. Pathol. 41 (2014): 427-436
Beatty, G. et al., J Immunol 166 (2001): 2276-2282
Becker, M. A. et al., Mol. Cancer Ther. 14 (2015): 973-981
Beggs, J. D., Nature 275 (1978): 104-109
Benada, J. et al., Biomolecules. 5 (2015): 1912-1937
Benjamini, Y. et al., Journal of the Royal Statistical Society. Series B (Methodological), Vol. 57 (1995): 289-300
Bentz, S. et al., Digestion 88 (2013): 182-192
Berard, A. R. et al., Proteomics. 15 (2015): 2113-2135
Berman, R. S. et al., National Cancer Institute: PDQ(R) Colon Cancer Treatment (2015a)
Berman, R. S. et al., National Cancer Institute: PDQ(R) Rectal Cancer Treatment (2015b)
Berndt, S. I. et al., Nat Commun. 6 (2015): 6889

TABLE 15

Absolute copy numbers. The table lists the results of absolute peptide quantitation in tumor samples. The median number of copies per cell are indicated for each peptide: <100 = +; >=100 = ++; >=1,000 +++; >=10,000 = ++++. The number of samples, in which evaluable, high quality MS data are available is indicated.

| SEQ ID No. | Peptide Code | Copies per cell (median) | Number of samples |
|---|---|---|---|
| 70 | DNMT3B-001 | ++ | 16 |
| 323 | KIAA0226L-002 | ++ | 19 |
| 325 | ZNF-003 | ++ | 14 |

Bie, L. et al., PLoS. One. 6 (2011): e25631
Bill, K. L. et al., Lab Invest (2015)
Binsky-Ehrenreich, I. et al., Oncogene 33 (2014): 1006-1016
Black, J. D. et al., Toxins. (Basel) 7 (2015): 1116-1125
Bo, H. et al., BMC. Cancer 13 (2013): 496
Bockelman, C. et al., Cancer Biol Ther. 13 (2012): 289-295
Boeva, V. et al., PLoS. One. 8 (2013): e72182
Bogdanov, K. V. et al., Tsitologiia 50 (2008): 590-596
Bogni, A. et al., Leukemia 20 (2006): 239-246
Boldt, H. B. et al., Endocrinology 152 (2011): 1470-1478
Bormann, F. et al., Mol. Genet. Genomics 286 (2011): 279-291
Boulter, J. M. et al., Protein Eng 16 (2003): 707-711
Braumuller, H. et al., Nature (2013)
Bray, F. et al., Int J Cancer 132 (2013): 1133-1145
Brenner, S. et al., Cancer Lett. 356 (2015): 517-524
Bridgewater, J. et al., J Hepatol. 60 (2014): 1268-1289
Brocker, E. B. et al., Int. J Cancer 41 (1988): 562-567
Brossart, P. et al., Blood 90 (1997): 1594-1599
Bruckdorfer, T. et al., Curr. Pharm. Biotechnol. 5 (2004): 29-43
Bryant, N. L. et al., J Neurooncol. 101 (2011): 179-188
Burgess, A. W. et al., Exp. Cell Res 317 (2011): 2748-2758
Butler, J. E. et al., J Immunol. 182 (2009): 6600-6609
Butterfield, L. H. et al., Clin Cancer Res 12 (2006): 2817-2825
Butterfield, L. H. et al., Clin Cancer Res 9 (2003): 5902-5908
Byrd, J. C. et al., N. Engl. J Med. 369 (2013): 32-42
Byrns, M. C. et al., J Steroid Biochem. Mol. Biol 125 (2011): 95-104
Cai, C. J. et al., Sichuan. Da. Xue. Xue. Bao. Yi. Xue. Ban. 41 (2010): 941-945
Camoes, M. J. et al., PLoS. One. 7 (2012): e49819
Cao, S. et al., J Virol. 89 (2015): 713-729
Cao, W. et al., J Biol Chem 282 (2007): 18922-18928
Carballido, E. et al., Cancer Control 19 (2012): 54-67
Carbonnelle-Puscian, A. et al., Leukemia 23 (2009): 952-960
Card, K. F. et al., Cancer Immunol Immunother. 53 (2004): 345-357
Carlsten, M. et al., Cancer Res 67 (2007): 1317-1325
Carr, J. C. et al., Surgery 152 (2012): 998-1007
Carr, J. C. et al., Ann. Surg. Oncol 20 Suppl 3 (2013): S739-S746
Cassoni, P. et al., J Neuroendocrinol. 16 (2004): 362-364
Catellani, S. et al., Blood 109 (2007): 2078-2085
Cavard, C. et al., J Pathol. 218 (2009): 201-209
Chae, Y. K. et al., Oncotarget. 6 (2015): 37117-37134
Chang, Y. S. et al., Cancer Chemother. Pharmacol. 59 (2007): 561-574
Chanock, S. J. et al., Hum. Immunol. 65 (2004): 1211-1223
Chapiro, J. et al., Radiol. Med. 119 (2014): 476-482
Che, J. et al., Tumour. Biol 36 (2015): 6559-6568
Chen, H. S. et al., Zhonghua Gan Zang. Bing. Za Zhi 11 (2003): 145-148
Chen, H. W. et al., Mol. Carcinog 52 (2013): 647-659
Chen, J. et al., Cancer Chemother. Pharmacol. 75 (2015): 1217-1227
Chen, R. S. et al., Oncogene 28 (2009): 599-609
Chen, W. L. et al., BMC. Cancer 12 (2012): 273
Chen, Y. et al., Am. J Physiol Lung Cell Mol. Physiol 306 (2014): L797-L807
Cheong, S. C. et al., Oral Oncol 45 (2009): 712-719
Chinwalla, V. et al., Oncogene 22 (2003): 1400-1410
Chisholm, K. M. et al., PLoS. One. 7 (2012): e30748
Choi, H. H. et al., Oncotarget. 6 (2015a): 19721-19734
Choi, H. H. et al., Oncotarget. 6 (2015b): 11779-11793
Chudnovsky, Y. et al., Cell Rep. 6 (2014): 313-324
Cicek, M. et al., PLoS. One. 6 (2011): e17522
Cipriano, R. et al., Oncotarget. 4 (2013): 729-738
Cipriano, R. et al., Mol. Cancer Res 12 (2014): 1156-1165
Cohen, C. J. et al., J Mol Recognit. 16 (2003a): 324-332
Cohen, C. J. et al., J Immunol 170 (2003b): 4349-4361
Cohen, S. N. et al., Proc. Natl. Acad. Sci. U.S.A 69 (1972): 2110-2114
Cohen, Y. et al., Hematology. 19 (2014): 286-292
Coligan, J. E. et al., Current Protocols in Protein Science (1995)
Colombetti, S. et al., J Immunol. 176 (2006): 2730-2738
Coosemans, A. et al., Anticancer Res 33 (2013): 5495-5500
Cotterchio, M. et al., PLoS. One. 10 (2015): e0125273
Counter, C. M. et al., Blood 85 (1995): 2315-2320
Courtial, N. et al., FASEB J 26 (2012): 523-532
Crawford, H. C. et al., Curr. Pharm. Des 15 (2009): 2288-2299
Cribier, B. et al., Br. J Dermatol. 144 (2001): 977-982
Cui, D. et al., Oncogene 33 (2014): 2225-2235
Dahlman, K. B. et al., PLoS. One. 7 (2012): e34414
Dai, X. et al., J Virol. 88 (2014): 12694-12702
de Kruijf, E. M. et al., BMC. Cancer 12 (2012): 24
De, S. et al., Cancer Res 69 (2009): 8035-8042
Dedes, K. J. et al., Sci. Transl. Med. 2 (2010): 53ra75
Dengjel, J. et al., Clin Cancer Res 12 (2006): 4163-4170
Denkberg, G. et al., J Immunol 171 (2003): 2197-2207
Dhanoa, B. S. et al., Hum. Genomics 7 (2013): 13
Ding, M. et al., Oncotarget. 6 (2015): 7686-7700
Donnard, E. et al., Oncotarget. 5 (2014): 9199-9213
Drayton, R. M. et al., Clin Cancer Res 20 (2014): 1990-2000
Drutskaya, M. S. et al., IUBMB. Life 62 (2010): 283-289
Du, C. et al., Gastric. Cancer 18 (2015): 516-525
Du, H. et al., Protein Pept. Lett. 16 (2009): 486-489
Duffy, M. J. et al., Clin Cancer Res 15 (2009): 1140-1144
Dufour, C. et al., Cancer 118 (2012): 3812-3821
Economopoulou, P. et al., Ann. Transl. Med. 4 (2016): 173
Ehlken, H. et al., Int. J Cancer 108 (2004): 307-313
Eichhorst, B. F. et al., Blood 107 (2006): 885-891
Eijsink, J. J. et al., Int. J Cancer 130 (2012): 1861-1869
Eisele, G. et al., Brain 129 (2006): 2416-2425
Elbelt, U. et al., J Clin Endocrinol. Metab 100 (2015): E119-E128
Elsnerova, K. et al., Oncol Rep. (2016)
Emens, L. A., Expert. Rev. Anticancer Ther. 12 (2012): 1597-1611
Engelmann, J C et al., PLoS. Comput. Biol 11 (2015): e1004293
Enguita-German, M. et al., World J Hepatol. 6 (2014): 716-737
Er, T. K. et al., J Mol. Med. (Berl) (2016)
Eruslanov, E. et al., Clin. Cancer Res. 19 (2013): 1670-1680
Espiard, S. et al., Endocrinol. Metab Clin North Am. 44 (2015): 311-334
Estey, E. H., Am. J Hematol. 89 (2014): 1063-1081
Etcheverry, A. et al., BMC. Genomics 11 (2010): 701
Faget, J. et al., Oncoimmunology 2 (2013): e23185
Falk, K. et al., Nature 351 (1991): 290-296
Fang, M. et al., Mol. Cell Biol 33 (2013): 2635-2647
Fang, Y. et al., Tumour. Biol 33 (2012): 2299-2306
Farrell, A. S. et al., Mol. Cancer Res 12 (2014): 924-939
Ferlay et al., GLOBOCAN 2012 v1.0, Cancer Incidence and Mortality Worldwide: IARC CancerBase No. 11 [Internet], (2013), globocan.iarc.fr Fernandez-Calotti, P. X. et al., Haematologica 97 (2012): 943-951
Fevre-Montange, M. et al., J Neuropathol. Exp. Neurol. 65 (2006): 675-684
Finocchiaro, G. et al., Ann. Transl. Med. 3 (2015): 83
Fiorito, V. et al., Biochim. Biophys. Acta 1839 (2014): 259-264
Fokas, E. et al., Cell Death. Dis. 3 (2012): e441
Fong, L. et al., Proc. Natl. Acad. Sci. U.S.A 98 (2001): 8809-8814
Ford-Hutchinson, A. W., Eicosanoids 4 (1991): 65-74
Forsey, R. W. et al., Biotechnol. Lett. 31 (2009): 819-823
Fremont, S. et al., EMBO Rep. 14 (2013): 364-372
Fritz, P. et al., Pathol. Res Pract. 208 (2012): 203-209
Fuge, O. et al., Res Rep. Urol. 7 (2015): 65-79
Fujita, H. et al., J Histochem. Cytochem. 63 (2015): 217-227
Fukuyama, R. et al., Oncogene 27 (2008): 6044-6055
Furman, R. R. et al., N. Engl. J Med. 370 (2014): 997-1007
Furukawa, T. et al., Sci. Rep. 1 (2011): 161
Gabrielson, M. et al., Biochem. Biophys. Res Commun. 469 (2016): 1090-1096
Gabrielson, M. et al., Oncol Rep. 29 (2013): 1268-1274
Gabrilovich, D. I. et al., Nat Med. 2 (1996): 1096-1103
Galazis, N. et al., Gynecol. Endocrinol. 29 (2013): 638-644
Gandhi, A. V. et al., Ann Surg. Oncol 20 Suppl 3 (2013): S636-S643
Gao, M. et al., Diagn. Pathol. 8 (2013): 205
Garbe, C. et al., J Invest Dermatol. 100 (1993): 239S-244S
Garcia-Irigoyen, O. et al., Hepatology 62 (2015): 166-178
Gattinoni, L. et al., Nat Rev. Immunol 6 (2006): 383-393
Gazy, I. et al., Mutat. Res Rev Mutat. Res 763 (2015): 267-279
Gelsi-Boyer, V. et al., Mol. Cancer Res 3 (2005): 655-667
Ghosh, A. et al., Int. J Biol Sci. 12 (2016): 30-41
Giannopoulos, K. et al., Leukemia 24 (2010): 798-805
Giannopoulos, K. et al., Int. J Oncol 29 (2006): 95-103
Gnjatic, S. et al., Proc Natl. Acad. Sci. U.S.A 100 (2003): 8862-8867
Godkin, A. et al., Int. Immunol 9 (1997): 905-911
Goede, V. et al., N. Engl. J Med. 370 (2014): 1101-1110
Gonda, T. J. et al., Expert. Opin. Biol Ther. 8 (2008): 713-717
Goni, M. H. et al., Anticancer Res 13 (1993): 1155-1160
Granziero, L. et al., Blood 97 (2001): 2777-2783
Green, J. et al., Cochrane. Database. Syst. Rev (2005): CD002225
Green, M. R. et al., Molecular Cloning, A Laboratory Manual 4th (2012)
Greenfield, E. A., Antibodies: A Laboratory Manual 2nd (2014)
Grimm, M. et al., J Transl. Med. 12 (2014): 208
Grinberg-Rashi, H. et al., Clin Cancer Res 15 (2009): 1755-1761
Grivas, P. D. et al., Semin Cancer Biol 35 (2015): 125-132
Gruel, N. et al., Breast Cancer Res 16 (2014): R46
Gunawardana, C. et al., Br. J Haematol. 142 (2008): 606-609
Guo, P. et al., Onco. Targets. Ther. 8 (2015a): 73-79
Guo, T. et al., Int. J Cancer (2016)
Guo, Z. et al., Tumour. Biol 36 (2015b): 3583-3589
Guo, Z. et al., Tumour. Biol 36 (2015c): 4777-4783
Guyonnet, Duperat, V et al., Biochem. J 305 (Pt 1) (1995): 211-219
Hallek, Michael et al., ASH Annual Meeting Abstracts 112 (2008): 325
Halon, A. et al., Arch. Gynecol. Obstet. 287 (2013): 563-570
Handkiewicz-Junak, D. et al., Eur. J Nucl. Med. Mol Imaging (2016)
Hapgood, G. et al., Blood 126 (2015): 17-25
Harig, S. et al., Blood 98 (2001): 2999-3005
Hayette, S. et al., Oncogene 19 (2000): 4446-4450
He, H. et al., Diagn. Mol. Pathol. 21 (2012): 143-149
He, M. et al., J Dig. Dis. 12 (2011): 393-400
Heerma van Voss, M. R. et al., Histopathology 65 (2014): 814-827
Heishima, K. et al., PLoS. One. 10 (2015): e0137361
Hill, S. J. et al., Genes Dev. 28 (2014): 1957-1975
Hinrichs, C. S. et al., Nat. Biotechnol. 31 (2013): 999-1008
Hirahata, M. et al., Cancer Med. (2016)
Hirano, Y. et al., Genes Cells 11 (2006): 1295-1304
Hlavac, V. et al., Medicine (Baltimore) 93 (2014): e255
Holla, S. et al., Mol. Cancer 13 (2014): 210
Holtl, L. et al., Clin. Cancer Res. 8 (2002): 3369-3376
Hong, L. et al., Hum. Pathol. 45 (2014): 2423-2429
Honore, B. et al., Exp. Cell Res 294 (2004): 199-209
Horig, H. et al., Cancer Immunol Immunother. 49 (2000): 504-514
Hu, X. T. et al., Zhonghua Zhong. Liu Za Zhi. 30 (2008): 515-518
Hu, X. T. et al., Oncol Rep. 22 (2009): 1247-1252
Huang, P. Y. et al., Leuk. Lymphoma 55 (2014): 2085-2092
Huang, Y. et al., Clin Epigenetics. 8 (2016): 9
Huang, Y. et al., PLoS. One. 8 (2013a): e82519
Huang, Y. et al., Cell Biosci. 3 (2013b): 16
Huang, Y. X. et al., Nan. Fang Yi. Ke. Da. Xue. Xue. Bao. 29 (2009): 1329-1332
Hubertus, J. et al., Oncol Rep. 25 (2011): 817-823
Huisman, C. et al., Mol. Ther. (2015)
Huisman, C. et al., Mol. Oncol 7 (2013): 669-679
Hung, C. F. et al., Immunol. Rev 222 (2008): 43-69
Hus, I. et al., Oncol Rep. 20 (2008): 443-451
Hussein, S. et al., Sci. Rep. 5 (2015): 15752
Huu, N. T. et al., FEBS J 282 (2015): 4727-4746
Hwang, M. L. et al., J Immunol. 179 (2007): 5829-5838
Ihn, H. J. et al., Exp. Biol Med. (Maywood.) 240 (2015): 1690-1697
Ilm, K. et al., Mol. Cancer 14 (2015): 38
Imai, K. et al., Br. J Cancer 104 (2011): 300-307
Inoue, K. et al., Subcell. Biochem. 85 (2014): 17-40
Ishida, T. et al., Leukemia 20 (2006): 2162-2168
Ishizone, S. et al., Cancer Sci. 97 (2006): 119-126
Iunusova, N. V. et al., Izv. Akad. Nauk Ser. Biol (2014): 448-455
Iunusova, N. V. et al., Izv. Akad. Nauk Ser. Biol (2013): 284-291
Iwakawa, R. et al., Carcinogenesis 36 (2015): 616-621
Jager, D. et al., Cancer Res 60 (2000): 3584-3591
Jaiswal, A. S. et al., Bioorg. Med. Chem Lett. 24 (2014): 4850-4853
Januchowski, R. et al., Biomed. Pharmacother. 67 (2013): 240-245
Januchowski, R. et al., Biomed. Pharmacother. 68 (2014): 447-453
Jelinek, J. et al., PLoS. One. 6 (2011): e22110
Jenne, D. E. et al., Am. J Hum. Genet. 69 (2001): 516-527
Jiang, H. et al., Int. J Mol. Med. 35 (2015a): 1374-1380
Jiang, H. et al., Exp. Ther. Med. 8 (2014a): 769-774
Jiang, H. N. et al., PLoS. One. 8 (2013): e67637
Jiang, L. et al., Cell Cycle 14 (2015b): 2881-2885
Jiang, L. et al., Oncotarget. 5 (2014b): 7663-7676
Jiang, Y. et al., Mol. Cell 53 (2014c): 75-87
Jiao, X. L. et al., Eur. Rev Med. Pharmacol. Sci. 18 (2014): 509-515
Johnson, M. A. et al., Growth Horm. IGF. Res 24 (2014): 164-173

Jones, R. T. et al., Urol. Clin North Am. 43 (2016): 77-86
Ju, W. et al., Oncol. Res. 18 (2009): 47-56
Jung, G. et al., Proc Natl Acad Sci USA 84 (1987): 4611-4615
Junttila, M. R. et al., Cell Cycle 7 (2008): 592-596
Kachakova, D. et al., J BUON. 18 (2013): 660-668
Kadeh, H. et al., Asian Pac. J Cancer Prev. 16 (2015): 6609-6613
Kalikin, L. M. et al., Genomics 57 (1999): 36-42
Kalos, M. et al., Sci. Transl. Med. 3 (2011): 95ra73
Kang, Y. K. et al., Cancer Res 68 (2008): 7887-7896
Kanthan, R. et al., J Oncol 2015 (2015): 967472
Kanzaki, H. et al., Oncol Rep. 18 (2007): 1171-1175
Kanzaki, H. et al., J Cancer Res Clin Oncol 134 (2008): 211-217
Kanzawa, M. et al., Pathobiology 80 (2013): 235-244
Karim, H. et al., Biochem. Biophys. Res Commun. 411 (2011): 156-161
Karrman, K. et al., Br. J Haematol. 144 (2009): 546-551
Kasiappan, R. et al., Mol. Cancer 9 (2010): 311
Katkoori, V. R. et al., PLoS. One. 7 (2012): e30020
Kato, S. et al., Int. J Oncol 29 (2006): 33-40
Kaufman, H. L. et al., Clin Cancer Res 14 (2008): 4843-4849
Kayser, G. et al., Pathology 43 (2011): 719-724
Kelavkar, U. et al., Curr. Urol. Rep. 3 (2002): 207-214
Kelavkar, U. P. et al., Prostaglandins Other Lipid Mediat. 82 (2007): 185-197
Khanna, A. et al., Int. J Cancer 138 (2016): 525-532
Khanna, A. et al., Cancer Res 73 (2013): 6548-6553
Khatamianfar, V. et al., BMJ Open. 2 (2012)
Kibbe, A. H., Handbook of Pharmaceutical Excipients rd (2000)
Kim, D. S. et al., J Proteome. Res 9 (2010a): 3710-3719
Kim, H. S. et al., Korean J Intern. Med. 25 (2010b): 399-407
Kim, J et al., J Biol Chem 286 (2011): 43294-43300
Kim, J H. et al., J Prev. Med. Public Health 49 (2016): 61-68
Kim, J W. et al., Cancer Sci. 100 (2009): 1468-1478
Kim, J Y. et al., BMB. Rep. 47 (2014a): 451-456
Kim, K. et al., Mol. Cancer Res 6 (2008): 426-434
Kim, S M. et al., Int. J Cancer 134 (2014b): 114-124
Kim, Y. D. et al., Int. J Mol. Med. 29 (2012): 656-662
Kindla, J. et al., Cancer Biol Ther. 11 (2011): 584-591
Kirschner, L. S. et al., Horm. Cancer 7 (2016): 9-16
Kitchen, M. O. et al., Epigenetics. 11 (2016): 237-246
Kiyomitsu, T. et al., Mol. Cell Biol 31 (2011): 998-1011
Kleylein-Sohn, J. et al., J Cell Sci. 125 (2012): 5391-5402
Klopfleisch, R. et al., J Proteome. Res 9 (2010): 6380-6391
Knollman, H. et al., Ther. Adv. Urol. 7 (2015a): 312-330
Knollman, H. et al., Ther. Adv. Urol. 7 (2015b): 312-330
Kocer, B. et al., Pathol. Int. 52 (2002): 470-477
Kohnz, R. A. et al., ACS Chem Biol 10 (2015): 1624-1630
Kohonen-Corish, M. R. et al., Oncogene 26 (2007): 4435-4441
Koido, S. et al., World J Gastroenterol. 19 (2013): 8531-8542
Kong, D. S. et al., Oncotarget. (2016)
Krackhardt, A. M. et al., Blood 100 (2002): 2123-2131
Krieg, A. M., Nat Rev. Drug Discov. 5 (2006): 471-484
Kronenberger, K. et al., J Immunother. 31 (2008): 723-730
Krupenko, S. A. et al., Cell Growth Differ. 13 (2002): 227-236
Kubota, T. et al., Cell Cycle 12 (2013): 2570-2579
Kuchenbaecker, K. B. et al., Nat Genet. 47 (2015): 164-171
Kuefer, M. U. et al., Oncogene 22 (2003): 1418-1424
Kumar, A. et al., Cell Biochem. Biophys. 67 (2013): 837-851
Kumar, R. et al., DNA Repair (Amst) 15 (2014): 54-59
Kunimoto, K. et al., J Cell Physiol 220 (2009): 621-631
Kuwada, M. et al., Cancer Lett. 369 (2015): 212-221
Landi, D. et al., Cancer 118 (2012): 4670-4680
Lanier, M. H. et al., Mol. Biol Cell 26 (2015): 4577-4588
Lee, D. G. et al., Curr. Cancer Drug Targets. 11 (2011): 966-975
Lee, J. H. et al., Ann. Surg. 249 (2009a): 933-941
Lee, K. Y. et al., Yonsei Med. J 50 (2009b): 60-67
Lee, M. A. et al., BMC. Cancer 14 (2014a): 125 Lee, S. Y. et al., Eur. J Cancer 50 (2014b): 698-705
Lee, W. C. et al., J Immunother. 28 (2005): 496-504
Lei, N. et al., Oncol Rep. 32 (2014): 1689-1694
Leitlinie Endometriumkarzinom, 032/034, (2008)
Leitlinie Magenkarzinom, 032-0090L, (2012)
Leitlinien für Diagnostik and Therapie in der Neurologie, 030/099, (2014)
Leonetti, M. D. et al., Proc. Natl. Acad. Sci. U.S.A 109 (2012): 19274-19279
Leung, J. et al., Immune. Netw. 14 (2014): 265-276
Li, J. et al., Mol. Biol Rep. 41 (2014): 8071-8079
Li, J. et al., Zhongguo Fei. Ai. Za Zhi. 18 (2015a): 16-22
Li, J. et al., Tumour. Biol (2016)
Li, J. F. et al., Zhonghua Wei Chang Wai Ke. Za Zhi 15 (2012a): 388-391
Li, L. et al., Pharmacogenet. Genomics 22 (2012b): 105-116
Li, W. Q. et al., Carcinogenesis 34 (2013): 1536-1542
Li, Y. et al., Cancer Biol Ther. 16 (2015b): 1316-1322
Li, Y. et al., Cancer Epidemiol. 39 (2015c): 8-13
Li, Y. F. et al., Int. J Biol Sci. 8 (2012c): 1168-1177
Liang, Y. C. et al., Oncotarget. 6 (2015): 38046-38060
Liao, W. et al., Oncotarget. 5 (2014): 10271-10279
Liddy, N. et al., Nat Med. 18 (2012): 980-987
Lin, C. et al., Oncotarget. 6 (2015): 8434-8453
Lin, J. C. et al., RNA. 20 (2014): 1621-1631
Lin, Y. W. et al., Eur. J Cancer 45 (2009): 2041-2049
Lin, Z. et al., Diagn. Pathol. 8 (2013): 133
Lindqvist, B. M. et al., Epigenetics. 7 (2012): 300-306
Linhares, N. D. et al., Eur. J Med. Genet. 57 (2014): 643-648
Linher-Melville, K. et al., Mol. Cell Biochem. 405 (2015): 205-221
Linkov, F. et al., Eur. Cytokine Netw. 20 (2009): 21-26
Listerman, I. et al., Cancer Res 73 (2013): 2817-2828
Liu, C. et al., Int. J Clin Exp. Pathol. 8 (2015): 7446-7449
Liu, L. et al., Biochem. J 451 (2013a): 55-60
Liu, M. et al., Asian Pac. J Cancer Prev. 14 (2013b): 6281-6286
Liu, Q. et al., Med. Oncol 31 (2014a): 882
Liu, T. et al., DNA Repair (Amst) 11 (2012): 131-138
Liu, W. J. et al., Leuk. Lymphoma 55 (2014b): 2691-2698
Liu, X. et al., Mol. Biol Rep. 41 (2014c): 7471-7478
Ljunggren, H. G. et al., J Exp. Med. 162 (1985): 1745-1759
Lleonart, M. E. et al., Oncol Rep. 16 (2006): 603-608
Llovet, J. M. et al., N. Engl. J Med. 359 (2008): 378-390
Lobito, A. A. et al., J Biol Chem 286 (2011): 18969-18981
Loddo, M. et al., J Pathol. 233 (2014): 344-356
Lollini, P. L. et al., Int. J Cancer 55 (1993): 320-329
Longenecker, B. M. et al., Ann N.Y. Acad. Sci. 690 (1993): 276-291
Lonsdale, J., Nat. Genet. 45 (2013): 580-585
Lu, G. et al., Cancer Cell 26 (2014): 222-234
Lucas, S. et al., Int. J Cancer 87 (2000): 55-60
Luhrig, S. et al., Cell Div. 8 (2013): 3
Luis, Espinoza J. et al., Cancer Sci. 104 (2013): 657-662
Lukas, T. J. et al., Proc. Natl. Acad. Sci. U.S.A 78 (1981): 2791-2795

Lukka, H. et al., Clin Oncol (R Coll. Radiol.) 14 (2002): 203-212
Luna, B. et al., Mol. Neurobiol. 52 (2015): 1341-1363
Lundblad, R. L., Chemical Reagents for Protein Modification 3rd (2004)
Ma, J. et al., Pathol. Oncol Res 19 (2013a): 821-832
Ma, L. D. et al., Zhongguo Shi Yan. Xue. Ye. Xue. Za Zhi. 21 (2013b): 1429-1434
Ma, T. et al., Zhonghua Yi. Xue. Za Zhi. 94 (2014): 3005-3007
Maggioni, A. et al., Protein Expr. Purif. 101 (2014): 165-171
Mahomed, F., Oral Oncol 47 (2011): 797-803
Mantel, A. et al., Exp. Dermatol. 23 (2014): 573-578
Mantia-Smaldone, G. M. et al., Hum. Vaccin. Immunother. 8 (2012): 1179-1191
Marchio, C. et al., J Clin Pathol. 63 (2010): 220-228
Marechal, R. et al., Clin Cancer Res 15 (2009): 2913-2919
Marine, J. C., Nat Rev Cancer 12 (2012): 455-464
Markus, M. A. et al., Genomics 107 (2016): 138-144
Marten, A. et al., Cancer Immunol. Immunother. 51 (2002): 637-644
Martin, R. W. et al., Cancer Res 67 (2007): 9658-9665
Martinez, I. et al., Eur. J Cancer 43 (2007): 415-432
Marzec, K. A. et al., Biomed. Res Int. 2015 (2015): 638526
Mason, C. C. et al., Leukemia (2015)
Massari, F. et al., Cancer Treat. Rev. 41 (2015): 114-121
Massoner, P. et al., PLoS. One. 8 (2013): e55207
Matsueda, S. et al., World J Gastroenterol. 20 (2014): 1657-1666
Matsuura, N. et al., Nihon Rinsho 53 (1995): 1643-1647
Maus, M. V. et al., Blood 123 (2014): 2625-2635
Mayr, C. et al., Exp. Hematol. 34 (2006): 44-53
Mayr, C. et al., Blood 105 (2005): 1566-1573
McGilvray, R. W. et al., Int. J Cancer 127 (2010): 1412-1420
Medeiros, A. C. et al., Cancer Epidemiol. Biomarkers Prev. 3 (1994): 331-333
Mehta, J. et al., PLoS. One. 10 (2015): e0120622
Mei, J. Z. et al., Nan. Fang Yi. Ke. Da. Xue. Xue. Bao. 27 (2007): 887-889
Mencia, N. et al., Biochem. Pharmacol. 82 (2011): 1572-1582
Mendoza-Maldonado, R. et al., PLoS. One. 5 (2010): e13720
Meziere, C. et al., J Immunol 159 (1997): 3230-3237
Migliorini, D. et al., J Clin Invest 121 (2011): 1329-1343
Milutin, Gasperov N. et al., PLoS. One. 10 (2015): e0129452
Missero, C. et al., Exp. Dermatol. 23 (2014): 143-146
Miyagi, Y. et al., Clin Cancer Res 7 (2001): 3950-3962
Miyamoto, K. et al., Int. J Cancer 116 (2005): 407-414
Mohanraj, L. et al., Recent Pat Anticancer Drug Discov 6 (2011): 166-177
Mohelnikova-Duchonova, B. et al., Cancer Chemother. Pharmacol. 72 (2013): 669-682
Molina, J. R. et al., Mayo Clin Proc. 83 (2008): 584-594
Morgan, R. A. et al., Science 314 (2006): 126-129
Mori, M. et al., Transplantation 64 (1997): 1017-1027
Morin, P. J., Cancer Res 65 (2005): 9603-9606
Morita, T. et al., Int. J Cancer 109 (2004): 525-532
Mortara, L. et al., Clin Cancer Res. 12 (2006): 3435-3443
Moser, J. J. et al., J Neurosci. Res 85 (2007): 3619-3631
Mou, X. et al., Sci. Rep. 4 (2014): 6138
Moulton, H. M. et al., Clin Cancer Res 8 (2002): 2044-2051
Mueller, L. N. et al., J Proteome. Res 7 (2008): 51-61
Mueller, L. N. et al., Proteomics. 7 (2007): 3470-3480
Mukhopadhyay, P. et al., Biochim Biophys. Acta 1815 (2011): 224-240
Muller, M. R. et al., Blood 103 (2004): 1763-1769
Mumberg, D. et al., Proc. Natl. Acad. Sci. U.S.A 96 (1999): 8633-8638
Nagashio, R. et al., Sci. Rep. 5 (2015): 8649
Naito, T. et al., J Biol Chem 290 (2015): 15004-15017
Nakajima, H. et al., Cancer Sci. 105 (2014): 1093-1099
Nakano, K. et al., Exp. Cell Res 287 (2003): 219-227
Nakarai, C. et al., Clin Exp. Med. 15 (2015): 333-341
Nakashima, A. et al., Biochem. Biophys. Res Commun. 361 (2007): 218-223
National Cancer Institute, (May 6, 2015)
Nguyen, M. H. et al., Int. J Oncol 41 (2012): 1285-1296
Ni, I. B. et al., Hematol. Rep. 4 (2012): e19
Ni, L. et al., J Cell Biochem. 106 (2009): 920-928
Nobusawa, S. et al., Brain Tumor Pathol. 31 (2014): 229-233
O'Brien, S. et al., Lancet Oncol 15 (2014): 48-58
O'Geen, H. et al., PLoS. Genet. 3 (2007): e89
Obama, K. et al., Clin Cancer Res 14 (2008): 1333-1339
Oehler, V. G. et al., Blood 114 (2009): 3292-3298
Ogasawara, N. et al., J Biochem. 149 (2011): 321-330
Ogbomo, H. et al., Neoplasia. 10 (2008): 1402-1410
Ogiso, Y. et al., Cancer Res 62 (2002): 5008-5012
Oh, Y. et al., J Biol. Chem 287 (2012): 17517-17529
Okabe, N. et al., Int. J Oncol 46 (2015): 999-1006
Okuno, K. et al., Exp. Ther Med. 2 (2011): 73-79
Olkhanud, P. B. et al., Cancer Res 69 (2009): 5996-6004
Olszewski-Hamilton, U. et al., Biomark. Cancer 3 (2011): 31-40
Orentas, R. J. et al., Front Oncol 2 (2012): 194
Orzol, P. et al., Histol. Histopathol. 30 (2015): 503-521
Ouyang, M. et al., BMC. Cancer 15 (2015): 132
Ozawa, H. et al., Ann. Surg. Oncol 17 (2010): 2341-2348
Ozeki, N. et al., Int. J Mol. Sci. 17 (2016)
Palma, M. et al., Cancer Immunol Immunother. 57 (2008): 1705-1710
Palmer, D. H. et al., Hepatology 49 (2009): 124-132
Palomba, M. L., Curr. Oncol Rep. 14 (2012): 433-440
Pan, J. et al., Leuk. Res 36 (2012): 889-894
Pannu, V. et al., Oncotarget. 6 (2015): 6076-6091
Parikh, R. A. et al., Genes Chromosomes. Cancer 53 (2014): 25-37
Parikh, S. A. et al., Blood 118 (2011): 2062-2068
Parisi, M. A., Am. J Med. Genet. C. Semin. Med. Genet. 151C (2009): 326-340
Park, E. et al., Mol. Cell 50 (2013): 908-918
Park, M. J. et al., Immunol. Invest 40 (2011): 367-382
Park, Y. R. et al., Cancer Genomics Proteomics. 13 (2016): 83-90
Parplys, A. C. et al., DNA Repair (Amst) 24 (2014): 87-97
Pasmant, E. et al., Mol. Med. 17 (2011): 79-87
Patil, A. A. et al., Oncotarget. 5 (2014): 6414-6424
Pattabiraman, D. R. et al., Leukemia 27 (2013): 269-277
Pawar, S. et al., J Ovarian. Res 7 (2014): 53
Payne, S. R. et al., Prostate 69 (2009): 1257-1269
Peng, B. et al., Mol. Biosyst. 11 (2015): 105-114
Pequeux, C. et al., Cancer Res 62 (2002): 4623-4629
Perrais, M. et al., J Biol Chem 276 (2001): 15386-15396
Petrini, I., Ann. Transl. Med. 3 (2015): 82
Phan, G. Q. et al., Cancer Control 20 (2013): 289-297
Phe, V. et al., BJU. Int. 104 (2009): 896-901
Piasecka, D. et al., Postepy Biochem. 61 (2015): 198-206
Pinheiro, J. et al., nlme: Linear and Nonlinear Mixed Effects Models (CRAN.R-project.org/packe=nlme) (2015)
Plebanski, M. et al., Eur. J Immunol 25 (1995): 1783-1787
Porta, C. et al., Virology 202 (1994): 949-955
Porter, D. L. et al., N. Engl. J Med. 365 (2011): 725-733
Potapenko, I. O. et al., Mol. Oncol 9 (2015): 861-876

Przybyl, J. et al., Int. J Biochem. Cell Biol 53 (2014): 505-513
Qian, M. X. et al., Cell 153 (2013): 1012-1024
Qiu, J. et al., Leukemia 17 (2003): 1891-1900
Quinn, D. I. et al., Urol. Oncol. (2015)
Qureshi, R. et al., Cancer Lett. 356 (2015): 321-331
Rainer, J. et al., Mol. Endocrinol. 26 (2012): 178-193
Raja, S. B. et al., J Cell Sci. 125 (2012): 703-713
Rajadhyaksha, A. M. et al., Am. J Hum. Genet. 87 (2010): 643-654
Rajkumar, T. et al., BMC. Cancer 11 (2011): 80
Rakic, M. et al., Hepatobiliary. Surg. Nutr. 3 (2014): 221-226
Rammensee, H. G. et al., Immunogenetics 50 (1999): 213-219
Ramsay, R. G. et al., Expert. Opin. Ther. Targets. 7 (2003): 235-248
RefSeq, The NCBI handbook [Internet], Chapter 18, (2002)
Reid-Lombardo, K. M. et al., Cancer Epidemiol. Biomarkers Prev. 20 (2011): 1251-1254
Reinisch, W. et al., J Immunother. 25 (2002): 489-499
Reinmuth, N. et al., Dtsch. Med. Wochenschr. 140 (2015): 329-333
Relogio, A. et al., PLoS. Genet. 10 (2014): e1004338
Rendon-Huerta, E. et al., J Gastrointest. Cancer 41 (2010): 52-59
Resende, C. et al., *Helicobacter.* 16 Suppl 1 (2011): 38-44
Richards, S. et al., J Natl. Cancer Inst. 91 (1999): 861-868
Ricke, R. M. et al., Cell Cycle 10 (2011): 3645-3651
Rincon, R. et al., Oncotarget. 6 (2015): 4299-4314
Rini, B. I. et al., Curr. Opin. Oncol. 20 (2008): 300-306
Rini, B. I. et al., Cancer 107 (2006): 67-74
Riordan, J. D. et al., PLoS. Genet. 9 (2013): e1003441
Ritter, A. et al., Cell Cycle 14 (2015): 3755-3767
Robak, T. et al., Expert. Opin. Biol. Ther 14 (2014): 651-661
Roca, H. et al., PLoS. One. 8 (2013): e76773
Rock, K. L. et al., Science 249 (1990): 918-921
Rodenko, B. et al., Nat Protoc. 1 (2006): 1120-1132
Rodini, C. O. et al., Int. J Oncol 40 (2012): 1180-1188
Rodriguez, F. J. et al., J Neuropathol. Exp. Neurol. 67 (2008): 1194-1204
Romanuik, T. L. et al., BMC. Med. Genomics 3 (2010): 43
Ronchi, C. L. et al., Neoplasia. 14 (2012): 206-218
Rouanne, M. et al., Crit Rev Oncol Hematol. 98 (2016): 106-115
Rucki, A. A. et al., World J Gastroenterol. 20 (2014): 2237-2246
Rudland, P. S. et al., Am. J Pathol. 176 (2010): 2935-2947
Rutkowski, M. J. et al., Mol Cancer Res 8 (2010): 1453-1465
Ryu, B. et al., PLoS. One. 2 (2007): e594
S3-Leitlinie Exokrines Pankreaskarzinom, 032-0100L, (2013)
S3-Leitlinie Lungenkarzinom, 020/007, (2011)
S3-Leitlinie maligne Ovarialtumore, 032-0350L, (2013)
S3-Leitlinie Mammakarzinom, 032-0450L, (2012)
S3-Leitlinie Melanom, 032-0240L, (2013)
S3-Leitlinie Prostatakarzinom, 043/0220L, (2014)
S3-Leitlinie Zervixkarzinom, 032/0330L, (2014)
Sadeque, A. et al., BMC. Med. Genomics 5 (2012): 59
Saeki, M. et al., PLoS. One. 8 (2013): e67326
Safarpour, D. et al., Arch. Pathol. Lab Med. 139 (2015): 612-617
Saiki, R. K. et al., Science 239 (1988): 487-491
Salim, H. et al., Genes Chromosomes. Cancer 52 (2013): 895-911
Salman, B. et al., Oncoimmunology. 2 (2013): e26662
Sandoval, J. et al., J Clin Oncol 31 (2013): 4140-4147
Sangro, B. et al., J Clin Oncol 22 (2004): 1389-1397
Sankaranarayanan, P. et al., PLoS. One. 10 (2015): e0121396
Santarlasci, V. et al., Eur. J Immunol. 44 (2014): 654-661
Sarma, S. N. et al., Environ. Toxicol. Pharmacol. 32 (2011): 285-295
Sasao, T. et al., Reproduction. 128 (2004): 709-716
Satija, Y. K. et al., Int. J Cancer 133 (2013): 2759-2768
Sato, N. et al., Genes Chromosomes. Cancer 49 (2010): 353-367
Savaskan, N. E. et al., Ann. Anat. 192 (2010): 309-313
Savaskan, N. E. et al., Curr. Neuropharmacol. 13 (2015): 258-265
Sawada, G. et al., Oncol Rep. 30 (2013): 1971-1975
Schetelig, J. et al., J Clin Oncol 26 (2008): 5094-5100
Scheurer, B. et al., Immunopharmacology 38 (1997): 167-175
Schmidt, S. M. et al., Cancer Res 64 (2004): 1164-1170
Schreiber, M. et al., J Biol Chem 273 (1998): 3509-3516
Seeger, F. H. et al., Immunogenetics 49 (1999): 571-576
Seidl, C. et al., Invest New Drugs 28 (2010): 49-60
Seppanen, M. et al., Acta Obstet. Gynecol. Scand. 87 (2008): 902-909
Shareef, M. M. et al., Arab. J Gastroenterol. 16 (2015): 105-112
Sharma, R. K. et al., Clin Exp. Metastasis 33 (2016): 263-275
Sharpe, D. J. et al., Oncotarget. 5 (2014): 8803-8815
Shen, C. et al., Cancer Res 73 (2013): 3393-3401
Shen, Y. et al., Oncotarget. 6 (2015a): 20396-20403
Shen, Y. et al., Cancer Cell Microenviron. 2 (2015b)
Sherman, F. et al., Laboratory Course Manual for Methods in Yeast Genetics (1986)
Sherman, S. K. et al., Surgery 154 (2013): 1206-1213
Shi, M. et al., World J Gastroenterol. 10 (2004): 1146-1151
Shi, Z. et al., Tumour. Biol 36 (2015): 8519-8529
Shimizu, F. et al., Lab Invest 83 (2003): 187-197
Shioji, G. et al., J Hum. Genet. 50 (2005): 507-515
Showel, M. M. et al., F1000Prime. Rep. 6 (2014): 96
Siegel, S. et al., Blood 102 (2003): 4416-4423
Siew, Y. Y. et al., Int. Immunol. 27 (2015): 621-632
Silva, L. P. et al., Anal. Chem. 85 (2013): 9536-9542
Silvestris, F. et al., Adv. Exp. Med. Biol 714 (2011): 113-128
Singh, V. et al., Curr. Cancer Drug Targets. 13 (2013): 379-399
Singh-Jasuja, H. et al., Cancer Immunol. Immunother. 53 (2004): 187-195
Skawran, B. et al., Mod. Pathol. 21 (2008): 505-516
Small, E. J. et al., J Clin Oncol. 24 (2006): 3089-3094
Smetsers, S. et al., Fam. Cancer 11 (2012): 661-665
Smith, P. et al., Clin Cancer Res 13 (2007): 4061-4068
Sohrabi, A. et al., Asian Pac. J Cancer Prev. 15 (2014): 6745-6748
Song, H. R. et al., Mol. Carcinog 52 Suppl 1 (2013): E155-E160
Sonora, C. et al., J Histochem. Cytochem. 54 (2006): 289-299
Spaner, D. E. et al., Cancer Immunol Immunother. 54 (2005): 635-646
Srivastava, N. et al., Cancer Manag. Res. 6 (2014): 279-289
Stacey, S. N. et al., Nat Commun. 6 (2015): 6825
Stahl, M. et al., Ann. Oncol. 24 Suppl 6 (2013): vi51-vi56
Stangel, D. et al., J Surg. Res 197 (2015): 91-100
Stein, U., Expert. Opin. Ther. Targets. 17 (2013): 1039-1052
Steinberg, R. L. et al., Urol. Oncol (2016a)
Steinberg, R. L. et al., Urol. Oncol (2016b)

Steinway, S. N. et al., PLoS. One. 10 (2015): e0128159
Stenman, G. et al., Cell Cycle 9 (2010): 2986-2995
Stevanovic, S. et al., J Clin Oncol 33 (2015): 1543-1550
Stintzing, S., F1000Prime. Rep. 6 (2014): 108
Stratakis, C. A. et al., DNA Seq. 9 (1998): 227-230
Struyf, S. et al., Am. J Pathol. 163 (2003): 2065-2075
Sturm, M. et al., BMC. Bioinformatics. 9 (2008): 163
Su, Z. et al., Cancer Res. 63 (2003): 2127-2133
Subhash, V. V. et al., BMC. Cancer 15 (2015): 550
Sui, Y. et al., Oncogene 26 (2007): 822-835
Sukocheva, O. A. et al., World J Gastroenterol. 21 (2015): 6146-6156
Sun, S. et al., Gene 584 (2016): 90-96
Sun, W. et al., World J Gastroenterol. 19 (2013): 2913-2920
Sutherland, C. L. et al., Blood 108 (2006): 1313-1319
Suzuki, N. et al., J Orthop. Res 32 (2014): 915-922
Tabares-Seisdedos, R. et al., Mol. Psychiatry 14 (2009): 563-589
Takahashi, M. et al., Int. J Oncol 27 (2005): 1483-1487
Takatsu, H. et al., J Biol Chem 286 (2011): 38159-38167
Takayama, M. A. et al., Genes Cells 5 (2000a): 481-490
Takayama, T. et al., Cancer 68 (1991): 2391-2396
Takayama, T. et al., Lancet 356 (2000b): 802-807
Taketani, T. et al., Cancer Res 62 (2002): 33-37
Tang, C. et al., Int. J Clin Exp. Pathol. 7 (2014): 4782-4794
Tatenhorst, L. et al., J Neuropathol. Exp. Neurol. 63 (2004): 210-222
Taverniti, V. et al., Nucleic Acids Res 43 (2015): 482-492
Taylor, M. et al., Breast Cancer Res 9 (2007): R46
Terabayashi, T. et al., PLoS. One. 7 (2012): e39714
Teufel, R. et al., Cell Mol Life Sci. 62 (2005): 1755-1762
Thakkar, J. P. et al., Cancer Epidemiol. Biomarkers Prev. 23 (2014): 1985-1996
Tian, Y. et al., Diagn. Pathol. 9 (2014): 42
Ting, L. et al., DNA Repair (Amst) 9 (2010): 1241-1248
Toda, M. et al., Meta Gene 2 (2014): 686-693
Toomey, P. G. et al., Cancer Control 20 (2013): 32-42
Torelli, G. F. et al., Haematologica 99 (2014): 1248-1254
Tran, E. et al., Science 344 (2014): 641-645
Tsujikawa, T. et al., Int. J Cancer 132 (2013): 2755-2766
Tumova, L. et al., Mol. Cancer Ther. 13 (2014): 812-822
Urata, Y. N. et al., Sci. Rep. 5 (2015): 13676
Ushiku, T. et al., Histopathology 61 (2012): 1043-1056
Utrera, R. et al., EMBO J 17 (1998): 5015-5025
Vainio, P. et al., Am. J Pathol. 178 (2011a): 525-536
Vainio, P. et al., Oncotarget. 2 (2011b): 1176-1190
Valque, H. et al., PLoS. One. 7 (2012): e46699
van de Klundert, M. A. et al., PLoS. One. 7 (2012): e48940
Van Ginkel, P. R. et al., Biochim. Biophys. Acta 1448 (1998): 290-297
van Muijen, G. N. et al., Recent Results Cancer Res 139 (1995): 105-122
Van, Seuningen, I et al., Biochem. J 348 Pt 3 (2000): 675-686
Vater, I. et al., Leukemia 29 (2015): 677-685
Ventela, S. et al., Oncotarget. 6 (2015): 144-158
Verreman, K. et al., Biochem. J 439 (2011): 469-477
Vici, P. et al., J Exp. Clin Cancer Res 33 (2014): 29
Von Hoff, D. D. et al., N. Engl. J Med. 369 (2013): 1691-1703
von Rundstedt, F. C. et al., Transl. Androl Urol. 4 (2015): 244-253
Wallrapp, C. et al., Ann. Oncol 10 Suppl 4 (1999): 64-68
Walsh, M. D. et al., Mod. Pathol. 26 (2013): 1642-1656
Walter, S. et al., J Immunol 171 (2003): 4974-4978
Walter, S. et al., Nat Med. 18 (2012): 1254-1261
Walton, E. L. et al., Biology. (Basel) 3 (2014): 578-605
Wan, W. et al., World J Surg. Oncol 12 (2014): 185
Wang, C. et al., Nucleic Acids Res 43 (2015a): 4893-4908
Wang, C. Q. et al., Oral Surg. Oral Med. Oral Pathol. Oral Radiol. 117 (2014a): 353-360
Wang, D. et al., Chin Med. Sci. J 14 (1999a): 107-111
Wang, G. et al., Tumour. Biol 36 (2015b): 1055-1065
Wang, G. H. et al., Oncol Lett. 5 (2013a): 544-548
Wang, H. et al., Carcinogenesis 30 (2009a): 1314-1319
Wang, J. et al., Ann. Surg. Oncol 22 (2015c): 685-692
Wang, J. et al., J Exp. Clin Cancer Res 34 (2015d): 13
Wang, J. W. et al., Oncogene 23 (2004): 4089-4097
Wang, L. et al., J Cutan. Pathol. 42 (2015e): 361-367
Wang, L. et al., Mol. Biol Rep. 38 (2011a): 229-236
Wang, L. et al., Diagn. Pathol. 8 (2013b): 190
Wang, N. et al., Arch. Gynecol. Obstet. 283 (2011b): 103-108
Wang, Q. et al., Cell 138 (2009b): 245-256
Wang, Q. et al., BMC. Cancer 11 (2011c): 271
Wang, Q. et al., Onco. Targets. Ther. 8 (20151): 1971-1977
Wang, Q. et al., PLoS. One. 8 (2013c): e61640
Wang, Q. et al., Mol. Cell Biochem. 405 (2015g): 97-104
Wang, S. et al., J Cell Sci. 120 (2007): 567-577
Wang, W. Z. et al., J Exp. Clin Cancer Res 29 (2010): 140
Wang, X. W. et al., Gut Liver 8 (2014b): 487-494
Wang, X. Z. et al., Oncogene 18 (1999b): 5718-5721
Wang, Y. et al., Cancer Cell 26 (2014c): 374-389
Wang, Y. P. et al., Ai. Zheng. 27 (2008): 243-248
Wang, Z. et al., J Cancer Res Clin Oncol 141 (2015h): 1353-1361
Wang, Z. et al., Oncotarget. (2016)
Wang, Z. et al., Glycobiology 22 (2012): 930-938
Watanabe, N. et al., J Biol Chem 278 (2003): 26102-26110
Watts, C. A. et al., Chem Biol 20 (2013): 1399-1410
Wells, J. et al., J Biol Chem 284 (2009): 29125-29135
Weng, Y. R. et al., Carcinogenesis 35 (2014): 1389-1398
Wheler, J. J. et al., BMC. Cancer 15 (2015): 442
Whitaker, H. C. et al., Oncogene 33 (2014): 5274-5287
Wierda, W. G. et al., Blood 118 (2011): 5126-5129
Wierinckx, A. et al., Endocr. Relat Cancer 14 (2007): 887-900
Wilhelm, S. M. et al., Cancer Res 64 (2004): 7099-7109
Willcox, B. E. et al., Protein Sci. 8 (1999): 2418-2423
Williams, G. L. et al., Cell Cycle 6 (2007): 1699-1704
Wilson, P. M. et al., Nat Rev. Clin Oncol 11 (2014): 282-298
Wilzen, A. et al., Int. J Oncol 34 (2009): 697-705
Wittig, B. et al., Hum. Gene Ther. 12 (2001): 267-278
Wlcek, K. et al., Cancer Biol Ther. 11 (2011): 801-811
Wong, R. P. et al., Pigment Cell Melanoma Res 25 (2012): 213-218
World Cancer Report, (2014)
World Health Organization, (2014)
Wu, J. et al., ACS Chem Biol 8 (2013): 2201-2208
Wu, Y. et al., Cancer Lett. 356 (2015): 646-655
Xie, B. et al., Pathol. Oncol Res 19 (2013): 611-617
Xie, C. et al., Biochem. Biophys. Res Commun. 445 (2014): 263-268
Xiong, D. et al., Carcinogenesis 33 (2012): 1797-1805
Xu, X. et al., Oncogene 26 (2007): 7371-7379
Xu, X. et al., J Biol Chem 289 (2014): 8881-8890
Xue, J. H. et al., Acta Pharmacol. Sin. 32 (2011): 1019-1024
Yamada, T. et al., Br. J Cancer 108 (2013): 2495-2504
Yamashita, J. et al., Acta Derm. Venereol. 92 (2012): 593-597
Yamazoe, S. et al., J Exp. Clin Cancer Res 29 (2010): 53
Yan-Chun, L. et al., Appl. Immunohistochem. Mol. Morphol. (2015)
Yan-Fang, T. et al., PLoS. One. 10 (2015): e0126566

Yang, J. J. et al., Haematologica 99 (2014a): e11-e13
Yang, L. et al., J Biol Chem 291 (2016): 3905-3917
Yang, L. et al., PLoS. One. 10 (2015a): e0133896
Yang, T. T. et al., Sci. Rep. 5 (2015b): 14096
Yang, Y. et al., Oncol Lett. 9 (2015c): 1833-1838
Yang, Y. et al., PLoS. One. 9 (2014b): e97578
Yang, Y. M. et al., Cancer Sci. 102 (2011): 1264-1271
Yao, Y. et al., Cell Physiol Biochem. 35 (2015): 983-996
Ye, B. G. et al., Oncotarget. (2016)
Yeh, I. et al., Nat. Commun. 6 (2015): 7174
Yeh, S. et al., Proc. Natl. Acad. Sci. U.S.A 97 (2000): 11256-11261
Yonezawa, S. et al., Pathol. Int. 49 (1999): 45-54
Yoshimaru, T. et al., Nat Commun. 4 (2013): 2443
Yoshimaru, T. et al., Sci. Rep. 4 (2014): 7355
Young, A. et al., BMC. Cancer 14 (2014): 808
Yu, C. J. et al., Int. J Cancer 69 (1996): 457-465
Yu, H. et al., Nat Chem Biol 11 (2015a): 847-854
Yu, T. et al., Cell Res 24 (2014): 1214-1230
Yu, X. et al., Tumour. Biol 36 (2015b): 967-972
Yuan, M. et al., Oncotarget. 5 (2014): 2820-2826
Zaganjor, E. et al., Proc. Natl. Acad. Sci. U.S.A 111 (2014): 10568-10573
Zamuner, F. T. et al., Mol. Cancer Ther. 14 (2015): 828-834
Zaremba, S. et al., Cancer Res. 57 (1997): 4570-4577
Zavala-Zendejas, V. E. et al., Cancer Invest 29 (2011): 1-11
Zekri, A. R. et al., BMC. Res Notes 1 (2008): 106
Zeng, B. et al., Curr. Cancer Drug Targets. 13 (2013a): 103-116
Zeng, S. et al., Eur. J Cancer 49 (2013b): 3752-3762
Zeng, X. et al., Ai. Zheng. 26 (2007): 1080-1084
Zeng, X. X. et al., Eur. Rev Med. Pharmacol. Sci. 19 (2015): 4353-4361
Zhan, W. et al., PLoS. One. 10 (2015): e0142596
Zhang, B. et al., J Huazhong. Univ Sci. Technolog. Med. Sci. 30 (2010a): 322-325
Zhang, G. et al., BMC. Cancer 14 (2014): 310
Zhang, J. et al., Theor. Biol Med. Model. 9 (2012a): 53
Zhang, Q. et al., Zhongguo Fei. Ai. Za Zhi. 13 (2010b): 612-616
Zhang, W. et al., Clin Cancer Res 7 (2001): 822s-829s
Zhang, W. et al., Biochem. J (2016)
Zhang, X. et al., EMBO J 30 (2011): 2177-2189
Zhang, X. et al., Med. Oncol 32 (2015): 148
Zhang, X. et al., Int. J Med. Sci. 10 (2013a): 1795-1804
Zhang, Y. et al., Gene 497 (2012b): 93-97
Zhang, Y. et al., J Ovarian. Res 6 (2013b): 55
Zhao, J. et al., Int. J Med. Sci. 11 (2014a): 1089-1097
Zhao, J. G. et al., FEBS Lett. 588 (2014b): 4536-4542
Zhen, T. et al., Oncotarget. 5 (2014): 3756-3769
Zheng, M. et al., Breast Cancer Res Treat. 148 (2014): 423-436
Zheng, M. Z. et al., J Transl. Med. 5 (2007): 36
Zhong, M. et al., Mol. Cancer Res 8 (2010): 1164-1172
Zhong, T. et al., Biomed. Pharmacother. 69 (2015): 317-325
Zhou, X. et al., J Cancer Res Clin Oncol 141 (2015): 961-969
Zhou, Y. et al., Front Biosci. (Landmark. Ed) 16 (2011): 1109-1131
Zhou, Z. et al., Gastroenterology 147 (2014): 1043-1054
Zhu, H. H. et al., Asian Pac. J Trop. Med. 7 (2014): 488-491
Zhu, J. et al., Int. J Clin Exp. Pathol. 8 (2015a): 9479-9486
Zhu, P. et al., Oncol Lett. 10 (2015b): 1487-1494
Zighelboim, I. et al., J Clin Oncol 27 (2009): 3091-3096
Zimmerman, K. M. et al., Mol. Cancer Res 11 (2013): 370-380
Zocchi, M. R. et al., Blood 119 (2012): 1479-1489
Zou, J. X. et al., Mol. Cancer Res 12 (2014): 539-549
Zou, T. T. et al., Oncogene 21 (2002): 4855-4862

SEQUENCE LISTING

```
Sequence total quantity: 419
SEQ ID NO: 1              moltype = AA  length = 9
FEATURE                   Location/Qualifiers
source                    1..9
                          mol_type = protein
                          organism = Homo sapiens
SEQUENCE: 1
PLWGKVFYL                                                                  9

SEQ ID NO: 2              moltype = AA  length = 9
FEATURE                   Location/Qualifiers
source                    1..9
                          mol_type = protein
                          organism = Homo sapiens
SEQUENCE: 2
ALYGKLLKL                                                                  9

SEQ ID NO: 3              moltype = AA  length = 9
FEATURE                   Location/Qualifiers
source                    1..9
                          mol_type = protein
                          organism = Homo sapiens
SEQUENCE: 3
TLLGKQVTL                                                                  9

SEQ ID NO: 4              moltype = AA  length = 9
FEATURE                   Location/Qualifiers
source                    1..9
                          mol_type = protein
                          organism = Homo sapiens
SEQUENCE: 4
ELAEIVFKV                                                                  9

SEQ ID NO: 5              moltype = AA  length = 9
```

-continued

```
FEATURE              Location/Qualifiers
source               1..9
                     mol_type = protein
                     organism = Homo sapiens
SEQUENCE: 5
SLFGQEVYC                                                                        9

SEQ ID NO: 6         moltype = AA  length = 9
FEATURE              Location/Qualifiers
source               1..9
                     mol_type = protein
                     organism = Homo sapiens
SEQUENCE: 6
FLDPAQRDL                                                                        9

SEQ ID NO: 7         moltype = AA  length = 9
FEATURE              Location/Qualifiers
source               1..9
                     mol_type = protein
                     organism = Homo sapiens
SEQUENCE: 7
AAAAKVPEV                                                                        9

SEQ ID NO: 8         moltype = AA  length = 9
FEATURE              Location/Qualifiers
source               1..9
                     mol_type = protein
                     organism = Homo sapiens
SEQUENCE: 8
KLGPFLLNA                                                                        9

SEQ ID NO: 9         moltype = AA  length = 9
FEATURE              Location/Qualifiers
source               1..9
                     mol_type = protein
                     organism = Homo sapiens
SEQUENCE: 9
FLGDYVENL                                                                        9

SEQ ID NO: 10        moltype = AA  length = 10
FEATURE              Location/Qualifiers
source               1..10
                     mol_type = protein
                     organism = Homo sapiens
SEQUENCE: 10
KTLDVFNIIL                                                                      10

SEQ ID NO: 11        moltype = AA  length = 10
FEATURE              Location/Qualifiers
source               1..10
                     mol_type = protein
                     organism = Homo sapiens
SEQUENCE: 11
GVLKVFLENV                                                                      10

SEQ ID NO: 12        moltype = AA  length = 10
FEATURE              Location/Qualifiers
source               1..10
                     mol_type = protein
                     organism = Homo sapiens
SEQUENCE: 12
GLIYEETRGV                                                                      10

SEQ ID NO: 13        moltype = AA  length = 9
FEATURE              Location/Qualifiers
source               1..9
                     mol_type = protein
                     organism = Homo sapiens
SEQUENCE: 13
VLRDNIQGI                                                                        9

SEQ ID NO: 14        moltype = AA  length = 11
FEATURE              Location/Qualifiers
source               1..11
                     mol_type = protein
                     organism = Homo sapiens
SEQUENCE: 14
LLDHLSFINK I                                                                    11
```

-continued

| | | |
|---|---|---|
| SEQ ID NO: 15<br>FEATURE<br>source | moltype = AA   length = 9<br>Location/Qualifiers<br>1..9<br>mol_type = protein<br>organism = Homo sapiens | |
| SEQUENCE: 15<br>ALGDYVHAC | | 9 |
| SEQ ID NO: 16<br>FEATURE<br>source | moltype = AA   length = 9<br>Location/Qualifiers<br>1..9<br>mol_type = protein<br>organism = Homo sapiens | |
| SEQUENCE: 16<br>HLYNNEEQV | | 9 |
| SEQ ID NO: 17<br>FEATURE<br>source | moltype = AA   length = 9<br>Location/Qualifiers<br>1..9<br>mol_type = protein<br>organism = Homo sapiens | |
| SEQUENCE: 17<br>ILHEHHIFL | | 9 |
| SEQ ID NO: 18<br>FEATURE<br>source | moltype = AA   length = 11<br>Location/Qualifiers<br>1..11<br>mol_type = protein<br>organism = Homo sapiens | |
| SEQUENCE: 18<br>YVLNEEDLQK V | | 11 |
| SEQ ID NO: 19<br>FEATURE<br>source | moltype = AA   length = 9<br>Location/Qualifiers<br>1..9<br>mol_type = protein<br>organism = Homo sapiens | |
| SEQUENCE: 19<br>TLLPTVLTL | | 9 |
| SEQ ID NO: 20<br>FEATURE<br>source | moltype = AA   length = 9<br>Location/Qualifiers<br>1..9<br>mol_type = protein<br>organism = Homo sapiens | |
| SEQUENCE: 20<br>ALDGHLYAI | | 9 |
| SEQ ID NO: 21<br>FEATURE<br>source | moltype = AA   length = 9<br>Location/Qualifiers<br>1..9<br>mol_type = protein<br>organism = Homo sapiens | |
| SEQUENCE: 21<br>SLYHRVLLY | | 9 |
| SEQ ID NO: 22<br>FEATURE<br>source | moltype = AA   length = 9<br>Location/Qualifiers<br>1..9<br>mol_type = protein<br>organism = Homo sapiens | |
| SEQUENCE: 22<br>MLSDLTLQL | | 9 |
| SEQ ID NO: 23<br>FEATURE<br>source | moltype = AA   length = 9<br>Location/Qualifiers<br>1..9<br>mol_type = protein<br>organism = Homo sapiens | |
| SEQUENCE: 23<br>AQTVVVIKA | | 9 |
| SEQ ID NO: 24<br>FEATURE<br>source | moltype = AA   length = 10<br>Location/Qualifiers<br>1..10<br>mol_type = protein<br>organism = Homo sapiens | |
| SEQUENCE: 24<br>FLWNGEDSAL | | 10 |

```
SEQ ID NO: 25            moltype = AA  length = 9
FEATURE                  Location/Qualifiers
source                   1..9
                         mol_type = protein
                         organism = Homo sapiens
SEQUENCE: 25
IQADDFRTL                                                                    9

SEQ ID NO: 26            moltype = AA  length = 9
FEATURE                  Location/Qualifiers
source                   1..9
                         mol_type = protein
                         organism = Homo sapiens
SEQUENCE: 26
KVDGVVIQL                                                                    9

SEQ ID NO: 27            moltype = AA  length = 9
FEATURE                  Location/Qualifiers
source                   1..9
                         mol_type = protein
                         organism = Homo sapiens
SEQUENCE: 27
KVFGDLDQV                                                                    9

SEQ ID NO: 28            moltype = AA  length = 10
FEATURE                  Location/Qualifiers
source                   1..10
                         mol_type = protein
                         organism = Homo sapiens
SEQUENCE: 28
TLYSMDLMKV                                                                  10

SEQ ID NO: 29            moltype = AA  length = 9
FEATURE                  Location/Qualifiers
source                   1..9
                         mol_type = protein
                         organism = Homo sapiens
SEQUENCE: 29
TLCNKTFTA                                                                    9

SEQ ID NO: 30            moltype = AA  length = 9
FEATURE                  Location/Qualifiers
source                   1..9
                         mol_type = protein
                         organism = Homo sapiens
SEQUENCE: 30
TVIDECTRI                                                                    9

SEQ ID NO: 31            moltype = AA  length = 12
FEATURE                  Location/Qualifiers
source                   1..12
                         mol_type = protein
                         organism = Homo sapiens
SEQUENCE: 31
ALSDETKNNW EV                                                               12

SEQ ID NO: 32            moltype = AA  length = 10
FEATURE                  Location/Qualifiers
source                   1..10
                         mol_type = protein
                         organism = Homo sapiens
SEQUENCE: 32
ILADEAFFSV                                                                  10

SEQ ID NO: 33            moltype = AA  length = 14
FEATURE                  Location/Qualifiers
source                   1..14
                         mol_type = protein
                         organism = Homo sapiens
SEQUENCE: 33
LLLPLLPPLS PSLG                                                             14

SEQ ID NO: 34            moltype = AA  length = 12
FEATURE                  Location/Qualifiers
source                   1..12
                         mol_type = protein
                         organism = Homo sapiens
SEQUENCE: 34
```

```
LLPKKTESHH KT                                                                           12

SEQ ID NO: 35          moltype = AA  length = 10
FEATURE                Location/Qualifiers
source                 1..10
                       mol_type = protein
                       organism = Homo sapiens SEQUENCE: 35
YVLPKLYVKL                                                                              10

SEQ ID NO: 36          moltype = AA  length = 9
FEATURE                Location/Qualifiers
source                 1..9
                       mol_type = protein
                       organism = Homo sapiens SEQUENCE: 36
KLYGIEIEV                                                                               9

SEQ ID NO: 37          moltype = AA  length = 13
FEATURE                Location/Qualifiers
source                 1..13
                       mol_type = protein
                       organism = Homo sapiens SEQUENCE: 37
ALINDILGEL VKL                                                                          13

SEQ ID NO: 38          moltype = AA  length = 9
FEATURE                Location/Qualifiers
source                 1..9
                       mol_type = protein
                       organism = Homo sapiens SEQUENCE: 38
KMQEDLVTL                                                                               9

SEQ ID NO: 39          moltype = AA  length = 9
FEATURE                Location/Qualifiers
source                 1..9
                       mol_type = protein
                       organism = Homo sapiens SEQUENCE: 39
ALMAVVSGL                                                                               9

SEQ ID NO: 40          moltype = AA  length = 11
FEATURE                Location/Qualifiers
source                 1..11
                       mol_type = protein
                       organism = Homo sapiens SEQUENCE: 40
SLLALPQDLQ A                                                                            11

SEQ ID NO: 41          moltype = AA  length = 9
FEATURE                Location/Qualifiers
source                 1..9
                       mol_type = protein
                       organism = Homo sapiens SEQUENCE: 41
FVLPLVVTL                                                                               9

SEQ ID NO: 42          moltype = AA  length = 9
FEATURE                Location/Qualifiers
source                 1..9
                       mol_type = protein
                       organism = Homo sapiens SEQUENCE: 42
VLSPFILTL                                                                               9

SEQ ID NO: 43          moltype = AA  length = 9
FEATURE                Location/Qualifiers
source                 1..9
                       mol_type = protein
                       organism = Homo sapiens SEQUENCE: 43
LLWAGPVTA                                                                               9

SEQ ID NO: 44          moltype = AA  length = 9
FEATURE                Location/Qualifiers
source                 1..9
                       mol_type = protein
                       organism = Homo sapiens
```

| | | |
|---|---|---|
| SEQUENCE: 44<br>GLLWQIIKV | | 9 |
| SEQ ID NO: 45<br>FEATURE<br>source | moltype = AA  length = 9<br>Location/Qualifiers<br>1..9<br>mol_type = protein<br>organism = Homo sapiens | |
| SEQUENCE: 45<br>VLGPTPELV | | 9 |
| SEQ ID NO: 46<br>FEATURE<br>source | moltype = AA  length = 10<br>Location/Qualifiers<br>1..10<br>mol_type = protein<br>organism = Homo sapiens | |
| SEQUENCE: 46<br>SLAKHGIVAL | | 10 |
| SEQ ID NO: 47<br>FEATURE<br>source | moltype = AA  length = 9<br>Location/Qualifiers<br>1..9<br>mol_type = protein<br>organism = Homo sapiens | |
| SEQUENCE: 47<br>GLYQAQVNL | | 9 |
| SEQ ID NO: 48<br>FEATURE<br>source | moltype = AA  length = 9<br>Location/Qualifiers<br>1..9<br>mol_type = protein<br>organism = Homo sapiens | |
| SEQUENCE: 48<br>TLDHKPVTV | | 9 |
| SEQ ID NO: 49<br>FEATURE<br>source | moltype = AA  length = 9<br>Location/Qualifiers<br>1..9<br>mol_type = protein<br>organism = Homo sapiens | |
| SEQUENCE: 49<br>LLDESKLTL | | 9 |
| SEQ ID NO: 50<br>FEATURE<br>source | moltype = AA  length = 9<br>Location/Qualifiers<br>1..9<br>mol_type = protein<br>organism = Homo sapiens | |
| SEQUENCE: 50<br>EYALLYHTL | | 9 |
| SEQ ID NO: 51<br>FEATURE<br>source | moltype = AA  length = 9<br>Location/Qualifiers<br>1..9<br>mol_type = protein<br>organism = Homo sapiens | |
| SEQUENCE: 51<br>LLLDGDFTL | | 9 |
| SEQ ID NO: 52<br>FEATURE<br>source | moltype = AA  length = 9<br>Location/Qualifiers<br>1..9<br>mol_type = protein<br>organism = Homo sapiens | |
| SEQUENCE: 52<br>ELLSSIFFL | | 9 |
| SEQ ID NO: 53<br>FEATURE<br>source | moltype = AA  length = 9<br>Location/Qualifiers<br>1..9<br>mol_type = protein<br>organism = Homo sapiens | |
| SEQUENCE: 53<br>SLLSHVIVA | | 9 |
| SEQ ID NO: 54<br>FEATURE<br>source | moltype = AA  length = 10<br>Location/Qualifiers<br>1..10<br>mol_type = protein | |

```
                                        organism = Homo sapiens
SEQUENCE: 54
FINPKGNWLL                                                                              10

SEQ ID NO: 55           moltype = AA   length = 9
FEATURE                 Location/Qualifiers
source                  1..9
                        mol_type = protein
                        organism = Homo sapiens
SEQUENCE: 55
IASAIVNEL                                                                               9

SEQ ID NO: 56           moltype = AA   length = 9
FEATURE                 Location/Qualifiers
source                  1..9
                        mol_type = protein
                        organism = Homo sapiens
SEQUENCE: 56
KILDLTRVL                                                                               9

SEQ ID NO: 57           moltype = AA   length = 9
FEATURE                 Location/Qualifiers
source                  1..9
                        mol_type = protein
                        organism = Homo sapiens
SEQUENCE: 57
VLISSTVRL                                                                               9

SEQ ID NO: 58           moltype = AA   length = 9
FEATURE                 Location/Qualifiers
source                  1..9
                        mol_type = protein
                        organism = Homo sapiens
SEQUENCE: 58
ALDDSLTSL                                                                               9

SEQ ID NO: 59           moltype = AA   length = 9
FEATURE                 Location/Qualifiers
source                  1..9
                        mol_type = protein
                        organism = Homo sapiens
SEQUENCE: 59
ALTKILAEL                                                                               9

SEQ ID NO: 60           moltype = AA   length = 9
FEATURE                 Location/Qualifiers
source                  1..9
                        mol_type = protein
                        organism = Homo sapiens
SEQUENCE: 60
FLIDTSASM                                                                               9

SEQ ID NO: 61           moltype = AA   length = 9
FEATURE                 Location/Qualifiers
source                  1..9
                        mol_type = protein
                        organism = Homo sapiens
SEQUENCE: 61
HLPDFVKQL                                                                               9

SEQ ID NO: 62           moltype = AA   length = 9
FEATURE                 Location/Qualifiers
source                  1..9
                        mol_type = protein
                        organism = Homo sapiens
SEQUENCE: 62
SLFNQEVQI                                                                               9

SEQ ID NO: 63           moltype = AA   length = 10
FEATURE                 Location/Qualifiers
source                  1..10
                        mol_type = protein
                        organism = Homo sapiens
SEQUENCE: 63
TLSSERDFAL                                                                              10

SEQ ID NO: 64           moltype = AA   length = 9
FEATURE                 Location/Qualifiers
source                  1..9
```

-continued

```
                        mol_type = protein
                        organism = Homo sapiens
SEQUENCE: 64
GLSSSSYEL                                                               9

SEQ ID NO: 65           moltype = AA   length = 9
FEATURE                 Location/Qualifiers
source                  1..9
                        mol_type = protein
                        organism = Homo sapiens
SEQUENCE: 65
KLDGICWQV                                                               9

SEQ ID NO: 66           moltype = AA   length = 9
FEATURE                 Location/Qualifiers
source                  1..9
                        mol_type = protein
                        organism = Homo sapiens
SEQUENCE: 66
FITDFYTTV                                                               9

SEQ ID NO: 67           moltype = AA   length = 9
FEATURE                 Location/Qualifiers
source                  1..9
                        mol_type = protein
                        organism = Homo sapiens
SEQUENCE: 67
GVIETVTSL                                                               9

SEQ ID NO: 68           moltype = AA   length = 9
FEATURE                 Location/Qualifiers
source                  1..9
                        mol_type = protein
                        organism = Homo sapiens
SEQUENCE: 68
ALYGFFFKI                                                               9

SEQ ID NO: 69           moltype = AA   length = 10
FEATURE                 Location/Qualifiers
source                  1..10
                        mol_type = protein
                        organism = Homo sapiens
SEQUENCE: 69
GIYDGILHSI                                                              10

SEQ ID NO: 70           moltype = AA   length = 9
FEATURE                 Location/Qualifiers
source                  1..9
                        mol_type = protein
                        organism = Homo sapiens
SEQUENCE: 70
GLFSQHFNL                                                               9

SEQ ID NO: 71           moltype = AA   length = 9
FEATURE                 Location/Qualifiers
source                  1..9
                        mol_type = protein
                        organism = Homo sapiens
SEQUENCE: 71
GLITVDIAL                                                               9

SEQ ID NO: 72           moltype = AA   length = 9
FEATURE                 Location/Qualifiers
source                  1..9
                        mol_type = protein
                        organism = Homo sapiens
SEQUENCE: 72
GMIGFQVLL                                                               9

SEQ ID NO: 73           moltype = AA   length = 9
FEATURE                 Location/Qualifiers
source                  1..9
                        mol_type = protein
                        organism = Homo sapiens
SEQUENCE: 73
GVPDTIATL                                                               9

SEQ ID NO: 74           moltype = AA   length = 9
FEATURE                 Location/Qualifiers
```

```
source                      1..9
                            mol_type = protein
                            organism = Homo sapiens
SEQUENCE: 74
ILDETLENV                                                                   9

SEQ ID NO: 75               moltype = AA   length = 9
FEATURE                     Location/Qualifiers
source                      1..9
                            mol_type = protein
                            organism = Homo sapiens
SEQUENCE: 75
ILDNVKNLL                                                                   9

SEQ ID NO: 76               moltype = AA   length = 12
FEATURE                     Location/Qualifiers
source                      1..12
                            mol_type = protein
                            organism = Homo sapiens
SEQUENCE: 76
ILLDESNFNH FL                                                              12

SEQ ID NO: 77               moltype = AA   length = 9
FEATURE                     Location/Qualifiers
source                      1..9
                            mol_type = protein
                            organism = Homo sapiens
SEQUENCE: 77
IVLSTIASV                                                                   9

SEQ ID NO: 78               moltype = AA   length = 9
FEATURE                     Location/Qualifiers
source                      1..9
                            mol_type = protein
                            organism = Homo sapiens
SEQUENCE: 78
LLWGHPRVA                                                                   9

SEQ ID NO: 79               moltype = AA   length = 9
FEATURE                     Location/Qualifiers
source                      1..9
                            mol_type = protein
                            organism = Homo sapiens
SEQUENCE: 79
SLVPLQILL                                                                   9

SEQ ID NO: 80               moltype = AA   length = 9
FEATURE                     Location/Qualifiers
source                      1..9
                            mol_type = protein
                            organism = Homo sapiens
SEQUENCE: 80
TLDEYLTYL                                                                   9

SEQ ID NO: 81               moltype = AA   length = 9
FEATURE                     Location/Qualifiers
source                      1..9
                            mol_type = protein
                            organism = Homo sapiens
SEQUENCE: 81
VLFLGKLLV                                                                   9

SEQ ID NO: 82               moltype = AA   length = 8
FEATURE                     Location/Qualifiers
source                      1..8
                            mol_type = protein
                            organism = Homo sapiens
SEQUENCE: 82
VLLRVLIL                                                                    8

SEQ ID NO: 83               moltype = AA   length = 9
FEATURE                     Location/Qualifiers
source                      1..9
                            mol_type = protein
                            organism = Homo sapiens
SEQUENCE: 83
ELLEYLPQL                                                                   9

SEQ ID NO: 84               moltype = AA   length = 9
```

```
FEATURE              Location/Qualifiers
source               1..9
                     mol_type = protein
                     organism = Homo sapiens
SEQUENCE: 84
FLEEEITRV                                                                   9

SEQ ID NO: 85        moltype = AA  length = 10
FEATURE              Location/Qualifiers
source               1..10
                     mol_type = protein
                     organism = Homo sapiens
SEQUENCE: 85
STLDGSLHAV                                                                 10

SEQ ID NO: 86        moltype = AA  length = 9
FEATURE              Location/Qualifiers
source               1..9
                     mol_type = protein
                     organism = Homo sapiens
SEQUENCE: 86
LLVTSLVVV                                                                   9

SEQ ID NO: 87        moltype = AA  length = 10
FEATURE              Location/Qualifiers
source               1..10
                     mol_type = protein
                     organism = Homo sapiens
SEQUENCE: 87
YLTEVFLHVV                                                                 10

SEQ ID NO: 88        moltype = AA  length = 11
FEATURE              Location/Qualifiers
source               1..11
                     mol_type = protein
                     organism = Homo sapiens
SEQUENCE: 88
ILLNTEDLAS L                                                               11

SEQ ID NO: 89        moltype = AA  length = 9
FEATURE              Location/Qualifiers
source               1..9
                     mol_type = protein
                     organism = Homo sapiens
SEQUENCE: 89
YLVAHNLLL                                                                   9

SEQ ID NO: 90        moltype = AA  length = 11
FEATURE              Location/Qualifiers
source               1..11
                     mol_type = protein
                     organism = Homo sapiens
SEQUENCE: 90
GAVAEEVLSS I                                                               11

SEQ ID NO: 91        moltype = AA  length = 10
FEATURE              Location/Qualifiers
source               1..10
                     mol_type = protein
                     organism = Homo sapiens
SEQUENCE: 91
SSLEPQIQPV                                                                 10

SEQ ID NO: 92        moltype = AA  length = 10
FEATURE              Location/Qualifiers
source               1..10
                     mol_type = protein
                     organism = Homo sapiens
SEQUENCE: 92
LLRGPPVARA                                                                 10

SEQ ID NO: 93        moltype = AA  length = 9
FEATURE              Location/Qualifiers
source               1..9
                     mol_type = protein
                     organism = Homo sapiens
SEQUENCE: 93
SLLTQPIFL                                                                   9
```

```
SEQ ID NO: 94            moltype = AA   length = 18
FEATURE                  Location/Qualifiers
source                   1..18
                         mol_type = protein
                         organism = Homo sapiens
SEQUENCE: 94
LKMENKEVLP QLVDAVTS                                                        18

SEQ ID NO: 95            moltype = AA   length = 21
FEATURE                  Location/Qualifiers
source                   1..21
                         mol_type = protein
                         organism = Homo sapiens
SEQUENCE: 95
GLYLPLFKPS VSTSKAIGGG P                                                    21

SEQ ID NO: 96            moltype = AA   length = 9
FEATURE                  Location/Qualifiers
source                   1..9
                         mol_type = protein
                         organism = Homo sapiens
SEQUENCE: 96
YYTQYSQTI                                                                   9

SEQ ID NO: 97            moltype = AA   length = 9
FEATURE                  Location/Qualifiers
source                   1..9
                         mol_type = protein
                         organism = Homo sapiens
SEQUENCE: 97
TYTFLKETF                                                                   9

SEQ ID NO: 98            moltype = AA   length = 10
FEATURE                  Location/Qualifiers
source                   1..10
                         mol_type = protein
                         organism = Homo sapiens
SEQUENCE: 98
VFPRLHNVLF                                                                 10

SEQ ID NO: 99            moltype = AA   length = 9
FEATURE                  Location/Qualifiers
source                   1..9
                         mol_type = protein
                         organism = Homo sapiens
SEQUENCE: 99
QYILAVPVL                                                                   9

SEQ ID NO: 100           moltype = AA   length = 13
FEATURE                  Location/Qualifiers
source                   1..13
                         mol_type = protein
                         organism = Homo sapiens
SEQUENCE: 100
VYIESRIGTS TSF                                                             13

SEQ ID NO: 101           moltype = AA   length = 10
FEATURE                  Location/Qualifiers
source                   1..10
                         mol_type = protein
                         organism = Homo sapiens
SEQUENCE: 101
IYIPVLPPHL                                                                 10

SEQ ID NO: 102           moltype = AA   length = 9
FEATURE                  Location/Qualifiers
source                   1..9
                         mol_type = protein
                         organism = Homo sapiens
SEQUENCE: 102
VYPFENFEF                                                                   9

SEQ ID NO: 103           moltype = AA   length = 11
FEATURE                  Location/Qualifiers
source                   1..11
                         mol_type = protein
                         organism = Homo sapiens
SEQUENCE: 103
NYIPVKNGKQ F                                                               11
```

```
SEQ ID NO: 104         moltype = AA   length = 9
FEATURE                Location/Qualifiers
source                 1..9
                       mol_type = protein
                       organism = Homo sapiens
SEQUENCE: 104
SYLTWHQQI                                                                  9

SEQ ID NO: 105         moltype = AA   length = 10
FEATURE                Location/Qualifiers
source                 1..10
                       mol_type = protein
                       organism = Homo sapiens
SEQUENCE: 105
IYNETITDLL                                                                10

SEQ ID NO: 106         moltype = AA   length = 10
FEATURE                Location/Qualifiers
source                 1..10
                       mol_type = protein
                       organism = Homo sapiens
SEQUENCE: 106
IYNETVRDLL                                                                10

SEQ ID NO: 107         moltype = AA   length = 9
FEATURE                Location/Qualifiers
source                 1..9
                       mol_type = protein
                       organism = Homo sapiens
SEQUENCE: 107
KYFPYLVVI                                                                  9

SEQ ID NO: 108         moltype = AA   length = 9
FEATURE                Location/Qualifiers
source                 1..9
                       mol_type = protein
                       organism = Homo sapiens
SEQUENCE: 108
PYLVVIHTL                                                                  9

SEQ ID NO: 109         moltype = AA   length = 9
FEATURE                Location/Qualifiers
source                 1..9
                       mol_type = protein
                       organism = Homo sapiens
SEQUENCE: 109
LFITGGQFF                                                                  9

SEQ ID NO: 110         moltype = AA   length = 9
FEATURE                Location/Qualifiers
source                 1..9
                       mol_type = protein
                       organism = Homo sapiens
SEQUENCE: 110
SYPKIIEEF                                                                  9

SEQ ID NO: 111         moltype = AA   length = 9
FEATURE                Location/Qualifiers
source                 1..9
                       mol_type = protein
                       organism = Homo sapiens
SEQUENCE: 111
VYVQILQKL                                                                  9

SEQ ID NO: 112         moltype = AA   length = 9
FEATURE                Location/Qualifiers
source                 1..9
                       mol_type = protein
                       organism = Homo sapiens
SEQUENCE: 112
IYNFVESKL                                                                  9

SEQ ID NO: 113         moltype = AA   length = 9
FEATURE                Location/Qualifiers
source                 1..9
                       mol_type = protein
                       organism = Homo sapiens
SEQUENCE: 113
```

IYSFHTLSF                                                                    9

SEQ ID NO: 114          moltype = AA  length = 9
FEATURE                 Location/Qualifiers
source                  1..9
                        mol_type = protein
                        organism = Homo sapiens SEQUENCE: 114
QYLDGTWSL                                                                    9

SEQ ID NO: 115          moltype = AA  length = 9
FEATURE                 Location/Qualifiers
source                  1..9
                        mol_type = protein
                        organism = Homo sapiens SEQUENCE: 115
RYLNKSFVL                                                                    9

SEQ ID NO: 116          moltype = AA  length = 9
FEATURE                 Location/Qualifiers
source                  1..9
                        mol_type = protein
                        organism = Homo sapiens SEQUENCE: 116
AYVIAVHLF                                                                    9

SEQ ID NO: 117          moltype = AA  length = 9
FEATURE                 Location/Qualifiers
source                  1..9
                        mol_type = protein
                        organism = Homo sapiens SEQUENCE: 117
IYLSDLTYI                                                                    9

SEQ ID NO: 118          moltype = AA  length = 9
FEATURE                 Location/Qualifiers
source                  1..9
                        mol_type = protein
                        organism = Homo sapiens SEQUENCE: 118
KYLNSVQYI                                                                    9

SEQ ID NO: 119          moltype = AA  length = 9
FEATURE                 Location/Qualifiers
source                  1..9
                        mol_type = protein
                        organism = Homo sapiens SEQUENCE: 119
VYRVYVTTF                                                                    9

SEQ ID NO: 120          moltype = AA  length = 9
FEATURE                 Location/Qualifiers
source                  1..9
                        mol_type = protein
                        organism = Homo sapiens SEQUENCE: 120
GYIEHFSLW                                                                    9

SEQ ID NO: 121          moltype = AA  length = 11
FEATURE                 Location/Qualifiers
source                  1..11
                        mol_type = protein
                        organism = Homo sapiens SEQUENCE: 121
RYGLPAAWST F                                                                11

SEQ ID NO: 122          moltype = AA  length = 9
FEATURE                 Location/Qualifiers
source                  1..9
                        mol_type = protein
                        organism = Homo sapiens SEQUENCE: 122
EYQARIPEF                                                                    9

SEQ ID NO: 123          moltype = AA  length = 9
FEATURE                 Location/Qualifiers
source                  1..9
                        mol_type = protein
                        organism = Homo sapiens

```
SEQUENCE: 123
VYTPVLEHL                                                                          9

SEQ ID NO: 124          moltype = AA  length = 9
FEATURE                 Location/Qualifiers
source                  1..9
                        mol_type = protein
                        organism = Homo sapiens
SEQUENCE: 124
TYKDYVDLF                                                                          9

SEQ ID NO: 125          moltype = AA  length = 11
FEATURE                 Location/Qualifiers
source                  1..11
                        mol_type = protein
                        organism = Homo sapiens
SEQUENCE: 125
VFSRDFGLLV F                                                                      11

SEQ ID NO: 126          moltype = AA  length = 13
FEATURE                 Location/Qualifiers
source                  1..13
                        mol_type = protein
                        organism = Homo sapiens
SEQUENCE: 126
PYDPALGSPS RLF                                                                    13

SEQ ID NO: 127          moltype = AA  length = 9
FEATURE                 Location/Qualifiers
source                  1..9
                        mol_type = protein
                        organism = Homo sapiens
SEQUENCE: 127
QYFTGNPLF                                                                          9

SEQ ID NO: 128          moltype = AA  length = 9
FEATURE                 Location/Qualifiers
source                  1..9
                        mol_type = protein
                        organism = Homo sapiens
SEQUENCE: 128
VYPFDWQYI                                                                          9

SEQ ID NO: 129          moltype = AA  length = 9
FEATURE                 Location/Qualifiers
source                  1..9
                        mol_type = protein
                        organism = Homo sapiens
SEQUENCE: 129
KYIDYLMTW                                                                          9

SEQ ID NO: 130          moltype = AA  length = 10
FEATURE                 Location/Qualifiers
source                  1..10
                        mol_type = protein
                        organism = Homo sapiens
SEQUENCE: 130
VYAHIYHQHF                                                                        10

SEQ ID NO: 131          moltype = AA  length = 11
FEATURE                 Location/Qualifiers
source                  1..11
                        mol_type = protein
                        organism = Homo sapiens
SEQUENCE: 131
EYLDRIGQLF F                                                                      11

SEQ ID NO: 132          moltype = AA  length = 9
FEATURE                 Location/Qualifiers
source                  1..9
                        mol_type = protein
                        organism = Homo sapiens
SEQUENCE: 132
RYPALFPVL                                                                          9

SEQ ID NO: 133          moltype = AA  length = 10
FEATURE                 Location/Qualifiers
source                  1..10
                        mol_type = protein
```

```
SEQUENCE: 133
KYLEDMKTYF                                                              10

SEQ ID NO: 134          moltype = AA  length = 9
FEATURE                 Location/Qualifiers
source                  1..9
                        mol_type = protein
                        organism = Homo sapiens
SEQUENCE: 134
AYIPTPIYF                                                               9

SEQ ID NO: 135          moltype = AA  length = 9
FEATURE                 Location/Qualifiers
source                  1..9
                        mol_type = protein
                        organism = Homo sapiens
SEQUENCE: 135
VYEAMVPLF                                                               9

SEQ ID NO: 136          moltype = AA  length = 10
FEATURE                 Location/Qualifiers
source                  1..10
                        mol_type = protein
                        organism = Homo sapiens
SEQUENCE: 136
IYPEWPVVFF                                                              10

SEQ ID NO: 137          moltype = AA  length = 9
FEATURE                 Location/Qualifiers
source                  1..9
                        mol_type = protein
                        organism = Homo sapiens
SEQUENCE: 137
EYLHNCSYF                                                               9

SEQ ID NO: 138          moltype = AA  length = 9
FEATURE                 Location/Qualifiers
source                  1..9
                        mol_type = protein
                        organism = Homo sapiens
SEQUENCE: 138
VYNAVSTSF                                                               9

SEQ ID NO: 139          moltype = AA  length = 9
FEATURE                 Location/Qualifiers
source                  1..9
                        mol_type = protein
                        organism = Homo sapiens
SEQUENCE: 139
IFGIFPNQF                                                               9

SEQ ID NO: 140          moltype = AA  length = 9
FEATURE                 Location/Qualifiers
source                  1..9
                        mol_type = protein
                        organism = Homo sapiens
SEQUENCE: 140
RYLINSYDF                                                               9

SEQ ID NO: 141          moltype = AA  length = 10
FEATURE                 Location/Qualifiers
source                  1..10
                        mol_type = protein
                        organism = Homo sapiens
SEQUENCE: 141
SYNGHLTIWF                                                              10

SEQ ID NO: 142          moltype = AA  length = 9
FEATURE                 Location/Qualifiers
source                  1..9
                        mol_type = protein
                        organism = Homo sapiens
SEQUENCE: 142
VYVDDIYVI                                                               9

SEQ ID NO: 143          moltype = AA  length = 9
FEATURE                 Location/Qualifiers
source                  1..9
```

```
                                mol_type = protein
                                organism = Homo sapiens
SEQUENCE: 143
KYIFQLNEI                                                                    9

SEQ ID NO: 144                  moltype = AA  length = 10
FEATURE                         Location/Qualifiers
source                          1..10
                                mol_type = protein
                                organism = Homo sapiens
SEQUENCE: 144
VFASLPGFLF                                                                  10

SEQ ID NO: 145                  moltype = AA  length = 9
FEATURE                         Location/Qualifiers
source                          1..9
                                mol_type = protein
                                organism = Homo sapiens
SEQUENCE: 145
VYALKVRTI                                                                    9

SEQ ID NO: 146                  moltype = AA  length = 9
FEATURE                         Location/Qualifiers
source                          1..9
                                mol_type = protein
                                organism = Homo sapiens
SEQUENCE: 146
NYYERIHAL                                                                    9

SEQ ID NO: 147                  moltype = AA  length = 9
FEATURE                         Location/Qualifiers
source                          1..9
                                mol_type = protein
                                organism = Homo sapiens
SEQUENCE: 147
LYLAFPLAF                                                                    9

SEQ ID NO: 148                  moltype = AA  length = 9
FEATURE                         Location/Qualifiers
source                          1..9
                                mol_type = protein
                                organism = Homo sapiens
SEQUENCE: 148
SYGTVSQIF                                                                    9

SEQ ID NO: 149                  moltype = AA  length = 8
FEATURE                         Location/Qualifiers
source                          1..8
                                mol_type = protein
                                organism = Homo sapiens
SEQUENCE: 149
SYGTVSQI                                                                     8

SEQ ID NO: 150                  moltype = AA  length = 10
FEATURE                         Location/Qualifiers
source                          1..10
                                mol_type = protein
                                organism = Homo sapiens
SEQUENCE: 150
IYITRQFVQF                                                                  10

SEQ ID NO: 151                  moltype = AA  length = 9
FEATURE                         Location/Qualifiers
source                          1..9
                                mol_type = protein
                                organism = Homo sapiens
SEQUENCE: 151
AYISGLDVF                                                                    9

SEQ ID NO: 152                  moltype = AA  length = 12
FEATURE                         Location/Qualifiers
source                          1..12
                                mol_type = protein
                                organism = Homo sapiens
SEQUENCE: 152
KFFDDLGDEL LF                                                               12

SEQ ID NO: 153                  moltype = AA  length = 13
FEATURE                         Location/Qualifiers
```

```
source                        1..13
                              mol_type = protein
                              organism = Homo sapiens
SEQUENCE: 153
VYVPFGGKSM ITF                                                              13

SEQ ID NO: 154                moltype = AA  length = 9
FEATURE                       Location/Qualifiers
source                        1..9
                              mol_type = protein
                              organism = Homo sapiens
SEQUENCE: 154
VYGVPTPHF                                                                    9

SEQ ID NO: 155                moltype = AA  length = 9
FEATURE                       Location/Qualifiers
source                        1..9
                              mol_type = protein
                              organism = Homo sapiens
SEQUENCE: 155
IYKWITDNF                                                                    9

SEQ ID NO: 156                moltype = AA  length = 10
FEATURE                       Location/Qualifiers
source                        1..10
                              mol_type = protein
                              organism = Homo sapiens
SEQUENCE: 156
YYMELTKLLL                                                                  10

SEQ ID NO: 157                moltype = AA  length = 11
FEATURE                       Location/Qualifiers
source                        1..11
                              mol_type = protein
                              organism = Homo sapiens
SEQUENCE: 157
DYIPASGFAL F                                                                11

SEQ ID NO: 158                moltype = AA  length = 12
FEATURE                       Location/Qualifiers
source                        1..12
                              mol_type = protein
                              organism = Homo sapiens
SEQUENCE: 158
IYEETRGVLK VF                                                               12

SEQ ID NO: 159                moltype = AA  length = 9
FEATURE                       Location/Qualifiers
source                        1..9
                              mol_type = protein
                              organism = Homo sapiens
SEQUENCE: 159
IYEETRGVL                                                                    9

SEQ ID NO: 160                moltype = AA  length = 9
FEATURE                       Location/Qualifiers
source                        1..9
                              mol_type = protein
                              organism = Homo sapiens
SEQUENCE: 160
RYGDGGSSF                                                                    9

SEQ ID NO: 161                moltype = AA  length = 9
FEATURE                       Location/Qualifiers
source                        1..9
                              mol_type = protein
                              organism = Homo sapiens
SEQUENCE: 161
KYPDIVQQF                                                                    9

SEQ ID NO: 162                moltype = AA  length = 9
FEATURE                       Location/Qualifiers
source                        1..9
                              mol_type = protein
                              organism = Homo sapiens
SEQUENCE: 162
KYTSYILAF                                                                    9

SEQ ID NO: 163                moltype = AA  length = 10
```

| | | |
|---|---|---|
| FEATURE | Location/Qualifiers | |
| source | 1..10 | |
| | mol_type = protein | |
| | organism = Homo sapiens | |
| SEQUENCE: 163 | | |
| RYLTISNLQF | | 10 |
| | | |
| SEQ ID NO: 164 | moltype = AA length = 9 | |
| FEATURE | Location/Qualifiers | |
| source | 1..9 | |
| | mol_type = protein | |
| | organism = Homo sapiens | |
| SEQUENCE: 164 | | |
| HYVPATKVF | | 9 |
| | | |
| SEQ ID NO: 165 | moltype = AA length = 11 | |
| FEATURE | Location/Qualifiers | |
| source | 1..11 | |
| | mol_type = protein | |
| | organism = Homo sapiens | |
| SEQUENCE: 165 | | |
| EYFTPLLSGQ F | | 11 |
| | | |
| SEQ ID NO: 166 | moltype = AA length = 9 | |
| FEATURE | Location/Qualifiers | |
| source | 1..9 | |
| | mol_type = protein | |
| | organism = Homo sapiens | |
| SEQUENCE: 166 | | |
| FYTLPFHLI | | 9 |
| | | |
| SEQ ID NO: 167 | moltype = AA length = 9 | |
| FEATURE | Location/Qualifiers | |
| source | 1..9 | |
| | mol_type = protein | |
| | organism = Homo sapiens | |
| SEQUENCE: 167 | | |
| RYGFYYVEF | | 9 |
| | | |
| SEQ ID NO: 168 | moltype = AA length = 9 | |
| FEATURE | Location/Qualifiers | |
| source | 1..9 | |
| | mol_type = protein | |
| | organism = Homo sapiens | |
| SEQUENCE: 168 | | |
| RYLEAALRL | | 9 |
| | | |
| SEQ ID NO: 169 | moltype = AA length = 10 | |
| FEATURE | Location/Qualifiers | |
| source | 1..10 | |
| | mol_type = protein | |
| | organism = Homo sapiens | |
| SEQUENCE: 169 | | |
| NYITGKGDVF | | 10 |
| | | |
| SEQ ID NO: 170 | moltype = AA length = 9 | |
| FEATURE | Location/Qualifiers | |
| source | 1..9 | |
| | mol_type = protein | |
| | organism = Homo sapiens | |
| SEQUENCE: 170 | | |
| QYPFHVPLL | | 9 |
| | | |
| SEQ ID NO: 171 | moltype = AA length = 9 | |
| FEATURE | Location/Qualifiers | |
| source | 1..9 | |
| | mol_type = protein | |
| | organism = Homo sapiens | |
| SEQUENCE: 171 | | |
| NYEDHFPLL | | 9 |
| | | |
| SEQ ID NO: 172 | moltype = AA length = 9 | |
| FEATURE | Location/Qualifiers | |
| source | 1..9 | |
| | mol_type = protein | |
| | organism = Homo sapiens | |
| SEQUENCE: 172 | | |
| VFIFKGNEF | | 9 |

-continued

| | | |
|---|---|---|
| SEQ ID NO: 173<br>FEATURE<br>source | moltype = AA   length = 9<br>Location/Qualifiers<br>1..9<br>mol_type = protein<br>organism = Homo sapiens | |
| SEQUENCE: 173<br>QYLEKYYNL | | 9 |
| SEQ ID NO: 174<br>FEATURE<br>source | moltype = AA   length = 10<br>Location/Qualifiers<br>1..10<br>mol_type = protein<br>organism = Homo sapiens | |
| SEQUENCE: 174<br>VYEKNGYIYF | | 10 |
| SEQ ID NO: 175<br>FEATURE<br>source | moltype = AA   length = 9<br>Location/Qualifiers<br>1..9<br>mol_type = protein<br>organism = Homo sapiens | |
| SEQUENCE: 175<br>LYSPVPFTL | | 9 |
| SEQ ID NO: 176<br>FEATURE<br>source | moltype = AA   length = 9<br>Location/Qualifiers<br>1..9<br>mol_type = protein<br>organism = Homo sapiens | |
| SEQUENCE: 176<br>FYINGQYQF | | 9 |
| SEQ ID NO: 177<br>FEATURE<br>source | moltype = AA   length = 10<br>Location/Qualifiers<br>1..10<br>mol_type = protein<br>organism = Homo sapiens | |
| SEQUENCE: 177<br>VYFKAGLDVF | | 10 |
| SEQ ID NO: 178<br>FEATURE<br>source | moltype = AA   length = 9<br>Location/Qualifiers<br>1..9<br>mol_type = protein<br>organism = Homo sapiens | |
| SEQUENCE: 178<br>NYSSAVQKF | | 9 |
| SEQ ID NO: 179<br>FEATURE<br>source | moltype = AA   length = 11<br>Location/Qualifiers<br>1..11<br>mol_type = protein<br>organism = Homo sapiens | |
| SEQUENCE: 179<br>TYIPVGLGRL L | | 11 |
| SEQ ID NO: 180<br>FEATURE<br>source | moltype = AA   length = 9<br>Location/Qualifiers<br>1..9<br>mol_type = protein<br>organism = Homo sapiens | |
| SEQUENCE: 180<br>KYLQVVGMF | | 9 |
| SEQ ID NO: 181<br>FEATURE<br>source | moltype = AA   length = 9<br>Location/Qualifiers<br>1..9<br>mol_type = protein<br>organism = Homo sapiens | |
| SEQUENCE: 181<br>VYPPYLNYL | | 9 |
| SEQ ID NO: 182<br>FEATURE<br>source | moltype = AA   length = 10<br>Location/Qualifiers<br>1..10<br>mol_type = protein<br>organism = Homo sapiens | |
| SEQUENCE: 182<br>AYAQLGYLLF | | 10 |

```
SEQ ID NO: 183          moltype = AA  length = 9
FEATURE                 Location/Qualifiers
source                  1..9
                        mol_type = protein
                        organism = Homo sapiens
SEQUENCE: 183
PYLQDVPRI                                                                9

SEQ ID NO: 184          moltype = AA  length = 10
FEATURE                 Location/Qualifiers
source                  1..10
                        mol_type = protein
                        organism = Homo sapiens
SEQUENCE: 184
IYSVGAFENF                                                              10

SEQ ID NO: 185          moltype = AA  length = 9
FEATURE                 Location/Qualifiers
source                  1..9
                        mol_type = protein
                        organism = Homo sapiens
SEQUENCE: 185
QYLVHVNDL                                                                9

SEQ ID NO: 186          moltype = AA  length = 9
FEATURE                 Location/Qualifiers
source                  1..9
                        mol_type = protein
                        organism = Homo sapiens
SEQUENCE: 186
VFTTSSNIF                                                                9

SEQ ID NO: 187          moltype = AA  length = 9
FEATURE                 Location/Qualifiers
source                  1..9
                        mol_type = protein
                        organism = Homo sapiens
SEQUENCE: 187
AYAANVHYL                                                                9

SEQ ID NO: 188          moltype = AA  length = 9
FEATURE                 Location/Qualifiers
source                  1..9
                        mol_type = protein
                        organism = Homo sapiens
SEQUENCE: 188
GYKTFFNEF                                                                9

SEQ ID NO: 189          moltype = AA  length = 9
FEATURE                 Location/Qualifiers
source                  1..9
                        mol_type = protein
                        organism = Homo sapiens
SEQUENCE: 189
AYFKQSSVF                                                                9

SEQ ID NO: 190          moltype = AA  length = 9
FEATURE                 Location/Qualifiers
source                  1..9
                        mol_type = protein
                        organism = Homo sapiens
SEQUENCE: 190
LYSELTETL                                                                9

SEQ ID NO: 191          moltype = AA  length = 12
FEATURE                 Location/Qualifiers
source                  1..12
                        mol_type = protein
                        organism = Homo sapiens
SEQUENCE: 191
TYPDGTYTGR IF                                                           12

SEQ ID NO: 192          moltype = AA  length = 9
FEATURE                 Location/Qualifiers
source                  1..9
                        mol_type = protein
                        organism = Homo sapiens
SEQUENCE: 192
```

-continued

```
RYSTFSEIF                                                                        9

SEQ ID NO: 193         moltype = AA   length = 11
FEATURE                Location/Qualifiers
source                 1..11
                       mol_type = protein
                       organism = Homo sapiens SEQUENCE: 193
LYLENNAQTQ F                                                                    11

SEQ ID NO: 194         moltype = AA   length = 9
FEATURE                Location/Qualifiers
source                 1..9
                       mol_type = protein
                       organism = Homo sapiens SEQUENCE: 194
VYQSLSNSL                                                                        9

SEQ ID NO: 195         moltype = AA   length = 9
FEATURE                Location/Qualifiers
source                 1..9
                       mol_type = protein
                       organism = Homo sapiens SEQUENCE: 195
AYIKGGWIL                                                                        9

SEQ ID NO: 196         moltype = AA   length = 9
FEATURE                Location/Qualifiers
source                 1..9
                       mol_type = protein
                       organism = Homo sapiens SEQUENCE: 196
GYIRGSWQF                                                                        9

SEQ ID NO: 197         moltype = AA   length = 9
FEATURE                Location/Qualifiers
source                 1..9
                       mol_type = protein
                       organism = Homo sapiens SEQUENCE: 197
IFTDIFHYL                                                                        9

SEQ ID NO: 198         moltype = AA   length = 9
FEATURE                Location/Qualifiers
source                 1..9
                       mol_type = protein
                       organism = Homo sapiens SEQUENCE: 198
DYVGFTLKI                                                                        9

SEQ ID NO: 199         moltype = AA   length = 9
FEATURE                Location/Qualifiers
source                 1..9
                       mol_type = protein
                       organism = Homo sapiens SEQUENCE: 199
SYLNHLNNL                                                                        9

SEQ ID NO: 200         moltype = AA   length = 9
FEATURE                Location/Qualifiers
source                 1..9
                       mol_type = protein
                       organism = Homo sapiens SEQUENCE: 200
VFIHHLPQF                                                                        9

SEQ ID NO: 201         moltype = AA   length = 9
FEATURE                Location/Qualifiers
source                 1..9
                       mol_type = protein
                       organism = Homo sapiens SEQUENCE: 201
GYNPNRVFF                                                                        9

SEQ ID NO: 202         moltype = AA   length = 9
FEATURE                Location/Qualifiers
source                 1..9
                       mol_type = protein
                       organism = Homo sapiens
```

```
SEQUENCE: 202
RYVEGIVSL                                                                                    9

SEQ ID NO: 203        moltype = AA  length = 11
FEATURE               Location/Qualifiers
source                1..11
                      mol_type = protein
                      organism = Homo sapiens
SEQUENCE: 203
VYNVEVKNAE F                                                                                11

SEQ ID NO: 204        moltype = AA  length = 9
FEATURE               Location/Qualifiers
source                1..9
                      mol_type = protein
                      organism = Homo sapiens
SEQUENCE: 204
EYLSTCSKL                                                                                    9

SEQ ID NO: 205        moltype = AA  length = 9
FEATURE               Location/Qualifiers
source                1..9
                      mol_type = protein
                      organism = Homo sapiens
SEQUENCE: 205
VYPVVLNQI                                                                                    9

SEQ ID NO: 206        moltype = AA  length = 9
FEATURE               Location/Qualifiers
source                1..9
                      mol_type = protein
                      organism = Homo sapiens
SEQUENCE: 206
NYLDVATFL                                                                                    9

SEQ ID NO: 207        moltype = AA  length = 11
FEATURE               Location/Qualifiers
source                1..11
                      mol_type = protein
                      organism = Homo sapiens
SEQUENCE: 207
LYSDAFKFIV F                                                                                11

SEQ ID NO: 208        moltype = AA  length = 9
FEATURE               Location/Qualifiers
source                1..9
                      mol_type = protein
                      organism = Homo sapiens
SEQUENCE: 208
TYLEKIDGF                                                                                    9

SEQ ID NO: 209        moltype = AA  length = 10
FEATURE               Location/Qualifiers
source                1..10
                      mol_type = protein
                      organism = Homo sapiens
SEQUENCE: 209
AFIETPIPLF                                                                                  10

SEQ ID NO: 210        moltype = AA  length = 10
FEATURE               Location/Qualifiers
source                1..10
                      mol_type = protein
                      organism = Homo sapiens
SEQUENCE: 210
IYAGVGEFSF                                                                                  10

SEQ ID NO: 211        moltype = AA  length = 9
FEATURE               Location/Qualifiers
source                1..9
                      mol_type = protein
                      organism = Homo sapiens
SEQUENCE: 211
VFKSEGAYF                                                                                    9

SEQ ID NO: 212        moltype = AA  length = 10
FEATURE               Location/Qualifiers
source                1..10
                      mol_type = protein
```

```
                              organism = Homo sapiens
SEQUENCE: 212
SYAPPSEDLF                                                                  10

SEQ ID NO: 213            moltype = AA   length = 11
FEATURE                   Location/Qualifiers
source                    1..11
                          mol_type = protein
                          organism = Homo sapiens
SEQUENCE: 213
SYAPPSEDLF L                                                                11

SEQ ID NO: 214            moltype = AA   length = 9
FEATURE                   Location/Qualifiers
source                    1..9
                          mol_type = protein
                          organism = Homo sapiens
SEQUENCE: 214
KYLMELTLI                                                                   9

SEQ ID NO: 215            moltype = AA   length = 9
FEATURE                   Location/Qualifiers
source                    1..9
                          mol_type = protein
                          organism = Homo sapiens
SEQUENCE: 215
SYVASFFLL                                                                   9

SEQ ID NO: 216            moltype = AA   length = 9
FEATURE                   Location/Qualifiers
source                    1..9
                          mol_type = protein
                          organism = Homo sapiens
SEQUENCE: 216
FYVNVKEQF                                                                   9

SEQ ID NO: 217            moltype = AA   length = 9
FEATURE                   Location/Qualifiers
source                    1..9
                          mol_type = protein
                          organism = Homo sapiens
SEQUENCE: 217
IYISNSIYF                                                                   9

SEQ ID NO: 218            moltype = AA   length = 10
FEATURE                   Location/Qualifiers
source                    1..10
                          mol_type = protein
                          organism = Homo sapiens
SEQUENCE: 218
LYSELNKWSF                                                                  10

SEQ ID NO: 219            moltype = AA   length = 9
FEATURE                   Location/Qualifiers
source                    1..9
                          mol_type = protein
                          organism = Homo sapiens
SEQUENCE: 219
SYLKAVFNL                                                                   9

SEQ ID NO: 220            moltype = AA   length = 9
FEATURE                   Location/Qualifiers
source                    1..9
                          mol_type = protein
                          organism = Homo sapiens
SEQUENCE: 220
SYSEIKDFL                                                                   9

SEQ ID NO: 221            moltype = AA   length = 9
FEATURE                   Location/Qualifiers
source                    1..9
                          mol_type = protein
                          organism = Homo sapiens
SEQUENCE: 221
KYIGNLDLL                                                                   9

SEQ ID NO: 222            moltype = AA   length = 9
FEATURE                   Location/Qualifiers
source                    1..9
```

```
                              mol_type = protein
                              organism = Homo sapiens
SEQUENCE: 222
HYSTLVHMF                                                                    9

SEQ ID NO: 223                moltype = AA  length = 9
FEATURE                       Location/Qualifiers
source                        1..9
                              mol_type = protein
                              organism = Homo sapiens
SEQUENCE: 223
TFITQSPLL                                                                    9

SEQ ID NO: 224                moltype = AA  length = 9
FEATURE                       Location/Qualifiers
source                        1..9
                              mol_type = protein
                              organism = Homo sapiens
SEQUENCE: 224
PYFFANQEF                                                                    9

SEQ ID NO: 225                moltype = AA  length = 9
FEATURE                       Location/Qualifiers
source                        1..9
                              mol_type = protein
                              organism = Homo sapiens
SEQUENCE: 225
TYTNTLERL                                                                    9

SEQ ID NO: 226                moltype = AA  length = 9
FEATURE                       Location/Qualifiers
source                        1..9
                              mol_type = protein
                              organism = Homo sapiens
SEQUENCE: 226
MYLKLVQLF                                                                    9

SEQ ID NO: 227                moltype = AA  length = 9
FEATURE                       Location/Qualifiers
source                        1..9
                              mol_type = protein
                              organism = Homo sapiens
SEQUENCE: 227
IYRFITERF                                                                    9

SEQ ID NO: 228                moltype = AA  length = 9
FEATURE                       Location/Qualifiers
source                        1..9
                              mol_type = protein
                              organism = Homo sapiens
SEQUENCE: 228
IYQYVADNF                                                                    9

SEQ ID NO: 229                moltype = AA  length = 9
FEATURE                       Location/Qualifiers
source                        1..9
                              mol_type = protein
                              organism = Homo sapiens
SEQUENCE: 229
IYQFVADSF                                                                    9

SEQ ID NO: 230                moltype = AA  length = 9
FEATURE                       Location/Qualifiers
source                        1..9
                              mol_type = protein
                              organism = Homo sapiens
SEQUENCE: 230
TYGMVMVTF                                                                    9

SEQ ID NO: 231                moltype = AA  length = 9
FEATURE                       Location/Qualifiers
source                        1..9
                              mol_type = protein
                              organism = Homo sapiens
SEQUENCE: 231
AFADVSVKF                                                                    9

SEQ ID NO: 232                moltype = AA  length = 9
FEATURE                       Location/Qualifiers
```

```
source                      1..9
                            mol_type = protein
                            organism = Homo sapiens SEQUENCE: 232
YYLSDSPLL                                                                   9

SEQ ID NO: 233              moltype = AA  length = 11
FEATURE                     Location/Qualifiers
source                      1..11
                            mol_type = protein
                            organism = Homo sapiens SEQUENCE: 233
QYLTAAALHN L                                                               11

SEQ ID NO: 234              moltype = AA  length = 9
FEATURE                     Location/Qualifiers
source                      1..9
                            mol_type = protein
                            organism = Homo sapiens SEQUENCE: 234
SYLPAIWLL                                                                   9

SEQ ID NO: 235              moltype = AA  length = 9
FEATURE                     Location/Qualifiers
source                      1..9
                            mol_type = protein
                            organism = Homo sapiens SEQUENCE: 235
VYKDSIYYI                                                                   9

SEQ ID NO: 236              moltype = AA  length = 9
FEATURE                     Location/Qualifiers
source                      1..9
                            mol_type = protein
                            organism = Homo sapiens SEQUENCE: 236
VYLPKIPSW                                                                   9

SEQ ID NO: 237              moltype = AA  length = 9
FEATURE                     Location/Qualifiers
source                      1..9
                            mol_type = protein
                            organism = Homo sapiens SEQUENCE: 237
KYVGQLAVL                                                                   9

SEQ ID NO: 238              moltype = AA  length = 9
FEATURE                     Location/Qualifiers
source                      1..9
                            mol_type = protein
                            organism = Homo sapiens SEQUENCE: 238
SYLEKVRQL                                                                   9

SEQ ID NO: 239              moltype = AA  length = 9
FEATURE                     Location/Qualifiers
source                      1..9
                            mol_type = protein
                            organism = Homo sapiens SEQUENCE: 239
VYAIFRILL                                                                   9

SEQ ID NO: 240              moltype = AA  length = 9
FEATURE                     Location/Qualifiers
source                      1..9
                            mol_type = protein
                            organism = Homo sapiens SEQUENCE: 240
YYFFVQEKI                                                                   9

SEQ ID NO: 241              moltype = AA  length = 9
FEATURE                     Location/Qualifiers
source                      1..9
                            mol_type = protein
                            organism = Homo sapiens SEQUENCE: 241
SYVKVLHHL                                                                   9

SEQ ID NO: 242              moltype = AA  length = 9
```

```
FEATURE              Location/Qualifiers
source               1..9
                     mol_type = protein
                     organism = Homo sapiens
SEQUENCE: 242
VYGEPRELL                                                                  9

SEQ ID NO: 243       moltype = AA  length = 9
FEATURE              Location/Qualifiers
source               1..9
                     mol_type = protein
                     organism = Homo sapiens
SEQUENCE: 243
SYLELANTL                                                                  9

SEQ ID NO: 244       moltype = AA  length = 12
FEATURE              Location/Qualifiers
source               1..12
                     mol_type = protein
                     organism = Homo sapiens
SEQUENCE: 244
VHFEDTGKTL LF                                                             12

SEQ ID NO: 245       moltype = AA  length = 9
FEATURE              Location/Qualifiers
source               1..9
                     mol_type = protein
                     organism = Homo sapiens
SEQUENCE: 245
LYPQLFVVL                                                                  9

SEQ ID NO: 246       moltype = AA  length = 9
FEATURE              Location/Qualifiers
source               1..9
                     mol_type = protein
                     organism = Homo sapiens
SEQUENCE: 246
KYLSVQLTL                                                                  9

SEQ ID NO: 247       moltype = AA  length = 9
FEATURE              Location/Qualifiers
source               1..9
                     mol_type = protein
                     organism = Homo sapiens
SEQUENCE: 247
SFTKTSPNF                                                                  9

SEQ ID NO: 248       moltype = AA  length = 9
FEATURE              Location/Qualifiers
source               1..9
                     mol_type = protein
                     organism = Homo sapiens
SEQUENCE: 248
AFPTFSVQL                                                                  9

SEQ ID NO: 249       moltype = AA  length = 9
FEATURE              Location/Qualifiers
source               1..9
                     mol_type = protein
                     organism = Homo sapiens
SEQUENCE: 249
RYHPTTCTI                                                                  9

SEQ ID NO: 250       moltype = AA  length = 10
FEATURE              Location/Qualifiers
source               1..10
                     mol_type = protein
                     organism = Homo sapiens
SEQUENCE: 250
KYPDIASPTF                                                                10

SEQ ID NO: 251       moltype = AA  length = 9
FEATURE              Location/Qualifiers
source               1..9
                     mol_type = protein
                     organism = Homo sapiens
SEQUENCE: 251
VYTKALSSL                                                                  9
```

-continued

```
SEQ ID NO: 252          moltype = AA   length = 13
FEATURE                 Location/Qualifiers
source                  1..13
                        mol_type = protein
                        organism = Homo sapiens
SEQUENCE: 252
AFGQETNVPL NNF                                                              13

SEQ ID NO: 253          moltype = AA   length = 9
FEATURE                 Location/Qualifiers
source                  1..9
                        mol_type = protein
                        organism = Homo sapiens
SEQUENCE: 253
IYGFFNENF                                                                    9

SEQ ID NO: 254          moltype = AA   length = 9
FEATURE                 Location/Qualifiers
source                  1..9
                        mol_type = protein
                        organism = Homo sapiens
SEQUENCE: 254
KYLESSATF                                                                    9

SEQ ID NO: 255          moltype = AA   length = 9
FEATURE                 Location/Qualifiers
source                  1..9
                        mol_type = protein
                        organism = Homo sapiens
SEQUENCE: 255
VYQKIILKF                                                                    9

SEQ ID NO: 256          moltype = AA   length = 9
FEATURE                 Location/Qualifiers
source                  1..9
                        mol_type = protein
                        organism = Homo sapiens
SEQUENCE: 256
VFGKSAYLF                                                                    9

SEQ ID NO: 257          moltype = AA   length = 12
FEATURE                 Location/Qualifiers
source                  1..12
                        mol_type = protein
                        organism = Homo sapiens
SEQUENCE: 257
IFIDNSTQPL HF                                                               12

SEQ ID NO: 258          moltype = AA   length = 9
FEATURE                 Location/Qualifiers
source                  1..9
                        mol_type = protein
                        organism = Homo sapiens
SEQUENCE: 258
AYAQLGYLL                                                                    9

SEQ ID NO: 259          moltype = AA   length = 11
FEATURE                 Location/Qualifiers
source                  1..11
                        mol_type = protein
                        organism = Homo sapiens
SEQUENCE: 259
YFIKSPPSQL F                                                                11

SEQ ID NO: 260          moltype = AA   length = 9
FEATURE                 Location/Qualifiers
source                  1..9
                        mol_type = protein
                        organism = Homo sapiens
SEQUENCE: 260
VYMNVMTRL                                                                    9

SEQ ID NO: 261          moltype = AA   length = 9
FEATURE                 Location/Qualifiers
source                  1..9
                        mol_type = protein
                        organism = Homo sapiens
SEQUENCE: 261
GYIKLINFI                                                                    9
```

| | | |
|---|---|---|
| SEQ ID NO: 262<br>FEATURE<br>source | moltype = AA  length = 9<br>Location/Qualifiers<br>1..9<br>mol_type = protein<br>organism = Homo sapiens | |
| SEQUENCE: 262<br>VYSSQFETI | | 9 |
| SEQ ID NO: 263<br>FEATURE<br>source | moltype = AA  length = 9<br>Location/Qualifiers<br>1..9<br>mol_type = protein<br>organism = Homo sapiens | |
| SEQUENCE: 263<br>RYILENHDF | | 9 |
| SEQ ID NO: 264<br>FEATURE<br>source | moltype = AA  length = 9<br>Location/Qualifiers<br>1..9<br>mol_type = protein<br>organism = Homo sapiens | |
| SEQUENCE: 264<br>LYTETRLQF | | 9 |
| SEQ ID NO: 265<br>FEATURE<br>source | moltype = AA  length = 9<br>Location/Qualifiers<br>1..9<br>mol_type = protein<br>organism = Homo sapiens | |
| SEQUENCE: 265<br>SYLNEAFSF | | 9 |
| SEQ ID NO: 266<br>FEATURE<br>source | moltype = AA  length = 9<br>Location/Qualifiers<br>1..9<br>mol_type = protein<br>organism = Homo sapiens | |
| SEQUENCE: 266<br>KYTDWTEFL | | 9 |
| SEQ ID NO: 267<br>FEATURE<br>source | moltype = AA  length = 12<br>Location/Qualifiers<br>1..12<br>mol_type = protein<br>organism = Homo sapiens | |
| SEQUENCE: 267<br>SFLNIEKTEI LF | | 12 |
| SEQ ID NO: 268<br>FEATURE<br>source | moltype = AA  length = 9<br>Location/Qualifiers<br>1..9<br>mol_type = protein<br>organism = Homo sapiens | |
| SEQUENCE: 268<br>IFITKALQI | | 9 |
| SEQ ID NO: 269<br>FEATURE<br>source | moltype = AA  length = 9<br>Location/Qualifiers<br>1..9<br>mol_type = protein<br>organism = Homo sapiens | |
| SEQUENCE: 269<br>QYPYLQAFF | | 9 |
| SEQ ID NO: 270<br>FEATURE<br>source | moltype = AA  length = 11<br>Location/Qualifiers<br>1..11<br>mol_type = protein<br>organism = Homo sapiens | |
| SEQUENCE: 270<br>YYSQESKVLY L | | 11 |
| SEQ ID NO: 271<br>FEATURE<br>source | moltype = AA  length = 9<br>Location/Qualifiers<br>1..9<br>mol_type = protein<br>organism = Homo sapiens | |
| SEQUENCE: 271 | | |

```
RFLMKSYSF                                                                                9

SEQ ID NO: 272         moltype = AA   length = 9
FEATURE                Location/Qualifiers
source                 1..9
                       mol_type = protein
                       organism = Homo sapiens
SEQUENCE: 272
RYVFPLPYL                                                                                9

SEQ ID NO: 273         moltype = AA   length = 10
FEATURE                Location/Qualifiers
source                 1..10
                       mol_type = protein
                       organism = Homo sapiens
SEQUENCE: 273
IYGEKLQFIF                                                                               10

SEQ ID NO: 274         moltype = AA   length = 11
FEATURE                Location/Qualifiers
source                 1..11
                       mol_type = protein
                       organism = Homo sapiens
SEQUENCE: 274
KQLDIANYEL F                                                                             11

SEQ ID NO: 275         moltype = AA   length = 9
FEATURE                Location/Qualifiers
source                 1..9
                       mol_type = protein
                       organism = Homo sapiens
SEQUENCE: 275
KYGTLDVTF                                                                                9

SEQ ID NO: 276         moltype = AA   length = 9
FEATURE                Location/Qualifiers
source                 1..9
                       mol_type = protein
                       organism = Homo sapiens
SEQUENCE: 276
QYLDVLHAL                                                                                9

SEQ ID NO: 277         moltype = AA   length = 9
FEATURE                Location/Qualifiers
source                 1..9
                       mol_type = protein
                       organism = Homo sapiens
SEQUENCE: 277
FYTFPFQQL                                                                                9

SEQ ID NO: 278         moltype = AA   length = 9
FEATURE                Location/Qualifiers
source                 1..9
                       mol_type = protein
                       organism = Homo sapiens
SEQUENCE: 278
KYVNLVMYF                                                                                9

SEQ ID NO: 279         moltype = AA   length = 9
FEATURE                Location/Qualifiers
source                 1..9
                       mol_type = protein
                       organism = Homo sapiens
SEQUENCE: 279
VWLPASVLF                                                                                9

SEQ ID NO: 280         moltype = AA   length = 10
FEATURE                Location/Qualifiers
source                 1..10
                       mol_type = protein
                       organism = Homo sapiens
SEQUENCE: 280
TYNPNLQDKL                                                                               10

SEQ ID NO: 281         moltype = AA   length = 11
FEATURE                Location/Qualifiers
source                 1..11
                       mol_type = protein
                       organism = Homo sapiens
```

-continued

```
SEQUENCE: 281
NYSPGLVSLI L                                                                    11

SEQ ID NO: 282          moltype = AA  length = 9
FEATURE                 Location/Qualifiers
source                  1..9
                        mol_type = protein
                        organism = Homo sapiens
SEQUENCE: 282
NYLVDPVTI                                                                       9

SEQ ID NO: 283          moltype = AA  length = 9
FEATURE                 Location/Qualifiers
source                  1..9
                        mol_type = protein
                        organism = Homo sapiens
SEQUENCE: 283
EYQEIFQQL                                                                       9

SEQ ID NO: 284          moltype = AA  length = 9
FEATURE                 Location/Qualifiers
source                  1..9
                        mol_type = protein
                        organism = Homo sapiens
SEQUENCE: 284
DYLKDPVTI                                                                       9

SEQ ID NO: 285          moltype = AA  length = 11
FEATURE                 Location/Qualifiers
source                  1..11
                        mol_type = protein
                        organism = Homo sapiens
SEQUENCE: 285
VYVGDALLHA I                                                                    11

SEQ ID NO: 286          moltype = AA  length = 9
FEATURE                 Location/Qualifiers
source                  1..9
                        mol_type = protein
                        organism = Homo sapiens
SEQUENCE: 286
SYGTILSHI                                                                       9

SEQ ID NO: 287          moltype = AA  length = 12
FEATURE                 Location/Qualifiers
source                  1..12
                        mol_type = protein
                        organism = Homo sapiens
SEQUENCE: 287
IYNPNLLTAS KF                                                                   12

SEQ ID NO: 288          moltype = AA  length = 10
FEATURE                 Location/Qualifiers
source                  1..10
                        mol_type = protein
                        organism = Homo sapiens
SEQUENCE: 288
VYPDTVALTF                                                                      10

SEQ ID NO: 289          moltype = AA  length = 9
FEATURE                 Location/Qualifiers
source                  1..9
                        mol_type = protein
                        organism = Homo sapiens
SEQUENCE: 289
FFHEGQYVF                                                                       9

SEQ ID NO: 290          moltype = AA  length = 10
FEATURE                 Location/Qualifiers
source                  1..10
                        mol_type = protein
                        organism = Homo sapiens
SEQUENCE: 290
KYGDFKLLEF                                                                      10

SEQ ID NO: 291          moltype = AA  length = 10
FEATURE                 Location/Qualifiers
source                  1..10
                        mol_type = protein
```

-continued

```
                        organism = Homo sapiens
SEQUENCE: 291
YYLGSGRETF                                                              10

SEQ ID NO: 292          moltype = AA  length = 9
FEATURE                 Location/Qualifiers
source                  1..9
                        mol_type = protein
                        organism = Homo sapiens
SEQUENCE: 292
FYPQIINTF                                                               9

SEQ ID NO: 293          moltype = AA  length = 11
FEATURE                 Location/Qualifiers
source                  1..11
                        mol_type = protein
                        organism = Homo sapiens
SEQUENCE: 293
VYPHFSTTNL I                                                            11

SEQ ID NO: 294          moltype = AA  length = 10
FEATURE                 Location/Qualifiers
source                  1..10
                        mol_type = protein
                        organism = Homo sapiens
SEQUENCE: 294
RFPVQGTVTF                                                              10

SEQ ID NO: 295          moltype = AA  length = 9
FEATURE                 Location/Qualifiers
source                  1..9
                        mol_type = protein
                        organism = Homo sapiens
SEQUENCE: 295
SYLVIHERI                                                               9

SEQ ID NO: 296          moltype = AA  length = 9
FEATURE                 Location/Qualifiers
source                  1..9
                        mol_type = protein
                        organism = Homo sapiens
SEQUENCE: 296
SYQVIFQHF                                                               9

SEQ ID NO: 297          moltype = AA  length = 9
FEATURE                 Location/Qualifiers
source                  1..9
                        mol_type = protein
                        organism = Homo sapiens
SEQUENCE: 297
TYIDTRTVF                                                               9

SEQ ID NO: 298          moltype = AA  length = 9
FEATURE                 Location/Qualifiers
source                  1..9
                        mol_type = protein
                        organism = Homo sapiens
SEQUENCE: 298
AYKSEVVYF                                                               9

SEQ ID NO: 299          moltype = AA  length = 9
FEATURE                 Location/Qualifiers
source                  1..9
                        mol_type = protein
                        organism = Homo sapiens
SEQUENCE: 299
KYQYVLNEF                                                               9

SEQ ID NO: 300          moltype = AA  length = 9
FEATURE                 Location/Qualifiers
source                  1..9
                        mol_type = protein
                        organism = Homo sapiens
SEQUENCE: 300
TYPSQLPSL                                                               9

SEQ ID NO: 301          moltype = AA  length = 9
FEATURE                 Location/Qualifiers
source                  1..9
```

```
                           mol_type = protein
                           organism = Homo sapiens
SEQUENCE: 301
KFDDVTMLF                                                            9

SEQ ID NO: 302            moltype = AA   length = 9
FEATURE                   Location/Qualifiers
source                    1..9
                          mol_type = protein
                          organism = Homo sapiens
SEQUENCE: 302
LYLPVHYGF                                                            9

SEQ ID NO: 303            moltype = AA   length = 9
FEATURE                   Location/Qualifiers
source                    1..9
                          mol_type = protein
                          organism = Homo sapiens
SEQUENCE: 303
LYSVIKEDF                                                            9

SEQ ID NO: 304            moltype = AA   length = 9
FEATURE                   Location/Qualifiers
source                    1..9
                          mol_type = protein
                          organism = Homo sapiens
SEQUENCE: 304
EYNEVANLF                                                            9

SEQ ID NO: 305            moltype = AA   length = 9
FEATURE                   Location/Qualifiers
source                    1..9
                          mol_type = protein
                          organism = Homo sapiens
SEQUENCE: 305
NYENKQYLF                                                            9

SEQ ID NO: 306            moltype = AA   length = 9
FEATURE                   Location/Qualifiers
source                    1..9
                          mol_type = protein
                          organism = Homo sapiens
SEQUENCE: 306
VYPAEQPQI                                                            9

SEQ ID NO: 307            moltype = AA   length = 9
FEATURE                   Location/Qualifiers
source                    1..9
                          mol_type = protein
                          organism = Homo sapiens
SEQUENCE: 307
GYAFTLPLF                                                            9

SEQ ID NO: 308            moltype = AA   length = 9
FEATURE                   Location/Qualifiers
source                    1..9
                          mol_type = protein
                          organism = Homo sapiens
SEQUENCE: 308
TFDGHGVFF                                                            9

SEQ ID NO: 309            moltype = AA   length = 9
FEATURE                   Location/Qualifiers
source                    1..9
                          mol_type = protein
                          organism = Homo sapiens
SEQUENCE: 309
KYYRQTLLF                                                            9

SEQ ID NO: 310            moltype = AA   length = 9
FEATURE                   Location/Qualifiers
source                    1..9
                          mol_type = protein
                          organism = Homo sapiens
SEQUENCE: 310
IYAPTLLVF                                                            9

SEQ ID NO: 311            moltype = AA   length = 9
FEATURE                   Location/Qualifiers
```

```
source                  1..9
                        mol_type = protein
                        organism = Homo sapiens
SEQUENCE: 311
EYLQNLNHI                                                               9

SEQ ID NO: 312          moltype = AA  length = 9
FEATURE                 Location/Qualifiers
source                  1..9
                        mol_type = protein
                        organism = Homo sapiens
SEQUENCE: 312
SYTSVLSRL                                                               9

SEQ ID NO: 313          moltype = AA  length = 9
FEATURE                 Location/Qualifiers
source                  1..9
                        mol_type = protein
                        organism = Homo sapiens
SEQUENCE: 313
KYTHFIQSF                                                               9

SEQ ID NO: 314          moltype = AA  length = 9
FEATURE                 Location/Qualifiers
source                  1..9
                        mol_type = protein
                        organism = Homo sapiens
SEQUENCE: 314
RYFKGDYSI                                                               9

SEQ ID NO: 315          moltype = AA  length = 10
FEATURE                 Location/Qualifiers
source                  1..10
                        mol_type = protein
                        organism = Homo sapiens
SEQUENCE: 315
FYIPHVPVSF                                                              10

SEQ ID NO: 316          moltype = AA  length = 10
FEATURE                 Location/Qualifiers
source                  1..10
                        mol_type = protein
                        organism = Homo sapiens
SEQUENCE: 316
VYFEGSDFKF                                                              10

SEQ ID NO: 317          moltype = AA  length = 10
FEATURE                 Location/Qualifiers
source                  1..10
                        mol_type = protein
                        organism = Homo sapiens
SEQUENCE: 317
VFDTSIAQLF                                                              10

SEQ ID NO: 318          moltype = AA  length = 10
FEATURE                 Location/Qualifiers
source                  1..10
                        mol_type = protein
                        organism = Homo sapiens
SEQUENCE: 318
TYSNSAFQYF                                                              10

SEQ ID NO: 319          moltype = AA  length = 9
FEATURE                 Location/Qualifiers
source                  1..9
                        mol_type = protein
                        organism = Homo sapiens
SEQUENCE: 319
KYSDVKNLI                                                               9

SEQ ID NO: 320          moltype = AA  length = 10
FEATURE                 Location/Qualifiers
source                  1..10
                        mol_type = protein
                        organism = Homo sapiens
SEQUENCE: 320
KFILALKVLF                                                              10

SEQ ID NO: 321          moltype = AA  length = 9
```

-continued

```
FEATURE                 Location/Qualifiers
source                  1..9
                        mol_type = protein
                        organism = Homo sapiens
SEQUENCE: 321
SLWFKPEEL                                                                    9

SEQ ID NO: 322          moltype = AA  length = 10
FEATURE                 Location/Qualifiers
source                  1..10
                        mol_type = protein
                        organism = Homo sapiens
SEQUENCE: 322
ALVSGGVAQA                                                                  10

SEQ ID NO: 323          moltype = AA  length = 9
FEATURE                 Location/Qualifiers
source                  1..9
                        mol_type = protein
                        organism = Homo sapiens
SEQUENCE: 323
ILSVVNSQL                                                                    9

SEQ ID NO: 324          moltype = AA  length = 9
FEATURE                 Location/Qualifiers
source                  1..9
                        mol_type = protein
                        organism = Homo sapiens
SEQUENCE: 324
AIFDFCPSV                                                                    9

SEQ ID NO: 325          moltype = AA  length = 9
FEATURE                 Location/Qualifiers
source                  1..9
                        mol_type = protein
                        organism = Homo sapiens
SEQUENCE: 325
RLLPKVQEV                                                                    9

SEQ ID NO: 326          moltype = AA  length = 9
FEATURE                 Location/Qualifiers
source                  1..9
                        mol_type = protein
                        organism = Homo sapiens
SEQUENCE: 326
SLLPLVWKI                                                                    9

SEQ ID NO: 327          moltype = AA  length = 9
FEATURE                 Location/Qualifiers
source                  1..9
                        mol_type = protein
                        organism = Homo sapiens
SEQUENCE: 327
SIGDIFLKY                                                                    9

SEQ ID NO: 328          moltype = AA  length = 9
FEATURE                 Location/Qualifiers
source                  1..9
                        mol_type = protein
                        organism = Homo sapiens
SEQUENCE: 328
SVDSAPAAV                                                                    9

SEQ ID NO: 329          moltype = AA  length = 11
FEATURE                 Location/Qualifiers
source                  1..11
                        mol_type = protein
                        organism = Homo sapiens
SEQUENCE: 329
FAWEPSFRDQ V                                                                11

SEQ ID NO: 330          moltype = AA  length = 9
FEATURE                 Location/Qualifiers
source                  1..9
                        mol_type = protein
                        organism = Homo sapiens
SEQUENCE: 330
FLWPKEVEL                                                                    9
```

-continued

| | | |
|---|---|---|
| SEQ ID NO: 331<br>FEATURE<br>source | moltype = AA length = 9<br>Location/Qualifiers<br>1..9<br>mol_type = protein<br>organism = Homo sapiens | |
| SEQUENCE: 331<br>AIWKELISL | | 9 |
| SEQ ID NO: 332<br>FEATURE<br>source | moltype = AA length = 9<br>Location/Qualifiers<br>1..9<br>mol_type = protein<br>organism = Homo sapiens | |
| SEQUENCE: 332<br>AVTKYTSAK | | 9 |
| SEQ ID NO: 333<br>FEATURE<br>source | moltype = AA length = 9<br>Location/Qualifiers<br>1..9<br>mol_type = protein<br>organism = Homo sapiens | |
| SEQUENCE: 333<br>GTFLEGVAK | | 9 |
| SEQ ID NO: 334<br>FEATURE<br>source | moltype = AA length = 9<br>Location/Qualifiers<br>1..9<br>mol_type = protein<br>organism = Homo sapiens | |
| SEQUENCE: 334<br>GRADALRVL | | 9 |
| SEQ ID NO: 335<br>FEATURE<br>source | moltype = AA length = 10<br>Location/Qualifiers<br>1..10<br>mol_type = protein<br>organism = Homo sapiens | |
| SEQUENCE: 335<br>VLLAAGPSAA | | 10 |
| SEQ ID NO: 336<br>FEATURE<br>source | moltype = AA length = 10<br>Location/Qualifiers<br>1..10<br>mol_type = protein<br>organism = Homo sapiens | |
| SEQUENCE: 336<br>GLMDGSPHFL | | 10 |
| SEQ ID NO: 337<br>FEATURE<br>source | moltype = AA length = 9<br>Location/Qualifiers<br>1..9<br>mol_type = protein<br>organism = Homo sapiens | |
| SEQUENCE: 337<br>KVLGKIEKV | | 9 |
| SEQ ID NO: 338<br>FEATURE<br>source | moltype = AA length = 10<br>Location/Qualifiers<br>1..10<br>mol_type = protein<br>organism = Homo sapiens | |
| SEQUENCE: 338<br>LLYDGKLSSA | | 10 |
| SEQ ID NO: 339<br>FEATURE<br>source | moltype = AA length = 9<br>Location/Qualifiers<br>1..9<br>mol_type = protein<br>organism = Homo sapiens | |
| SEQUENCE: 339<br>VLGPGPPPL | | 9 |
| SEQ ID NO: 340<br>FEATURE<br>source | moltype = AA length = 9<br>Location/Qualifiers<br>1..9<br>mol_type = protein<br>organism = Homo sapiens | |
| SEQUENCE: 340<br>SVAKTILKR | | 9 |

| | | |
|---|---|---|
| SEQ ID NO: 341<br>FEATURE<br>source | moltype = AA   length = 9<br>Location/Qualifiers<br>1..9<br>mol_type = protein<br>organism = Homo sapiens | |
| SEQUENCE: 341<br>SYLTQHQRI | | 9 |
| SEQ ID NO: 342<br>FEATURE<br>source | moltype = AA   length = 9<br>Location/Qualifiers<br>1..9<br>mol_type = protein<br>organism = Homo sapiens | |
| SEQUENCE: 342<br>NYAFLHRTL | | 9 |
| SEQ ID NO: 343<br>FEATURE<br>source | moltype = AA   length = 9<br>Location/Qualifiers<br>1..9<br>mol_type = protein<br>organism = Homo sapiens | |
| SEQUENCE: 343<br>NYLGGTSTI | | 9 |
| SEQ ID NO: 344<br>FEATURE<br>source | moltype = AA   length = 9<br>Location/Qualifiers<br>1..9<br>mol_type = protein<br>organism = Homo sapiens | |
| SEQUENCE: 344<br>EYNSDLHQF | | 9 |
| SEQ ID NO: 345<br>FEATURE<br>source | moltype = AA   length = 10<br>Location/Qualifiers<br>1..10<br>mol_type = protein<br>organism = Homo sapiens | |
| SEQUENCE: 345<br>EYNSDLHQFF | | 10 |
| SEQ ID NO: 346<br>FEATURE<br>source | moltype = AA   length = 9<br>Location/Qualifiers<br>1..9<br>mol_type = protein<br>organism = Homo sapiens | |
| SEQUENCE: 346<br>IYVIPQPHF | | 9 |
| SEQ ID NO: 347<br>FEATURE<br>source | moltype = AA   length = 8<br>Location/Qualifiers<br>1..8<br>mol_type = protein<br>organism = Homo sapiens | |
| SEQUENCE: 347<br>VYAEVNSL | | 8 |
| SEQ ID NO: 348<br>FEATURE<br>source | moltype = AA   length = 9<br>Location/Qualifiers<br>1..9<br>mol_type = protein<br>organism = Homo sapiens | |
| SEQUENCE: 348<br>IYLEHTESI | | 9 |
| SEQ ID NO: 349<br>FEATURE<br>source | moltype = AA   length = 9<br>Location/Qualifiers<br>1..9<br>mol_type = protein<br>organism = Homo sapiens | |
| SEQUENCE: 349<br>QYSIISNVF | | 9 |
| SEQ ID NO: 350<br>FEATURE<br>source | moltype = AA   length = 9<br>Location/Qualifiers<br>1..9<br>mol_type = protein<br>organism = Homo sapiens | |
| SEQUENCE: 350 | | |

```
KYGNFIDKL                                                                             9

SEQ ID NO: 351          moltype = AA  length = 9
FEATURE                 Location/Qualifiers
source                  1..9
                        mol_type = protein
                        organism = Homo sapiens SEQUENCE: 351
IFHEVPLKF                                                                             9

SEQ ID NO: 352          moltype = AA  length = 10
FEATURE                 Location/Qualifiers
source                  1..10
                        mol_type = protein
                        organism = Homo sapiens SEQUENCE: 352
QYGGDLTNTF                                                                           10

SEQ ID NO: 353          moltype = AA  length = 9
FEATURE                 Location/Qualifiers
source                  1..9
                        mol_type = protein
                        organism = Homo sapiens SEQUENCE: 353
TYGKIDLGF                                                                             9

SEQ ID NO: 354          moltype = AA  length = 10
FEATURE                 Location/Qualifiers
source                  1..10
                        mol_type = protein
                        organism = Homo sapiens SEQUENCE: 354
VYNEQIRDLL                                                                           10

SEQ ID NO: 355          moltype = AA  length = 9
FEATURE                 Location/Qualifiers
source                  1..9
                        mol_type = protein
                        organism = Homo sapiens SEQUENCE: 355
IYVTGGHLF                                                                             9

SEQ ID NO: 356          moltype = AA  length = 9
FEATURE                 Location/Qualifiers
source                  1..9
                        mol_type = protein
                        organism = Homo sapiens SEQUENCE: 356
NYMPGQLTI                                                                             9

SEQ ID NO: 357          moltype = AA  length = 9
FEATURE                 Location/Qualifiers
source                  1..9
                        mol_type = protein
                        organism = Homo sapiens SEQUENCE: 357
QFITSTNTF                                                                             9

SEQ ID NO: 358          moltype = AA  length = 9
FEATURE                 Location/Qualifiers
source                  1..9
                        mol_type = protein
                        organism = Homo sapiens SEQUENCE: 358
YYSEVPVKL                                                                             9

SEQ ID NO: 359          moltype = AA  length = 9
FEATURE                 Location/Qualifiers
source                  1..9
                        mol_type = protein
                        organism = Homo sapiens SEQUENCE: 359
NYGVLHVTF                                                                             9

SEQ ID NO: 360          moltype = AA  length = 9
FEATURE                 Location/Qualifiers
source                  1..9
                        mol_type = protein
                        organism = Homo sapiens
```

-continued

```
SEQUENCE: 360
VFSPDGHLF                                                              9

SEQ ID NO: 361         moltype = AA  length = 12
FEATURE                Location/Qualifiers
source                 1..12
                       mol_type = protein
                       organism = Homo sapiens
SEQUENCE: 361
TYADIGGLDN QI                                                         12

SEQ ID NO: 362         moltype = AA  length = 9
FEATURE                Location/Qualifiers
source                 1..9
                       mol_type = protein
                       organism = Homo sapiens
SEQUENCE: 362
VYNYAEQTL                                                              9

SEQ ID NO: 363         moltype = AA  length = 9
FEATURE                Location/Qualifiers
source                 1..9
                       mol_type = protein
                       organism = Homo sapiens
SEQUENCE: 363
SYAELGTTI                                                              9

SEQ ID NO: 364         moltype = AA  length = 11
FEATURE                Location/Qualifiers
source                 1..11
                       mol_type = protein
                       organism = Homo sapiens
SEQUENCE: 364
KYLNENQLSQ L                                                          11

SEQ ID NO: 365         moltype = AA  length = 9
FEATURE                Location/Qualifiers
source                 1..9
                       mol_type = protein
                       organism = Homo sapiens
SEQUENCE: 365
VFIDHPVHL                                                              9

SEQ ID NO: 366         moltype = AA  length = 9
FEATURE                Location/Qualifiers
source                 1..9
                       mol_type = protein
                       organism = Homo sapiens
SEQUENCE: 366
QYLELAHSL                                                              9

SEQ ID NO: 367         moltype = AA  length = 9
FEATURE                Location/Qualifiers
source                 1..9
                       mol_type = protein
                       organism = Homo sapiens
SEQUENCE: 367
LYQDHMQYI                                                              9

SEQ ID NO: 368         moltype = AA  length = 9
FEATURE                Location/Qualifiers
source                 1..9
                       mol_type = protein
                       organism = Homo sapiens
SEQUENCE: 368
KYQNVKHNL                                                              9

SEQ ID NO: 369         moltype = AA  length = 9
FEATURE                Location/Qualifiers
source                 1..9
                       mol_type = protein
                       organism = Homo sapiens
SEQUENCE: 369
VYTHEVVTL                                                              9

SEQ ID NO: 370         moltype = AA  length = 9
FEATURE                Location/Qualifiers
source                 1..9
                       mol_type = protein
```

-continued

```
                          organism = Homo sapiens
SEQUENCE: 370
RFIGIPNQF                                                            9

SEQ ID NO: 371            moltype = AA   length = 9
FEATURE                   Location/Qualifiers
source                    1..9
                          mol_type = protein
                          organism = Homo sapiens
SEQUENCE: 371
AYSHLRYVF                                                            9

SEQ ID NO: 372            moltype = AA   length = 11
FEATURE                   Location/Qualifiers
source                    1..11
                          mol_type = protein
                          organism = Homo sapiens
SEQUENCE: 372
VYVIEPHSME F                                                        11

SEQ ID NO: 373            moltype = AA   length = 9
FEATURE                   Location/Qualifiers
source                    1..9
                          mol_type = protein
                          organism = Homo sapiens
SEQUENCE: 373
GYISNGELF                                                            9

SEQ ID NO: 374            moltype = AA   length = 9
FEATURE                   Location/Qualifiers
source                    1..9
                          mol_type = protein
                          organism = Homo sapiens
SEQUENCE: 374
VFLPRVTEL                                                            9

SEQ ID NO: 375            moltype = AA   length = 9
FEATURE                   Location/Qualifiers
source                    1..9
                          mol_type = protein
                          organism = Homo sapiens
SEQUENCE: 375
KYTDYILKI                                                            9

SEQ ID NO: 376            moltype = AA   length = 11
FEATURE                   Location/Qualifiers
source                    1..11
                          mol_type = protein
                          organism = Homo sapiens
SEQUENCE: 376
VYTPVASRQS L                                                        11

SEQ ID NO: 377            moltype = AA   length = 9
FEATURE                   Location/Qualifiers
source                    1..9
                          mol_type = protein
                          organism = Homo sapiens
SEQUENCE: 377
QYTPHSHQF                                                            9

SEQ ID NO: 378            moltype = AA   length = 9
FEATURE                   Location/Qualifiers
source                    1..9
                          mol_type = protein
                          organism = Homo sapiens
SEQUENCE: 378
VYIAELEKI                                                            9

SEQ ID NO: 379            moltype = AA   length = 9
FEATURE                   Location/Qualifiers
source                    1..9
                          mol_type = protein
                          organism = Homo sapiens
SEQUENCE: 379
VFIAQGYTL                                                            9

SEQ ID NO: 380            moltype = AA   length = 9
FEATURE                   Location/Qualifiers
source                    1..9
```

```
                            mol_type = protein
                            organism = Homo sapiens
SEQUENCE: 380
VYTGIDHHW                                                       9

SEQ ID NO: 381              moltype = AA  length = 9
FEATURE                     Location/Qualifiers
source                      1..9
                            mol_type = protein
                            organism = Homo sapiens
SEQUENCE: 381
KYPASSSVF                                                       9

SEQ ID NO: 382              moltype = AA  length = 10
FEATURE                     Location/Qualifiers
source                      1..10
                            mol_type = protein
                            organism = Homo sapiens
SEQUENCE: 382
AYLPPLQQVF                                                      10

SEQ ID NO: 383              moltype = AA  length = 10
FEATURE                     Location/Qualifiers
source                      1..10
                            mol_type = protein
                            organism = Homo sapiens
SEQUENCE: 383
RYKPGEPITF                                                      10

SEQ ID NO: 384              moltype = AA  length = 10
FEATURE                     Location/Qualifiers
source                      1..10
                            mol_type = protein
                            organism = Homo sapiens
SEQUENCE: 384
RYFDVGLHNF                                                      10

SEQ ID NO: 385              moltype = AA  length = 9
FEATURE                     Location/Qualifiers
source                      1..9
                            mol_type = protein
                            organism = Homo sapiens
SEQUENCE: 385
QYIEELQKF                                                       9

SEQ ID NO: 386              moltype = AA  length = 9
FEATURE                     Location/Qualifiers
source                      1..9
                            mol_type = protein
                            organism = Homo sapiens
SEQUENCE: 386
TFSDVEAHF                                                       9

SEQ ID NO: 387              moltype = AA  length = 9
FEATURE                     Location/Qualifiers
source                      1..9
                            mol_type = protein
                            organism = Homo sapiens
SEQUENCE: 387
KYTEKLEEI                                                       9

SEQ ID NO: 388              moltype = AA  length = 9
FEATURE                     Location/Qualifiers
source                      1..9
                            mol_type = protein
                            organism = Homo sapiens
SEQUENCE: 388
IYGEKTYAF                                                       9

SEQ ID NO: 389              moltype = AA  length = 10
FEATURE                     Location/Qualifiers
source                      1..10
                            mol_type = protein
                            organism = Homo sapiens
SEQUENCE: 389
EYLPEFLHTF                                                      10

SEQ ID NO: 390              moltype = AA  length = 9
FEATURE                     Location/Qualifiers
```

```
source                  1..9
                        mol_type = protein
                        organism = Homo sapiens
SEQUENCE: 390
RYLWATVTI                                                                  9

SEQ ID NO: 391          moltype = AA   length = 10
FEATURE                 Location/Qualifiers
source                  1..10
                        mol_type = protein
                        organism = Homo sapiens
SEQUENCE: 391
LYQILQGIVF                                                                10

SEQ ID NO: 392          moltype = AA   length = 11
FEATURE                 Location/Qualifiers
source                  1..11
                        mol_type = protein
                        organism = Homo sapiens
SEQUENCE: 392
RYLDSLKAIV F                                                              11

SEQ ID NO: 393          moltype = AA   length = 9
FEATURE                 Location/Qualifiers
source                  1..9
                        mol_type = protein
                        organism = Homo sapiens
SEQUENCE: 393
KYIEAIQWI                                                                  9

SEQ ID NO: 394          moltype = AA   length = 9
FEATURE                 Location/Qualifiers
source                  1..9
                        mol_type = protein
                        organism = Homo sapiens
SEQUENCE: 394
FYQPKIQQF                                                                  9

SEQ ID NO: 395          moltype = AA   length = 9
FEATURE                 Location/Qualifiers
source                  1..9
                        mol_type = protein
                        organism = Homo sapiens
SEQUENCE: 395
LYINKANIW                                                                  9

SEQ ID NO: 396          moltype = AA   length = 9
FEATURE                 Location/Qualifiers
source                  1..9
                        mol_type = protein
                        organism = Homo sapiens
SEQUENCE: 396
YYHFIFTTL                                                                  9

SEQ ID NO: 397          moltype = AA   length = 9
FEATURE                 Location/Qualifiers
source                  1..9
                        mol_type = protein
                        organism = Homo sapiens
SEQUENCE: 397
IYNGKLFDL                                                                  9

SEQ ID NO: 398          moltype = AA   length = 10
FEATURE                 Location/Qualifiers
source                  1..10
                        mol_type = protein
                        organism = Homo sapiens
SEQUENCE: 398
IYNGKLFDLL                                                                10

SEQ ID NO: 399          moltype = AA   length = 9
FEATURE                 Location/Qualifiers
source                  1..9
                        mol_type = protein
                        organism = Homo sapiens
SEQUENCE: 399
SYIDVLPEF                                                                  9

SEQ ID NO: 400          moltype = AA   length = 9
```

```
FEATURE                 Location/Qualifiers
source                  1..9
                        mol_type = protein
                        organism = Homo sapiens
SEQUENCE: 400
KYLEKYYNL                                                               9

SEQ ID NO: 401          moltype = AA  length = 10
FEATURE                 Location/Qualifiers
source                  1..10
                        mol_type = protein
                        organism = Homo sapiens
SEQUENCE: 401
VFMKDGFFYF                                                              10

SEQ ID NO: 402          moltype = AA  length = 10
FEATURE                 Location/Qualifiers
source                  1..10
                        mol_type = protein
                        organism = Homo sapiens
SEQUENCE: 402
VWSDVTPLTF                                                              10

SEQ ID NO: 403          moltype = AA  length = 10
FEATURE                 Location/Qualifiers
source                  1..10
                        mol_type = protein
                        organism = Homo sapiens
SEQUENCE: 403
TYKYVDINTF                                                              10

SEQ ID NO: 404          moltype = AA  length = 9
FEATURE                 Location/Qualifiers
source                  1..9
                        mol_type = protein
                        organism = Homo sapiens
SEQUENCE: 404
RYLEKFYGL                                                               9

SEQ ID NO: 405          moltype = AA  length = 9
FEATURE                 Location/Qualifiers
source                  1..9
                        mol_type = protein
                        organism = Homo sapiens
SEQUENCE: 405
NYPKSIHSF                                                               9

SEQ ID NO: 406          moltype = AA  length = 9
FEATURE                 Location/Qualifiers
source                  1..9
                        mol_type = protein
                        organism = Homo sapiens
SEQUENCE: 406
TYSEKTTLF                                                               9

SEQ ID NO: 407          moltype = AA  length = 9
FEATURE                 Location/Qualifiers
source                  1..9
                        mol_type = protein
                        organism = Homo sapiens
SEQUENCE: 407
VYGIRLEHF                                                               9

SEQ ID NO: 408          moltype = AA  length = 9
FEATURE                 Location/Qualifiers
source                  1..9
                        mol_type = protein
                        organism = Homo sapiens
SEQUENCE: 408
QYASRFVQL                                                               9

SEQ ID NO: 409          moltype = AA  length = 9
FEATURE                 Location/Qualifiers
source                  1..9
                        mol_type = protein
                        organism = Homo sapiens
SEQUENCE: 409
YFISHVLAF                                                               9
```

```
SEQ ID NO: 410         moltype = AA   length = 9
FEATURE                Location/Qualifiers
source                 1..9
                       mol_type = protein
                       organism = Homo sapiens
SEQUENCE: 410
RFLSGIINF                                                               9

SEQ ID NO: 411         moltype = AA   length = 9
FEATURE                Location/Qualifiers
source                 1..9
                       mol_type = protein
                       organism = Homo sapiens
SEQUENCE: 411
VYIGHTSTI                                                               9

SEQ ID NO: 412         moltype = AA   length = 9
FEATURE                Location/Qualifiers
source                 1..9
                       mol_type = protein
                       organism = Homo sapiens
SEQUENCE: 412
SYNPLWLRI                                                               9

SEQ ID NO: 413         moltype = AA   length = 9
FEATURE                Location/Qualifiers
source                 1..9
                       mol_type = protein
                       organism = Homo sapiens
SEQUENCE: 413
NYLLYVSNF                                                               9

SEQ ID NO: 414         moltype = AA   length = 9
FEATURE                Location/Qualifiers
source                 1..9
                       mol_type = protein
                       organism = Homo sapiens
SEQUENCE: 414
MYPYIYHVL                                                               9

SEQ ID NO: 415         moltype = AA   length = 9
FEATURE                Location/Qualifiers
source                 1..9
                       mol_type = protein
                       organism = Homo sapiens
SEQUENCE: 415
SYQKVIELF                                                               9

SEQ ID NO: 416         moltype = AA   length = 9
FEATURE                Location/Qualifiers
source                 1..9
                       mol_type = protein
                       organism = Homo sapiens
SEQUENCE: 416
AYSDGHFLF                                                               9

SEQ ID NO: 417         moltype = AA   length = 9
FEATURE                Location/Qualifiers
source                 1..9
                       mol_type = protein
                       organism = Homo sapiens
SEQUENCE: 417
VYKVVGNLL                                                               9

SEQ ID NO: 418         moltype = AA   length = 10
FEATURE                Location/Qualifiers
source                 1..10
                       mol_type = protein
                       organism = Homo sapiens
SEQUENCE: 418
ELAGIGILTV                                                             10
```

```
-continued

SEQ ID NO: 419      moltype = AA  length = 9
FEATURE             Location/Qualifiers
source              1..9
                    mol_type = protein
                    organism = Homo sapiens
SEQUENCE: 419
YLLPAIVHI                                                                  9
```

The invention claimed is:

1. A peptide consisting of the amino acid sequence VYALKVRTI (SEQ ID NO: 145) in the form of a pharmaceutically acceptable salt.

2. The peptide of claim 1, wherein said peptide has the ability to bind to an MHC class-I molecule, and wherein said peptide, when bound to said MHC, is capable of being recognized by CD8 T cells.

3. The peptide of claim 1, wherein the pharmaceutically acceptable salt is chloride salt.

4. The peptide of claim 1, wherein the pharmaceutically acceptable salt is acetate salt.

5. A composition comprising the peptide of claim 1 and a pharmaceutically acceptable carrier.

6. The composition of claim 5, wherein the peptide is in the form of a chloride salt.

7. The composition of claim 5, wherein the peptide is in the form of an acetate salt.

8. The composition of claim 5, further comprising an adjuvant selected from the group consisting of anti-CD40 antibody, imiquimod, resiquimod, GM-CSF, cyclophosphamide, sunitinib, bevacizumab, interferon-alpha, interferon-beta, CpG oligonucleotides and derivatives, poly-(I: C) and derivatives, RNA, sildenafil, particulate formulations with poly(lactide co-glycolide) (PLG), virosomes, interleukin (IL)-1, IL-2, IL-4, IL-7, IL-12, IL-13, IL-15, IL-21, and IL-23.

9. The composition of claim 8, wherein the adjuvant is IL-2.

10. The composition of claim 8, wherein the adjuvant is IL-7.

11. The composition of claim 8, wherein the adjuvant is IL-12.

12. The composition of claim 8, wherein the adjuvant is IL-15.

13. The composition of claim 8, wherein the adjuvant is IL-21.

14. A pegylated peptide consisting of the amino acid sequence of VYALKVRTI (SEQ ID NO: 145) or a pharmaceutically acceptable salt thereof.

15. The peptide of claim 14, wherein the pharmaceutically acceptable salt is chloride salt.

16. The peptide of claim 14, wherein the pharmaceutically acceptable salt is acetate salt.

17. A composition comprising the pegylated peptide of claim 14 or pharmaceutically acceptable salt thereof, and a pharmaceutically acceptable carrier.

18. The composition of claim 5, wherein the pharmaceutically acceptable carrier is selected from the group consisting of saline, Ringer's solution, dextrose solution, and sustained release preparation.

19. The peptide in the form of a pharmaceutically acceptable salt of claim 1, wherein said peptide is produced by solid phase peptide synthesis or produced by a yeast cell or bacterial cell expression system.

20. A composition comprising the peptide of claim 1, wherein the composition is a pharmaceutical composition and comprises water and a buffer.

* * * * *